United States Patent
Cygnar et al.

(10) Patent No.: US 12,252,544 B2
(45) Date of Patent: *Mar. 18, 2025

(54) ANTI-CD63 ANTIBODIES, CONJUGATES, AND USES THEREOF

(71) Applicant: Regeneron Pharmaceuticals, Inc., Tarrytown, NY (US)

(72) Inventors: Katherine Cygnar, New York, NY (US); Andrew Baik, Bronx, NY (US); Christopher Schoenherr, Piermont, NY (US); Andrew J. Murphy, Croton-on-Hudson, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 1029 days.

This patent is subject to a terminal disclaimer.

(21) Appl. No.: 17/056,301

(22) PCT Filed: May 17, 2019

(86) PCT No.: PCT/US2019/032922
§ 371 (c)(1),
(2) Date: Nov. 17, 2020

(87) PCT Pub. No.: WO2019/222663
PCT Pub. Date: Nov. 21, 2019

(65) Prior Publication Data
US 2021/0079109 A1  Mar. 18, 2021

Related U.S. Application Data

(60) Provisional application No. 62/777,592, filed on Dec. 10, 2018, provisional application No. 62/681,563, filed on Jun. 6, 2018, provisional application No. 62/673,098, filed on May 17, 2018.

(51) Int. Cl.
| | |
|---|---|
| *C07K 16/28* | (2006.01) |
| *A61K 39/00* | (2006.01) |
| *A61K 48/00* | (2006.01) |
| *C12N 9/34* | (2006.01) |

(52) U.S. Cl.
CPC ........ *C07K 16/2896* (2013.01); *C12N 9/2428* (2013.01); *A61K 2039/505* (2013.01); *A61K 48/00* (2013.01); *C07K 2317/21* (2013.01); *C07K 2317/31* (2013.01); *C07K 2317/622* (2013.01); *C07K 2317/77* (2013.01); *C07K 2317/92* (2013.01); *C07K 2319/00* (2013.01)

(58) Field of Classification Search
CPC ............ C07K 16/2896; C07K 2317/21; C07K 2317/31; C07K 2317/622; C07K 2317/77; C07K 2317/92; C07K 2319/00; C12N 9/2428; A61K 48/00; A61K 2039/505; A61K 38/47
See application file for complete search history.

(56) References Cited

U.S. PATENT DOCUMENTS

| | | |
|---|---|---|
| 4,444,878 A | 4/1984 | Paulus |
| 4,975,278 A | 12/1990 | Senter et al. |
| 5,030,717 A | 7/1991 | Tramontano et al. |
| 5,126,258 A | 6/1992 | Lerner et al. |
| 5,156,965 A | 10/1992 | Schochetman et al. |
| 5,208,020 A | 5/1993 | Chari et al. |
| 5,229,272 A | 7/1993 | Paul et al. |
| 5,500,362 A | 3/1996 | Robinson et al. |
| 5,585,108 A | 12/1996 | Ruddy et al. |
| 5,601,819 A | 2/1997 | Wong et al. |
| 5,602,021 A | 2/1997 | Davis et al. |
| 5,714,586 A | 2/1998 | Kunstmann et al. |
| 5,731,168 A | 3/1998 | Carter et al. |
| 5,821,337 A | 10/1998 | Carter et al. |
| 5,851,527 A | 12/1998 | Hansen |
| 5,858,351 A | 1/1999 | Podsakoff et al. |
| 5,962,313 A | 10/1999 | Podsakoff et al. |
| 6,235,714 B1 | 5/2001 | Paul et al. |
| 6,265,389 B1 | 7/2001 | Burke |
| 6,306,393 B1 | 10/2001 | Goldenberg et al. |
| 6,329,503 B1 | 12/2001 | Afar et al. |
| 6,335,011 B1 | 1/2002 | Podsakoff et al. |
| 6,372,205 B1 | 4/2002 | Duncan et al. |
| 6,387,674 B1 | 5/2002 | Trasciatti et al. |
| 6,479,265 B1 | 11/2002 | Napper et al. |
| 6,555,525 B2 | 4/2003 | Burke |
| 6,610,290 B2 | 8/2003 | Podsakoff et al. |
| 6,703,488 B1 | 3/2004 | Burton et al. |

(Continued)

FOREIGN PATENT DOCUMENTS

| | | | |
|---|---|---|---|
| CN | 104160033 A | 11/2014 | |
| CN | 109071658 A | * 12/2018 | ......... A61K 47/6803 |

(Continued)

OTHER PUBLICATIONS

Oksvold, et. al. Magnetic Bead-Based Isolation of Exosomes. In: Sioud, M. (eds) RNA Interference. Methods in Molecular Biology. 1218:465-481 (2015) (Year: 2015).*

(Continued)

*Primary Examiner* — Jessica H Roark
*Assistant Examiner* — Francesca Edgingtongiordan
(74) *Attorney, Agent, or Firm* — Alston & Bird LLP

(57) ABSTRACT

Antibodies, portions, and fusion proteins thereof to CD63 are provided. Also provided are nucleic acid sequences encoding same. Also provided are compositions comprising and methods of using same, e.g., for treating a patient in need thereof.

Figure 1:
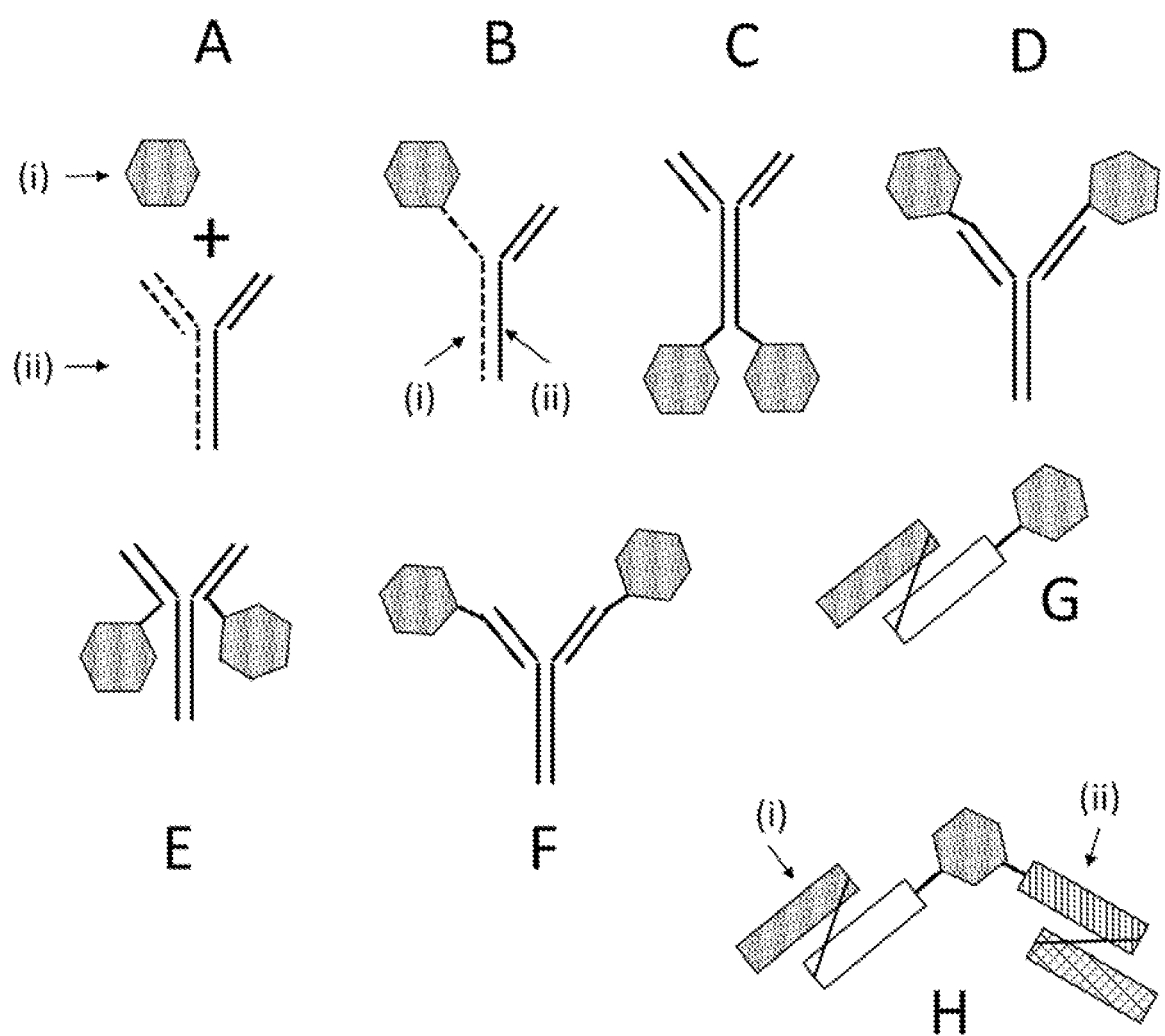

24 Claims, 2 Drawing Sheets
Specification includes a Sequence Listing.

(56) References Cited

U.S. PATENT DOCUMENTS

| | | |
|---|---|---|
| 6,855,804 B2 | 2/2005 | Paul et al. |
| 7,041,298 B2 | 5/2006 | Deshaies et al. |
| 7,105,348 B2 | 9/2006 | Murphy et al. |
| 7,223,556 B1 | 5/2007 | Zhou et al. |
| 7,235,641 B2 | 6/2007 | Kufer et al. |
| 7,335,504 B2 | 2/2008 | Haupts et al. |
| 7,371,539 B2 | 5/2008 | Church et al. |
| 7,431,923 B2 | 10/2008 | Young et al. |
| 7,442,777 B2 | 10/2008 | Young et al. |
| 7,560,424 B2 | 7/2009 | LeBowitz et al. |
| 7,704,492 B2 | 4/2010 | Podsakoff et al. |
| 7,750,116 B1 | 7/2010 | Doronina et al. |
| 7,754,681 B2 | 7/2010 | Feng |
| 7,771,997 B2 | 8/2010 | Chen et al. |
| 7,785,856 B2 | 8/2010 | LeBowitz et al. |
| 7,858,367 B2 | 12/2010 | Amalfitano et al. |
| 7,914,787 B2 | 3/2011 | Goldenberg et al. |
| 8,048,991 B2 | 11/2011 | Lundgren-Åkerlund |
| 8,058,399 B2 | 11/2011 | Jung |
| 8,257,745 B2 | 9/2012 | Ketelson et al. |
| 8,278,036 B2 | 10/2012 | Kariko et al. |
| 8,563,255 B2 | 10/2013 | Lundgren-Åkerlund |
| 8,586,713 B2 | 11/2013 | Davis et al. |
| 8,642,835 B2 | 2/2014 | Macdonald et al. |
| 8,679,478 B2 | 3/2014 | Koeberl |
| 8,785,168 B2 | 7/2014 | LeBowitz et al. |
| 8,815,226 B2 | 8/2014 | Yurkovetskiy et al. |
| 9,186,420 B2 | 11/2015 | Koeberl |
| 9,315,790 B2 | 4/2016 | Sakuraba et al. |
| 9,359,437 B2 | 6/2016 | Davis et al. |
| 9,453,241 B2 | 9/2016 | Pan |
| 9,545,450 B2 | 1/2017 | Do |
| 9,622,459 B2 | 4/2017 | Macdonald et al. |
| 9,738,717 B2 | 8/2017 | Azorsa |
| 9,849,195 B2 | 12/2017 | Davidson |
| 9,873,868 B2 | 1/2018 | Koeberl et al. |
| 9,950,076 B2 | 4/2018 | Nittoli et al. |
| 10,017,581 B2 | 7/2018 | Armstrong et al. |
| 10,087,253 B2 | 10/2018 | Lundgren-Åkerlund |
| 10,098,905 B2 | 10/2018 | Koeberl |
| 10,293,000 B2 | 3/2019 | Rebar |
| 10,512,676 B2 | 12/2019 | Char et al. |
| 10,556,015 B2 | 2/2020 | Zhang et al. |
| 10,759,864 B2 | 9/2020 | Sonoda et al. |
| 10,857,212 B2 | 12/2020 | Do et al. |
| 10,869,906 B2 | 12/2020 | Kishnani et al. |
| 10,912,804 B2 | 2/2021 | Byrne et al. |
| 11,129,903 B2 | 9/2021 | Andreev et al. |
| 11,191,844 B2 | 12/2021 | Andreev et al. |
| 11,208,458 B2 * | 12/2021 | Baik ................. C12N 9/24 |
| 11,352,446 B2 | 6/2022 | Cygnar et al. |
| 11,578,135 B2 | 2/2023 | Papadopoulos et al. |
| 2003/0219415 A1 | 11/2003 | Podsakoff et al. |
| 2004/0204379 A1 | 10/2004 | Cheng et al. |
| 2004/0248262 A1 | 12/2004 | Koeberl et al. |
| 2004/0258666 A1 | 12/2004 | Passini et al. |
| 2005/0142141 A1 | 6/2005 | Pardridge et al. |
| 2005/0220766 A1 | 10/2005 | Amalfitano et al. |
| 2005/0244400 A1 | 11/2005 | LeBowitz et al. |
| 2006/0078542 A1 | 4/2006 | Mah et al. |
| 2006/0099184 A1 | 5/2006 | Podsakoff et al. |
| 2006/0099205 A1 | 5/2006 | Adams et al. |
| 2006/0171926 A1 | 8/2006 | Passini et al. |
| 2006/0182745 A1 | 8/2006 | Kraft et al. |
| 2006/0210474 A1 | 9/2006 | Young et al. |
| 2007/0041978 A1 | 2/2007 | Hatiori et al. |
| 2007/0258987 A1 | 8/2007 | Francisco et al. |
| 2007/0280945 A1 | 12/2007 | Stevens et al. |
| 2008/0044408 A1 | 2/2008 | Young et al. |
| 2008/0069803 A1 | 3/2008 | Podsakoff et al. |
| 2008/0089891 A1 | 4/2008 | Hahn et al. |
| 2008/0269149 A1 | 10/2008 | Bowles et al. |
| 2008/0279945 A1 | 11/2008 | Mah et al. |
| 2008/0305497 A1 | 12/2008 | Kosmeder et al. |
| 2009/0117091 A1 | 5/2009 | LeBowitz et al. |
| 2009/0155262 A1 | 6/2009 | Young et al. |
| 2009/0191178 A1 | 7/2009 | Zankel et al. |
| 2010/0081796 A1 | 4/2010 | Brinkmann et al. |
| 2010/0129314 A1 | 5/2010 | Singh et al. |
| 2010/0183577 A1 | 7/2010 | Stern et al. |
| 2010/0221225 A1 | 9/2010 | Byrne et al. |
| 2010/0233173 A1 | 9/2010 | Wu et al. |
| 2010/0330034 A1 | 12/2010 | Bigler et al. |
| 2010/0331527 A1 | 12/2010 | Davis et al. |
| 2011/0184049 A1 | 7/2011 | Chuah et al. |
| 2011/0195454 A1 | 8/2011 | McWhirter et al. |
| 2011/0223147 A1 | 9/2011 | Lebowitz et al. |
| 2012/0034625 A1 | 2/2012 | Lundgren-Åkerlund |
| 2012/0093794 A1 | 4/2012 | LeBowitz et al. |
| 2012/0183502 A1 | 7/2012 | Meeker et al. |
| 2012/0228565 A1 | 9/2012 | Adams et al. |
| 2012/0265001 A1 | 10/2012 | Asmatulu et al. |
| 2012/0283503 A1 | 11/2012 | Ostrovska et al. |
| 2012/0322861 A1 | 12/2012 | Byrne et al. |
| 2013/0101546 A1 | 4/2013 | Yurkovetskiy et al. |
| 2013/0243775 A1 | 9/2013 | Papadopoulos et al. |
| 2013/0259833 A1 | 10/2013 | Pan |
| 2013/0267473 A1 | 10/2013 | Piens et al. |
| 2014/0099716 A1 | 4/2014 | Lundgren-Åkerlund |
| 2014/0186326 A1 | 7/2014 | Canfield et al. |
| 2014/0243504 A1 | 8/2014 | Davis et al. |
| 2014/0356366 A1 | 12/2014 | Cheong et al. |
| 2015/0056221 A1 | 2/2015 | Papadopoulos et al. |
| 2015/0196671 A1 | 7/2015 | Byrne et al. |
| 2015/0322149 A1 | 11/2015 | Bohrmann et al. |
| 2016/0089451 A1 | 3/2016 | Armstrong |
| 2016/0108133 A1 | 4/2016 | Armstrong et al. |
| 2016/0115229 A1 | 4/2016 | Azorsa |
| 2016/0319023 A1 | 11/2016 | Lundgren-Åkerlund |
| 2016/0369297 A1 | 12/2016 | Byrne et al. |
| 2016/0375147 A1 | 12/2016 | Nittoli et al. |
| 2017/0007715 A1 | 1/2017 | Andreev et al. |
| 2017/0028002 A1 | 2/2017 | Byrne et al. |
| 2017/0151346 A1 | 6/2017 | Zhao |
| 2017/0189497 A1 | 7/2017 | Do et al. |
| 2017/0209591 A1 | 7/2017 | Nittoli et al. |
| 2018/0002433 A1 | 1/2018 | Zhang et al. |
| 2018/0028676 A1 | 2/2018 | Armstrong |
| 2018/0036388 A1 | 2/2018 | McIvor et al. |
| 2018/0125949 A1 | 5/2018 | LeBowitz et al. |
| 2018/0236105 A1 | 8/2018 | Davidson et al. |
| 2018/0251571 A1 | 9/2018 | Armstrong et al. |
| 2018/0264090 A1 | 9/2018 | McIvor et al. |
| 2018/0271956 A1 | 9/2018 | McIvor et al. |
| 2018/0355017 A1 | 12/2018 | Baik et al. |
| 2018/0371440 A1 | 12/2018 | Koeberl et al. |
| 2019/0000984 A1 | 1/2019 | Andreev et al. |
| 2019/0030059 A1 | 1/2019 | Koeberl |
| 2019/0112588 A1 | 4/2019 | Baik et al. |
| 2019/0224246 A1 | 7/2019 | Rebar |
| 2019/0241633 A1 | 8/2019 | Fotin-Mleczek et al. |
| 2019/0269797 A1 | 9/2019 | Davidson et al. |
| 2019/0309061 A1 | 10/2019 | Papadopoulos et al. |
| 2019/0390184 A1 | 12/2019 | Mingozzi et al. |
| 2019/0390225 A1 | 12/2019 | Mingozzi et al. |
| 2020/0009267 A1 | 1/2020 | Davidson et al. |
| 2020/0095338 A1 | 3/2020 | Cygnar et al. |
| 2020/0248205 A1 | 8/2020 | Kirn et al. |
| 2020/0317798 A1 | 10/2020 | Sonoda et al. |
| 2020/0399623 A1 | 12/2020 | Baik et al. |
| 2020/0407746 A1 | 12/2020 | Vandendriessche et al. |
| 2021/0038739 A1 | 2/2021 | Takahashi et al. |
| 2021/0040464 A1 | 2/2021 | Armstrong et al. |
| 2021/0040503 A1 | 2/2021 | Mingozzi et al. |
| 2022/0008548 A1 | 1/2022 | Andreev et al. |
| 2022/0195011 A1 | 6/2022 | Baik et al. |
| 2022/0267477 A1 | 8/2022 | Cygnar et al. |
| 2023/0220100 A1 | 7/2023 | Cygnar et al. |
| 2023/0338477 A1 | 10/2023 | Baik et al. |

FOREIGN PATENT DOCUMENTS

| | | | |
|---|---|---|---|
| EP | 1716232 | B1 | 4/2010 |
| EP | 1587923 | B1 | 8/2011 |

(56) References Cited

FOREIGN PATENT DOCUMENTS

| | | |
|---|---|---|
| EP | 1879624 B1 | 9/2011 |
| EP | 1620133 B1 | 12/2015 |
| EP | 2475376 B1 | 3/2016 |
| EP | 2420256 B1 | 6/2016 |
| EP | 2279210 B1 | 4/2017 |
| EP | 2861263 B1 | 12/2017 |
| EP | 3315606 A1 | 5/2018 |
| EP | 2269658 B1 | 12/2018 |
| EP | 2687597 B1 | 12/2018 |
| EP | 3075386 B1 | 10/2019 |
| EP | 3292875 B1 | 5/2020 |
| EP | 2981551 B1 | 6/2020 |
| EP | 3272773 B1 | 7/2020 |
| EP | 3461905 B1 | 8/2020 |
| KR | 10-2017-0010896 | 2/2017 |
| WO | 1997/005266 A1 | 2/1997 |
| WO | WO 1998/016254 A1 | 4/1998 |
| WO | 1999/036437 A1 | 7/1999 |
| WO | 2001/036005 A2 | 5/2001 |
| WO | WO 2003/057179 A2 | 7/2003 |
| WO | WO 2004/023973 A2 | 3/2004 |
| WO | WO 2005/077333 A2 | 8/2005 |
| WO | 2005/089808 A2 | 9/2005 |
| WO | WO 2006/072166 A1 | 7/2006 |
| WO | WO 2006/108052 A2 | 10/2006 |
| WO | 2007/024323 A2 | 3/2007 |
| WO | WO 2007/075270 A1 | 7/2007 |
| WO | 2008/011710 A1 | 1/2008 |
| WO | 2008/011711 A1 | 1/2008 |
| WO | 2008/014404 A2 | 1/2008 |
| WO | WO 2008/022295 A1 | 2/2008 |
| WO | 2008/122039 A2 | 10/2008 |
| WO | WO 2008/143354 A1 | 11/2008 |
| WO | 2009/094561 A1 | 7/2009 |
| WO | 2010/010324 A1 | 1/2010 |
| WO | 2010/115552 A1 | 10/2010 |
| WO | 2010/119119 A1 | 10/2010 |
| WO | 2011/012316 A2 | 2/2011 |
| WO | 2011/018611 A1 | 2/2011 |
| WO | 2011/029823 A1 | 3/2011 |
| WO | 2011/130598 A1 | 10/2011 |
| WO | 2011/147986 A1 | 12/2011 |
| WO | 2012/005982 A2 | 1/2012 |
| WO | 2012/125987 A2 | 9/2012 |
| WO | 2012/143379 A1 | 10/2012 |
| WO | 2012/166559 A1 | 12/2012 |
| WO | 2013/053872 A1 | 4/2013 |
| WO | 2013/053873 A1 | 4/2013 |
| WO | 2013/055990 A1 | 4/2013 |
| WO | 2013/055993 A1 | 4/2013 |
| WO | 2013/068874 A1 | 5/2013 |
| WO | 2013/085925 A1 | 6/2013 |
| WO | 2013/138400 A1 | 9/2013 |
| WO | 2014/065661 A1 | 5/2014 |
| WO | WO 2014/085621 A1 | 6/2014 |
| WO | 2014/130723 A1 | 8/2014 |
| WO | 2014/145090 A1 | 9/2014 |
| WO | 2014/182970 A1 | 11/2014 |
| WO | WO 2014/185214 A2 | 11/2014 |
| WO | WO 2015/026907 A1 | 2/2015 |
| WO | 2015/031396 A1 | 3/2015 |
| WO | WO 2016/044947 A1 | 3/2016 |
| WO | WO 2016/065319 A1 | 4/2016 |
| WO | WO 2016/077840 A2 | 5/2016 |
| WO | WO 2016/085820 A1 | 6/2016 |
| WO | 2016/160615 A1 | 10/2016 |
| WO | WO 2016/179257 A2 | 11/2016 |
| WO | 2017/007796 A1 | 1/2017 |
| WO | 2017/190079 A1 | 2/2017 |
| WO | WO 2017/100467 A2 | 6/2017 |
| WO | 2017/134197 A1 | 8/2017 |
| WO | WO 2006/088503 A1 | 8/2017 |
| WO | WO 2017/131496 A1 | 8/2017 |
| WO | WO 2017/147414 A1 | 8/2017 |
| WO | WO 2018/031424 A1 | 2/2018 |
| WO | WO 2018/138322 A1 | 8/2018 |
| WO | WO 2018/213340 A1 | 11/2018 |
| WO | 2018/226861 A1 | 12/2018 |
| WO | WO 2019/075417 A1 | 4/2019 |
| WO | WO 2019/153009 A1 | 8/2019 |
| WO | WO-2019157224 A1 * | 8/2019 ............ A61K 38/47 |
| WO | WO 2019/197428 A1 | 10/2019 |
| WO | WO 2019/222411 A1 | 11/2019 |
| WO | WO 2019/222663 A1 | 11/2019 |
| WO | 2020/023390 A1 | 1/2020 |
| WO | 2020/041773 A1 | 2/2020 |
| WO | WO 2020/028841 A1 | 2/2020 |
| WO | 2020/223362 A1 | 5/2020 |
| WO | WO 2020/102645 A1 | 5/2020 |
| WO | WO 2020/117898 A1 | 6/2020 |
| WO | 2020/163480 A1 | 8/2020 |
| WO | 2021/005176 A1 | 1/2021 |

OTHER PUBLICATIONS

De Goeij et. al. J Exp Med 201(3):385-396. (2005) (Year: 2005).*
Gershoni et al., Epitope Mapping, Biodrugs 2007; 21 (3): 145-156p. 146 section 1.1 (Year: 2007).*
Blythe et al., Benchmarking B cell epitope prediction: Underperformance of existing methods, Protein Science (2005), 14:246-248 p. 246 (Year: 2005).*
Schreiber et al., 3D-Epitope-Explorer (3DEX): Localization of Conformational Epitopes within Three-Dimensional Structures of Proteins, Wiley Interscience, 42-44:60596 (2005) (Year: 2005).*
Davidson et. al. 143(1):13-20 (2014) (Year: 2014).*
Agarwal et al., "A Pictet-Spengler ligation for protein chemical modification," Proc. Natl. Acad. Sci., USA, 2013, 110:46-51.
Ahmad et al., "scFv Antibody: Principles and Clinical Application," Clinical and Developmental Immunology, vol. 2012, article ID 980250, 15 pages.
Al-Lazikani et al., "Standard Conformations for the Canonical Structures of Immunoglobulins," J. Mol. Biol., 1997, 273:927-948.
Altschul et al., "Basic Local Alignment Search Tool," J. Mol. Biol., 1990, 215:403-410.
Altschul et al., "Gapped BLAST and PSI-BLAST: a new generation of protein database search programs," Nucleic Acids Res., 1997, 25(17):3389-3402.
Andreev et al., "Abstract A131: Rapid constitutive internalization and degradation of prolactin receptor (PRLR) is associated with potent cell killing by PRLR antibody drug conjugates (ADC)," Molecular targets and Cancer Therapeutics, 14(12):supp. 2, Abstract No. A131 (Dec. 2015).
Andreev et al., "Bispecific Antibodies and Antibody-Drug Conjugates (ADCs) Bridging HER2 and Prolactin Receptor Improve Efficacy of HER2 ADCs," Mol. Cancer Ther., Apr. 2017, 16(4):681-693.
Angal et al. (1993) "A single amino acid substitution abolishes the heterogeneity of chimeric mouse/human (IgG4) antibody," Molecular Immunology 30(1):105-108 Abstract Only.
Anzai et al., "c-kit associated with the transmembrane 4 superfamily proteins constitutes a functionally distinct subunit in human hematopoietic progenitors," Blood, 2002, 99(12):4413-4421, doi:10.1182/blood.V99.12.4413.
Arnold et al. "Metabolic Biotinylation Provides a Unique Platform for the Purification and Targeting of Multiple AAV Vector Serotypes," Molecular Therapy, 2006, 14(1):97-106.
Arribas and Cutler, "Weibel-Palade Body Membrane Proteins Exhibit Differential Trafficking After Exocytosis in Endothelial Cells," Traffic, 2000, 1:783-793.
Aurnhammer et al., "Universal Real-Time PCR for the Detection and Quantification of Adeno-Associated Virus Serotype 2-Derived Inverted Terminal Repeat Sequences," Hum. Gene Ther. Methods, Part B, 2012, 23:18-28.
Azad et al., "A fully human CXCR4 antibody demonstrates diagnostic utility and therapeutic efficacy in solid tumor xenografts," Oncotarget, 2016, 7(11):12344-12358.
Baik et al., "Next-generation antibody-guided enzyme replacement therapy in Pompe disease mice," Molecular Genetics and Metabolism, 2018, 123(2):S21 Abstract Only.

(56) References Cited

OTHER PUBLICATIONS

Banerjee et al., "Targeted and armed oncolytic adenovirus via chemoselective modification," Bioorganic and Medicinal Chemistry Letters, 2011, 21(17):4985-4988.
Bareford and Swaan, "Endocytic mechanisms for targeted drug delivery," Advanced Drug Delivery Reviews, Elsevier, Amsterdam, NL, 2007, 59(8):748-758.
Bartlett et al., "Infectious Entry Pathway of Adeno-Associated Virus and Adeno-Associated Virus Vectors," Journal of Virology, 2000, 74(6):2777-2785.
Barzel et al., "Promoterless gene targeting without nucleases ameliorates hemophilia B in mice," Nature, 2015, 517(7534):360-364.
Battig et al., "Programmable Release of Multiple Protein Drugs from Aptamer-Functionalized Hydrogels via Nucleic Acid Hybridization," J. Am. Chem. Society., 2012, 134:12410-12413.
Beatty, "Trafficking from CD63-positive late endocytic multivesicular bodies is essential for intracellular development of Chlamydia trachomatis," Journal of Cell Science, 2006, 119(2):350-359.
Benedict et al., "Determination of the binding affinity of an anti-CD34 single-chain antibody using a novel, flow cytometry based assay," J Immunol Methods., 1997, 201(2):223-231.
Berditchevski et al., "Specific Association of CD63 with the VLA-3 and VLA-6 Integrins," Journal of Biological Chemistry, 1995, 270(30):17784-17790.
Berditchevski et al., "Characterization of Novel Complexes on the Cell Surface between Integrins and Proteins with 4 Transmembrane Domains (TM4 proteins)," Molecular Biology of the Cell, 1996, 7:193-207.
Berditchevski et al., "A Novel Link between Integrins, Transmembrane-4 Superfamily Proteins (CD63 and CD81), and Phosphatidylinositol 4-Kinase," Journal of Biological Chemistry, Jan. 1997, 272(5):2595-2598.
Berditchevski et al., "Generation of Monoclonal Antibodies to Integrin-associated Proteins," Journal of Biological Chemistry, Nov. 1997, 272(46):29174-29180.
Berditchevski et al., "Expression of the Palmitoylation-deficient CD151 Weakens the Association of $\alpha3\beta1$ Integrin with the Tetraspanin-enriched Microdomains and Affects Integrin-dependent Signaling," Journal of Biological Chemistry, 2002, 277(40):36991-37000.
Bian et al., "Selective gene transfer in vitro to tumor cells via recombinant Newcastle disease virus," Cancer Gene Ther., 2005, 12:295-303.
Bian et al., "In vivo efficacy of systemic tumor targeting of a viral RNA vector with oncolytic properties using a bispecific adapter protein," Int. J. Oncol., 2006, 29:1359-1369.
Blechacz and Russell, "Measles Virus as An Oncolytic Vector Platform," Current Gene Therapy, 2008, 8:162-175.
Bode et al., "Antibody-Directed Fibrinolysis: An Antibody Specific for Both Fibrin and Tissue Plasminogen Activator," Journal of Biological Chemistry, Jan. 1989, 264(2):944-948.
Boersma et al., "DARPins and other repeat protein scaffolds: advances in engineering and applications," Curr. Opin. Biotechnol., 2011, 22:849-885.
Bonardi et al., "Delivery of Saporin to Human B-Cell Lymphoma Using Bispecific Antibody: Targeting via CD22 but not CD19, CD37, or Immunoglobulin Results in Efficient Killing," Cancer Research, Jul. 1993, 53(13):3015-3021.
Boustany, "Lysosomal storage diseases—the horizon expands," Nat. Rev. Neurol., Oct. 2013, 9(10):583-598.
Brissinck et al., (1993) "Bispecific Antibodies in Lymphoma," Intern. Rev. Immunol., 10(2-3):187-194.
Campadelli-Fiume et al., "Rethinking herpes simplex virus: the way to oncolytic agents," Reviews in Medical Virology, 2011, 21:213-226.
Carrico et al., "Introducing genetically encoded aldehydes into proteins," Nat. Chem. Biol., 2007, 3:321-322.
Catelas et al., "Controlled Release of Bioactive Transforming Growth Factor Beta-1 from Fibrin Gels In Vitro," Tissue Engineering: Part C, 2008, 14(2):119-128.

Chadwick et al., "Modification of Retroviral Tropism by Display of IGF-I," Journal of Molecular Biology, 1999, 285:485-494.
Chen et al., "Fusion Protein Linkers: Property, Design and Functionality," Adv Drug Deliv Rev., 2013, 65(10):1357-1369.
Chiba, "Molecular Mechanism in $\alpha$-Glucosidase and Glucoamylase," Biosci. Biotechnol. Biochem., 1997, 61(8):1233-1239.
Chuah et al., "Liver-Specific Transcriptional Modules Identified by Genome-Wide In Silico Analysis Enable Efficient Gene Therapy in Mice and Non-Human Primates," Mol. Ther., 2014, 22(9):1605-1613.
Clynes et al., "Fc receptors are required in passive and active immunity to melanoma," Proc. Natl. Acad. Sci. (USA), 1998, 95:652-656.
Dalba et al., "Beyond Oncolytic Virotherapy: Replication-Competent Retrovirus Vectors for Selective and Stable Transduction of Tumors," Current Gene Therapy, 2005, 5:655-667.
De Goeij et al., "Efficient Payload Delivery by a Bispecific Antibody-Drug Conjugate Targeting HER2 and CD63," Mol. Cancer Ther., 2016, 15(11):2688-2697.
Derosa et al., "Therapeutic efficacy in a hemophilia B model using a biosynthetic mRNA liver depot system," Gene Therapy, 2016, 23:699-707.
Desnick and Schuchman, "Enzyme replacement therapy for lysosomal diseases: lessons from 20 years of experience and remaining challenges," 13 Annu. Rev. Genomics Hum. Genet., 2012, 13:307-335.
Devay et al., "Improved Lysosomal Trafficking Can Modulate the Potency of Antibody Drug Conjugates," Bioconjugate Chem., 2017, 28(4):1102-1114, DOI: 10.1021/acs.bioconjchem.7b00013.
Dimauro and Spiegel, "Progress and problems in muscle glycogenosis," Acta Myologica, Oct. 2011, 30(2):96-102.
Doronina et al., "Development of potent monoclonal antibody auristatin conjugates for cancer therapy," Nature Biotechnology, 2003, 21(7):778-784 and p. 941 Corrigendum.
Doyle et al., "CD63 is an essential cofactor to leukocyte recruitment by endothelial P-selectin," Blood, 2011, 118(15):4265-427.
Ducry and Stump, "Antibody-Drug Conjugates: Linking Cytotoxic Payloads to Monoclonal Antibodies," Bioconjugate Chem., 2010, 21:5-13.
Duffield et al., "The tetraspanin CD63 enhances the internalization of the H,K-ATPase $\beta$-subunit," Proc. Nail. Acad. Sci. USA, Dec. 2003, 100(26):15560-15565.
Egea et al., "Tissue inhibitor of metalloproteinase-1 (TIMP-1) regulates mesenchymal stem cells through let-7f microRNA and Wnt/$\beta$-catenin signaling," PNAS, 2012, 109(6):E309-E316.
Ehring, "Hydrogen Exchange/Electrospray Ionization Mass Spectrometry Studies of Structural Features of Proteins and Protein/Protein Interactions," Analytical Biochemistry, 1999, 267(2):252-259.
Einfeld, et al., "Reducing the Native Tropism of Adenovirus Vectors Requires Removal of both CAR and Integrin Interactions," J. Virol., 2001, 75(23):11284-11291.
Engen and Smith, "The Basics of Ion Chromatography," Anal. Chem., 2001, 73:256A-265A.
Engering and Pieters, "Association of distinct tetraspanins with MHC class II molecules at different subcellular locations in human immature dendritic cells," International Immunology, 2001, 13(2):127-134.
Erlwein et al., "Chimeric Ecotropic MLV Envelope Proteins that Carry EGF Receptor-Specific Ligands and the Pseudomonas Exotoxin A Translocation Domain to Target Gene Transfer to Human Cancer Cells," Virology, 2002, 302:333-341.
Ferland et al., "The effect of chloroquine on lysosomal prolactin receptors in rat liver," Endocrinology, 1984, 115(5):1842-1849.
Flannery et al., "Palmitoylation-dependent association with CD63 targets the CA2+ sensor synaptotagmin VII to lysosomes," J. Cell Biol., Nov. 2010, 191(3):599-613.
Galanis, "Therapeutic Potential of Oncolytic Measles Virus: Promises and Challenges," Clinical Pharmacology and Therapeutics, 2010, 88(5):620-625.
Galmiche et al., "Expression of a functional single chain antibody on the surface of extracellular enveloped vaccinia virus as a step towards selective tumour cell targeting," Journal of General Virology, 1997, 78:3019-3027.

(56) References Cited

OTHER PUBLICATIONS

Gao et al., "Novel adeno-associated viruses from rhesus monkeys as vectors for human gene therapy," PNAS, 2002, 99(18):11854-11859.
Genty et al., "Endocytosis and degradation of prolactin and its receptor in Chinese hamster ovary cells stably transfected with prolactin receptor cDNA," Mol. Cell Endocrinol., 1994, 99(2):221-228.
Geuijen et al. "Affinity ranking of antibodies using flow cytometry: Application in antibody phage display-based target discovery," J Immunol Methods, 2005, 302(1-2):68-77.
Ghaderi et al., "Production platforms for biotherapeutic glycoproteins. Occurrence, impact, and challenges of non-human sialylation," Biotechnol. Genet. Eng. Rev., 2012, 28:147-175.
Ghosh et al., "An Endocytosed TGN38 Chimeric Protein is Delivered to the TGN after Trafficking Through the Endocytic Recycling Compartment in CHO Cells," J. Cell Bioi., Aug. 1998, 142(4):923-936.
Gigout et al., "Altering AAV Tropism with Mosaic Viral Capsids," Molecular Therapy, 2005, 11(6):856-865.
Girod et al., "Genetic capsid modifications allow efficient re-targeting of adeno-associated virus type 2," Nature Medicine, 1999, 5(9):1052-1056.
Glasgow et al., "A Strategy for Adenovirus Vector Targeting with a Secreted Single Chain Antibody," PLOS One, 2009, 4(12):e8355, 12 pages.
Gonnet et al., "Exhaustive Matching of the Entire Protein Sequence Database," Science, 1992, 256: 1443-1445.
Grabow and Jaeger, "Loaded-up microsponges," Nature Materials, 2012, 11:268-269.
Gray et al., "Production of recombinant adeno-associated viral vectors and use in vitro and in vivo administration", Current Protocols in Neuroscience, 2011, Chapter: Unit 4.17, 36 pages, doi:10.1002/0471142301.ns0417s57.
Grifman et al., "Incorporation of Tumor-Targeting Peptides into Recombinant Adeno-associated Virus Capsids," Molecular Therapy, 2001, 3(6):964-975.
Guse et al., "Oncolytic vaccinia virus for the treatment of cancer," Expert Opinion on Biological Therapy, 2011, 11(5):595-608.
Haijema et al., "Switching Species Tropism: an Effective Way to Manipulate the Feline Coronavirus Genome," J. Virol., 2003, 77(8):4528-4538.
Hakomori, "Glycosphingolipids in Cellular Interaction, Differentiation, and Oncogenesis," Annual Review of Biochemistry, Jul. 1981, 50:733-764.
Hamblett et al., "Effects of Drug Loading on the Antitumor Activity of a Monoclonal Antibody Drug Conjugate," American Association for Cancer Research, Oct. 15, 2004, 10(20):7063-7070.
Hammond et al., "Single-Chain Antibody Displayed on a Recombinant Measles Virus Confers Entry through the Tumor-Associated Carcinoembryonic Antigen," Journal of Virology, 2001, 75(5):2087-2096.
Hemler, (2008) "Targeting of tetraspanin proteins—potential benefits and strategies," Nat. Rev. Drug. Discov. 7(9):747-758, doi: 10.1038/nrd2659.
Hemminki et al., "Targeting Oncolytic Adenoviral Agents to the Epidermal Growth Factor Pathway with a Secretory Fusion Molecule," Cancer Res., 2001, 61: 6377-6381.
Henning et al., "Genetic Modification of Adenovirus 5 Tropism by a Novel Class of Ligands Based on a Three-Helix Bundle Scaffold Derived from Staphylococcal Protein A," Human Gene Therapy, 2002, 13:1427-1439.
Hesselink et al., "Lysosomal dysfunction in muscle with special reference to glycogen storage disease type II," Biochim. Biophys. Acta., 2003, 1637(2):164-170.
Hirst et al., "Characterization of a Fourth Adaptor-related Protein Complex," Molecular Biology of the Cell, 1999, 10:2787-2802.
Hofer et al., "An engineered selenocysteine defines a unique class of antibody derivatives," Proc. Natl. Acad. Sci., USA, 2008, 105:12451-12456.
Hollander et al., "Selection of Reaction Additives Used in the Preparation of Monomeric Antibody-Calicheamicin Conjugates," Bioconjugate Chem., 2008, 19:358-361.
Holliger et al., ""Diabodies": Small bivalent and bispecific antibody fragments," PNAS USA, 1993, 90:6444-6448.
Jarantow et al., "Impact of Cell-surface Antigen Expression on Target Engagement and Function of an Epidermal Growth Factor Receptor x c-MET Bispecific Antibody," J Biol Chem., Oct. 9, 2015, 290(41):24689-24704, doi: 10.1074/jbc.M115.651653.
Jeger et al., "Site-Specific and Stoichiometric Modification of Antibodies by Bacterial Transglutaminase," Angew Chemie, Inter. Ed., 2010, 49:9995-9997.
Junghans et al., "Anti-Tac-H, a Humanized Antibody to the Interleukin 2 Receptor with New Features for Immunotherapy in Malignant and Immune Disorders," Cancer Res. 1990, 50:1495-1502.
Kabat et al., (1991) "Tabulation and Analysis of Amino Acid and Nucleic Acid Sequences of Precursors, V-Regions, C-Regions, J-Chain, T-Cell Receptors for Antigen, T-Cell Surface Antigens, alpha2-Microglobulins, Major Histocompatibility Antigens, Thy-1, Complement, C-Reactive Protein, Thymopoietin, Integrins, Post-gamma Globulin, a 2-Macroglobulins, and Other Related Proteins", Sequences of Proteins of Immunological Interest, Fifth Edition; NIH Publication No. 91-3242, National Institutes of Health, Bethesda, Md. (37 pages).
Kidd et al., "Fibrin hydrogels for lentiviral gene delivery in vitro and in vivo," Journal of Controlled Release, 2012, 157(1):80-85.
Kitani et al., "A Cell Surface Glycoprotein of Rat Basophilic Leukemia Cells Close to the High Affinity IgE Receptor (FcεRI)," Journal of Biological Chemistry, 1991, 266(3):1903-1909.
Klein et al., "Progress in overcoming the chain association issue in bispecific heterodimeric IgG antibodies," mAbs, 2012, 4:6 653-663 (12 pages).
Klimstra et al., "Targeting Sindbis virus-based vectors to Fc receptor-positive cell types," Virology, 2005, 338:9-21.
Kobayashi et al., "The Tetraspanin CD63/lamp3 Cycles between Endocytic and Secretory Compartments in Human Endothelial Cells," Molecular Biology, May 2000, 11:1829-1843.
Koeberl et al., "Enhanced efficacy of enzyme replacement therapy in Pompe disease through mannose-6-phosphate receptor expression in skeletal muscle," Mol. Genet. Metab., 2011, 103(2):107-112.
Kontermann, "Dual targeting strategies with bispecific antibodies," mAbs, 2012, 4(2):182-197.
Kraft et al., "Anti-CD63 antibodies suppress IgE-dependent allergic reactions in vitro and in vivo," JEM, 2005, 201(3):385-396.
Kraft et al., "The tetraspanin CD63 is required for efficient IgE-mediated mast cell degranulation and anaphylaxis," J. Immunol, 2013, 191(6):2871-2878.
Kufer et al., "A revival of bispecific antibodies," Trends Biotechnol., 2004, 22(5):238-244.
Langer, "New Methods of Drug Delivery," Science, 1990, 249:1527-1533.
Latysheva et al., "Syntenin-1 Is a New Component of Tetraspanin-Enriched Microdomains: Mechanisms and Consequences of the Interaction of Syntenin-1 with CD63," Molecular and Cellular Biology, Oct. 2006, 26(20):7707-7718.
Lee et al., "Impaired Retrograde Membrane Traffic Through Endosomes in a Mutant CHO Cell Defective in Phosphalidyl Serine Synthesis," Genes to Cells, 2012, 17:728-736.
Lekishvili et al., "The tumour-associated antigen L6 (L6-Ag) is recruited to the tetraspanin-enriched microdomains: implication for tumour cell motility," Journal of Cell Science, 2008, 121(5):685-694, doi:10.1242/jcs.020347.
Lieu et al., "The Golgin GCC88 Is Required for Efficient Retrograde Transport of Cargo from the Early Endosomes to the Trans-Golgi Network," Mol. Bioi. Cell, Dec. 2007, 18:4979-4991.
Lloyd et al., "Modelling the human immune response: performance of a 1011 human antibody repertoire against a broad panel of therapeutically relevant antigens," Protein Engineering, Design & Selection, 2009, 22(3):159-168.
Maecker et al., "The tetraspanin superfamily: molecular facilitators," FASEB J., May 1997, 11(6)428-442.

(56) References Cited

OTHER PUBLICATIONS

Maga et al., "Glycosylation-independent Lysosomal Targeting of Acid α-Glucosidase Enhances Muscle Glycogen Clearance in Pompe Mice," J. Biol. Chem., 2013, 288(3):1428-1438.

Mantegazza et al., "CD63 Tetraspanin Slows Down Cell Migration and Translocates to the Endosomal-Lysosomal—MIICs Route after Extracellular Stimuli in Human Immature Dendritic Cells," Blood, Aug. 2004, 104(4):1183-1190.

Martin et al., "Modeling antibody hypervariable loops: A combined algorithm," Proc. Natl. Acad. Sci. USA, 1989, 86:9268-9272.

Metzelaar et al., "CD63 antigen. A novel lysosomal membrane glycoprotein, cloned by a screening procedure for intracellular antigens in eukaryotic cells," J. Biol. Chem., 1991, 266(5):3239-3245.

Mordenti et al., "Interspecies Scaling of Clearance and Volume of Distribution Data for Five Therapeutic Proteins," Pharmaceutical Research, 1991, 8:1351-1359.

Muenzer, "Early initiation of enzyme replacement therapy for the mucopolysaccharidoses," Mol. Genet. Metab., Feb. 2014, 111(2):63-72.

Nakamura and Russell "Oncolytic measles viruses for cancer therapy," Expert Opinion on Biological Therapy, 2004, 4(10):1685-1692.

Nakano et al., "Herpes Simplex Virus Targeting to the EGF Receptor by a gD-Specific Soluble Bridging Molecule," Mol. Ther., Apr. 2005, 11(4):617-624.

Nicklin and Baker, "Tropism-Modified Adenoviral and Adeno-Associated Viral Vectors for Gene Therapy," Curr. Gene Ther., 2002, 2:273-293.

Nishibori et al., "The Protein CD63 Is in Platelet Dense Granules, Is Deficient in a Patient with Hermansky-Pudlak Syndrome, and Appears Identical to Granulophysin," J. Clin. Invest., 1993, 91(4):1775-1782.

Nishida-Aoki et al., "Disruption of Circulating Extracellular Vesicles as a Novel Therapeutic Strategy against Cancer Metastasis," Molecular Therapy, 2017, 25(1):181-191.

Nishida-Aoki et al., "Disruption of Circulating Extracellular Vesicles as a Novel Therapeutic Strategy against Cancer Metastasis," Molecular Therapy, 2017, 25(1):181-191 Supplemental Information (16 pages).

Ohno et al., "Cell-specific targeting of Sindbis virus vectors displaying IgG-binding domains of protein A," Nature Biotechnology, 1997, 15:763-767.

Oka and Bulleid, "Forming disulfides in the endoplasmic reticulum," Biochim Biophys Acta, 2013, 1833(11):2425-2429.

Papapetrou and Schambach, "Gene Insertion Into Genomic Safe Harbors for Human Gene Therapy," J. Molecular Therapy, Apr. 2016, 24(4):678-684.

Park et al., "Cancer gene therapy using adeno-associated virus vectors," Frontiers in Bioscience, Jan. 2008, 13:2653-2659.

Park et al., "Epidermal growth factor (EGF) receptor targeted delivery of PEGylated adenovirus," Biochemical and Biophysical Research Communications, 2008, 366:769-774.

Paul et al., "Specific Tumor Cell Targeting by a Recombinant MVA Expressing a Functional Single Chain Antibody on the Surface of Intracellular Mature Virus (IMV) Particles," Viral Immunology, 2007, 20(4):664-671.

Pearson, "Using the FASTA Program to Search Protein and DNA Sequence Databases," Chapter 26, Methods Mol. Biol., 1994, 26:307-331.

Pereboeva et al., "Targeting EGFR with metabolically biotinylated fiber-mosaic adenovirus," Gene Therapy, 2007, 14(8):627-637.

Phillips et al., "Dual Targeting of HER2-Positive Cancer with Trastuzumab Emtansine and Pertuzumab: Critical Role for Neuregulin Blockade in Antitumor Response to Combination Therapy," Clinical Cancer Research, 2014, 20(2):456-468.

Pizzato et al., "Evidence for nonspecific adsorption of targeted retrovirus vector particles to cells," Gene Therapy, 2001, 8:1088-1096.

Poljak et al., "Production and structure of diabodies," Structure, 1994, 2:1121-1123.

Pols and Klumperman, "Trafficking and Function of the Tetraspanin CD63," Exp. Cell Res., Oct. 2009, 315:1584-1592.

Ponnazhagan et al., "Conjugate-Based Targeting of Recombinant Adeno-Associated Virus Type 2 Vectors by Using Avidin-Linked Ligands," J. Virol., 2002, 76(24):12900-12907.

Powell et al., "Compendium of Excipients for Parenteral Formulations" PDA J. Pharm. Sci. Technol., 1998, 52:238-311.

Prabakaran et al., "Mannose 6-Phosphate Receptor and Sortilin Mediated Endocytosis of α-Galactosidase A in Kidney Endothelial Cells," PLoS One, 2012, 7(6):e39975, 9 pages.

Quetglas et al., "Alphavirus vectors for cancer therapy," Virus Research, 2010, 153:179-196.

Rabuka et al., "Site-specific chemical protein conjugation using genetically encoded aldehyde tags," Nat. Protocols, 2012, 7(6):1052-1067.

Reineke, "Antibody Epitope Mapping Using Arrays of Synthetic Peptides," Methods Mol. Biol., Chapter 26, 2004, 248:443-463.

Rhoden et al., "A Modeling and Experimental Investigation of the Effects of Antigen Density, Binding Affinity, and Antigen Expression Ratio on Bispecific Antibody Binding to Cell Surface Targets," J Biol. Chem. 291, May 2016, 291(21):11337-11347, doi: 10.1074/jbc.M116.714287.

Ridgway et al., "'Knobs-into-holes' engineering of antibody CH3 domains for heavy chain heterodimerization," Protein Eng., 1996, 9(7):617-621.

Říhová "Receptor-mediated targeted drug or toxin delivery," Advanced Drug Delivery Reviews, 1998, 29:273-289.

Rous et al., "Role of Adaptor Complex AP-3 in Targeting Wild-Type and Mutated CD63 to Lysosomes," Molecular Biology of the Cell, Mar. 2002, 13:1071-1082.

Rubinstein et al., "CD9, CD63, CD81, and CD82 are components of a surface tetraspan network connected to HLA-DR and VLA integrins," Eur. J. Immunol., 1996, 26:2657-2665.

Russell and Cosset, "Modifying the Host Range Properties of Retroviral Vectors," Journal of Gene Medicine, 1999, 1:300-311.

Russell and Peng, "Measles virus for cancer therapy," Current Topics in Microbiology and Immunology, 2009, 330:213-241.

Ryan et al., "Polyclonal Antibody Production Against Chito—Oligosaccharides," Food & Agriculture Immunol., 2001, 13:127-130.

Sapra et al., "Monoclonal antibody-based therapies in cancer: Advances and challenges," Pharmacol. & Therapeutics, 2013, 138:452-469.

Sasisekharan et al., "Glycomics Approach to Structure-Function Relationships of Glycosaminoglycans," Ann. Rev. Biomed. Eng., Dec. 2014, 8(1):181-231.

Schanzer et al., (Jul. 2014) "A Novel Glycoengineered Bispecific Antibody Format for Targeted Inhibition of Epidermal Growth Factor Receptor (EGFR) and Insulin-like Growth Factor Receptor Type I (IGF-1R) Demonstrating Unique Molecular Properties," J. Biol. Chem., 289(27):18693-18706.

Schröder et al., "Deficiency of the Tetraspanin CD63 Associated with Kidney Pathology but Normal Lysosomal Function," Mol. Cell. Biol., 2009, 29(4):1083-1094.

Schumacher et al., "Current Status: Site-Specific Antibody Drug Conjugates," J. Clin. Immunol., 2016, 36(Suppl 1):S100-S107.

Sefton, "Implantable Pumps," CRC Crit. Ref. Biomed. Eng., 1987, 14(3):201-240.

Senter, "Activation of Prodrugs by Antibody-Enzyme Conjugates: A New Approach to Cancer Therapy," FASEB J., 1990, 4:188-193.

Shah and Breakefield, "HSV Amplicon Vectors for Cancer Therapy," Current Gene Therapy, 2006, 6:361-370.

Shaunak et al., "Site-specific PEGylation of native disulfide bonds in therapeutic proteins," Nat. Chem. Biol., 2006, 2(6):312-313.

Shen et al., "A map of the cis-regulatory sequences in the mouse genome," Nature, 2012, 488(7409):116-120, doi:10.1038/nature11243.

Shi et al., "Insertional Mutagenesis of the Adeno-Associated Virus Type 2 (AAV2) Capsid Gene and Generation of AAV2 Vectors Targeted to Alternative Cell-Surface Receptors," Human Gene Therapy, 2001, 12:1697-1711.

(56) References Cited

OTHER PUBLICATIONS

Shi and Bartlett, "RGD Inclusion in VP3 Provides Adeno-Associated Virus Type 2 (AAV2)-Based Vectors with a Heparan Sulfate-Independent Cell Entry Mechanism," Molecular Therapy, Apr. 2003, 7(4):515-525.
Shields et al., "Lack of Fucose on Human IgG1 N-Linked Oligosaccharide Improves Binding to Human Fc RIII and Antibody-dependent Cellular Toxicity," Journal of Biological Chemistry, 2002, 277(30):26733-26740.
Shimamoto et al., "Peptibodies: A flexible alternative format to antibodies," Mabs, 2012, 4(5):586-591.
Skubitz et al., "CD63 associates with tyrosine kinase activity and CD11/CD18, and transmits an activation signal in neutrophils," Journal of Immunology, 1996, 157:3617-3626.
Spicer and Mikos, "Fibrin Glue as a Drug Delivery System," Journal of Controlled Release, 2010, 148(1):49-55.
Stachler and Bartlett, "Mosaic vectors comprised of modified AAV1 capsid proteins for efficient vector purification and targeting to vascular endothelial cells," Gene Ther., 2006, 13:926-931.
Stachler et al., "Site-specific Modification of AAV Vector Particles With Biophysical Probes and Targeting Ligands Using Biotin Ligase," Molecular Therapy, 2008, 16(8):1467-1473.
Tai and Kasahara, "Replication-competent retrovirus vectors for cancer gene therapy," Frontiers in Bioscience, 2008., 13:3083 3095.
Tajima et al., "Use of a Modified α-N-Acetylgalactosaminidase in the Development of Enzyme Replacement Therapy for Fabry Disease," Am. J. Hum. Genet., 2009, 85(5):569-580.
Takino et al., "Tetraspanin CD63 promotes targeting and lysosomal proteolysis of membrane-type 1 matrix metalloproteinase," Biochem. Biophys. Res. Commun., 2003, 304:160-166.
Tavare et al., "An effective immuno-PET imaging method to monitor CD8-dependent responses to immunotherapy," Cancer Res., 2016, 76(1):73-82.
Taylor et al., "A transgenic mouse that expresses a diversity of human sequence heavy and light chain immunoglobulins," Nucl. Acids Res., 1992, 20(23):6287-6295.
Tomer, "Characterization of a discontinuous epitope of the human immunodeficiency virus (HIV) core protein p24 by epitope excision and differential chemical modification followed by mass spectrometric peptide mapping analysis," Protein Science, 2000, 9:487-496.
Tuli et al., "Mechanism for amyloid precursor-like protein 2 enhancement of major histocompatibility complex class I molecule degradation," J Biol Chem. 2009, 284(49):34296-34307, doi: 10.1074/jbc.M109.039727. Epub Oct. 6, 2009.
Tuma and Hubbard, "Transcytosis: Crossing Cellular Barriers," Physiological Reviews, Jul. 1, 2003, 83(3):871-935.
Tutt et al., "TRISPECIFIC F(ab')3 Derivatives That Use Cooperative Signaling Via the TCR/CD3 Complex and CD2 to Activate and Redirect Resting Cytotoxic T Cells," J. Immunol., 1991, 147(1):60-69.
Valadi et al., "Exosome-mediated transfer of mRNAs and microRNAs is a novel mechanism of genetic exchange between cells," Nature Cell Biology, Jun. 2007, 9(6):654-659 and Supplementary Information (18 pages).
Van Beusechem et al., "Conditionally replicative adenovirus expressing a targeting adapter molecule exhibits enhanced oncolytic potency on CAR-deficient tumors," Gene Therapy, 2003, 10:1982-1991.
Verheije and Rottier, (2012) "Retargeting of Viruses to Generate Oncolytic Agents," Advances in Virology, 2012, 2012:1-15.
Vincent and Zurini, "Current strategies in antibody engineering: Fc engineering and pH-dependent antigen binding, bispecific antibodies and antibody drug conjugates," Biotechnol. J., 2012, 7:1444-1450.
Ward et al., "Binding activities of a repertoire of single immunoglobulin variable domains secreted from *Escherichia coli*," Nature, 1989, 341:544-546.
White et al., "Targeted Gene Delivery to Vascular Tissue In Vivo by Tropism-Modified Adeno-Associated Virus Vectors," Circulation, 2004, 109:513-519.
Wu et al., "Receptor-mediated in Vitro Gene Transformation by Soluble DNA Carrier System," J. Biol. Chem., 1987, 262(10):4429-4432.
Wurdinger et al., "Targeting non-human coronaviruses to human cancer cells using a bispecific single-chain antibody," Gene Therapy, 2005, 12:1394-1404.
Yauch and Hemler, "Specific interactions among transmembrane 4 superfamily (TM4SF) proteins and phosphoinositide 4-kinase," Biochem. J., 2000, 351:629-637.
Yi et al., "Antibody-mediated enzyme replacement therapy targeting both lysosomal and cytoplasmic glycogen in Pompe disease," J. Mol. Med., 2017, 95(5):513-521.
Yoshida et al., "A CD63 Mutant Inhibits T-cell Tropic Human Immunodeficiency Virus Type 1 Entry by Disrupting CXCR4 Trafficking to the Plasma Membrane," Traffic, Feb. 2008, 9:540-558.
Zhu et al., "Conjugation of Mannose-6-Phosphate-containing Oligosaccharides to Acid α-Glucosidase Improves the Clearance of Glycogen in Pompe Mice," J. Biol. Chem., 2004, 279(48):50336-50341.
Zolotukhin et al., "Recombinant adeno-associated virus purification using novel methods improves infectious titer and yield," Gene Ther., 1999, 6:973-985.
Invitation to Provide Informal Clarification with Respect to PCT/US2019/032922 Mailed Jul. 29, 2019.
International Search Report and Written Opinion with Respect to PCT/US2019/032922 Mailed Sep. 2, 2019.
Statement of Relatedness under MPEP 2001.06 with Respect to U.S. Appl. No. 17/056,301 dated Jan. 14, 2022.
Lee et al., "Novel strategy for a bispecific antibody: induction of dual target internalization and degradation," Oncogene, 2016, 35(34):4437-4446.
Statement of Relatedness under MPEP 2001.06 with Respect to U.S. Appl. No. 17/056,301 dated Aug. 17, 2022.
Audran et al., "Internalization of human macrophage surface antigens induced by monoclonal antibodies," Journal of Immunological Methods, 1995, 188:147-154.
Azorsa, et al. "CD63/Pltgp40: A Platelet Activation Antigen Identical to the Stage-Specific Melanoma-Associated Antigen ME491," Blood, 1991, 78(2):280-284.
Barrio, et al. "Monoclonal Antibody FC-5.01, Directed Against CD63 Antigen, is Internalized into Cytoplasmic Vesicles in the IIB-BR-G Human Breast Cancer Cell Line," Hybridoma, 1998, 17(6):517-525.
Dakour, et al. "Characterization of melanosome-associated proteins by establishment of monoclonal antibodies and immunoscreening of a melanoma cDNA library through an anti-melanosome antibody," Melanoma Research, 1993, 3(5):331-336.
Demetrick, et al. "ME491 Melanoma-Associated Glycoprotein Family: Antigenic Identity of ME491, NKI/C-3, Neuroglandular Antigen (NGA), and CD63 Proteins," Journal Natl. Cancer Inst., 1992; 84(6):422-429.
Ferrara et al., "Recombinant renewable polyclonal antibodies," mAbs, 2015, 7(1):32-41.
Hořejší and Vlček "Novel structurally distinct family of leucocyte surface glycoproteins including CD9, CD37, CD53 and CD63," FEBS, Aug. 1991, 288(1,2):1-4.
Huston et al., "Protein engineering of antibody binding sites: Recovery of specific activity in an anti-digoxin single-chain Fv analogue produced in *Escherichia coli*," PNAS, 1988, 85:16:5879-5883.
Israels and McMillan-Ward, "CD63 modulates spreading and tyrosine phosphorylation of platelets on immobilized fibrinogen," Thromb. Haemost., 2005, 93(2):311-318.
Kennel, et al. "Monoclonal Antibody to Rat CD63 Detects Different Molecular Form in Rat Tissue," Hybridoma, 1998, 17(6):509-515.
Knol, et al. "Monitoring human basophil activation via CD63 monoclonal antibody 435," J. Allergy Clin. Immunol., 1991, 88(3, Part 1):328-338.
Robinson e al., "Optimizing the stability of single-chain proteins by linker length and composition mutagenesis," PNAS, 1998, 95(11):5929-5934.

(56) References Cited

OTHER PUBLICATIONS

Verjan Garcia, et al., "SIRPa/CD172a Regulates Eosinophil Homeostasis," Journal of Immunology, 2011, 187:2268-2277.
Vischer and Wagner, "CD63 Is a Component of Weibel-Palade Bodies of Human Endothelial Cells," Blood, 1993, 82(4):1184-1191.
Statement of Relatedness under MPEP 2001.06 with Respect to U.S. Appl. No. 17/056,301 dated Aug. 3, 2022.
Almagro et al. "Progress and Challenges in the Design and Clinical Development of Antibodies for Cancer Therapy," Front. Immunol., 2018; 8:1751 (19 pages).
Brown et al., "Tolerance of single, but not multiple, amino acid replacements in antibody VH CDR 2: a means of minimizing B cell wastage from somatic hypermutation?," J Immunol, 1996, 156(9):3285-3291.
Chiu et al., "Antibody Structure and Function: The Basis for Engineering Therapeutics," Antibodies, Aug. 2019, 55 (80 pages) doi:10.3390/antib8040055.
Mazor et al., "Enhanced tumor-targeting selectivity by modulating bispecific antibody binding affinity and format valence," Scientific Reports, Jan. 9, 2017, 7:40098.
Rudikoff et al., "Single amino acid substitution altering antigen-binding specificity," Proc. Natl. Acad. Sci. USA, Mar. 1982, 79:1979-1983.
Saftig and Kluperman, "Lysosome biogenesis and lysosomal membrane proteins: trafficking meets function," Nature Reviews, Molecular Cell Biology, Sep. 2009, 10:623-635.
Statement of Relatedness under MPEP 2001.06 with Respect to U.S. Appl. No. 17/056,301 dated Nov. 15, 2023.
Jager et al., "High level transient production of recombinant antibodies and antibody fusion proteins in HEK293 cells," BMC Biotechnol., 13:52, (2013).
Spiess et al., "Alternative molecular formats and therapeutic applications for bispecific antibodies," Mol. Immunol., 67 (2 pt A):95-106, (2015).
Statement of Relatedness under MPEP 2001.06 with Respect to U.S. Appl. No. 17/056,301 dated Jun. 10, 2024.
Arai et al., "Design of the linkers which effectively separate domains of a bifunctional fusion protein," Protein Engineering, 2001, 14(8):529-532.
Author unknown, "Adeno-associated virus" Ed. by Masami Muramatsu, et al., Molecular Cell Biology Dictionary, Tokyo Kagaku Dojin, p. 21, (2002). English Translation.
Author Unknown, The Journal of the Japanese Society of Internal Medicine, (2009) vol. 98, No. 4, p. 875-882, submitted with the English Translation of Office Action dated Mar. 24, 2022 with respect to JP 2019-567722.
Baik et al., "Engineering tissue specific delivery of enzymes for lysosomal disease treatment," Abstracts, Molecular Genetics and Metabolism, 2016, 120:S23-S24.
Baik, et al., "Targeted delivery of acid alpha-glucosidase corrects skeletal muscle phenotypes in Pompe disease mice," Biorxiv, Apr. 23, 2020; retrieved from the internet Nov. 3, 2020 https://www.biorxiv.org/content/10.1101/2020.04.22.051672v1.full. pdf.
Berger et al., "Fusion protein technologies for biopharmaceuticals: Applications and challenges," mAbs, 2015, 7(3):456-460.
Boado et al., "Genetic Engineering of a Lysosomal Enzyme Fusion Protein for Targeted Delivery Across the Human Blood-Brain Barrier," Biotechnology and Bioengineering, Feb. 1, 2008, 99(2):475-484.
Boado et al., "IgG-enzyme fusion protein: pharmacokinetics and anti-drug antibody response in rhesus monkeys," Bioconjug. Chem., 24(1):97-104, (2013).
Boado et al., "IgG-Enzyme Fusion Protein: Pharmacokinetics and Anti-Drug Antibody Response in Rhesus Monkeys," Bioconjugate Chemistry, 2013, 24(1):97-104.
Braun et al., "Preclinical studies of lymphocyte gene therapy for mild Hunter syndrome (mucopolysaccharidosis type II)," Hum. Gene Ther., 7(3):283-290, (1996), Abstract.
Burkin and Kaufman, "The a7B1 integrin in muscle development and disease," Cell Tissue Res., 1999, 296:183-190.
Clevenger and Kline, "Prolactin receptor signal transduction," 10(10) Lupus, (2001) 10:706-718.
Corti et al., "Safety of Intradiaphragmatic Delivery of Adeno-Associated Virus-Mediated Alpha-Glucosidase (rAAV1-CMV-hGAA) Gene Therapy in Children Affected by Pompe Disease," Human Gene Therapy Clinical Development, 2017, 28(4):208-218.
Darvish-Damavandi et al., "Towards the development of an enzyme replacement therapy for the metabolic disorder propionic acidemia," Molecular Genetics and Metabolism Reports, 2016, 8(1):51-60.
Davies et al., "Human lgG4: a structural perspective," Immunol. Rev., 268(1):139-159, (2015).
De Franceschi et al., "Integrin traffic - the update," Journal of Cell Science, 2015, 128(5):839-852.
Dhital et al., "Mammalian Mucosal a-Glucosidases Coordinate with a-Amylase in the Initial Starch Hydrolysis Stage to Have a Role in Starch Digestion Beyond Glucogenesis," PLoS One, 2013, 8(4):e62546, 13 pages.
Dirks, "Brain tumor stem cells: bringing order to the chaos of brain cancer," J. Clin. Oncol., 26(17):2916-2924, (2008), Abstract only.
Elmallah et al., "Sustained Correction of Motoneuron Histopathology Following Intramuscular Delivery of AAV in Pompe Mice," The American Society of Gene & Cell Therapy, Apr. 2014, 22(4):702-712.
Falk et al., "Peripheral nerve and neuromuscular junction pathology in Pompe disease," Human Molecular Genetics, 2015, 24(3):625-636.
Ferrua et al., "Twenty-Five Years of Gene Therapy for ADA-SCID: From Bubble Babies to an Approved Drug," Hum. Gene Ther., 28(11):972-981, (2017), Abstract.
Fuentealba et al., "Low-Density Lipoprotein Receptor-Related Protein 1 (LRP1) Mediates Neuronal AB42 Uptake and Lysomal Trafficking," PLoS One 5(7): e11884, pp. 1-10, Jul. 2010.
Fukuda et al., "Autophagy and Mistargeting of Therapeutic Enzyme in Skeletal Muscle in Pompe Disease," Mol. Therapy, 2006, 14(6):831-839.
Fukuda et al., "Dysfunction of Endocytic and Autophagic Pathways in a Lysosomal Storage Disease," Ann Neurol, 2006, 59(4):700-708.
Fuller et al., "Isolation and characterisation of a recombinant, precursor form of lysosomal acid alpha-glucosidase," European Journal of Biochemistry, 1995, 234(3):903-909.
Geel et al., "Pompe disease: Current state of treatment modalities and animal models," Molecular Genetics and Metabolism, 2007, 92:299-307.
Gelperina et al., "The Potential Advantages of Nanoparticle Drug Delivery Systems in Chemotherapy of Tuberculosis," Am J Respir Crit Care Med., 172(12):1487-1490 (2005).
Haijema et al., "Live, Attenuated Coronavirus Vaccines through the Directed Deletion of Group-Specific Genes Provide Protection against Feline Infectious Peritonitis," J. Virology, 2004, 78(8):3863-3871.
Hordeaux et al., "Long-term neurologic and cardiac correction by intrathecal gene therapy in Pompe disease," Acta Neuropathologica Communications, 2017, 5:66 (19 pages).
Hsu et al., "Enhanced delivery of a-glucosidase for Pompe disease by ICAM-1-targeted nanocarriers: comparative performance of a strategy for three distinct lysosomal storage disorders," Nanomedicine, 8(5):731-739, (2012).
Huie et al., "Glycogen Storage Disease Type II: Identification of Four Novel Missense Mutations (D645N, G648S, R672W, R672Q) and Two Insertions/Deletions in the Acid α-Glucosidase Locus of Patients of Differing Phenotype," Biochem. Biophys. Res. Commun., 1998, 244(3):921-927.
Huie et al., "Increased Occurrence of Cleft Lip in Glycogen Storage Disease Type II (GSDII): Exclusion of a Contiguous Gene Syndrome in Two Patients by Presence of Intragenic Mutations Including a Novel Nonsense Mutation Gln58Stop," Am. J. Med. Genet., 1999, 85(1):5-8.
Kishnani, "Challenges of Enzyme Replacement Therapy: Poor Tissue Distribution in Lysosomal Diseases Using Pompe Disease as

(56) References Cited

OTHER PUBLICATIONS a Model." In: Rosenberg, A., Demeule, B. (eds) Biobetters. AAPS Advances in the Pharmaceutical Sciences Series, vol. 19. Springer, New York, NY (2015).
Lopez-Lararo, "The migration ability of stem cells can explain the existence of cancer of unknown primary site. Rethinking metastasis," Oncoscience, 2(5):467-475, (2015).
Mabey, "Epidemiology of sexually transmitted infections: worldwide," Medicine, 42(6):287-290, (2014), Abstract only.
Maesner et al., "Established cell surface markers efficiently isolate highly overlapping populations of skeletal muscle satellite cells by fluorescence-activated cell sorting," Skeletal Muscle, 2016, 6:35 (10 pages).
Matsui et al., "An orphan nuclear receptor, mROR alpha, and its spatial expression in adult mouse brain," Brain Res. Mol. Brain Res., 33(2):217-226, (1995).
Moody et al., "Receptor Crosslinking: A General Method to Trigger Internalization and Lysosomal Targeting of Therapeutic Receptor: Ligand Complexes," Molecular Therapy, 2015, 23(12):1888-1898.
Nishiyama et al., "Akt inactivation induces endoplasmic reticulum stress-independent autophagy in fibroblasts from patients with Pompe disease," Molecular Genetics and Metabolism, 2012, 107:490-495.
Ohashi et al., "Enzyme replacement therapy for lysosomal storage diseases," Pediatr. Endocrinol. Rev., 10 Suppl 1:26-34, (2012), Abstract.
Ozawa, K., "Gene therapy using AAV," Virus, (2007) vol. 57, No. 1, p. 47-56 (includes English translation).
Pacak et al. "Tissue specific promoters improve specificity of AAV9 mediated transgene expression following intra-vascular gene delivery in neonatal mice," Genetic Vaccines and Therapy, 2008 6:13 (5 pages).
Pardridge et al., "Plasma Pharmacokinetics of Valanafusp Alpha, a Human Insulin Receptor Antibody-Iduronidase Fusion Protein, in Patients with Mucopolysaccharidosis Type I," BioDrugs, 2018, 32(2):169-176.
Pardridge et al., "Reengineering biopharmaceuticals for targeted delivery across the blood- brain barrier," Methods Enzymol., 503:269-292, (2012).
Pardridge, "Blood-brain barrier drug delivery of IgG fusion proteins with a transferrin receptor monoclonal antibody," Expert Opin. Drug Deliv., 12(2):207-22, (Aug. 20, 2014).
Parenti et al., "Lysomal Storage Diseases: From Pathophysiology to Therapy," Ann. Rev. Med., 66:471-486, Jan. 2015.
Paterson et al., "Exploiting transferrin receptor for delivering drugs across the blood-brain barrier," Drug Discov. Today Technol., 20:49-52, (Oct. 27, 2016).
Puzzo et al., "Rescue of Pompe disease in mice by AAV-mediated liver delivery of secretable acid a-glucosidase," Science Translational Medicine, Nov. 29, 2017, 9(418):eaam6375 (12 pages).
Quezada-Calvillo et al., "Luminal Starch Substrate "Brake" on Maltase-Glucoamylase Activity is Located within the Glucoamylase Subunit," Journal of Nutrition, 2008, 138(4):685- 692.
Raben et al., "Enzyme replacement therapy in the mouse model of Pompe disease," Molecular Genetics and Metabolism, 2003, 80: 159-169.
Rofo et al., "Enhanced neprilysin-mediated degradation of hippocampal AB42 with a somatostatin peptide that enters the brain," Theranostics, 11(2): 789-804, (Jan. 2021).
Salem et al., "The Influence of SV40 polyA on Gene Expression of Baculovirus Expression Vector Systems," PLoS One, 10(12):e0145019, (2015).
Schänzer et al., "Quantification of muscle pathology in infantile Pompe disease," Neuromuscular Disorders, 2017, 27:141-152.
Sidman et al., "Temporal Neuropathological and Behavioral Phenotype of 6Neo/6Neo Pompe Disease Mice," Author Manuscript, J. Neuropathol. Exp. Neurol., Aug. 2008, 67(8):803-818.
Sim et al., "Human Intestinal Maltase-Glucoamylase: Crystal Structure of the N-Terminal Catalytic Subunit and Basis of Inhibition and Substrate Specificity," J. Mol. Biol., 2008, 375:782-792.
Sun et al., "New perspectives for ERT in Pompe disease: Extending the action of the enzyme to cytosolic targets," Molecular Genetics and Metabolism, 2016, 117:S110-S111, Abstract No. 295 doi: 10.1016/j.ymgme.2015.12.453.
Tanaka et al., "A novel approach to CNS dysfunction of Pompe disease with a fusion protein consisting of anti-transferrin receptor antibody and GAA enzyme," Mol. Genet. Metab., 129(2):S150-S151, (Feb. 2020).
Tran et al., "Survival comparison between glioblastoma multiforme and other incurable cancers," J. Clin. Neurosci., 17(4):417-421, (2010), Abstract only.
Umapathysivam et al., "Correlation of acid alpha-glucosidase and glycogen content in skin fibroblasts with age of onset in Pompe disease," Clin. Chim. Acta., 2005, 361:191-198.
Van Der Ploeg and Reuser "Lysosomal Storage Disease 2," Lancet, 2008, 372:1342-1353.
Wang et al., "Silence of MCL-1 upstream signaling by shRNA abrogates multiple myeloma growth," Exp. Hematol. Oncol., 3(1):27, (2014).
Xu et al., "Diversity in the CDR3 region of V(H) is sufficient for most antibody specificities," Immunity, 13(1):37-45, (2000).
Zhou et al., "Antibody-Mediated Enzyme Therapeutics and Applications in Glycogen Storage Diseases," Trends Mol. Med., 25(12):1094-1109, (2019).

* cited by examiner

SEQUENCE LISTING

<160> NUMBER OF SEQ ID NOS: 372

<210> SEQ ID NO 1
<211> LENGTH: 354
<212> TYPE: DNA
<213> ORGANISM: Homo sapiens

<400> SEQUENCE: 1

```
caggtgcagc tgcaggagtc gggcccgga ctgatgaagc cttcggagac cctgtccctc      60
acctgcactg tctctggtgg ctccttcagc agttactatt ggaactggat ccggcagtcc     120
ccagggaagg gactggagtg gattgggtat atccgttata gtggggacac caactacaag     180
ccctccctca agagtcgatt caccatatca attgacacgt ccaagaacct tttctccctg     240
aggctgaaat ctgtgaccgc tgcggacacg gccgtgtatt actgtgcgag gatgggactg     300
gggagtgatg cttttgatat ctggggccaa gggacaatgg tcaccgtctc ttca           354
```

<210> SEQ ID NO 2
<211> LENGTH: 118
<212> TYPE: PRT
<213> ORGANISM: Homo sapiens

<400> SEQUENCE: 2

```
Gln Val Gln Leu Gln Glu Ser Gly Pro Gly Leu Met Lys Pro Ser Glu
1               5                   10                  15

Thr Leu Ser Leu Thr Cys Thr Val Ser Gly Gly Ser Phe Ser Ser Tyr
            20                  25                  30

Tyr Trp Asn Trp Ile Arg Gln Ser Pro Gly Lys Gly Leu Glu Trp Ile
        35                  40                  45

Gly Tyr Ile Arg Tyr Ser Gly Asp Thr Asn Tyr Lys Pro Ser Leu Lys
    50                  55                  60

Ser Arg Phe Thr Ile Ser Ile Asp Thr Ser Lys Asn Leu Phe Ser Leu
65                  70                  75                  80

Arg Leu Lys Ser Val Thr Ala Ala Asp Thr Ala Val Tyr Tyr Cys Ala
                85                  90                  95

Arg Met Gly Leu Gly Ser Asp Ala Phe Asp Ile Trp Gly Gln Gly Thr
            100                 105                 110

Met Val Thr Val Ser Ser
        115
```

```
<210> SEQ ID NO 3
<211> LENGTH: 24
<212> TYPE: DNA
<213> ORGANISM: Homo sapiens

<400> SEQUENCE: 3
ggtggctcct tcagcagtta ctat                                         24

<210> SEQ ID NO 4
<211> LENGTH: 8
<212> TYPE: PRT
<213> ORGANISM: Homo sapiens

<400> SEQUENCE: 4

Gly Gly Ser Phe Ser Ser Tyr Tyr
1               5

<210> SEQ ID NO 5
<211> LENGTH: 21
<212> TYPE: DNA
<213> ORGANISM: Homo sapiens

<400> SEQUENCE: 5
atccgttata gtggggacac c                                            21

<210> SEQ ID NO 6
<211> LENGTH: 7
<212> TYPE: PRT
<213> ORGANISM: Homo sapiens

<400> SEQUENCE: 6

Ile Arg Tyr Ser Gly Asp Thr
1               5

<210> SEQ ID NO 7
<211> LENGTH: 36
<212> TYPE: DNA
<213> ORGANISM: Homo sapiens

<400> SEQUENCE: 7
gcgaggatgg gactggggag tgatgctttt gatatc                            36

<210> SEQ ID NO 8
<211> LENGTH: 12
<212> TYPE: PRT
<213> ORGANISM: Homo sapiens

<400> SEQUENCE: 8

Ala Arg Met Gly Leu Gly Ser Asp Ala Phe Asp Ile
1               5                   10

<210> SEQ ID NO 9
<211> LENGTH: 324
<212> TYPE: DNA
<213> ORGANISM: Homo sapiens

<400> SEQUENCE: 9
gaaattgtgt tgacgcagtc tccaggcacc ctgtctttgt ctccagggga aagagccacc     60
ctctcctgca gggccagtca gagtgttaac aacaattatt tagcctggta ccagcagaaa    120
cctggccagg ctcccaggct cctcatctat ggtgtattca cagggccac taacatccca    180 gacaggttca gtggcagtgg gtctgggaca gatttcactc tcaccatcag cagactggag    240
```

```
cctgaagatt tgcagtgta ttactgtcag cagtatggta gttcaccttg gacgttcggc    300
caagggacca aggtggaaat caaa                                          324
```

<210> SEQ ID NO 10
<211> LENGTH: 108
<212> TYPE: PRT
<213> ORGANISM: Homo sapiens

<400> SEQUENCE: 10

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Asn Asn Asn
            20                  25                  30

Tyr Leu Ala Trp Tyr Gln Gln Lys Pro Gly Gln Ala Pro Arg Leu Leu
        35                  40                  45

Ile Tyr Gly Val Phe Asn Arg Ala Thr Asn Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105
```

<210> SEQ ID NO 11
<211> LENGTH: 21
<212> TYPE: DNA
<213> ORGANISM: Homo sapiens

<400> SEQUENCE: 11

```
cagagtgtta acaacaatta t                                             21
```

<210> SEQ ID NO 12
<211> LENGTH: 7
<212> TYPE: PRT
<213> ORGANISM: Homo sapiens

<400> SEQUENCE: 12

```
Gln Ser Val Asn Asn Asn Tyr
1               5
```

<210> SEQ ID NO 13
<211> LENGTH: 9
<212> TYPE: DNA
<213> ORGANISM: Homo sapiens

<400> SEQUENCE: 13

```
ggtgtattc                                                            9
```

<210> SEQ ID NO 14
<211> LENGTH: 3
<212> TYPE: PRT
<213> ORGANISM: Homo sapiens

<400> SEQUENCE: 14

```
Gly Val Phe
1
```

<210> SEQ ID NO 15
<211> LENGTH: 27
<212> TYPE: DNA

<213> ORGANISM: Homo sapiens

<400> SEQUENCE: 15
cagcagtatg gtagttcacc ttggacg          27

<210> SEQ ID NO 16
<211> LENGTH: 9
<212> TYPE: PRT
<213> ORGANISM: Homo sapiens

<400> SEQUENCE: 16

Gln Gln Tyr Gly Ser Ser Pro Trp Thr
1               5

<210> SEQ ID NO 17
<211> LENGTH: 354
<212> TYPE: DNA
<213> ORGANISM: Homo sapiens

<400> SEQUENCE: 17
caggtgcagc tgcaggagtc gggcccaaga ctggtgaagc cttcggagac cctgtccctc      60
acctgcattg tctctggtgg ctccatcagt aatttctact ggaactggat ccggcagtcc     120
ccagggaagg gactggaatg gattggatat ttcttttaca ctgggactat cgactacaac     180
ccctccctca agagtcgagt caccatatca ctggacacgt ccaagaacca gttctccctg     240
aacctgcgtc ttctgaccgc cgcagacgcg gccgtttatt attgtgcgag gatggggctg     300
ggggctaatg cttttgacat ctggggccac gggacaatgg tcaccgtctc ttca           354

<210> SEQ ID NO 18
<211> LENGTH: 118
<212> TYPE: PRT
<213> ORGANISM: Homo sapiens

<400> SEQUENCE: 18

Gln Val Gln Leu Gln Glu Ser Gly Pro Arg Leu Val Lys Pro Ser Glu
1               5                   10                  15
Thr Leu Ser Leu Thr Cys Ile Val Ser Gly Gly Ser Ile Ser Asn Phe
            20                  25                  30
Tyr Trp Asn Trp Ile Arg Gln Ser Pro Gly Lys Gly Leu Glu Trp Ile
        35                  40                  45
Gly Tyr Phe Phe Tyr Thr Gly Thr Ile Asp Tyr Asn Pro Ser Leu Lys
    50                  55                  60
Ser Arg Val Thr Ile Ser Leu Asp Thr Ser Lys Asn Gln Phe Ser Leu
65                  70                  75                  80
Asn Leu Arg Leu Leu Thr Ala Ala Asp Ala Ala Val Tyr Tyr Cys Ala
                85                  90                  95
Arg Met Gly Leu Gly Ala Asn Ala Phe Asp Ile Trp Gly His Gly Thr
            100                 105                 110
Met Val Thr Val Ser Ser
        115

<210> SEQ ID NO 19
<211> LENGTH: 24
<212> TYPE: DNA
<213> ORGANISM: Homo sapiens

<400> SEQUENCE: 19
ggtggctcca tcagtaattt ctac          24

<210> SEQ ID NO 20
<211> LENGTH: 8
<212> TYPE: PRT
<213> ORGANISM: Homo sapiens

<400> SEQUENCE: 20

Gly Gly Ser Ile Ser Asn Phe Tyr
1               5

<210> SEQ ID NO 21
<211> LENGTH: 21
<212> TYPE: DNA
<213> ORGANISM: Homo sapiens

<400> SEQUENCE: 21
ttcttttaca ctgggactat c                                              21

<210> SEQ ID NO 22
<211> LENGTH: 7
<212> TYPE: PRT
<213> ORGANISM: Homo sapiens

<400> SEQUENCE: 22

Phe Phe Tyr Thr Gly Thr Ile
1               5

<210> SEQ ID NO 23
<211> LENGTH: 36
<212> TYPE: DNA
<213> ORGANISM: Homo sapiens

<400> SEQUENCE: 23
gcgaggatgg ggctgggggc taatgctttt gacatc                              36

<210> SEQ ID NO 24
<211> LENGTH: 12
<212> TYPE: PRT
<213> ORGANISM: Homo sapiens

<400> SEQUENCE: 24

Ala Arg Met Gly Leu Gly Ala Asn Ala Phe Asp Ile
1               5                   10

<210> SEQ ID NO 25
<211> LENGTH: 324
<212> TYPE: DNA
<213> ORGANISM: Homo sapiens

<400> SEQUENCE: 25
gaaattgtgt tgacgcagtc tccaggcacc ctgtctttgt ctcctggaga aagagccacc     60
ctctcctgca gggccagtca gcatgttagc agcaactact tagcctggta ccagcagaaa    120
cctggccagg ctcccaggct cctcatctat ggtggatcca gcagggccac tggcatccca    180
gacaggttca gtggcagtgg gtctgggaca gacttcactc tcaccatcag cagactggag    240
cctgcagatt ttgcagtgtt ttactgtcag cagtatggta actcaccttg gacgttcggc    300
caagggacca aggtggaaat gaaa                                           324

<210> SEQ ID NO 26
<211> LENGTH: 108
<212> TYPE: PRT
<213> ORGANISM: Homo sapiens -continued

```
<400> SEQUENCE: 26

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln His Val Ser Ser Asn
            20                  25                  30

Tyr Leu Ala Trp Tyr Gln Lys Pro Gly Gln Ala Pro Arg Leu Leu
        35                  40                  45

Ile Tyr Gly Gly Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Ala Asp Phe Ala Val Phe Tyr Cys Gln Gln Tyr Gly Asn Ser Pro
                85                  90                  95

Trp Thr Phe Gly Gln Gly Thr Lys Val Glu Met Lys
            100                 105

<210> SEQ ID NO 27
<211> LENGTH: 21
<212> TYPE: DNA
<213> ORGANISM: Homo sapiens

<400> SEQUENCE: 27
cagcatgtta gcagcaacta c                                          21

<210> SEQ ID NO 28
<211> LENGTH: 7
<212> TYPE: PRT
<213> ORGANISM: Homo sapiens

<400> SEQUENCE: 28

Gln His Val Ser Ser Asn Tyr
1               5

<210> SEQ ID NO 29
<211> LENGTH: 9
<212> TYPE: DNA
<213> ORGANISM: Homo sapiens

<400> SEQUENCE: 29 ggtggatcc                                                         9

<210> SEQ ID NO 30
<211> LENGTH: 3
<212> TYPE: PRT
<213> ORGANISM: Homo sapiens

<400> SEQUENCE: 30

Gly Gly Ser
1

<210> SEQ ID NO 31
<211> LENGTH: 27
<212> TYPE: DNA
<213> ORGANISM: Homo sapiens

<400> SEQUENCE: 31
cagcagtatg gtaactcacc ttggacg                                    27

<210> SEQ ID NO 32
<211> LENGTH: 9
<212> TYPE: PRT
```

<213> ORGANISM: Homo sapiens

<400> SEQUENCE: 32

Gln Gln Tyr Gly Asn Ser Pro Trp Thr
1               5

<210> SEQ ID NO 33
<211> LENGTH: 351
<212> TYPE: DNA
<213> ORGANISM: Homo sapiens

<400> SEQUENCE: 33

```
caggtgcaac tacaggagtc gggcccaaag gtggtgaagc cttcggagac cctgtccctc    60
acctgcactg tctctggtgg ctccatcagt agttactact ggaattggat ccgccagtcc   120
ccagggaagg gactggagtg gattggatat accaaaagag gtataccga ctacaacccc    180
tccctcagga gtcgcgtcac tatatcagaa gacacgtcca agaaccagtt ctccctgagg   240
atcagctctg tgaccgccgc agacacggcc gtatattact gtgcacaaat ggggtgggga   300
tcccatgctt ttgacatgtg gggccaaggg acaatggtcg ccgtctcttc a            351
```

<210> SEQ ID NO 34
<211> LENGTH: 117
<212> TYPE: PRT
<213> ORGANISM: Homo sapiens

<400> SEQUENCE: 34

Gln Val Gln Leu Gln Glu Ser Gly Pro Lys Val Val Lys Pro Ser Glu
1               5                   10                  15

Thr Leu Ser Leu Thr Cys Thr Val Ser Gly Gly Ser Ile Ser Ser Tyr
                20                  25                  30

Tyr Trp Asn Trp Ile Arg Gln Ser Pro Gly Lys Gly Leu Glu Trp Ile
            35                  40                  45

Gly Tyr Thr Lys Arg Gly Tyr Thr Asp Tyr Asn Pro Ser Leu Arg Ser
        50                  55                  60

Arg Val Thr Ile Ser Glu Asp Thr Ser Lys Asn Gln Phe Ser Leu Arg
65                  70                  75                  80

Ile Ser Ser Val Thr Ala Ala Asp Thr Ala Val Tyr Tyr Cys Ala Gln
                85                  90                  95

Met Gly Trp Gly Ser His Ala Phe Asp Met Trp Gly Gln Gly Thr Met
            100                 105                 110

Val Ala Val Ser Ser
        115

<210> SEQ ID NO 35
<211> LENGTH: 24
<212> TYPE: DNA
<213> ORGANISM: Homo sapiens

<400> SEQUENCE: 35
ggtggctcca tcagtagtta ctac                                          24

<210> SEQ ID NO 36
<211> LENGTH: 8
<212> TYPE: PRT
<213> ORGANISM: Homo sapiens

<400> SEQUENCE: 36

Gly Gly Ser Ile Ser Ser Tyr Tyr
1               5

```
<210> SEQ ID NO 37
<211> LENGTH: 18
<212> TYPE: DNA
<213> ORGANISM: Homo sapiens

<400> SEQUENCE: 37
accaaaagag ggtatacc                                                   18

<210> SEQ ID NO 38
<211> LENGTH: 6
<212> TYPE: PRT
<213> ORGANISM: Homo sapiens

<400> SEQUENCE: 38

Thr Lys Arg Gly Tyr Thr
1               5

<210> SEQ ID NO 39
<211> LENGTH: 36
<212> TYPE: DNA
<213> ORGANISM: Homo sapiens

<400> SEQUENCE: 39
gcacaaatgg ggtggggatc ccatgctttt gacatg                               36

<210> SEQ ID NO 40
<211> LENGTH: 12
<212> TYPE: PRT
<213> ORGANISM: Homo sapiens

<400> SEQUENCE: 40

Ala Gln Met Gly Trp Gly Ser His Ala Phe Asp Met
1               5                   10

<210> SEQ ID NO 41
<211> LENGTH: 324
<212> TYPE: DNA
<213> ORGANISM: Homo sapiens

<400> SEQUENCE: 41
gaaattgtgt tgacgcagtc tccaggcacc ctgtctttgt ctccagggga aagagccacc     60
ctctcctgca gggccagtca gagtgttagc agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta gctcaccttg gacgttcggc    300
caagggacca aggtggaaat caaa                                          324

<210> SEQ ID NO 42
<211> LENGTH: 108
<212> TYPE: PRT
<213> ORGANISM: Homo sapiens

<400> SEQUENCE: 42

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45
```

-continued

```
Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Trp Thr Phe Gly Gln Gly Thr Lys Val Glu Ile Lys
             100                 105

<210> SEQ ID NO 43
<211> LENGTH: 21
<212> TYPE: DNA
<213> ORGANISM: Homo sapiens

<400> SEQUENCE: 43
cagagtgtta gcagcagcta c                                            21

<210> SEQ ID NO 44
<211> LENGTH: 7
<212> TYPE: PRT
<213> ORGANISM: Homo sapiens

<400> SEQUENCE: 44

Gln Ser Val Ser Ser Ser Tyr
 1               5

<210> SEQ ID NO 45
<211> LENGTH: 9
<212> TYPE: DNA
<213> ORGANISM: Homo sapiens

<400> SEQUENCE: 45 ggtgcatcc                                                           9

<210> SEQ ID NO 46
<211> LENGTH: 3
<212> TYPE: PRT
<213> ORGANISM: Homo sapiens

<400> SEQUENCE: 46

Gly Ala Ser
 1

<210> SEQ ID NO 47
<211> LENGTH: 27
<212> TYPE: DNA
<213> ORGANISM: Homo sapiens

<400> SEQUENCE: 47
cagcagtatg gtagctcacc ttggacg                                      27

<210> SEQ ID NO 48
<211> LENGTH: 9
<212> TYPE: PRT
<213> ORGANISM: Homo sapiens

<400> SEQUENCE: 48

Gln Gln Tyr Gly Ser Ser Pro Trp Thr
 1               5

<210> SEQ ID NO 49
<211> LENGTH: 351
```

```
<212> TYPE: DNA
<213> ORGANISM: Homo sapiens

<400> SEQUENCE: 49
caggtgcaac tacaggagtc gggcccaaag gtggtgaagc cttcggagac cctgtccctc    60
acctgcactg tctctggtgg ctccatcagt agttactact ggaattggat ccgccagtcc   120
ccagggaagg gactggagtg gattggatat accaaaagag gtataccga ctacaacccc    180 tccctcagga gtcgcgtcac tatatcagaa gacacgtcca agaaccagtt ctccctgagg   240
atcagctctg tgaccgccgc agacacggcc gtatattact gtgcacaaat ggggtgggga   300
tcccatgctt ttgacatgtg gggccaaggg acaatggtcg ccgtctcttc a             351

<210> SEQ ID NO 50
<211> LENGTH: 117
<212> TYPE: PRT
<213> ORGANISM: Homo sapiens

<400> SEQUENCE: 50

Gln Val Gln Leu Gln Glu Ser Gly Pro Lys Val Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Asn Trp Ile Arg Gln Ser Pro Gly Lys Gly Leu Glu Trp Ile
        35                  40                  45

Gly Tyr Thr Lys Arg Gly Tyr Thr Asp Tyr Asn Pro Ser Leu Arg Ser
    50                  55                  60

Arg Val Thr Ile Ser Glu Asp Thr Ser Lys Asn Gln Phe Ser Leu Arg
65                  70                  75                  80

Ile Ser Ser Val Thr Ala Ala Asp Thr Ala Val Tyr Tyr Cys Ala Gln
                85                  90                  95

Met Gly Trp Gly Ser His Ala Phe Asp Met Trp Gly Gln Gly Thr Met
            100                 105                 110

Val Ala Val Ser Ser
        115

<210> SEQ ID NO 51
<211> LENGTH: 24
<212> TYPE: DNA
<213> ORGANISM: Homo sapiens

<400> SEQUENCE: 51
ggtggctcca tcagtagtta ctac                                            24

<210> SEQ ID NO 52
<211> LENGTH: 8
<212> TYPE: PRT
<213> ORGANISM: Homo sapiens

<400> SEQUENCE: 52

Gly Gly Ser Ile Ser Ser Tyr Tyr
1               5

<210> SEQ ID NO 53
<211> LENGTH: 18
<212> TYPE: DNA
<213> ORGANISM: Homo sapiens

<400> SEQUENCE: 53
accaaaagag ggtatacc                                                   18
```

<210> SEQ ID NO 54
<211> LENGTH: 6
<212> TYPE: PRT
<213> ORGANISM: Homo sapiens

<400> SEQUENCE: 54

Thr Lys Arg Gly Tyr Thr
1               5

<210> SEQ ID NO 55
<211> LENGTH: 36
<212> TYPE: DNA
<213> ORGANISM: Homo sapiens

<400> SEQUENCE: 55
gcacaaatgg ggtggggatc ccatgctttt gacatg                                 36

<210> SEQ ID NO 56
<211> LENGTH: 12
<212> TYPE: PRT
<213> ORGANISM: Homo sapiens

<400> SEQUENCE: 56

Ala Gln Met Gly Trp Gly Ser His Ala Phe Asp Met
1               5                   10

<210> SEQ ID NO 57
<211> LENGTH: 324
<212> TYPE: DNA
<213> ORGANISM: Homo sapiens

<400> SEQUENCE: 57
gaaattgtgt tgacgcagtc tccaggcacc ctgtctttgt ctccagggga aagagccacc        60
ctctcctgca gggccagtca gagtgttaat agtaggtact tagcctggta ccagcagaaa       120
cctggccagg ctcccaggct cctcatctat ggtgcatcca gcagggccac tggcatccca       180
gacaggtgca gtggcagtgg gtccgggaca gacttcactc tcaccatcag cagactggag       240
cctgaagatt ttgcagtgta ttactgtcag cagtatggta gctcaccttg gacgttcggc       300
caggggacca aggtggaaat caaa                                             324

<210> SEQ ID NO 58
<211> LENGTH: 108
<212> TYPE: PRT
<213> ORGANISM: Homo sapiens

<400> SEQUENCE: 58

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Asn Ser Arg
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Cys Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
           100                  105

<210> SEQ ID NO 59
<211> LENGTH: 21
<212> TYPE: DNA
<213> ORGANISM: Homo sapiens

<400> SEQUENCE: 59
cagagtgtta atagtaggta c                                        21

<210> SEQ ID NO 60
<211> LENGTH: 7
<212> TYPE: PRT
<213> ORGANISM: Homo sapiens

<400> SEQUENCE: 60

Gln Ser Val Asn Ser Arg Tyr
1               5

<210> SEQ ID NO 61
<211> LENGTH: 9
<212> TYPE: DNA
<213> ORGANISM: Homo sapiens

<400> SEQUENCE: 61 ggtgcatcc                                                      9

<210> SEQ ID NO 62
<211> LENGTH: 3
<212> TYPE: PRT
<213> ORGANISM: Homo sapiens

<400> SEQUENCE: 62

Gly Ala Ser
1

<210> SEQ ID NO 63
<211> LENGTH: 27
<212> TYPE: DNA
<213> ORGANISM: Homo sapiens

<400> SEQUENCE: 63
cagcagtatg gtagctcacc ttggacg                         27

<210> SEQ ID NO 64
<211> LENGTH: 9
<212> TYPE: PRT
<213> ORGANISM: Homo sapiens

<400> SEQUENCE: 64

Gln Gln Tyr Gly Ser Ser Pro Trp Thr
1               5

<210> SEQ ID NO 65
<211> LENGTH: 357
<212> TYPE: DNA
<213> ORGANISM: Homo sapiens

<400> SEQUENCE: 65
caggtgcagt tggtggagtc tgggggaggc ttggtcaagc ctggagggtc cctgagactc    60
tcctgtgcag cctcgggatt catcttcagt gactactaca taaactggat tcgccaggct  120
ccagggaagg ggctggagtg ggtttcatat actagcagta gtggtagtac cacttattac  180

```
gaagactctg tgaagggccg attcaccatg tccagggaca atgccaggaa tttagtgtac    240
ctgcaaatga acagcctgag agccgaggac acggccgcgt attactgtgt gagagatctg    300
agatacaacg atggtttgga cgtctggggc caagggacca cggtcaccgt ctcctca       357
```

<210> SEQ ID NO 66
<211> LENGTH: 119
<212> TYPE: PRT
<213> ORGANISM: Homo sapiens

<400> SEQUENCE: 66

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Ile Phe Ser Asp Tyr
            20                  25                  30

Tyr Ile Asn Trp Ile Arg Gln Ala Pro Gly Lys Gly Leu Glu Trp Val
        35                  40                  45

Ser Tyr Thr Ser Ser Gly Ser Thr Thr Tyr Tyr Glu Asp Ser Val
    50                  55                  60

Lys Gly Arg Phe Thr Met Ser Arg Asp Asn Ala Arg Asn Leu Val Tyr
65                  70                  75                  80

Leu Gln Met Asn Ser Leu Arg Ala Glu Asp Thr Ala Ala Tyr Tyr Cys
                85                  90                  95

Val Arg Asp Leu Arg Tyr Asn Asp Gly Leu Asp Val Trp Gly Gln Gly
            100                 105                 110

Thr Thr Val Thr Val Ser Ser
        115
```

<210> SEQ ID NO 67
<211> LENGTH: 24
<212> TYPE: DNA
<213> ORGANISM: Homo sapiens

<400> SEQUENCE: 67

```
ggattcatct tcagtgacta ctac                                            24
```

<210> SEQ ID NO 68
<211> LENGTH: 8
<212> TYPE: PRT
<213> ORGANISM: Homo sapiens

<400> SEQUENCE: 68

```
Gly Phe Ile Phe Ser Asp Tyr Tyr
1               5
```

<210> SEQ ID NO 69
<211> LENGTH: 24
<212> TYPE: DNA
<213> ORGANISM: Homo sapiens

<400> SEQUENCE: 69

```
actagcagta gtggtagtac cact                                            24
```

<210> SEQ ID NO 70
<211> LENGTH: 8
<212> TYPE: PRT
<213> ORGANISM: Homo sapiens

<400> SEQUENCE: 70

```
Thr Ser Ser Ser Gly Ser Thr Thr
```

<210> SEQ ID NO 71
<211> LENGTH: 36
<212> TYPE: DNA
<213> ORGANISM: Homo sapiens

<400> SEQUENCE: 71
gtgagagatc tgagatacaa cgatggtttg gacgtc                              36

<210> SEQ ID NO 72
<211> LENGTH: 12
<212> TYPE: PRT
<213> ORGANISM: Homo sapiens

<400> SEQUENCE: 72

Val Arg Asp Leu Arg Tyr Asn Asp Gly Leu Asp Val
1               5                   10

<210> SEQ ID NO 73
<211> LENGTH: 324
<212> TYPE: DNA
<213> ORGANISM: Homo sapiens

<400> SEQUENCE: 73
gacatcctgc tgacccagtc tccatcctcc ctgtctgcat ctgtaggaga cagagtcacc      60
atcacttgcc gggcaagtca gagcattcgc acctatttaa attggtatca gcagaaacca     120
gggagagccc ctaagctcct ggtctatgct gcatccagtt tgcaaagtgg ggtcccatca     180
aggttcagtg gcagtggatc tgggacagat ttcactctca ccatcagcag tctgcaacct     240
gaagattttg caacttactt ctgtcaacag agttatgata accctccgat caccttcggc     300
caggggacac gactggcgat taaa                                            324

<210> SEQ ID NO 74
<211> LENGTH: 108
<212> TYPE: PRT
<213> ORGANISM: Homo sapiens

<400> SEQUENCE: 74

Asp Ile Leu Leu Thr Gln Ser Pro Ser Ser Leu Ser Ala Ser Val Gly
1               5                   10                  15

Asp Arg Val Thr Ile Thr Cys Arg Ala Ser Gln Ser Ile Arg Thr Tyr
            20                  25                  30

Leu Asn Trp Tyr Gln Gln Lys Pro Gly Arg Ala Pro Lys Leu Leu Val
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ser Tyr Asp Asn Pro Pro
                85                  90                  95

Ile Thr Phe Gly Gln Gly Thr Arg Leu Ala Ile Lys
            100                 105

<210> SEQ ID NO 75
<211> LENGTH: 18
<212> TYPE: DNA
<213> ORGANISM: Homo sapiens

<400> SEQUENCE: 75

```
cagagcattc gcacctat                                                  18

<210> SEQ ID NO 76
<211> LENGTH: 6
<212> TYPE: PRT
<213> ORGANISM: Homo sapiens

<400> SEQUENCE: 76

Gln Ser Ile Arg Thr Tyr
1               5

<210> SEQ ID NO 77
<211> LENGTH: 9
<212> TYPE: DNA
<213> ORGANISM: Homo sapiens

<400> SEQUENCE: 77 gctgcatcc                                                             9

<210> SEQ ID NO 78
<211> LENGTH: 3
<212> TYPE: PRT
<213> ORGANISM: Homo sapiens

<400> SEQUENCE: 78

Ala Ala Ser
1

<210> SEQ ID NO 79
<211> LENGTH: 30
<212> TYPE: DNA
<213> ORGANISM: Homo sapiens

<400> SEQUENCE: 79
caacagagtt atgataaccc tccgatcacc                                     30

<210> SEQ ID NO 80
<211> LENGTH: 10
<212> TYPE: PRT
<213> ORGANISM: Homo sapiens

<400> SEQUENCE: 80

Gln Gln Ser Tyr Asp Asn Pro Pro Ile Thr
1               5                   10

<210> SEQ ID NO 81
<211> LENGTH: 354
<212> TYPE: DNA
<213> ORGANISM: Homo sapiens

<400> SEQUENCE: 81
caggtgcagc tgcaggagtc gggcccagga ctggtgaagc cttcggagac cctgtccctc    60
acctgcactg tctctggtgg ctccatcagt agttactact ggaactggat ccggcagtcc   120
ccagagaagg gactggagtg gattggatat atctatatca gtgggaccac caactacaac   180
ccctccctca agagtcgagt caccatatca gtagacacgt caagaatcag gttctccctg   240
aagctgaact ctgtgaccgc tgcggacacg gccgtgtatt actgtgcgag gatggggctg   300
gggagggagg ctttttgatat ctggggccaa gggacaatgg tcaccgtctc ttca        354

<210> SEQ ID NO 82
<211> LENGTH: 118
```

```
<212> TYPE: PRT
<213> ORGANISM: Homo sapiens

<400> SEQUENCE: 82

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Asn Trp Ile Arg Gln Ser Pro Glu Lys Gly Leu Glu Trp Ile
        35                  40                  45

Gly Tyr Ile Tyr Ile Ser Gly Thr Thr Asn Tyr Asn Pro Ser Leu Lys
    50                  55                  60

Ser Arg Val Thr Ile Ser Val Asp Thr Phe Lys Asn Gln Phe Ser Leu
65                  70                  75                  80

Lys Leu Asn Ser Val Thr Ala Ala Asp Thr Ala Val Tyr Tyr Cys Ala
                85                  90                  95

Arg Met Gly Leu Gly Arg Glu Ala Phe Asp Ile Trp Gly Gln Gly Thr
            100                 105                 110

Met Val Thr Val Ser Ser
        115

<210> SEQ ID NO 83
<211> LENGTH: 24
<212> TYPE: DNA
<213> ORGANISM: Homo sapiens

<400> SEQUENCE: 83
ggtggctcca tcagtagtta ctac                                              24

<210> SEQ ID NO 84
<211> LENGTH: 8
<212> TYPE: PRT
<213> ORGANISM: Homo sapiens

<400> SEQUENCE: 84

Gly Gly Ser Ile Ser Ser Tyr Tyr
1               5

<210> SEQ ID NO 85
<211> LENGTH: 21
<212> TYPE: DNA
<213> ORGANISM: Homo sapiens

<400> SEQUENCE: 85
atctatatca gtgggaccac c                                                 21

<210> SEQ ID NO 86
<211> LENGTH: 7
<212> TYPE: PRT
<213> ORGANISM: Homo sapiens

<400> SEQUENCE: 86

Ile Tyr Ile Ser Gly Thr Thr
1               5

<210> SEQ ID NO 87
<211> LENGTH: 36
<212> TYPE: DNA
<213> ORGANISM: Homo sapiens

<400> SEQUENCE: 87
```

```
gcgaggatgg ggctggggag ggaggctttt gatatc                                      36
```

<210> SEQ ID NO 88
<211> LENGTH: 12
<212> TYPE: PRT
<213> ORGANISM: Homo sapiens

<400> SEQUENCE: 88

```
Ala Arg Met Gly Leu Gly Arg Glu Ala Phe Asp Ile
1               5                   10
```

<210> SEQ ID NO 89
<211> LENGTH: 324
<212> TYPE: DNA
<213> ORGANISM: Homo sapiens

<400> SEQUENCE: 89

```
gaaattgtgt tgacgcagtc tccaggcacc ctgtctttgt ctccagggga aagagccacc     60
ctctcctgca gggccagtca gagtgttagc aacaactact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta gctcaccttg gacgttcggc    300
caagggacca aggtggaaat caaa                                           324
```

<210> SEQ ID NO 90
<211> LENGTH: 108
<212> TYPE: PRT
<213> ORGANISM: Homo sapiens

<400> SEQUENCE: 90

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asn Asn
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105
```

<210> SEQ ID NO 91
<211> LENGTH: 21
<212> TYPE: DNA
<213> ORGANISM: Homo sapiens

<400> SEQUENCE: 91

```
cagagtgtta gcaacaacta c                                               21
```

<210> SEQ ID NO 92
<211> LENGTH: 7
<212> TYPE: PRT
<213> ORGANISM: Homo sapiens

<400> SEQUENCE: 92

Gln Ser Val Ser Asn Asn Tyr
1               5

<210> SEQ ID NO 93
<211> LENGTH: 9
<212> TYPE: DNA
<213> ORGANISM: Homo sapiens

<400> SEQUENCE: 93 ggtgcatcc                                                                  9

<210> SEQ ID NO 94
<211> LENGTH: 3
<212> TYPE: PRT
<213> ORGANISM: Homo sapiens

<400> SEQUENCE: 94

Gly Ala Ser
1

<210> SEQ ID NO 95
<211> LENGTH: 27
<212> TYPE: DNA
<213> ORGANISM: Homo sapiens

<400> SEQUENCE: 95
cagcagtatg gtagctcacc ttggacg                                             27

<210> SEQ ID NO 96
<211> LENGTH: 9
<212> TYPE: PRT
<213> ORGANISM: Homo sapiens

<400> SEQUENCE: 96

Gln Gln Tyr Gly Ser Ser Pro Trp Thr
1               5

<210> SEQ ID NO 97
<211> LENGTH: 357
<212> TYPE: DNA
<213> ORGANISM: Homo sapiens

<400> SEQUENCE: 97
caggtgcaac tggaggagtc tgggggaggc gtggtcaagg ctggagggtc cctgagactc         60
tcctgtgtag cctctggatt caccttcagt gactattaca taaactggat ccgccaggct        120
ccagggaagg ggctggagtg ggtttcgtac attaataatg gtggttatac catttactac        180
gcagactctg tgaagggccg attcaccatg tccaggaca acgccaagaa ctcagtatat         240
ctagaaatga acggcctgag agccgaggac acggcctttt attactgtgt gagagaccca        300
cggagttatt atgggtttga ctattgggc agggaaccc tggtcaccgt ctcctca             357

<210> SEQ ID NO 98
<211> LENGTH: 119
<212> TYPE: PRT
<213> ORGANISM: Homo sapiens

<400> SEQUENCE: 98

Gln Val Gln Leu Glu Glu Ser Gly Gly Gly Val Val Lys Ala Gly Gly
1               5                   10                  15

Ser Leu Arg Leu Ser Cys Val Ala Ser Gly Phe Thr Phe Ser Asp Tyr
            20                  25                  30

```
Tyr Ile Asn Trp Ile Arg Gln Ala Pro Gly Lys Gly Leu Glu Trp Val
        35                  40                  45
Ser Tyr Ile Asn Asn Gly Gly Tyr Thr Ile Tyr Tyr Ala Asp Ser Val
    50                  55                  60
Lys Gly Arg Phe Thr Met Ser Arg Asp Asn Ala Lys Asn Ser Val Tyr
65                  70                  75                  80
Leu Glu Met Asn Gly Leu Arg Ala Glu Asp Thr Ala Phe Tyr Tyr Cys
                85                  90                  95
Val Arg Asp Pro Arg Ser Tyr Tyr Gly Phe Asp Tyr Trp Gly Gln Gly
                100                 105                 110
Thr Leu Val Thr Val Ser Ser
            115
```

<210> SEQ ID NO 99
<211> LENGTH: 24
<212> TYPE: DNA
<213> ORGANISM: Homo sapiens

<400> SEQUENCE: 99
ggattcacct tcagtgacta ttac                                        24

<210> SEQ ID NO 100
<211> LENGTH: 8
<212> TYPE: PRT
<213> ORGANISM: Homo sapiens

<400> SEQUENCE: 100

```
Gly Phe Thr Phe Ser Asp Tyr Tyr
1               5
```

<210> SEQ ID NO 101
<211> LENGTH: 24
<212> TYPE: DNA
<213> ORGANISM: Homo sapiens

<400> SEQUENCE: 101
attaataatg gtggttatac catt                                        24

<210> SEQ ID NO 102
<211> LENGTH: 8
<212> TYPE: PRT
<213> ORGANISM: Homo sapiens

<400> SEQUENCE: 102

```
Ile Asn Asn Gly Gly Tyr Thr Ile
1               5
```

<210> SEQ ID NO 103
<211> LENGTH: 36
<212> TYPE: DNA
<213> ORGANISM: Homo sapiens

<400> SEQUENCE: 103
gtgagagacc cacggagtta ttatgggttt gactat                           36

<210> SEQ ID NO 104
<211> LENGTH: 12
<212> TYPE: PRT
<213> ORGANISM: Homo sapiens

<400> SEQUENCE: 104

Val Arg Asp Pro Arg Ser Tyr Tyr Gly Phe Asp Tyr
1               5                   10

<210> SEQ ID NO 105
<211> LENGTH: 324
<212> TYPE: DNA
<213> ORGANISM: Homo sapiens

<400> SEQUENCE: 105
gacatccaga tgacccagtc tccatcctcc ctgtctgcat ctgtaggaga cagagtcacc      60
atcacttgcc gggcaagtca gagcattagc agttatttaa attggaatca gcagaaacca     120
gggaaagccc cgaagctcct gatctatgta gcatccagtt tgcaaagtgg ggtcccatca     180
aggttcagtg gcagtggatc tgggacagat ttcactctca ccatcagcgg tctacaacct    240
gaagattttg caccttacta ctgtcaacag agttacatta cccctccgat caccttcggc    300
caagggacac gactggatat taaa                                            324

<210> SEQ ID NO 106
<211> LENGTH: 108
<212> TYPE: PRT
<213> ORGANISM: Homo sapiens

<400> SEQUENCE: 106

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Asn Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
    50                  55                  60

Ser Gly Ser Gly Thr Asp Phe Thr Leu Thr Ile Ser Gly Leu Gln Pro
65                  70                  75                  80

Glu Asp Phe Ala Pro Tyr Tyr Cys Gln Gln Ser Tyr Ile Thr Pro Pro
                85                  90                  95

Ile Thr Phe Gly Gln Gly Thr Arg Leu Asp Ile Lys
            100                 105

<210> SEQ ID NO 107
<211> LENGTH: 18
<212> TYPE: DNA
<213> ORGANISM: Homo sapiens

<400> SEQUENCE: 107
cagagcatta gcagttat                                                    18

<210> SEQ ID NO 108
<211> LENGTH: 6
<212> TYPE: PRT
<213> ORGANISM: Homo sapiens

<400> SEQUENCE: 108

Gln Ser Ile Ser Ser Tyr
1               5

<210> SEQ ID NO 109
<211> LENGTH: 9
<212> TYPE: DNA
<213> ORGANISM: Homo sapiens

<400> SEQUENCE: 109 gtagcatcc                                                                                          9

<210> SEQ ID NO 110
<211> LENGTH: 3
<212> TYPE: PRT
<213> ORGANISM: Homo sapiens

<400> SEQUENCE: 110

Val Ala Ser
1

<210> SEQ ID NO 111
<211> LENGTH: 30
<212> TYPE: DNA
<213> ORGANISM: Homo sapiens

<400> SEQUENCE: 111
caacagagtt acattacccc tccgatcacc                                                                  30

<210> SEQ ID NO 112
<211> LENGTH: 10
<212> TYPE: PRT
<213> ORGANISM: Homo sapiens

<400> SEQUENCE: 112

Gln Gln Ser Tyr Ile Thr Pro Pro Ile Thr
1               5                   10

<210> SEQ ID NO 113
<211> LENGTH: 357
<212> TYPE: DNA
<213> ORGANISM: Homo sapiens

<400> SEQUENCE: 113
caggtgcaac tggaggagtc tgggggaggc gtggtcaagg ctggagggtc cctgagactc       60
tcctgtgcag cctctggatt caccttcagt gactattaca taaattggat ccgccaggct      120
ccagggaagg ggctggagtg ggtttcgtac attaataatg gtggttatac catatactac      180
gcagactctg tgaagggccg attcaccatg tccagggaca acgccaagaa ctcagtatat      240
ctgcaaatga acggcctgag agccgaggac acggcctttt attactgtgt gagagaccca      300
cggagttatt atgggtttga ctattggggc cagggaaccc tggtcaccgt ctcctca         357

<210> SEQ ID NO 114
<211> LENGTH: 119
<212> TYPE: PRT
<213> ORGANISM: Homo sapiens

<400> SEQUENCE: 114

Gln Val Gln Leu Glu Glu Ser Gly Gly Gly Val Val Lys Ala Gly Gly
1               5                   10                  15

Ser Leu Arg Leu Ser Cys Ala Ala Ser Gly Phe Thr Phe Ser Asp Tyr
            20                  25                  30

Tyr Ile Asn Trp Ile Arg Gln Ala Pro Gly Lys Gly Leu Glu Trp Val
        35                  40                  45

Ser Tyr Ile Asn Asn Gly Gly Tyr Thr Ile Tyr Tyr Ala Asp Ser Val
    50                  55                  60

Lys Gly Arg Phe Thr Met Ser Arg Asp Asn Ala Lys Asn Ser Val Tyr
65                  70                  75                  80

Leu Gln Met Asn Gly Leu Arg Ala Glu Asp Thr Ala Phe Tyr Tyr Cys
            85                  90                  95

Val Arg Asp Pro Arg Ser Tyr Tyr Gly Phe Asp Tyr Trp Gly Gln Gly
            100                 105                 110

Thr Leu Val Thr Val Ser Ser
            115

<210> SEQ ID NO 115
<211> LENGTH: 24
<212> TYPE: DNA
<213> ORGANISM: Homo sapiens

<400> SEQUENCE: 115
ggattcacct tcagtgacta ttac                                           24

<210> SEQ ID NO 116
<211> LENGTH: 8
<212> TYPE: PRT
<213> ORGANISM: Homo sapiens

<400> SEQUENCE: 116

Gly Phe Thr Phe Ser Asp Tyr Tyr
1               5

<210> SEQ ID NO 117
<211> LENGTH: 24
<212> TYPE: DNA
<213> ORGANISM: Homo sapiens

<400> SEQUENCE: 117
attaataatg gtggttatac cata                                           24

<210> SEQ ID NO 118
<211> LENGTH: 8
<212> TYPE: PRT
<213> ORGANISM: Homo sapiens

<400> SEQUENCE: 118

Ile Asn Asn Gly Gly Tyr Thr Ile
1               5

<210> SEQ ID NO 119
<211> LENGTH: 36
<212> TYPE: DNA
<213> ORGANISM: Homo sapiens

<400> SEQUENCE: 119
gtgagagacc cacggagtta ttatgggttt gactat                              36

<210> SEQ ID NO 120
<211> LENGTH: 12
<212> TYPE: PRT
<213> ORGANISM: Homo sapiens

<400> SEQUENCE: 120

Val Arg Asp Pro Arg Ser Tyr Tyr Gly Phe Asp Tyr
1               5                   10

<210> SEQ ID NO 121
<211> LENGTH: 324
<212> TYPE: DNA
<213> ORGANISM: Homo sapiens

<400> SEQUENCE: 121

```
gacatccaga tgacccagtc tccatcctcc ctgtctgcat ctgtaggaga cagagtcacc    60
atcacttgcc gggcaagtca gagtattagc aggttttac attggtatca gcagaaacca   120
gggaaagccc ctaagctcct gatctatggt gcatccagtt tgcaaagtgg ggtcccatca   180
aggttcagtg gcagtggatc tgggacagat ttcactctca ccatcagcac tctgcaacct   240
gaagactttg caacttacta ctgtcaacag agttatagta cccctccgat cactttcggc   300
caagggacac gactggagat taaa                                          324
```

<210> SEQ ID NO 122
<211> LENGTH: 108
<212> TYPE: PRT
<213> ORGANISM: Homo sapiens

<400> SEQUENCE: 122

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Phe
            20                  25                  30

Leu His Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Thr Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 123
<211> LENGTH: 18
<212> TYPE: DNA
<213> ORGANISM: Homo sapiens

<400> SEQUENCE: 123

```
cagagtatta gcaggttt                                                  18
```

<210> SEQ ID NO 124
<211> LENGTH: 6
<212> TYPE: PRT
<213> ORGANISM: Homo sapiens

<400> SEQUENCE: 124

Gln Ser Ile Ser Arg Phe
1               5

<210> SEQ ID NO 125
<211> LENGTH: 9
<212> TYPE: DNA
<213> ORGANISM: Homo sapiens

<400> SEQUENCE: 125

```
ggtgcatcc                                                             9
```

<210> SEQ ID NO 126
<211> LENGTH: 3
<212> TYPE: PRT
<213> ORGANISM: Homo sapiens

<400> SEQUENCE: 126

Gly Ala Ser
1

<210> SEQ ID NO 127
<211> LENGTH: 30
<212> TYPE: DNA
<213> ORGANISM: Homo sapiens

<400> SEQUENCE: 127
caacagagtt atagtacccc tccgatcact                                    30

<210> SEQ ID NO 128
<211> LENGTH: 10
<212> TYPE: PRT
<213> ORGANISM: Homo sapiens

<400> SEQUENCE: 128

Gln Gln Ser Tyr Ser Thr Pro Pro Ile Thr
1               5                   10

<210> SEQ ID NO 129
<211> LENGTH: 351
<212> TYPE: DNA
<213> ORGANISM: Homo sapiens

<400> SEQUENCE: 129
caggtgcacc tggtggagtc tgggggaggc ttggtcaagc ctggagggtc cctgagactc     60
tcctgtgcag cctctggatt catcttcagt gactactaca tgagctggat ccgacaggct    120
ccagggaagg gctggagtg gtttcatac atcagaggta gtggttataa cgcagactct     180
gtgcagggtc ggttcaccat ctccagggac aacgccaaga actcactgtt tctgcaaatg    240
aacagcctga gagccgagga cacggccgtg tattactgtg cgagaggata cagctttggt    300
tacggcttct ttgactactg gggccaggga accctggtca ccgtctcctc a             351

<210> SEQ ID NO 130
<211> LENGTH: 117
<212> TYPE: PRT
<213> ORGANISM: Homo sapiens

<400> SEQUENCE: 130

Gln Val His Leu Val Glu Ser Gly Gly Gly Leu Val Lys Pro Gly Gly
1               5                   10                  15

Ser Leu Arg Leu Ser Cys Ala Ala Ser Gly Phe Ile Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Arg Gly Ser Gly Tyr Asn Ala Asp Ser Val Gln Gly Arg
    50                  55                  60

Phe Thr Ile Ser Arg Asp Asn Ala Lys Asn Ser Leu Phe Leu Gln Met
65                  70                  75                  80

Asn Ser Leu Arg Ala Glu Asp Thr Ala Val Tyr Tyr Cys Ala Arg Gly
                85                  90                  95

Tyr Ser Phe Gly Tyr Gly Phe Phe Asp Tyr Trp Gly Gln Gly Thr Leu
            100                 105                 110

Val Thr Val Ser Ser
        115

```
<210> SEQ ID NO 131
<211> LENGTH: 24
<212> TYPE: DNA
<213> ORGANISM: Homo sapiens

<400> SEQUENCE: 131
ggattcatct tcagtgacta ctac                                            24

<210> SEQ ID NO 132
<211> LENGTH: 8
<212> TYPE: PRT
<213> ORGANISM: Homo sapiens

<400> SEQUENCE: 132

Gly Phe Ile Phe Ser Asp Tyr Tyr
1               5

<210> SEQ ID NO 133
<211> LENGTH: 18
<212> TYPE: DNA
<213> ORGANISM: Homo sapiens

<400> SEQUENCE: 133
atcagaggta gtggttat                                                   18

<210> SEQ ID NO 134
<211> LENGTH: 6
<212> TYPE: PRT
<213> ORGANISM: Homo sapiens

<400> SEQUENCE: 134

Ile Arg Gly Ser Gly Tyr
1               5

<210> SEQ ID NO 135
<211> LENGTH: 39
<212> TYPE: DNA
<213> ORGANISM: Homo sapiens

<400> SEQUENCE: 135
gcgagaggat acagctttgg ttacggcttc tttgactac                             39

<210> SEQ ID NO 136
<211> LENGTH: 13
<212> TYPE: PRT
<213> ORGANISM: Homo sapiens

<400> SEQUENCE: 136

Ala Arg Gly Tyr Ser Phe Gly Tyr Gly Phe Phe Asp Tyr
1               5                   10

<210> SEQ ID NO 137
<211> LENGTH: 324
<212> TYPE: DNA
<213> ORGANISM: Homo sapiens

<400> SEQUENCE: 137
gacatccaga tgacccagtc tccatcctcc ctgtctgcat ctgtaggaga cagagtcacc      60
atcacttgcc gggcaagtca gagcattagc agctatttaa attggtatca gcagaaacca    120
gggagagccc ctaagctcct gatctatgct gcatccagtt tacaaagtgg ggtcccatca    180
aggttcagtg gcagtggatc tgggacagat ttcactctca ccatcagcag tctgcaacct    240
gaagattttg caacttacta ctgtcaacag agttacagtc accctccgat caccttcggc    300
```
caagggacac gactggagat taaa                                              324

<210> SEQ ID NO 138
<211> LENGTH: 108
<212> TYPE: PRT
<213> ORGANISM: Homo sapiens

<400> SEQUENCE: 138

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Arg Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser His Pro Pro
                85                  90                  95

Ile Thr Phe Gly Gln Gly Thr Arg Leu Glu Ile Lys
            100                 105

<210> SEQ ID NO 139
<211> LENGTH: 18
<212> TYPE: DNA
<213> ORGANISM: Homo sapiens

<400> SEQUENCE: 139
cagagcatta gcagctat                                                      18

<210> SEQ ID NO 140
<211> LENGTH: 6
<212> TYPE: PRT
<213> ORGANISM: Homo sapiens

<400> SEQUENCE: 140

Gln Ser Ile Ser Ser Tyr
1               5

<210> SEQ ID NO 141
<211> LENGTH: 9
<212> TYPE: DNA
<213> ORGANISM: Homo sapiens

<400> SEQUENCE: 141 gctgcatcc                                                                 9

<210> SEQ ID NO 142
<211> LENGTH: 3
<212> TYPE: PRT
<213> ORGANISM: Homo sapiens

<400> SEQUENCE: 142

Ala Ala Ser
1

<210> SEQ ID NO 143
<211> LENGTH: 30
<212> TYPE: DNA
<213> ORGANISM: Homo sapiens

<400> SEQUENCE: 143
caacagagtt acagtcaccc tccgatcacc                                         30

<210> SEQ ID NO 144
<211> LENGTH: 10
<212> TYPE: PRT
<213> ORGANISM: Homo sapiens

<400> SEQUENCE: 144

Gln Gln Ser Tyr Ser His Pro Pro Ile Thr
1               5                   10

<210> SEQ ID NO 145
<211> LENGTH: 357
<212> TYPE: DNA
<213> ORGANISM: Homo sapiens

<400> SEQUENCE: 145
caggtgcagc tggtggagtc tgggggaggc ttggtcaagc ctggagggtc cctgagactc      60
tcctgtgcag cctctggatt caccttcact gactacttca tgaactggat ccgccaggct     120
ccagggaagg ggctggagtg gtttcatac attagtaata gtggtgctat aaaataccaa      180
gcagactctg tgaagggccg attcaccatc tccagggaca acgccaagaa ttctttgtat     240
ctgcaaatga acagcctgag agccgacgac acggccgtgt attactgtgt gagagaccca    300
cggagctact atgggtttga ctattggggc cagggaaccc tggtcaccgt ctcctca       357

<210> SEQ ID NO 146
<211> LENGTH: 119
<212> TYPE: PRT
<213> ORGANISM: Homo sapiens

<400> SEQUENCE: 146

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Asp Tyr
            20                  25                  30

Phe Met Asn Trp Ile Arg Gln Ala Pro Gly Lys Gly Leu Glu Trp Val
        35                  40                  45

Ser Tyr Ile Ser Asn Ser Gly Ala Ile Lys Tyr Gln Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Val Arg Asp Pro Arg Ser Tyr Tyr Gly Phe Asp Tyr Trp Gly Gln Gly
            100                 105                 110

Thr Leu Val Thr Val Ser Ser
        115

<210> SEQ ID NO 147
<211> LENGTH: 24
<212> TYPE: DNA
<213> ORGANISM: Homo sapiens

<400> SEQUENCE: 147
ggattcacct tcactgacta cttc                                              24

```
<210> SEQ ID NO 148
<211> LENGTH: 8
<212> TYPE: PRT
<213> ORGANISM: Homo sapiens

<400> SEQUENCE: 148

Gly Phe Thr Phe Thr Asp Tyr Phe
1               5

<210> SEQ ID NO 149
<211> LENGTH: 24
<212> TYPE: DNA
<213> ORGANISM: Homo sapiens

<400> SEQUENCE: 149
attagtaata gtggtgctat aaaa                                           24

<210> SEQ ID NO 150
<211> LENGTH: 8
<212> TYPE: PRT
<213> ORGANISM: Homo sapiens

<400> SEQUENCE: 150

Ile Ser Asn Ser Gly Ala Ile Lys
1               5

<210> SEQ ID NO 151
<211> LENGTH: 36
<212> TYPE: DNA
<213> ORGANISM: Homo sapiens

<400> SEQUENCE: 151
gtgagagacc cacggagcta ctatgggttt gactat                              36

<210> SEQ ID NO 152
<211> LENGTH: 12
<212> TYPE: PRT
<213> ORGANISM: Homo sapiens

<400> SEQUENCE: 152

Val Arg Asp Pro Arg Ser Tyr Tyr Gly Phe Asp Tyr
1               5                   10

<210> SEQ ID NO 153
<211> LENGTH: 324
<212> TYPE: DNA
<213> ORGANISM: Homo sapiens

<400> SEQUENCE: 153
gacatccaga tgacccagtc tccatcctcc ctgtctgcat ctgtaggaga cagagtcacc    60
atcacttgcc gggcaagtca gagcattagg aatttttaa  attggtatca gcagaaacca   120
gggaaagccc ctaggctcct gatctatgct gcatccagtt tgcaaagtgg ggtcccatca   180
aggttcagtg gcggtggatc tgggacagat ttcactctca ccatcagcag tctgcaacct   240
gaagattttg caacttacta ctgtcaacag agttacagta accctccgat caccttcggc   300
caagggacac gactggagat taaa                                         324

<210> SEQ ID NO 154
<211> LENGTH: 108
<212> TYPE: PRT
<213> ORGANISM: Homo sapiens

<400> SEQUENCE: 154
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Asn Phe
            20                  25                  30

Leu Asn Trp Tyr Gln Lys Pro Gly Lys Ala Pro Arg Leu Leu Ile
        35                  40                  45

Tyr Ala Ala Ser Ser Leu Gln Ser Gly Val Pro Ser Arg Phe Ser Gly
50                  55                  60

Gly Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Asn Pro Pro
                85                  90                  95

Ile Thr Phe Gly Gln Gly Thr Arg Leu Glu Ile Lys
            100                 105

<210> SEQ ID NO 155
<211> LENGTH: 18
<212> TYPE: DNA
<213> ORGANISM: Homo sapiens

<400> SEQUENCE: 155
cagagcatta ggaattttt                                          18

<210> SEQ ID NO 156
<211> LENGTH: 6
<212> TYPE: PRT
<213> ORGANISM: Homo sapiens

<400> SEQUENCE: 156

Gln Ser Ile Arg Asn Phe
1               5

<210> SEQ ID NO 157
<211> LENGTH: 9
<212> TYPE: DNA
<213> ORGANISM: Homo sapiens

<400> SEQUENCE: 157 gctgcatcc                                                      9

<210> SEQ ID NO 158
<211> LENGTH: 3
<212> TYPE: PRT
<213> ORGANISM: Homo sapiens

<400> SEQUENCE: 158

Ala Ala Ser
1

<210> SEQ ID NO 159
<211> LENGTH: 30
<212> TYPE: DNA
<213> ORGANISM: Homo sapiens

<400> SEQUENCE: 159
caacagagtt acagtaaccc tccgatcacc                              30

<210> SEQ ID NO 160
<211> LENGTH: 10
<212> TYPE: PRT
<213> ORGANISM: Homo sapiens

<400> SEQUENCE: 160

Gln Gln Ser Tyr Ser Asn Pro Pro Ile Thr
1               5                   10

<210> SEQ ID NO 161
<211> LENGTH: 357
<212> TYPE: DNA
<213> ORGANISM: Homo sapiens

<400> SEQUENCE: 161
caggtgcaac tggaggagtc tgggggaggc gtggtcaagg ctggagggtc cctgagactc    60
tcctgtgcag cctctggatt caccttcagt gactattaca tgaactggat ccgccaggct   120
ccagggaagg ggctggagtg gtttcgtac attaataatg gtggttatac catatactac    180
gcagactctg tgaagggccg attcaccatg tccagggaca acgccaagaa ctcagtgtat   240
ctgcaaatga acggcctgag agccgaggac acggcctttt attactgtgt gagagaccca   300
cggagctatt atgggtttga ctactgggc cagggaaccc tggtcatcgt ctcctca       357

<210> SEQ ID NO 162
<211> LENGTH: 119
<212> TYPE: PRT
<213> ORGANISM: Homo sapiens

<400> SEQUENCE: 162

Gln Val Gln Leu Glu Glu Ser Gly Gly Gly Val Val Lys Ala Gly
1               5                   10                  15

Ser Leu Arg Leu Ser Cys Ala Ala Ser Gly Phe Thr Phe Ser Asp Tyr
            20                  25                  30

Tyr Met Asn Trp Ile Arg Gln Ala Pro Gly Lys Gly Leu Glu Trp Val
        35                  40                  45

Ser Tyr Ile Asn Asn Gly Gly Tyr Thr Ile Tyr Tyr Ala Asp Ser Val
    50                  55                  60

Lys Gly Arg Phe Thr Met Ser Arg Asp Asn Ala Lys Asn Ser Val Tyr
65                  70                  75                  80

Leu Gln Met Asn Gly Leu Arg Ala Glu Asp Thr Ala Phe Tyr Tyr Cys
                85                  90                  95

Val Arg Asp Pro Arg Ser Tyr Tyr Gly Phe Asp Tyr Trp Gly Gln Gly
            100                 105                 110

Thr Leu Val Ile Val Ser Ser
        115

<210> SEQ ID NO 163
<211> LENGTH: 24
<212> TYPE: DNA
<213> ORGANISM: Homo sapiens

<400> SEQUENCE: 163
ggattcacct tcagtgacta ttac                                           24

<210> SEQ ID NO 164
<211> LENGTH: 8
<212> TYPE: PRT
<213> ORGANISM: Homo sapiens

<400> SEQUENCE: 164

Gly Phe Thr Phe Ser Asp Tyr Tyr
1               5

<210> SEQ ID NO 165
<211> LENGTH: 24
<212> TYPE: DNA
<213> ORGANISM: Homo sapiens

<400> SEQUENCE: 165
attaataatg gtggttatac cata                                            24

<210> SEQ ID NO 166
<211> LENGTH: 8
<212> TYPE: PRT
<213> ORGANISM: Homo sapiens

<400> SEQUENCE: 166

Ile Asn Asn Gly Gly Tyr Thr Ile
1               5

<210> SEQ ID NO 167
<211> LENGTH: 36
<212> TYPE: DNA
<213> ORGANISM: Homo sapiens

<400> SEQUENCE: 167
gtgagagacc cacggagcta ttatgggttt gactac                               36

<210> SEQ ID NO 168
<211> LENGTH: 12
<212> TYPE: PRT
<213> ORGANISM: Homo sapiens

<400> SEQUENCE: 168

Val Arg Asp Pro Arg Ser Tyr Tyr Gly Phe Asp Tyr
1               5                   10

<210> SEQ ID NO 169
<211> LENGTH: 324
<212> TYPE: DNA
<213> ORGANISM: Homo sapiens

<400> SEQUENCE: 169
gacatccaga tgacccagtc tccatcctcc ctgtctgcat ctgtaggaga cagagtcacc      60
atcacttgcc gggcaagtca gagtattagc aggttttac attggtatca gcagaaacca     120
gggaaagccc ctaagctcct gatctatggt gcatccagtt tgcaaagtgg ggtcccatca     180
aggttcagtg gcagtggatc tgggacagat tcactctca ccatcagcag tctgcaacct     240
gaagattttg caacttacta ctgtcaacag agttatagca cccctccgat cactttcggc     300
caagggacac gactggagat taaa                                           324

<210> SEQ ID NO 170
<211> LENGTH: 108
<212> TYPE: PRT
<213> ORGANISM: Homo sapiens

<400> SEQUENCE: 170

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Phe
            20                  25                  30

Leu His Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Pro
                 85                  90                  95

Ile Thr Phe Gly Gln Gly Thr Arg Leu Glu Ile Lys
                100                 105

<210> SEQ ID NO 171
<211> LENGTH: 18
<212> TYPE: DNA
<213> ORGANISM: Homo sapiens

<400> SEQUENCE: 171
cagagtatta gcaggttt                                                   18

<210> SEQ ID NO 172
<211> LENGTH: 6
<212> TYPE: PRT
<213> ORGANISM: Homo sapiens

<400> SEQUENCE: 172

Gln Ser Ile Ser Arg Phe
1               5

<210> SEQ ID NO 173
<211> LENGTH: 9
<212> TYPE: DNA
<213> ORGANISM: Homo sapiens

<400> SEQUENCE: 173 ggtgcatcc                                                              9

<210> SEQ ID NO 174
<211> LENGTH: 3
<212> TYPE: PRT
<213> ORGANISM: Homo sapiens

<400> SEQUENCE: 174

Gly Ala Ser
1

<210> SEQ ID NO 175
<211> LENGTH: 30
<212> TYPE: DNA
<213> ORGANISM: Homo sapiens

<400> SEQUENCE: 175
caacagagtt atagcacccc tccgatcact                                      30

<210> SEQ ID NO 176
<211> LENGTH: 10
<212> TYPE: PRT
<213> ORGANISM: Homo sapiens

<400> SEQUENCE: 176

Gln Gln Ser Tyr Ser Thr Pro Pro Ile Thr
1               5                   10

<210> SEQ ID NO 177
<211> LENGTH: 357
<212> TYPE: DNA

<213> ORGANISM: Homo sapiens

<400> SEQUENCE: 177

```
caggtgcaac tggtggagtc tgggggaggc ttggtcaagc ctggagggtc cctgagactc    60
tcctgtgcaa cctctggatt caccttcggt gactactaca tgaactggtt tcgccaggct   120
ccagggaagg ggctggactg ggtttcatac attagtagta gtggtagtac cagatactac   180
gcagactctg tgaggggccg attcaccatc tccagggaca cgccaagaa ttcactgtac   240
ctgcaaatga acagtctgag agccgaggac acggccgtct attactgtgt gagagatctc   300
cgctactact acggtatgga cgtatggggc caagggacca cggtcaccgt ctcctca     357
```

<210> SEQ ID NO 178
<211> LENGTH: 119
<212> TYPE: PRT
<213> ORGANISM: Homo sapiens

<400> SEQUENCE: 178

```
Gln Val Gln Leu Val Glu Ser Gly Gly Gly Leu Val Lys Pro Gly Gly
1               5                   10                  15
Ser Leu Arg Leu Ser Cys Ala Thr Ser Gly Phe Thr Phe Gly Asp Tyr
            20                  25                  30
Tyr Met Asn Trp Phe Arg Gln Ala Pro Gly Lys Gly Leu Asp Trp Val
        35                  40                  45
Ser Tyr Ile Ser Ser Ser Gly Ser Thr Arg Tyr Tyr Ala Asp Ser Val
    50                  55                  60
Arg Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Val Arg Asp Leu Arg Tyr Tyr Tyr Gly Met Asp Val Trp Gly Gln Gly
            100                 105                 110
Thr Thr Val Thr Val Ser Ser
        115
```

<210> SEQ ID NO 179
<211> LENGTH: 24
<212> TYPE: DNA
<213> ORGANISM: Homo sapiens

<400> SEQUENCE: 179

```
ggattcacct tcggtgacta ctac                                           24
```

<210> SEQ ID NO 180
<211> LENGTH: 8
<212> TYPE: PRT
<213> ORGANISM: Homo sapiens

<400> SEQUENCE: 180

```
Gly Phe Thr Phe Gly Asp Tyr Tyr
1               5
```

<210> SEQ ID NO 181
<211> LENGTH: 24
<212> TYPE: DNA
<213> ORGANISM: Homo sapiens

<400> SEQUENCE: 181

```
attagtagta gtggtagtac caga                                           24
```

<210> SEQ ID NO 182
<211> LENGTH: 8
<212> TYPE: PRT
<213> ORGANISM: Homo sapiens

<400> SEQUENCE: 182

Ile Ser Ser Ser Gly Ser Thr Arg
1               5

<210> SEQ ID NO 183
<211> LENGTH: 36
<212> TYPE: DNA
<213> ORGANISM: Homo sapiens

<400> SEQUENCE: 183
gtgagagatc tccgctacta ctacggtatg gacgta                                36

<210> SEQ ID NO 184
<211> LENGTH: 12
<212> TYPE: PRT
<213> ORGANISM: Homo sapiens

<400> SEQUENCE: 184

Val Arg Asp Leu Arg Tyr Tyr Tyr Gly Met Asp Val
1               5                   10

<210> SEQ ID NO 185
<211> LENGTH: 324
<212> TYPE: DNA
<213> ORGANISM: Homo sapiens

<400> SEQUENCE: 185
gaaattgtgt tgacgcagtc tccaggcacc ctgtctttgt ctccagggga aagagccacc      60
ctctcctgca gggccagtca gagtgttagc aacaactact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcaccttg gacgttcggc     300
caagggacca aggtggaaat caaa                                            324

<210> SEQ ID NO 186
<211> LENGTH: 108
<212> TYPE: PRT
<213> ORGANISM: Homo sapiens

<400> SEQUENCE: 186

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asn Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys

```
<210> SEQ ID NO 187
<211> LENGTH: 21
<212> TYPE: DNA
<213> ORGANISM: Homo sapiens

<400> SEQUENCE: 187
cagagtgtta gcaacaacta c                                             21

<210> SEQ ID NO 188
<211> LENGTH: 7
<212> TYPE: PRT
<213> ORGANISM: Homo sapiens

<400> SEQUENCE: 188

Gln Ser Val Ser Asn Asn Tyr
1               5

<210> SEQ ID NO 189
<211> LENGTH: 9
<212> TYPE: DNA
<213> ORGANISM: Homo sapiens

<400> SEQUENCE: 189 ggtgcatcc                                                            9

<210> SEQ ID NO 190
<211> LENGTH: 3
<212> TYPE: PRT
<213> ORGANISM: Homo sapiens

<400> SEQUENCE: 190

Gly Ala Ser
1

<210> SEQ ID NO 191
<211> LENGTH: 27
<212> TYPE: DNA
<213> ORGANISM: Homo sapiens

<400> SEQUENCE: 191
cagcagtatg gtagctcacc ttggacg                                       27

<210> SEQ ID NO 192
<211> LENGTH: 9
<212> TYPE: PRT
<213> ORGANISM: Homo sapiens

<400> SEQUENCE: 192

Gln Gln Tyr Gly Ser Ser Pro Trp Thr
1               5

<210> SEQ ID NO 193
<211> LENGTH: 351
<212> TYPE: DNA
<213> ORGANISM: Homo sapiens

<400> SEQUENCE: 193
caggtgcaac tgcaggagtc gggcccagga ctggtgaagc cttcggagac cctgtccctc    60
acctgcactg tctctggtgg ctccatcagt agttactact ggaactggat ccggcagtcc   120
ccagggaagg gactggagtg gattgggtat accaaaaaaa ggagtaccaa ctacaacccc   180
```

```
tccctcagga gtcgagtcac tatatcagaa gacacgtcca agaaccagtt ctccctgaag       240
atgagctctg tgaccgccgc agacacggcc gtatattact gtgcaaaaat ggggtgggga       300
tcccatgctt ttgatatatg gggccaaggg acaatggtca ccgtctcttc a              351
```

<210> SEQ ID NO 194
<211> LENGTH: 117
<212> TYPE: PRT
<213> ORGANISM: Homo sapiens

<400> SEQUENCE: 194

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Asn Trp Ile Arg Gln Ser Pro Gly Lys Gly Leu Glu Trp Ile
        35                  40                  45

Gly Tyr Thr Lys Lys Arg Ser Thr Asn Tyr Asn Pro Ser Leu Arg Ser
    50                  55                  60

Arg Val Thr Ile Ser Glu Asp Thr Ser Lys Asn Gln Phe Ser Leu Lys
65                  70                  75                  80

Met Ser Ser Val Thr Ala Ala Asp Thr Ala Val Tyr Tyr Cys Ala Lys
                85                  90                  95

Met Gly Trp Gly Ser His Ala Phe Asp Ile Trp Gly Gln Gly Thr Met
            100                 105                 110

Val Thr Val Ser Ser
        115
```

<210> SEQ ID NO 195
<211> LENGTH: 24
<212> TYPE: DNA
<213> ORGANISM: Homo sapiens

<400> SEQUENCE: 195

```
ggtggctcca tcagtagtta ctac                                              24
```

<210> SEQ ID NO 196
<211> LENGTH: 8
<212> TYPE: PRT
<213> ORGANISM: Homo sapiens

<400> SEQUENCE: 196

```
Gly Gly Ser Ile Ser Ser Tyr Tyr
1               5
```

<210> SEQ ID NO 197
<211> LENGTH: 18
<212> TYPE: DNA
<213> ORGANISM: Homo sapiens

<400> SEQUENCE: 197

```
accaaaaaaa ggagtacc                                                     18
```

<210> SEQ ID NO 198
<211> LENGTH: 6
<212> TYPE: PRT
<213> ORGANISM: Homo sapiens

<400> SEQUENCE: 198

```
Thr Lys Lys Arg Ser Thr
1               5
```

<210> SEQ ID NO 199
<211> LENGTH: 36
<212> TYPE: DNA
<213> ORGANISM: Homo sapiens

<400> SEQUENCE: 199
gcaaaaatgg ggtggggatc ccatgctttt gatata                36

<210> SEQ ID NO 200
<211> LENGTH: 12
<212> TYPE: PRT
<213> ORGANISM: Homo sapiens

<400> SEQUENCE: 200

Ala Lys Met Gly Trp Gly Ser His Ala Phe Asp Ile
1               5                   10

<210> SEQ ID NO 201
<211> LENGTH: 324
<212> TYPE: DNA
<213> ORGANISM: Homo sapiens

<400> SEQUENCE: 201
gaaattgtgt tgacgcagtc tccaggcacc ctgtctttgt ctccagggga aagagccacc     60
ctctcctgca gggccagtca gagtgttagc agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta gctcaccttg gacgttcggc    300
caagggacca aggtggaaat caaa                                           324

<210> SEQ ID NO 202
<211> LENGTH: 108
<212> TYPE: PRT
<213> ORGANISM: Homo sapiens

<400> SEQUENCE: 202

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 203
<211> LENGTH: 21
<212> TYPE: DNA
<213> ORGANISM: Homo sapiens

<400> SEQUENCE: 203

```
cagagtgtta gcagcagcta c                                              21
```

<210> SEQ ID NO 204
<211> LENGTH: 7
<212> TYPE: PRT
<213> ORGANISM: Homo sapiens

<400> SEQUENCE: 204

Gln Ser Val Ser Ser Tyr
1               5

<210> SEQ ID NO 205
<211> LENGTH: 9
<212> TYPE: DNA
<213> ORGANISM: Homo sapiens

<400> SEQUENCE: 205

```
ggtgcatcc                                                             9
```

<210> SEQ ID NO 206
<211> LENGTH: 3
<212> TYPE: PRT
<213> ORGANISM: Homo sapiens

<400> SEQUENCE: 206

Gly Ala Ser
1

<210> SEQ ID NO 207
<211> LENGTH: 27
<212> TYPE: DNA
<213> ORGANISM: Homo sapiens

<400> SEQUENCE: 207

```
cagcagtatg gtagctcacc ttggacg                                        27
```

<210> SEQ ID NO 208
<211> LENGTH: 9
<212> TYPE: PRT
<213> ORGANISM: Homo sapiens

<400> SEQUENCE: 208

Gln Gln Tyr Gly Ser Ser Pro Trp Thr
1               5

<210> SEQ ID NO 209
<211> LENGTH: 354
<212> TYPE: DNA
<213> ORGANISM: Homo sapiens

<400> SEQUENCE: 209

```
caggtgcagc tgcaggaggc gggcccagga ctggtgaagc cttcggagac cctgtccctc     60
acctgcattg tctctggtgg ctccatcagt ggtttctact ggaattggat ccggcagccc    120
ccagggaagg gactggaatg gattggatat tcctttaca gtgggactat cgactacaac    180
ccctccctca agagccgagt caccatatca gtggacacgt ccaaaaacca attctttctg    240
aagttgagtt ttgtgaccgc cgctgacacg gccgtttatt actgtgtgag gatgggactg    300
ggggctaatg cttttgacat ctggggccga ggacaatgg tcaccgtctc ttca           354
```

<210> SEQ ID NO 210
<211> LENGTH: 118
<212> TYPE: PRT

<213> ORGANISM: Homo sapiens

<400> SEQUENCE: 210

```
Gln Val Gln Leu Gln Glu Ala Gly Pro Gly Leu Val Lys Pro Ser Glu
1               5                  10                  15
Thr Leu Ser Leu Thr Cys Ile Val Ser Gly Gly Ser Ile Ser Gly Phe
            20                  25                  30
Tyr Trp Asn Trp Ile Arg Gln Pro Pro Gly Lys Gly Leu Glu Trp Ile
        35                  40                  45
Gly Tyr Phe Leu Tyr Ser Gly Thr Ile Asp Tyr Asn Pro Ser Leu Lys
    50                  55                  60
Ser Arg Val Thr Ile Ser Val Asp Thr Ser Lys Asn Gln Phe Phe Leu
65                  70                  75                  80
Lys Leu Ser Phe Val Thr Ala Ala Asp Thr Ala Val Tyr Tyr Cys Val
                85                  90                  95
Arg Met Gly Leu Gly Ala Asn Ala Phe Asp Ile Trp Gly Arg Gly Thr
            100                 105                 110
Met Val Thr Val Ser Ser
        115
```

<210> SEQ ID NO 211
<211> LENGTH: 24
<212> TYPE: DNA
<213> ORGANISM: Homo sapiens

<400> SEQUENCE: 211
ggtggctcca tcagtggttt ctac                                   24

<210> SEQ ID NO 212
<211> LENGTH: 8
<212> TYPE: PRT
<213> ORGANISM: Homo sapiens

<400> SEQUENCE: 212

```
Gly Gly Ser Ile Ser Gly Phe Tyr
1               5
```

<210> SEQ ID NO 213
<211> LENGTH: 21
<212> TYPE: DNA
<213> ORGANISM: Homo sapiens

<400> SEQUENCE: 213
ttcctttaca gtgggactat c                                      21

<210> SEQ ID NO 214
<211> LENGTH: 7
<212> TYPE: PRT
<213> ORGANISM: Homo sapiens

<400> SEQUENCE: 214

```
Phe Leu Tyr Ser Gly Thr Ile
1               5
```

<210> SEQ ID NO 215
<211> LENGTH: 36
<212> TYPE: DNA
<213> ORGANISM: Homo sapiens

<400> SEQUENCE: 215
gtgaggatgg gactgggggc taatgctttt gacatc                      36

<210> SEQ ID NO 216
<211> LENGTH: 12
<212> TYPE: PRT
<213> ORGANISM: Homo sapiens

<400> SEQUENCE: 216

```
Val Arg Met Gly Leu Gly Ala Asn Ala Phe Asp Ile
1               5                   10
```

<210> SEQ ID NO 217
<211> LENGTH: 324
<212> TYPE: DNA
<213> ORGANISM: Homo sapiens

<400> SEQUENCE: 217

```
gaaattgtgt tgacgcagtc tccaggcacc ctgtctttgt ctccagggga aagagccacc      60
ctctcctgca gggccagtca gactgttagt aggagtttct tagcctggta ccagcagaaa     120
cctggccagg ctcccaggct cctcatctat ggtccatcca gcagggccac tggcatccca     180
gacaggttca gtggcagtgg gtctgggaca gatttcactc tcaccatcag cagactggag     240
cctgaagatt ttgcggtgta ttactgtcaa caatatggta actcaccttg gacgttcggc     300
caagggacca aggtggaaat caaa                                            324
```

<210> SEQ ID NO 218
<211> LENGTH: 108
<212> TYPE: PRT
<213> ORGANISM: Homo sapiens

<400> SEQUENCE: 218

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Thr Val Ser Arg Ser
            20                  25                  30

Phe Leu Ala Trp Tyr Gln Gln Lys Pro Gly Gln Ala Pro Arg Leu Leu
        35                  40                  45

Ile Tyr Gly Pro Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asn Ser Pro
                85                  90                  95

Trp Thr Phe Gly Gln Gly Thr Lys Val Glu Ile Lys
            100                 105
```

<210> SEQ ID NO 219
<211> LENGTH: 21
<212> TYPE: DNA
<213> ORGANISM: Homo sapiens

<400> SEQUENCE: 219

```
cagactgtta gtaggagttt c                                                21
```

<210> SEQ ID NO 220
<211> LENGTH: 7
<212> TYPE: PRT
<213> ORGANISM: Homo sapiens

<400> SEQUENCE: 220

Gln Thr Val Ser Arg Ser Phe
1               5

<210> SEQ ID NO 221
<211> LENGTH: 9
<212> TYPE: DNA
<213> ORGANISM: Homo sapiens

<400> SEQUENCE: 221 ggtccatcc                                                                 9

<210> SEQ ID NO 222
<211> LENGTH: 3
<212> TYPE: PRT
<213> ORGANISM: Homo sapiens

<400> SEQUENCE: 222

Gly Pro Ser
1

<210> SEQ ID NO 223
<211> LENGTH: 27
<212> TYPE: DNA
<213> ORGANISM: Homo sapiens

<400> SEQUENCE: 223
caacaatatg gtaactcacc ttggacg                                            27

<210> SEQ ID NO 224
<211> LENGTH: 9
<212> TYPE: PRT
<213> ORGANISM: Homo sapiens

<400> SEQUENCE: 224

Gln Gln Tyr Gly Asn Ser Pro Trp Thr
1               5

<210> SEQ ID NO 225
<211> LENGTH: 357
<212> TYPE: DNA
<213> ORGANISM: Homo sapiens

<400> SEQUENCE: 225
caggtccagc tggtggagtc tgggggaggc ttggtcaagc ctggagggtc cctgagactc        60
tcctgtgcag tttctggatt cacctacact gactacttca tgaactggat ccgacaggct       120
ccagggaagg ggctggaatg ggtttcatat attagtaata gtggtgctat caaatactac       180
gcagactctg tgaagggccg attcaccatc tccagggaca acgccaagaa ttctttgtat       240
ctgcaaatga acggcctgag agccgacgac acggccgtgt attactgtgt gagagaccct       300
cgaagctact atgggtttga ctattgggc cagggaaccc tggtcaccgt ctcctca          357

<210> SEQ ID NO 226
<211> LENGTH: 119
<212> TYPE: PRT
<213> ORGANISM: Homo sapiens

<400> SEQUENCE: 226

Gln Val Gln Leu Val Glu Ser Gly Gly Gly Leu Val Lys Pro Gly Gly
1               5                   10                  15

Ser Leu Arg Leu Ser Cys Ala Val Ser Gly Phe Thr Tyr Thr Asp Tyr
            20                  25                  30

```
Phe Met Asn Trp Ile Arg Gln Ala Pro Gly Lys Gly Leu Glu Trp Val
             35                  40                  45
Ser Tyr Ile Ser Asn Ser Gly Ala Ile Lys Tyr Tyr Ala Asp Ser Val
     50                  55                  60
Lys Gly Arg Phe Thr Ile Ser Arg Asp Asn Ala Lys Asn Ser Leu Tyr
 65                  70                  75                  80
Leu Gln Met Asn Gly Leu Arg Ala Asp Asp Thr Ala Val Tyr Tyr Cys
                 85                  90                  95
Val Arg Asp Pro Arg Ser Tyr Tyr Gly Phe Asp Tyr Trp Gly Gln Gly
             100                 105                 110
Thr Leu Val Thr Val Ser Ser
        115
```

```
<210> SEQ ID NO 227
<211> LENGTH: 24
<212> TYPE: DNA
<213> ORGANISM: Homo sapiens

<400> SEQUENCE: 227
ggattcacct acactgacta cttc                                    24

<210> SEQ ID NO 228
<211> LENGTH: 8
<212> TYPE: PRT
<213> ORGANISM: Homo sapiens

<400> SEQUENCE: 228

Gly Phe Thr Tyr Thr Asp Tyr Phe
 1               5

<210> SEQ ID NO 229
<211> LENGTH: 24
<212> TYPE: DNA
<213> ORGANISM: Homo sapiens

<400> SEQUENCE: 229
attagtaata gtggtgctat caaa                                    24

<210> SEQ ID NO 230
<211> LENGTH: 8
<212> TYPE: PRT
<213> ORGANISM: Homo sapiens

<400> SEQUENCE: 230

Ile Ser Asn Ser Gly Ala Ile Lys
 1               5

<210> SEQ ID NO 231
<211> LENGTH: 36
<212> TYPE: DNA
<213> ORGANISM: Homo sapiens

<400> SEQUENCE: 231
gtgagagacc ctcgaagcta ctatgggttt gactat                       36

<210> SEQ ID NO 232
<211> LENGTH: 12
<212> TYPE: PRT
<213> ORGANISM: Homo sapiens

<400> SEQUENCE: 232

Val Arg Asp Pro Arg Ser Tyr Tyr Gly Phe Asp Tyr
```

<210> SEQ ID NO 233
<211> LENGTH: 324
<212> TYPE: DNA
<213> ORGANISM: Homo sapiens

<400> SEQUENCE: 233

```
gacatccaga tgacccagtc tccatcctcc ctgtctgcat ctgtaggtga cagagtcacc        60
atcacttgcc gggcaagtca gagcattagt aactttttaa attggtatca gcagaaacca       120
gggaaagccc ctaggctcct gatctatggt gcatccaatt tgcaaagtgg ggtcccatca       180
aggttcagtg gcggtggatc tgggacagat ttcactctca ccatcagcag tctgcaacct       240
gcagattttg caacttacta ctgtcagcag agtttcagta accctccggt caccttcggc       300
caagggacac gactggagat taac                                              324
```

<210> SEQ ID NO 234
<211> LENGTH: 108
<212> TYPE: PRT
<213> ORGANISM: Homo sapiens

<400> SEQUENCE: 234

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Phe
            20                  25                  30

Leu Asn Trp Tyr Gln Gln Lys Pro Gly Lys Ala Pro Arg Leu Leu Ile
        35                  40                  45

Tyr Gly Ala Ser Asn Leu Gln Ser Gly Val Pro Ser Arg Phe Ser Gly
    50                  55                  60

Gly Gly Ser Gly Thr Asp Phe Thr Leu Thr Ile Ser Ser Leu Gln Pro
65                  70                  75                  80

Ala Asp Phe Ala Thr Tyr Tyr Cys Gln Gln Ser Phe Ser Asn Pro Pro
                85                  90                  95

Val Thr Phe Gly Gln Gly Thr Arg Leu Glu Ile Asn
            100                 105

<210> SEQ ID NO 235
<211> LENGTH: 18
<212> TYPE: DNA
<213> ORGANISM: Homo sapiens

<400> SEQUENCE: 235

```
cagagcatta gtaacttt                                                      18
```

<210> SEQ ID NO 236
<211> LENGTH: 6
<212> TYPE: PRT
<213> ORGANISM: Homo sapiens

<400> SEQUENCE: 236

Gln Ser Ile Ser Asn Phe
1               5

<210> SEQ ID NO 237
<211> LENGTH: 9
<212> TYPE: DNA
<213> ORGANISM: Homo sapiens

<400> SEQUENCE: 237

```
ggtgcatcc                                                                  9
```

<210> SEQ ID NO 238
<211> LENGTH: 3
<212> TYPE: PRT
<213> ORGANISM: Homo sapiens

<400> SEQUENCE: 238

Gly Ala Ser
1

<210> SEQ ID NO 239
<211> LENGTH: 30
<212> TYPE: DNA
<213> ORGANISM: Homo sapiens

<400> SEQUENCE: 239

```
cagcagagtt tcagtaaccc tccggtcacc                                          30
```

<210> SEQ ID NO 240
<211> LENGTH: 10
<212> TYPE: PRT
<213> ORGANISM: Homo sapiens

<400> SEQUENCE: 240

Gln Gln Ser Phe Ser Asn Pro Pro Val Thr
1               5                   10

<210> SEQ ID NO 241
<211> LENGTH: 357
<212> TYPE: DNA
<213> ORGANISM: Homo sapiens

<400> SEQUENCE: 241

```
caggtgcagt tggtggagtc tgggggaggc ttggtccagc ctggagggtc cctgagactc          60
tcctgtgcag cctctggatt catcttcggt gactactaca ttaactggat tcgccaggct         120
ccagggaagg ggctgcagtg ggtttcatat actagtagta gtggtagtac cacttactac         180
gaagactctg tgaagggccg attcaccatg tccaggaca atgccaagaa tttagtatac          240
ctgcaaatga acagcctgag agccgaggac acggccgcgt attattgtgt gagagatctg         300
agatacaacg atggtttgga cgtctggggc caagggacca cggtcatcgt ctcctca           357
```

<210> SEQ ID NO 242
<211> LENGTH: 119
<212> TYPE: PRT
<213> ORGANISM: Homo sapiens

<400> SEQUENCE: 242

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Gly Asp Tyr
            20                  25                  30

Tyr Ile Asn Trp Ile Arg Gln Ala Pro Gly Lys Gly Leu Gln Trp Val
        35                  40                  45

Ser Tyr Thr Ser Ser Ser Gly Ser Thr Thr Tyr Tyr Glu Asp Ser Val
    50                  55                  60

Lys Gly Arg Phe Thr Met Ser Arg Asp Asn Ala Lys Asn Leu Val Tyr
65                  70                  75                  80

Leu Gln Met Asn Ser Leu Arg Ala Glu Asp Thr Ala Ala Tyr Tyr Cys

```
                85                  90                  95

Val Arg Asp Leu Arg Tyr Asn Asp Gly Leu Asp Val Trp Gly Gln Gly
            100                 105                 110

Thr Thr Val Ile Val Ser Ser
        115

<210> SEQ ID NO 243
<211> LENGTH: 24
<212> TYPE: DNA
<213> ORGANISM: Homo sapiens

<400> SEQUENCE: 243
ggattcatct tcggtgacta ctac                                            24

<210> SEQ ID NO 244
<211> LENGTH: 8
<212> TYPE: PRT
<213> ORGANISM: Homo sapiens

<400> SEQUENCE: 244

Gly Phe Ile Phe Gly Asp Tyr Tyr
1               5

<210> SEQ ID NO 245
<211> LENGTH: 24
<212> TYPE: DNA
<213> ORGANISM: Homo sapiens

<400> SEQUENCE: 245
actagtagta gtggtagtac cact                                            24

<210> SEQ ID NO 246
<211> LENGTH: 8
<212> TYPE: PRT
<213> ORGANISM: Homo sapiens

<400> SEQUENCE: 246

Thr Ser Ser Ser Gly Ser Thr Thr
1               5

<210> SEQ ID NO 247
<211> LENGTH: 36
<212> TYPE: DNA
<213> ORGANISM: Homo sapiens

<400> SEQUENCE: 247
gtgagagatc tgagatacaa cgatggtttg gacgtc                               36

<210> SEQ ID NO 248
<211> LENGTH: 12
<212> TYPE: PRT
<213> ORGANISM: Homo sapiens

<400> SEQUENCE: 248

Val Arg Asp Leu Arg Tyr Asn Asp Gly Leu Asp Val
1               5                   10

<210> SEQ ID NO 249
<211> LENGTH: 324
<212> TYPE: DNA
<213> ORGANISM: Homo sapiens

<400> SEQUENCE: 249
```

```
gacatcctgc tgacccagtc tccatcctcc ctgtctgcat ttgtaggaga cagagtcacc    60
atcacttgcc gggcaagtca gaacattcgc acctatctaa attggtatca gcagaaacca   120
gggagagccc ctaagctcct ggtctatgct gcatccactt tgcaaagtgg ggtcccatca   180
aggttcagtg gcagtggatc tgggacagac ttcactctca ccatcagcag tctgcaacct   240
gaagattttg caagttactt ctgtcaacag agttacgata cccctccgat caccttcggc   300
caagggacac gactggcgat taaa                                          324
```

<210> SEQ ID NO 250
<211> LENGTH: 108
<212> TYPE: PRT
<213> ORGANISM: Homo sapiens

<400> SEQUENCE: 250

```
Asp Ile Leu Leu Thr Gln Ser Pro Ser Ser Leu Ser Ala Phe Val Gly
 1               5                  10                  15

Asp Arg Val Thr Ile Thr Cys Arg Ala Ser Gln Asn Ile Arg Thr Tyr
             20                  25                  30

Leu Asn Trp Tyr Gln Gln Lys Pro Gly Arg Ala Pro Lys Leu Leu Val
         35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Ser Tyr Phe Cys Gln Gln Ser Tyr Asp Asn Pro Pro
                 85                  90                  95

Ile Thr Phe Gly Gln Gly Thr Arg Leu Ala Ile Lys
            100                 105
```

<210> SEQ ID NO 251
<211> LENGTH: 18
<212> TYPE: DNA
<213> ORGANISM: Homo sapiens

<400> SEQUENCE: 251

```
cagaacattc gcacctat                                                  18
```

<210> SEQ ID NO 252
<211> LENGTH: 6
<212> TYPE: PRT
<213> ORGANISM: Homo sapiens

<400> SEQUENCE: 252

```
Gln Asn Ile Arg Thr Tyr
 1               5
```

<210> SEQ ID NO 253
<211> LENGTH: 9
<212> TYPE: DNA
<213> ORGANISM: Homo sapiens

<400> SEQUENCE: 253

```
gctgcatcc                                                             9
```

<210> SEQ ID NO 254
<211> LENGTH: 3
<212> TYPE: PRT
<213> ORGANISM: Homo sapiens

<400> SEQUENCE: 254

Ala Ala Ser
1

<210> SEQ ID NO 255
<211> LENGTH: 30
<212> TYPE: DNA
<213> ORGANISM: Homo sapiens

<400> SEQUENCE: 255
caacagagtt acgataaccc tccgatcacc                                    30

<210> SEQ ID NO 256
<211> LENGTH: 10
<212> TYPE: PRT
<213> ORGANISM: Homo sapiens

<400> SEQUENCE: 256

Gln Gln Ser Tyr Asp Asn Pro Pro Ile Thr
1               5                   10

<210> SEQ ID NO 257
<211> LENGTH: 360
<212> TYPE: DNA
<213> ORGANISM: Homo sapiens

<400> SEQUENCE: 257
gaagtgcaac tggtggagtc tgggggaggc ttggtacagc ctggcaggtc cctgagactc    60
tcctgtacag cctctggatt cacctttggt gatcatgcca tgcactgggt ccgacaagct   120
cccgggaagg gcctggaggg ggtctcaagt attaattgga atagtggtat cataggctat   180
gcggagtctg tgaagggccg attcaccatc tccagagaca cgccaagaa ctccctgtat   240 ctgcaaatga acaatctgag agctgaggac acgggcttat attactgtgc aaggatatt   300 ggcgtggcaa cgcttggtat tgactactgg ggccagggaa ccctggtcac cgtctcctca   360

<210> SEQ ID NO 258
<211> LENGTH: 120
<212> TYPE: PRT
<213> ORGANISM: Homo sapiens

<400> SEQUENCE: 258

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp His
            20                  25                  30

Ala Met His Trp Val Arg Gln Ala Pro Gly Lys Gly Leu Glu Gly Val
        35                  40                  45

Ser Ser Ile Asn Trp Asn Ser Gly Ile Ile Gly Tyr Ala Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Asn Leu Arg Ala Glu Asp Thr Gly Leu Tyr Tyr Cys
                85                  90                  95

Ala Arg Asp Ile Gly Val Ala Thr Leu Gly Ile Asp Tyr Trp Gly Gln
            100                 105                 110

Gly Thr Leu Val Thr Val Ser Ser
        115                 120

<210> SEQ ID NO 259

```
<211> LENGTH: 24
<212> TYPE: DNA
<213> ORGANISM: Homo sapiens

<400> SEQUENCE: 259
ggattcacct ttggtgatca tgcc                                          24

<210> SEQ ID NO 260
<211> LENGTH: 8
<212> TYPE: PRT
<213> ORGANISM: Homo sapiens

<400> SEQUENCE: 260

Gly Phe Thr Phe Gly Asp His Ala
1               5

<210> SEQ ID NO 261
<211> LENGTH: 24
<212> TYPE: DNA
<213> ORGANISM: Homo sapiens

<400> SEQUENCE: 261
attaattgga atagtggtat cata                                          24

<210> SEQ ID NO 262
<211> LENGTH: 8
<212> TYPE: PRT
<213> ORGANISM: Homo sapiens

<400> SEQUENCE: 262

Ile Asn Trp Asn Ser Gly Ile Ile
1               5

<210> SEQ ID NO 263
<211> LENGTH: 39
<212> TYPE: DNA
<213> ORGANISM: Homo sapiens

<400> SEQUENCE: 263
gcaagggata ttggcgtggc aacgcttggt attgactac                          39

<210> SEQ ID NO 264
<211> LENGTH: 13
<212> TYPE: PRT
<213> ORGANISM: Homo sapiens

<400> SEQUENCE: 264

Ala Arg Asp Ile Gly Val Ala Thr Leu Gly Ile Asp Tyr
1               5                   10

<210> SEQ ID NO 265
<211> LENGTH: 324
<212> TYPE: DNA
<213> ORGANISM: Homo sapiens

<400> SEQUENCE: 265
gacatccaga tgacccagtc tccatcctcc ctgtctgcat cagtaggaga cagagtcacc    60
atcacttgcc gggcaagtca gagcattagc agctactcaa attggtatca gcagaaacca   120
gggaaagccc ctaaactcct gatctatgct gcatccagtt tgcaaagtgg ggtcccatca   180
aggttcagtg gcagtggatc tgggacagat tcactctcac ccatcagcag tctgcaacct   240
gaagattttg caacttacta ctgtcaacag agtcacagta cccctccgat caccttcggc   300
```
caagggacac gactggagat taaa                                              324

<210> SEQ ID NO 266
<211> LENGTH: 108
<212> TYPE: PRT
<213> ORGANISM: Homo sapiens

<400> SEQUENCE: 266

Asp Ile Gln Met Thr Gln Ser Pro Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Ser Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser His Ser Thr Pro Pro
                85                  90                  95

Ile Thr Phe Gly Gln Gly Thr Arg Leu Glu Ile Lys
            100                 105

<210> SEQ ID NO 267
<211> LENGTH: 18
<212> TYPE: DNA
<213> ORGANISM: Homo sapiens

<400> SEQUENCE: 267
cagagcatta gcagctac                                                     18

<210> SEQ ID NO 268
<211> LENGTH: 6
<212> TYPE: PRT
<213> ORGANISM: Homo sapiens

<400> SEQUENCE: 268

Gln Ser Ile Ser Ser Tyr
1               5

<210> SEQ ID NO 269
<211> LENGTH: 9
<212> TYPE: DNA
<213> ORGANISM: Homo sapiens

<400> SEQUENCE: 269 gctgcatcc                                                                9

<210> SEQ ID NO 270
<211> LENGTH: 3
<212> TYPE: PRT
<213> ORGANISM: Homo sapiens

<400> SEQUENCE: 270

Ala Ala Ser
1

<210> SEQ ID NO 271
<211> LENGTH: 30
<212> TYPE: DNA
<213> ORGANISM: Homo sapiens

<400> SEQUENCE: 271
caacagagtc acagtacccc tccgatcacc                                30

<210> SEQ ID NO 272
<211> LENGTH: 10
<212> TYPE: PRT
<213> ORGANISM: Homo sapiens

<400> SEQUENCE: 272

Gln Gln Ser His Ser Thr Pro Pro Ile Thr
1               5                   10

<210> SEQ ID NO 273
<211> LENGTH: 357
<212> TYPE: DNA
<213> ORGANISM: Homo sapiens

<400> SEQUENCE: 273
caggtgcagc tggtggagtc tgggggaggc ttggtcaagc ctggagggtc cctgagactc     60
tcctgtgcaa cctctggatt caccttcact gactacttca tgaattggat ccgccaggct    120
ccagggaagg gactggagtg gtttcatac attagtaaca gtggttctat cagatattat     180
gcagactctg tgaggggccg attctccatc tccagggaca atgccaagaa ctccctgtat    240
ctgcaaatga gcagcctgag agccgatgac acggccgtgt attactgtgt gagagatccg    300
cgacaaatct acggtatgga cgtctgggc caagggacca cggtcaccgt ctcctca        357

<210> SEQ ID NO 274
<211> LENGTH: 119
<212> TYPE: PRT
<213> ORGANISM: Homo sapiens

<400> SEQUENCE: 274

Gln Val Gln Leu Val Glu Ser Gly Gly Gly Leu Val Lys Pro Gly Gly
1               5                   10                  15

Ser Leu Arg Leu Ser Cys Ala Thr Ser Gly Phe Thr Phe Thr Asp Tyr
            20                  25                  30

Phe Met Asn Trp Ile Arg Gln Ala Pro Gly Lys Gly Leu Glu Trp Val
        35                  40                  45

Ser Tyr Ile Ser Asn Ser Gly Ser Ile Arg Tyr Tyr Ala Asp Ser Val
    50                  55                  60

Arg Gly Arg Phe Ser Ile Ser Arg Asp Asn Ala Lys Asn Ser Leu Tyr
65                  70                  75                  80

Leu Gln Met Ser Ser Leu Arg Ala Asp Asp Thr Ala Val Tyr Tyr Cys
                85                  90                  95

Val Arg Asp Pro Arg Gln Ile Tyr Gly Met Asp Val Trp Gly Gln Gly
            100                 105                 110

Thr Thr Val Thr Val Ser Ser
        115

<210> SEQ ID NO 275
<211> LENGTH: 24
<212> TYPE: DNA
<213> ORGANISM: Homo sapiens

<400> SEQUENCE: 275
ggattcacct tcactgacta cttc                                      24

<210> SEQ ID NO 276

```
<211> LENGTH: 8
<212> TYPE: PRT
<213> ORGANISM: Homo sapiens

<400> SEQUENCE: 276

Gly Phe Thr Phe Thr Asp Tyr Phe
1               5

<210> SEQ ID NO 277
<211> LENGTH: 24
<212> TYPE: DNA
<213> ORGANISM: Homo sapiens

<400> SEQUENCE: 277
attagtaaca gtggttctat caga                                            24

<210> SEQ ID NO 278
<211> LENGTH: 8
<212> TYPE: PRT
<213> ORGANISM: Homo sapiens

<400> SEQUENCE: 278

Ile Ser Asn Ser Gly Ser Ile Arg
1               5

<210> SEQ ID NO 279
<211> LENGTH: 36
<212> TYPE: DNA
<213> ORGANISM: Homo sapiens

<400> SEQUENCE: 279
gtgagagatc cgcgacaaat ctacggtatg gacgtc                               36

<210> SEQ ID NO 280
<211> LENGTH: 12
<212> TYPE: PRT
<213> ORGANISM: Homo sapiens

<400> SEQUENCE: 280

Val Arg Asp Pro Arg Gln Ile Tyr Gly Met Asp Val
1               5                   10

<210> SEQ ID NO 281
<211> LENGTH: 324
<212> TYPE: DNA
<213> ORGANISM: Homo sapiens

<400> SEQUENCE: 281
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccgtca     180
aggttcagtg gcagtggatc tgggacagat ttcactctca ccatcagcag tctgcaacct     240
gaagattttg caacttacta ctgtcaacag agttacagta cccctccgat caccttcggc     300
caagggacac gactggagat taaa                                            324

<210> SEQ ID NO 282
<211> LENGTH: 108
<212> TYPE: PRT
<213> ORGANISM: Homo sapiens

<400> SEQUENCE: 282
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
                100                 105
```

<210> SEQ ID NO 283
<211> LENGTH: 18
<212> TYPE: DNA
<213> ORGANISM: Homo sapiens

<400> SEQUENCE: 283
cagagcatta gcagctat                                                   18

<210> SEQ ID NO 284
<211> LENGTH: 6
<212> TYPE: PRT
<213> ORGANISM: Homo sapiens

<400> SEQUENCE: 284

```
Gln Ser Ile Ser Ser Tyr
1               5
```

<210> SEQ ID NO 285
<211> LENGTH: 9
<212> TYPE: DNA
<213> ORGANISM: Homo sapiens

<400> SEQUENCE: 285 gctgcatcc                                                              9

<210> SEQ ID NO 286
<211> LENGTH: 3
<212> TYPE: PRT
<213> ORGANISM: Homo sapiens

<400> SEQUENCE: 286

```
Ala Ala Ser
1
```

<210> SEQ ID NO 287
<211> LENGTH: 30
<212> TYPE: DNA
<213> ORGANISM: Homo sapiens

<400> SEQUENCE: 287
caacagagtt acagtacccc tccgatcacc                                      30

<210> SEQ ID NO 288
<211> LENGTH: 10
<212> TYPE: PRT
<213> ORGANISM: Homo sapiens

<400> SEQUENCE: 288

Gln Gln Ser Tyr Ser Thr Pro Pro Ile Thr
1               5                   10

<210> SEQ ID NO 289
<211> LENGTH: 357
<212> TYPE: DNA
<213> ORGANISM: Homo sapiens

<400> SEQUENCE: 289
caggtgcagc tggtggagtc tgggggaggc ttggtcaagc ctcgagggtc cctgagactc    60
tcctgtgcag cctctggatt catcttcgat gactacttca tgaactggat ccgccaggct   120
ccagggaagg gctggagtg ggtttcatac attagtaata gtggtaatac caaatactac   180
gcagactctg tgaagggccg attcaccatc tccaggaca acgcctacaa ctctctgtat   240
ctgcaaatga acagcctgag agccgaggac acggccgtgt attactgtgt gagagatcct   300
agaagttact acggtatgga cgtctggggc caagggacca cggtcaccgt ctcctca     357

<210> SEQ ID NO 290
<211> LENGTH: 119
<212> TYPE: PRT
<213> ORGANISM: Homo sapiens

<400> SEQUENCE: 290

Gln Val Gln Leu Val Glu Ser Gly Gly Gly Leu Val Lys Pro Arg Gly
1               5                   10                  15

Ser Leu Arg Leu Ser Cys Ala Ala Ser Gly Phe Ile Phe Asp Asp Tyr
            20                  25                  30

Phe Met Asn Trp Ile Arg Gln Ala Pro Gly Lys Gly Leu Glu Trp Val
        35                  40                  45

Ser Tyr Ile Ser Asn Ser Gly Asn Thr Lys Tyr Tyr Ala Asp Ser Val
    50                  55                  60

Lys Gly Arg Phe Thr Ile Ser Arg Asp Asn Ala Tyr Asn Ser Leu Tyr
65                  70                  75                  80

Leu Gln Met Asn Ser Leu Arg Ala Glu Asp Thr Ala Val Tyr Tyr Cys
                85                  90                  95

Val Arg Asp Pro Arg Ser Tyr Tyr Gly Met Asp Val Trp Gly Gln Gly
            100                 105                 110

Thr Thr Val Thr Val Ser Ser
        115

<210> SEQ ID NO 291
<211> LENGTH: 24
<212> TYPE: DNA
<213> ORGANISM: Homo sapiens

<400> SEQUENCE: 291
ggattcatct tcgatgacta cttc                                            24

<210> SEQ ID NO 292
<211> LENGTH: 8
<212> TYPE: PRT
<213> ORGANISM: Homo sapiens

<400> SEQUENCE: 292

Gly Phe Ile Phe Asp Asp Tyr Phe
1               5

```
<210> SEQ ID NO 293
<211> LENGTH: 24
<212> TYPE: DNA
<213> ORGANISM: Homo sapiens

<400> SEQUENCE: 293
attagtaata gtggtaatac caaa                                          24

<210> SEQ ID NO 294
<211> LENGTH: 8
<212> TYPE: PRT
<213> ORGANISM: Homo sapiens

<400> SEQUENCE: 294

Ile Ser Asn Ser Gly Asn Thr Lys
1               5

<210> SEQ ID NO 295
<211> LENGTH: 36
<212> TYPE: DNA
<213> ORGANISM: Homo sapiens

<400> SEQUENCE: 295
gtgagagatc ctagaagtta ctacggtatg gacgtc                             36

<210> SEQ ID NO 296
<211> LENGTH: 12
<212> TYPE: PRT
<213> ORGANISM: Homo sapiens

<400> SEQUENCE: 296

Val Arg Asp Pro Arg Ser Tyr Tyr Gly Met Asp Val
1               5                   10

<210> SEQ ID NO 297
<211> LENGTH: 357
<212> TYPE: DNA
<213> ORGANISM: Homo sapiens

<400> SEQUENCE: 297
caggtgcagc tggtggagtc tgggggaggc ttggtcaagc ctggagggtc cctgagactc    60
tcctgtgcag cctctggatt caccttcagt gactactaca tgaactggat ccgccaggct   120
ccagggaagg ggctggagtg ggtttcatac attaatggtg gtggttatac catgtactac   180
gcagactctg tgaagggccg attcaccatc tccagggaca acgccaagaa ctcactttat   240
ctgcaaatga acagcctgag agccgaggac acggccgtgt attactgtgc gagagataga   300
aggactacag tatctattga ctactggggc cagggaaccc tggtcaccgt ctcctca      357

<210> SEQ ID NO 298
<211> LENGTH: 39
<212> TYPE: PRT
<213> ORGANISM: Homo sapiens

<400> SEQUENCE: 298

Leu Gln Met Asn Ser Leu Arg Ala Glu Asp Thr Ala Val Tyr Tyr Cys
1               5                   10                  15

Ala Arg Asp Arg Arg Thr Thr Val Ser Ile Asp Tyr Trp Gly Gln Gly
            20                  25                  30

Thr Leu Val Thr Val Ser Ser
        35
```

```
<210> SEQ ID NO 299
<211> LENGTH: 24
<212> TYPE: DNA
<213> ORGANISM: Homo sapiens

<400> SEQUENCE: 299
ggattcacct tcagtgacta ctac                                            24

<210> SEQ ID NO 300
<211> LENGTH: 8
<212> TYPE: PRT
<213> ORGANISM: Homo sapiens

<400> SEQUENCE: 300

Gly Phe Thr Phe Ser Asp Tyr Tyr
1               5

<210> SEQ ID NO 301
<211> LENGTH: 24
<212> TYPE: DNA
<213> ORGANISM: Homo sapiens

<400> SEQUENCE: 301
attaatggtg gtggttatac catg                                            24

<210> SEQ ID NO 302
<211> LENGTH: 8
<212> TYPE: PRT
<213> ORGANISM: Homo sapiens

<400> SEQUENCE: 302

Ile Asn Gly Gly Gly Tyr Thr Met
1               5

<210> SEQ ID NO 303
<211> LENGTH: 36
<212> TYPE: DNA
<213> ORGANISM: Homo sapiens

<400> SEQUENCE: 303
gcgagagata gaaggactac agtatctatt gactac                               36

<210> SEQ ID NO 304
<211> LENGTH: 12
<212> TYPE: PRT
<213> ORGANISM: Homo sapiens

<400> SEQUENCE: 304

Ala Arg Asp Arg Arg Thr Thr Val Ser Ile Asp Tyr
1               5                   10

<210> SEQ ID NO 305
<211> LENGTH: 360
<212> TYPE: DNA
<213> ORGANISM: Homo sapiens

<400> SEQUENCE: 305
gaagtgcagc tggtggagtc tgggggagcc ttggtacagc ctggcaggtc cctgagactc      60
tcctgtgcag cctctggatt cacctttgat gattatgcca tgcactgggt ccggcaagct     120
ccagggaagg gcctagagtg ggtctcaggt attagttgga atagtggtac catgggctat     180
gcggactctg tgaagggccg attcaccatt tccagagaca cgccaagaa gtccctgtat      240 ctgcaaatga atagtctgag agctgaggac acggccttgt attactgtgg aaaaggtcta     300
```
cttcaccagt gggaggtact tgactactgg ggccagggaa ccctggtcac cgtctcctca    360

<210> SEQ ID NO 306
<211> LENGTH: 120
<212> TYPE: PRT
<213> ORGANISM: Homo sapiens

<400> SEQUENCE: 306

Glu Val Gln Leu Val Glu Ser Gly Gly Ala Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Thr Met Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Gly Lys Gly Leu Leu His Gln Trp Glu Val Leu Asp Tyr Trp Gly Gln
            100                 105                 110

Gly Thr Leu Val Thr Val Ser Ser
        115                 120

<210> SEQ ID NO 307
<211> LENGTH: 24
<212> TYPE: DNA
<213> ORGANISM: Homo sapiens

<400> SEQUENCE: 307
ggattcacct ttgatgatta tgcc                                          24

<210> SEQ ID NO 308
<211> LENGTH: 8
<212> TYPE: PRT
<213> ORGANISM: Homo sapiens

<400> SEQUENCE: 308

Gly Phe Thr Phe Asp Asp Tyr Ala
1               5

<210> SEQ ID NO 309
<211> LENGTH: 24
<212> TYPE: DNA
<213> ORGANISM: Homo sapiens

<400> SEQUENCE: 309
attagttgga atagtggtac catg                                          24

<210> SEQ ID NO 310
<211> LENGTH: 8
<212> TYPE: PRT
<213> ORGANISM: Homo sapiens

<400> SEQUENCE: 310

Ile Ser Trp Asn Ser Gly Thr Met
1               5

<210> SEQ ID NO 311

<210> SEQ ID NO 311
<211> LENGTH: 39
<212> TYPE: DNA
<213> ORGANISM: Homo sapiens

<400> SEQUENCE: 311
ggaaaaggtc tacttcacca gtgggaggta cttgactac                                   39

<210> SEQ ID NO 312
<211> LENGTH: 13
<212> TYPE: PRT
<213> ORGANISM: Homo sapiens

<400> SEQUENCE: 312

Gly Lys Gly Leu Leu His Gln Trp Glu Val Leu Asp Tyr
1               5                   10

<210> SEQ ID NO 313
<211> LENGTH: 357
<212> TYPE: DNA
<213> ORGANISM: Homo sapiens

<400> SEQUENCE: 313
caggtgcagc tggtggagtc tgggggaggc ttggtcaagc ctggagggtc cctgagactc            60
tcctgtgcag cctctggatt catcttcact gattacttca tgaactggat ccgccaggct           120
ccaggaaagg gactggagtg gtttcgtac attagtaata gtggtaatat tttatactat           180
gcagactctg tgaagggccg attcaccatc tccagggaca acgccaaggc gtccctgtat           240
ctgcaaatga gcagccttaa agccgaggac acggccgtgt attactgtgt gagagatccc           300
cgtatgttct acggtatgga cgtctggggc caggggacca cggtcaccgt ctcctca              357

<210> SEQ ID NO 314
<211> LENGTH: 119
<212> TYPE: PRT
<213> ORGANISM: Homo sapiens

<400> SEQUENCE: 314

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Ile Phe Thr Asp Tyr
            20                  25                  30

Phe Met Asn Trp Ile Arg Gln Ala Pro Gly Lys Gly Leu Glu Trp Val
        35                  40                  45

Ser Tyr Ile Ser Asn Ser Gly Asn Ile Leu Tyr Tyr Ala Asp Ser Val
    50                  55                  60

Lys Gly Arg Phe Thr Ile Ser Arg Asp Asn Ala Lys Ala Ser Leu Tyr
65                  70                  75                  80

Leu Gln Met Ser Ser Leu Lys Ala Glu Asp Thr Ala Val Tyr Tyr Cys
                85                  90                  95

Val Arg Asp Pro Arg Met Phe Tyr Gly Met Asp Val Trp Gly Gln Gly
            100                 105                 110

Thr Thr Val Thr Val Ser Ser
        115

<210> SEQ ID NO 315
<211> LENGTH: 24
<212> TYPE: DNA
<213> ORGANISM: Homo sapiens

<400> SEQUENCE: 315

```
ggattcatct tcactgatta cttc                                          24
```

<210> SEQ ID NO 316
<211> LENGTH: 8
<212> TYPE: PRT
<213> ORGANISM: Homo sapiens

<400> SEQUENCE: 316

Gly Phe Ile Phe Thr Asp Tyr Phe
1               5

<210> SEQ ID NO 317
<211> LENGTH: 24
<212> TYPE: DNA
<213> ORGANISM: Homo sapiens

<400> SEQUENCE: 317

```
attagtaata gtggtaatat ttta                                          24
```

<210> SEQ ID NO 318
<211> LENGTH: 8
<212> TYPE: PRT
<213> ORGANISM: Homo sapiens

<400> SEQUENCE: 318

Ile Ser Asn Ser Gly Asn Ile Leu
1               5

<210> SEQ ID NO 319
<211> LENGTH: 36
<212> TYPE: DNA
<213> ORGANISM: Homo sapiens

<400> SEQUENCE: 319

```
gtgagagatc cccgtatgtt ctacggtatg gacgtc                             36
```

<210> SEQ ID NO 320
<211> LENGTH: 12
<212> TYPE: PRT
<213> ORGANISM: Homo sapiens

<400> SEQUENCE: 320

Val Arg Asp Pro Arg Met Phe Tyr Gly Met Asp Val
1               5                   10

<210> SEQ ID NO 321
<211> LENGTH: 357
<212> TYPE: DNA
<213> ORGANISM: Homo sapiens

<400> SEQUENCE: 321

```
caggtgcagc tggtggagtc tgggggaggc ttggtcaagc ctggagggtc cctgagactc    60
tcctgtgcag cctctggatt caccttcagt gactactata tgaattggat ccgccaggct   120
ccagggaagg gactggagtg gattacatac attaataatg gtggctatac caaatactac   180
gcagactctg tgaagggccg attcatcatc tccagggaca acaccaagaa ttcagtgcat   240
ttgcaaatga atagcctgag agccgaggac acggccgtgt attactgtgt gagagatccc   300
cgtatgtatt atggtatgga cgtctggggc caagggacca cggtcaccgt ctcctca      357
```

<210> SEQ ID NO 322
<211> LENGTH: 119
<212> TYPE: PRT

<213> ORGANISM: Homo sapiens

<400> SEQUENCE: 322

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Asn Trp Ile Arg Gln Ala Pro Gly Lys Gly Leu Glu Trp Ile
        35                  40                  45

Thr Tyr Ile Asn Asn Gly Gly Tyr Thr Lys Tyr Tyr Ala Asp Ser Val
    50                  55                  60

Lys Gly Arg Phe Ile Ile Ser Arg Asp Asn Thr Lys Asn Ser Val His
65                  70                  75                  80

Leu Gln Met Asn Ser Leu Arg Ala Glu Asp Thr Ala Val Tyr Tyr Cys
                85                  90                  95

Val Arg Asp Pro Arg Met Tyr Tyr Gly Met Asp Val Trp Gly Gln Gly
            100                 105                 110

Thr Thr Val Thr Val Ser Ser
        115

<210> SEQ ID NO 323
<211> LENGTH: 24
<212> TYPE: DNA
<213> ORGANISM: Homo sapiens

<400> SEQUENCE: 323
ggattcacct tcagtgacta ctat                                      24

<210> SEQ ID NO 324
<211> LENGTH: 8
<212> TYPE: PRT
<213> ORGANISM: Homo sapiens

<400> SEQUENCE: 324

Gly Phe Thr Phe Ser Asp Tyr Tyr
1               5

<210> SEQ ID NO 325
<211> LENGTH: 24
<212> TYPE: DNA
<213> ORGANISM: Homo sapiens

<400> SEQUENCE: 325
attaataatg gtggctatac caaa                                      24

<210> SEQ ID NO 326
<211> LENGTH: 8
<212> TYPE: PRT
<213> ORGANISM: Homo sapiens

<400> SEQUENCE: 326

Ile Asn Asn Gly Gly Tyr Thr Lys
1               5

<210> SEQ ID NO 327
<211> LENGTH: 36
<212> TYPE: DNA
<213> ORGANISM: Homo sapiens

<400> SEQUENCE: 327
gtgagagatc cccgtatgta ttatggtatg gacgtc                         36

<210> SEQ ID NO 328
<211> LENGTH: 12
<212> TYPE: PRT
<213> ORGANISM: Homo sapiens

<400> SEQUENCE: 328

Val Arg Asp Pro Arg Met Tyr Tyr Gly Met Asp Val
1               5                   10

<210> SEQ ID NO 329
<211> LENGTH: 357
<212> TYPE: DNA
<213> ORGANISM: Homo sapiens

<400> SEQUENCE: 329
caggtgcagc tggtggagtc tgggggaggc ttggtcaagc ctggagggtc cctgagactc      60
tcctgtgcag cctctggatt ctccttcagt gactactaca ttacctggat ccgccaggct     120
ccagggaagg ggctggagtg ggtttcatac attaatactg gtggttatac catgtattac     180
gcagactctg tgaagggccg attcaccatc tccagggaca acgccaagaa ctcactgtat     240
cttcaaatga acaacctgag agccgaggac acggccgtgt attattgtac gagagatagg     300
agatacaact ttggtcttga ctactggggc cagggaaccc tggtcaccgt ctcctca        357

<210> SEQ ID NO 330
<211> LENGTH: 119
<212> TYPE: PRT
<213> ORGANISM: Homo sapiens

<400> SEQUENCE: 330

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Asp Tyr
            20                  25                  30

Tyr Ile Thr Trp Ile Arg Gln Ala Pro Gly Lys Gly Leu Glu Trp Val
        35                  40                  45

Ser Tyr Ile Asn Thr Gly Gly Tyr Thr Met Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Asn Leu Arg Ala Glu Asp Thr Ala Val Tyr Tyr Cys
                85                  90                  95

Thr Arg Asp Arg Arg Tyr Asn Phe Gly Leu Asp Tyr Trp Gly Gln Gly
            100                 105                 110

Thr Leu Val Thr Val Ser Ser
        115

<210> SEQ ID NO 331
<211> LENGTH: 24
<212> TYPE: DNA
<213> ORGANISM: Homo sapiens

<400> SEQUENCE: 331
ggattctcct tcagtgacta ctac                                            24

<210> SEQ ID NO 332
<211> LENGTH: 8
<212> TYPE: PRT
<213> ORGANISM: Homo sapiens

<400> SEQUENCE: 332

Gly Phe Ser Phe Ser Asp Tyr Tyr
1               5

<210> SEQ ID NO 333
<211> LENGTH: 24
<212> TYPE: DNA
<213> ORGANISM: Homo sapiens

<400> SEQUENCE: 333
attaatactg gtggttatac catg                                          24

<210> SEQ ID NO 334
<211> LENGTH: 8
<212> TYPE: PRT
<213> ORGANISM: Homo sapiens

<400> SEQUENCE: 334

Ile Asn Thr Gly Gly Tyr Thr Met
1               5

<210> SEQ ID NO 335
<211> LENGTH: 36
<212> TYPE: DNA
<213> ORGANISM: Homo sapiens

<400> SEQUENCE: 335
acgagagata ggagatacaa ctttggtctt gactac                             36

<210> SEQ ID NO 336
<211> LENGTH: 12
<212> TYPE: PRT
<213> ORGANISM: Homo sapiens

<400> SEQUENCE: 336

Thr Arg Asp Arg Arg Tyr Asn Phe Gly Leu Asp Tyr
1               5                   10

<210> SEQ ID NO 337
<211> LENGTH: 238
<212> TYPE: PRT
<213> ORGANISM: Homo sapiens

<400> SEQUENCE: 337

Met Ala Val Glu Gly Gly Met Lys Cys Val Lys Phe Leu Leu Tyr Val
1               5                   10                  15

Leu Leu Leu Ala Phe Cys Ala Cys Ala Val Gly Leu Ile Ala Val Gly
            20                  25                  30

Val Gly Ala Gln Leu Val Leu Ser Gln Thr Ile Ile Gln Gly Ala Thr
        35                  40                  45

Pro Gly Ser Leu Leu Pro Val Val Ile Ile Ala Val Gly Val Phe Leu
    50                  55                  60

Phe Leu Val Ala Phe Val Gly Cys Cys Gly Ala Cys Lys Glu Asn Tyr
65                  70                  75                  80

Cys Leu Met Ile Thr Phe Ala Ile Phe Leu Ser Leu Ile Met Leu Val
                85                  90                  95

Glu Val Ala Ala Ala Ile Ala Gly Tyr Val Phe Arg Asp Lys Val Met
            100                 105                 110

Ser Glu Phe Asn Asn Asn Phe Arg Gln Gln Met Glu Asn Tyr Pro Lys
        115                 120                 125

Asn Asn His Thr Ala Ser Ile Leu Asp Arg Met Gln Ala Asp Phe Lys
            130                 135                 140

Cys Cys Gly Ala Ala Asn Tyr Thr Asp Trp Glu Lys Ile Pro Ser Met
145                 150                 155                 160

Ser Lys Asn Arg Val Pro Asp Ser Cys Cys Ile Asn Val Thr Val Gly
                165                 170                 175

Cys Gly Ile Asn Phe Asn Glu Lys Ala Ile His Lys Glu Gly Cys Val
                180                 185                 190

Glu Lys Ile Gly Gly Trp Leu Arg Lys Asn Val Leu Val Ala Ala
            195                 200                 205

Ala Ala Leu Gly Ile Ala Phe Val Glu Val Leu Gly Ile Val Phe Ala
            210                 215                 220

Cys Cys Leu Val Lys Ser Ile Arg Ser Gly Tyr Glu Val Met
225                 230                 235

<210> SEQ ID NO 338
<211> LENGTH: 125
<212> TYPE: PRT
<213> ORGANISM: Artificial Sequence
<220> FEATURE:
<223> OTHER INFORMATION: CD63 EC loop 2 MMH

<400> SEQUENCE: 338

Arg Asp Lys Val Met Ser Glu Phe Asn Asn Phe Arg Gln Gln Met
1               5                   10                  15

Glu Asn Tyr Pro Lys Asn Asn His Thr Ala Ser Ile Leu Asp Arg Met
                20                  25                  30

Gln Ala Asp Phe Lys Cys Cys Gly Ala Ala Asn Tyr Thr Asp Trp Glu
            35                  40                  45

Lys Ile Pro Ser Met Ser Lys Asn Arg Val Pro Asp Ser Cys Cys Ile
50                  55                  60

Asn Val Thr Val Gly Cys Gly Ile Asn Phe Asn Glu Lys Ala Ile His
65                  70                  75                  80

Lys Glu Gly Cys Val Glu Lys Ile Gly Gly Trp Leu Arg Lys Asn Val
                85                  90                  95

Leu Glu Gln Lys Leu Ile Ser Glu Glu Asp Leu Gly Gly Glu Gln Lys
                100                 105                 110

Leu Ile Ser Glu Glu Asp Leu His His His His His
            115                 120                 125

<210> SEQ ID NO 339
<211> LENGTH: 324
<212> TYPE: PRT
<213> ORGANISM: Artificial Sequence
<220> FEATURE:
<223> OTHER INFORMATION: CD63 EC loop 2 hFC

<400> SEQUENCE: 339

Arg Asp Lys Val Met Ser Glu Phe Asn Asn Phe Arg Gln Gln Met
1               5                   10                  15

Glu Asn Tyr Pro Lys Asn Asn His Thr Ala Ser Ile Leu Asp Arg Met
                20                  25                  30

Gln Ala Asp Phe Lys Cys Cys Gly Ala Ala Asn Tyr Thr Asp Trp Glu
            35                  40                  45

Lys Ile Pro Ser Met Ser Lys Asn Arg Val Pro Asp Ser Cys Cys Ile
50                  55                  60

Asn Val Thr Val Gly Cys Gly Ile Asn Phe Asn Glu Lys Ala Ile His

```
            65                  70                  75                  80
Lys Glu Gly Cys Val Glu Lys Ile Gly Gly Trp Leu Arg Lys Asn Val
                    85                  90                  95

Leu Asp Lys Thr His Thr Cys Pro Pro Cys Pro Ala Pro Glu Leu Leu
                100                 105                 110

Gly Gly Pro Ser Val Phe Leu Phe Pro Pro Lys Pro Lys Asp Thr Leu
                115                 120                 125

Met Ile Ser Arg Thr Pro Glu Val Thr Cys Val Val Val Asp Val Ser
            130                 135                 140

His Glu Asp Pro Glu Val Lys Phe Asn Trp Tyr Val Asp Gly Val Glu
145                 150                 155                 160

Val His Asn Ala Lys Thr Lys Pro Arg Glu Glu Gln Tyr Asn Ser Thr
                    165                 170                 175

Tyr Arg Val Val Ser Val Leu Thr Val Leu His Gln Asp Trp Leu Asn
                180                 185                 190

Gly Lys Glu Tyr Lys Cys Lys Val Ser Asn Lys Ala Leu Pro Ala Pro
            195                 200                 205

Ile Glu Lys Thr Ile Ser Lys Ala Lys Gly Gln Pro Arg Glu Pro Gln
        210                 215                 220

Val Tyr Thr Leu Pro Pro Ser Arg Asp Glu Leu Thr Lys Asn Gln Val
225                 230                 235                 240

Ser Leu Thr Cys Leu Val Lys Gly Phe Tyr Pro Ser Asp Ile Ala Val
                    245                 250                 255

Glu Trp Glu Ser Asn Gly Gln Pro Glu Asn Asn Tyr Lys Thr Thr Pro
                260                 265                 270

Pro Val Leu Asp Ser Asp Gly Ser Phe Phe Leu Tyr Ser Lys Leu Thr
            275                 280                 285

Val Asp Lys Ser Arg Trp Gln Gln Gly Asn Val Phe Ser Cys Ser Val
        290                 295                 300

Met His Glu Ala Leu His Asn His Tyr Thr Gln Lys Ser Leu Ser Leu
305                 310                 315                 320

Ser Pro Gly Lys

<210> SEQ ID NO 340
<211> LENGTH: 330
<212> TYPE: PRT
<213> ORGANISM: Artificial Sequence
<220> FEATURE:
<223> OTHER INFORMATION: synthetic

<400> SEQUENCE: 340

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                    85                  90                  95

Lys Val Glu Pro Lys Ser Cys Asp Lys Thr His Thr Cys Pro Pro Cys
                100                 105                 110
```

```
Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 341
<211> LENGTH: 330
<212> TYPE: PRT
<213> ORGANISM: Artificial Sequence
<220> FEATURE:
<223> OTHER INFORMATION: synthetic

<400> SEQUENCE: 341

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140
```

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn Arg Phe Thr
305                 310                 315                 320

Gln Lys Ser Leu Ser Leu Ser Pro Gly Lys
                325                 330

<210> SEQ ID NO 342
<211> LENGTH: 326
<212> TYPE: PRT
<213> ORGANISM: Artificial Sequence
<220> FEATURE:
<223> OTHER INFORMATION: synthetic

<400> SEQUENCE: 342

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175
```

```
Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 343
<211> LENGTH: 326
<212> TYPE: PRT
<213> ORGANISM: Artificial Sequence
<220> FEATURE:
<223> OTHER INFORMATION: synthetic

<400> SEQUENCE: 343

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205
```

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
            245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
        290                 295                 300

Ser Val Met His Glu Ala Leu His Asn Arg Phe Thr Gln Lys Ser Leu
305                 310                 315                 320

Ser Leu Ser Pro Gly Lys
                325

<210> SEQ ID NO 344
<211> LENGTH: 327
<212> TYPE: PRT
<213> ORGANISM: Artificial Sequence
<220> FEATURE:
<223> OTHER INFORMATION: synthetic

<400> SEQUENCE: 344

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

```
Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 345
<211> LENGTH: 327
<212> TYPE: PRT
<213> ORGANISM: Artificial Sequence
<220> FEATURE:
<223> OTHER INFORMATION: synthetic

<400> SEQUENCE: 345

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270
```

```
Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn Arg Phe Thr Gln Lys Ser
305                 310                 315                 320

Leu Ser Leu Ser Leu Gly Lys
                325

<210> SEQ ID NO 346
<211> LENGTH: 329
<212> TYPE: PRT
<213> ORGANISM: Artificial Sequence
<220> FEATURE:
<223> OTHER INFORMATION: synthetic

<400> SEQUENCE: 346

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Pro Val Ala Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser Gln Glu Asp Pro Glu Val Gln Phe Asn Trp Tyr
145                 150                 155                 160

Val Asp Gly Val Glu Val His Asn Ala Lys Thr Lys Pro Arg Glu Glu
                165                 170                 175

Gln Phe Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Gly Leu Pro Ser Ser Ile Glu Lys Thr Ile Ser Lys Ala Lys Gly Gln
    210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300
```

```
Phe Ser Cys Ser Val Met His Glu Ala Leu His Asn His Tyr Thr Gln
305                 310                 315                 320

Lys Ser Leu Ser Leu Ser Pro Gly Lys
            325

<210> SEQ ID NO 347
<211> LENGTH: 329
<212> TYPE: PRT
<213> ORGANISM: Artificial Sequence
<220> FEATURE:
<223> OTHER INFORMATION: synthetic

<400> SEQUENCE: 347

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Pro Val Ala Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser Gln Glu Asp Pro Glu Val Gln Phe Asn Trp Tyr
145                 150                 155                 160

Val Asp Gly Val Glu Val His Asn Ala Lys Thr Lys Pro Arg Glu Glu
                165                 170                 175

Gln Phe Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Gly Leu Pro Ser Ser Ile Glu Lys Thr Ile Ser Lys Ala Lys Gly Gln
    210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn Arg Phe Thr Gln
305                 310                 315                 320

Lys Ser Leu Ser Leu Ser Pro Gly Lys
            325
```

<210> SEQ ID NO 348
<211> LENGTH: 327
<212> TYPE: PRT
<213> ORGANISM: Artificial Sequence
<220> FEATURE:
<223> OTHER INFORMATION: CH sequence

<400> SEQUENCE: 348

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 349
<211> LENGTH: 326
<212> TYPE: PRT
<213> ORGANISM: Artificial Sequence -continued
<220> FEATURE:
<223> OTHER INFORMATION: synthetic

<400> SEQUENCE: 349

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Leu Gly Lys
                325

<210> SEQ ID NO 350
<211> LENGTH: 326
<212> TYPE: PRT
<213> ORGANISM: Artificial Sequence
<220> FEATURE:
<223> OTHER INFORMATION: synthetic

<400> SEQUENCE: 350

Ala Ser Thr Lys Gly Pro Ser Val Phe Pro Leu Ala Pro Cys Ser Arg

```
                1               5                    10                      15
            Ser Thr Ser Glu Ser Thr Ala Ala Leu Gly Cys Leu Val Lys Asp Tyr
                        20                  25                  30

Phe Pro Glu Pro Val Thr Val Ser Trp Asn Ser Gly Ala Leu Thr Ser
                        35                  40                  45

Gly Val His Thr Phe Pro Ala Val Leu Gln Ser Ser Gly Leu Tyr Ser
                        50                  55                  60

Leu Ser Ser Val Val Thr Val Pro Ser Ser Leu Gly Thr Lys Thr
            65                  70                  75                  80

Tyr Thr Cys Asn Val Asp His Lys Pro Ser Asn Thr Lys Val Asp Lys
                                85                  90                  95

Arg Val Glu Ser Lys Tyr Gly Pro Pro Cys Pro Pro Cys Pro Ala Pro
                            100                 105                 110

Pro Val Ala Gly Pro Ser Val Phe Leu Phe Pro Pro Lys Pro Lys Asp
                            115                 120                 125

Thr Leu Met Ile Ser Arg Thr Pro Glu Val Thr Cys Val Val Val Asp
                        130                 135                 140

Val Ser Gln Glu Asp Pro Glu Val Gln Phe Asn Trp Tyr Val Asp Gly
            145                 150                 155                 160

Val Glu Val His Asn Ala Lys Thr Lys Pro Arg Glu Glu Gln Phe Asn
                            165                 170                 175

Ser Thr Tyr Arg Val Val Ser Val Leu Thr Val Leu His Gln Asp Trp
                            180                 185                 190

Leu Asn Gly Lys Glu Tyr Lys Cys Lys Val Ser Asn Lys Gly Leu Pro
                        195                 200                 205

Ser Ser Ile Glu Lys Thr Ile Ser Lys Ala Lys Gly Gln Pro Arg Glu
            210                 215                 220

Pro Gln Val Tyr Thr Leu Pro Pro Ser Gln Glu Glu Met Thr Lys Asn
            225                 230                 235                 240

Gln Val Ser Leu Thr Cys Leu Val Lys Gly Phe Tyr Pro Ser Asp Ile
                            245                 250                 255

Ala Val Glu Trp Glu Ser Asn Gly Gln Pro Glu Asn Asn Tyr Lys Thr
                            260                 265                 270

Thr Pro Pro Val Leu Asp Ser Asp Gly Ser Phe Phe Leu Tyr Ser Arg
                        275                 280                 285

Leu Thr Val Asp Lys Ser Arg Trp Gln Glu Gly Asn Val Phe Ser Cys
                        290                 295                 300

Ser Val Met His Glu Ala Leu His Asn Arg Phe Thr Gln Lys Ser Leu
            305                 310                 315                 320

Ser Leu Ser Leu Gly Lys
                        325

<210> SEQ ID NO 351
<211> LENGTH: 327
<212> TYPE: PRT
<213> ORGANISM: Artificial Sequence
<220> FEATURE:
<223> OTHER INFORMATION: CH sequence

<400> SEQUENCE: 351

Ala Ser Thr Lys Gly Pro Ser Val Phe Pro Leu Ala Pro Cys Ser Arg
            1                   5                   10                  15

Ser Thr Ser Glu Ser Thr Ala Ala Leu Gly Cys Leu Val Lys Asp Tyr
                        20                  25                  30

Phe Pro Glu Pro Val Thr Val Ser Trp Asn Ser Gly Ala Leu Thr Ser
```

```
                35                  40                  45
Gly Val His Thr Phe Pro Ala Val Leu Gln Ser Ser Gly Leu Tyr Ser
            50                  55                  60
Leu Ser Ser Val Val Thr Val Pro Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Pro Cys Pro Ala Pro
            100                 105                 110
Glu Phe Leu Gly Gly Pro Ser Val Phe Leu Phe Pro Pro Lys Pro Lys
        115                 120                 125
Asp Thr Leu Met Ile Ser Arg Thr Pro Glu Val Thr Cys Val Val Val
    130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys Gly Gln Pro Arg
    210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Arg Leu Thr Val Asp Lys Ser Arg Trp Gln Glu Gly Asn Val Phe Ser
    290                 295                 300
Cys Ser Val Met His Glu Ala Leu His Asn Arg Phe Thr Gln Lys Ser
305                 310                 315                 320
Leu Ser Leu Ser Leu Gly Lys
                325

<210> SEQ ID NO 352
<211> LENGTH: 232
<212> TYPE: PRT
<213> ORGANISM: Artificial Sequence
<220> FEATURE:
<223> OTHER INFORMATION: synthetic

<400> SEQUENCE: 352

Glu Pro Lys Ser Cys Asp Lys Thr His Thr Cys Pro Pro Cys Pro Ala
1               5                   10                  15
Pro Glu Leu Leu Gly Gly Pro Ser Val Phe Leu Phe Pro Pro Lys Pro
            20                  25                  30
Lys Asp Thr Leu Met Ile Ser Arg Thr Pro Glu Val Thr Cys Val Val
        35                  40                  45
Val Asp Val Ser His Glu Asp Pro Glu Val Lys Phe Asn Trp Tyr Val
    50                  55                  60
Asp Gly Val Glu Val His Asn Ala Lys Thr Lys Pro Arg Glu Glu Gln
```

```
                65                  70                  75                  80
Tyr Asn Ser Thr Tyr Arg Val Val Ser Val Leu Thr Val Leu His Gln
                    85                  90                  95
Asp Trp Leu Asn Gly Lys Glu Tyr Lys Cys Lys Val Ser Asn Lys Ala
                100                 105                 110
Leu Pro Ala Pro Ile Glu Lys Thr Ile Ser Lys Ala Lys Gly Gln Pro
                115                 120                 125
Arg Glu Pro Gln Val Tyr Thr Leu Pro Pro Ser Arg Asp Glu Leu Thr
            130                 135                 140
Lys Asn Gln Val Ser Leu Thr Cys Leu Val Lys Gly Phe Tyr Pro Ser
145                 150                 155                 160
Asp Ile Ala Val Glu Trp Glu Ser Asn Gly Gln Pro Glu Asn Asn Tyr
                165                 170                 175
Lys Thr Thr Pro Pro Val Leu Asp Ser Asp Gly Ser Phe Phe Leu Tyr
                180                 185                 190
Ser Lys Leu Thr Val Asp Lys Ser Arg Trp Gln Gln Gly Asn Val Phe
                195                 200                 205
Ser Cys Ser Val Met His Glu Ala Leu His Asn His Tyr Thr Gln Lys
                210                 215                 220
Ser Leu Ser Leu Ser Pro Gly Lys
225                 230

<210> SEQ ID NO 353
<211> LENGTH: 232
<212> TYPE: PRT
<213> ORGANISM: Artificial Sequence
<220> FEATURE:
<223> OTHER INFORMATION: synthetic

<400> SEQUENCE: 353

Glu Pro Lys Ser Cys Asp Lys Thr His Thr Cys Pro Pro Cys Pro Ala
1               5                   10                  15
Pro Glu Leu Leu Gly Gly Pro Ser Val Phe Leu Phe Pro Pro Lys Pro
                20                  25                  30
Lys Asp Thr Leu Met Ile Ser Arg Thr Pro Glu Val Thr Cys Val Val
            35                  40                  45
Val Asp Val Ser His Glu Asp Pro Glu Val Lys Phe Asn Trp Tyr Val
        50                  55                  60
Asp Gly Val Glu Val His Asn Ala Lys Thr Lys Pro Arg Glu Glu Gln
65                  70                  75                  80
Tyr Asn Ser Thr Tyr Arg Val Val Ser Val Leu Thr Val Leu His Gln
                85                  90                  95
Asp Trp Leu Asn Gly Lys Glu Tyr Lys Cys Lys Val Ser Asn Lys Ala
                100                 105                 110
Leu Pro Ala Pro Ile Glu Lys Thr Ile Ser Lys Ala Lys Gly Gln Pro
                115                 120                 125
Arg Glu Pro Gln Val Tyr Thr Leu Pro Pro Ser Arg Asp Glu Leu Thr
            130                 135                 140
Lys Asn Gln Val Ser Leu Thr Cys Leu Val Lys Gly Phe Tyr Pro Ser
145                 150                 155                 160
Asp Ile Ala Val Glu Trp Glu Ser Asn Gly Gln Pro Glu Asn Asn Tyr
                165                 170                 175
Lys Thr Thr Pro Pro Val Leu Asp Ser Asp Gly Ser Phe Phe Leu Tyr
                180                 185                 190
Ser Lys Leu Thr Val Asp Lys Ser Arg Trp Gln Gln Gly Asn Val Phe
```

```
                195                 200                 205
Ser Cys Ser Val Met His Glu Ala Leu His Asn Arg Phe Thr Gln Lys
    210                 215                 220

Ser Leu Ser Leu Ser Pro Gly Lys
225                 230

<210> SEQ ID NO 354
<211> LENGTH: 228
<212> TYPE: PRT
<213> ORGANISM: Artificial Sequence
<220> FEATURE:
<223> OTHER INFORMATION: synthetic

<400> SEQUENCE: 354

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
130                 135                 140

Ser Leu Thr Cys Leu Val Lys Gly Phe Tyr Pro Ser Asp Ile Ser Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 355
<211> LENGTH: 228
<212> TYPE: PRT
<213> ORGANISM: Artificial Sequence
<220> FEATURE:
<223> OTHER INFORMATION: synthetic

<400> SEQUENCE: 355

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30
```

Met Ile Ser Arg Thr Pro Glu Val Thr Cys Val Val Asp Val Ser
        35                  40                  45

His Glu Asp Pro Glu Val Gln Phe Asn Trp Tyr Val Asp Gly Val Glu
 50                  55                  60

Val His Asn Ala Lys Thr Lys Pro Arg Glu Glu Gln Phe Asn Ser Thr
65                  70                  75                  80

Phe Arg Val Val Ser Val Leu Thr Val His Gln Asp Trp Leu Asn
                85                  90                  95

Gly Lys Glu Tyr Lys Cys Lys Val Ser Asn Lys Gly Leu Pro Ala Pro
                100                 105                 110

Ile Glu Lys Thr Ile Ser Lys Thr Lys Gly Gln Pro Arg Glu Pro Gln
                115                 120                 125

Val Tyr Thr Leu Pro Pro Ser Arg Glu Glu Met Thr Lys Asn Gln Val
130                 135                 140

Ser Leu Thr Cys Leu Val Lys Gly Phe Tyr Pro Ser Asp Ile Ser Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
                180                 185                 190

Val Asp Lys Ser Arg Trp Gln Gln Gly Asn Val Phe Ser Cys Ser Val
                195                 200                 205

Met His Glu Ala Leu His Asn Arg Phe Thr Gln Lys Ser Leu Ser Leu
                210                 215                 220

Ser Pro Gly Lys
225

<210> SEQ ID NO 356
<211> LENGTH: 229
<212> TYPE: PRT
<213> ORGANISM: Artificial Sequence
<220> FEATURE:
<223> OTHER INFORMATION: synthetic

<400> SEQUENCE: 356

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
 50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
                115                 120                 125

Gln Val Tyr Thr Leu Pro Pro Ser Gln Glu Glu Met Thr Lys Asn Gln
                130                 135                 140

Val Ser Leu Thr Cys Leu Val Lys Gly Phe Tyr Pro Ser Asp Ile Ala
145                 150                 155                 160

-continued

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn Arg Phe Thr Gln Lys Ser Leu Ser
    210                 215                 220

Leu Ser Leu Gly Lys
225

<210> SEQ ID NO 357
<211> LENGTH: 229
<212> TYPE: PRT
<213> ORGANISM: Artificial Sequence
<220> FEATURE:
<223> OTHER INFORMATION: synthetic

<400> SEQUENCE: 357

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 358
<211> LENGTH: 228
<212> TYPE: PRT
<213> ORGANISM: Artificial Sequence
<220> FEATURE:
<223> OTHER INFORMATION: Fc sequence

<400> SEQUENCE: 358

Glu Ser Lys Tyr Gly Pro Pro Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Leu Pro Ser Ser
                100                 105                 110

Ile Glu Lys Thr Ile Ser Lys Ala Lys Gly Gln Pro Arg Glu Pro Gln
            115                 120                 125

Val Tyr Thr Leu Pro Pro Ser Gln Glu Glu Met Thr Lys Asn Gln Val
        130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
                180                 185                 190

Val Asp Lys Ser Arg Trp Gln Glu Gly Asn Val Phe Ser Cys Ser Val
            195                 200                 205

Met His Glu Ala Leu His Asn His Tyr Thr Gln Lys Ser Leu Ser Leu
        210                 215                 220

Ser Leu Gly Lys
225

<210> SEQ ID NO 359
<211> LENGTH: 231
<212> TYPE: PRT
<213> ORGANISM: Artificial Sequence
<220> FEATURE:
<223> OTHER INFORMATION: synthetic

<400> SEQUENCE: 359

Glu Pro Lys Ser Cys Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser Gln Glu Asp Pro Glu Val Gln Phe Asn Trp Tyr Val Asp
    50                  55                  60

Gly Val Glu Val His Asn Ala Lys Thr Lys Pro Arg Glu Glu Gln Phe
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Gly Leu
                100                 105                 110

Pro Ser Ser Ile Glu Lys Thr Ile Ser Lys Ala Lys Gly Gln Pro Arg
            115                 120                 125

```
Glu Pro Gln Val Tyr Thr Leu Pro Pro Ser Arg Asp Glu Leu Thr Lys
            130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
            195                 200                 205

Cys Ser Val Met His Glu Ala Leu His Asn His Tyr Thr Gln Lys Ser
            210                 215                 220

Leu Ser Leu Ser Pro Gly Lys
225                 230

<210> SEQ ID NO 360
<211> LENGTH: 231
<212> TYPE: PRT
<213> ORGANISM: Artificial Sequence
<220> FEATURE:
<223> OTHER INFORMATION: synthetic

<400> SEQUENCE: 360

Glu Pro Lys Ser Cys Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
            35                  40                  45

Asp Val Ser Gln Glu Asp Pro Glu Val Gln Phe Asn Trp Tyr Val Asp
50                  55                  60

Gly Val Glu Val His Asn Ala Lys Thr Lys Pro Arg Glu Glu Gln Phe
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Gly Leu
            100                 105                 110

Pro Ser Ser Ile Glu Lys Thr Ile Ser Lys Ala Lys Gly Gln Pro Arg
            115                 120                 125

Glu Pro Gln Val Tyr Thr Leu Pro Pro Ser Arg Asp Glu Leu Thr Lys
            130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
            195                 200                 205

Cys Ser Val Met His Glu Ala Leu His Asn Arg Phe Thr Gln Lys Ser
            210                 215                 220

Leu Ser Leu Ser Pro Gly Lys
225                 230

<210> SEQ ID NO 361
```

<211> LENGTH: 228
<212> TYPE: PRT
<213> ORGANISM: Artificial Sequence
<220> FEATURE:
<223> OTHER INFORMATION: Fc sequence

<400> SEQUENCE: 361

Glu Ser Lys Tyr Gly Pro Pro Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Leu Pro Ser Ser
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205

Met His Glu Ala Leu His Asn Arg Phe Thr Gln Lys Ser Leu Ser Leu
    210                 215                 220

Ser Leu Gly Lys
225

<210> SEQ ID NO 362
<211> LENGTH: 229
<212> TYPE: PRT
<213> ORGANISM: Artificial Sequence
<220> FEATURE:
<223> OTHER INFORMATION: Fc sequence

<400> SEQUENCE: 362

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu

-continued

```
                85                  90                  95
Asn Gly Lys Glu Tyr Lys Cys Lys Val Ser Asn Lys Gly Leu Pro Ser
            100                 105                 110
Ser Ile Glu Lys Thr Ile Ser Lys Ala Lys Gly Gln Pro Arg Glu Pro
            115                 120                 125
Gln Val Tyr Thr Leu Pro Pro Ser Gln Glu Glu Met Thr Lys Asn Gln
            130                 135                 140
Val Ser Leu Thr Cys Leu Val Lys Gly Phe Tyr Pro Ser Asp Ile Ala
145                 150                 155                 160
Val Glu Trp Glu Ser Asn Gly Gln Pro Glu Asn Asn Tyr Lys Thr Thr
                165                 170                 175
Pro Pro Val Leu Asp Ser Asp Gly Ser Phe Phe Leu Tyr Ser Arg Leu
            180                 185                 190
Thr Val Asp Lys Ser Arg Trp Gln Glu Gly Asn Val Phe Ser Cys Ser
            195                 200                 205
Val Met His Glu Ala Leu His Asn His Tyr Thr Gln Lys Ser Leu Ser
210                 215                 220
Leu Ser Leu Gly Lys
225

<210> SEQ ID NO 363
<211> LENGTH: 229
<212> TYPE: PRT
<213> ORGANISM: Artificial Sequence
<220> FEATURE:
<223> OTHER INFORMATION: Fc sequence

<400> SEQUENCE: 363

Glu Ser Lys Tyr Gly Pro Pro Cys Pro Pro Cys Pro Ala Pro Glu Phe
1               5                   10                  15
Leu Gly Gly Pro Ser Val Phe Leu Phe Pro Pro Lys Pro Lys Asp Thr
            20                  25                  30
Leu Met Ile Ser Arg Thr Pro Glu Val Thr Cys Val Val Val Asp Val
        35                  40                  45
Ser Gln Glu Asp Pro Glu Val Gln Phe Asn Trp Tyr Val Asp Gly Val
50                  55                  60
Glu Val His Asn Ala Lys Thr Lys Pro Arg Glu Glu Gln Phe Asn Ser
65                  70                  75                  80
Thr Tyr Arg Val Val Ser Val Leu Thr Val Leu His Gln Asp Trp Leu
                85                  90                  95
Asn Gly Lys Glu Tyr Lys Cys Lys Val Ser Asn Lys Gly Leu Pro Ser
            100                 105                 110
Ser Ile Glu Lys Thr Ile Ser Lys Ala Lys Gly Gln Pro Arg Glu Pro
            115                 120                 125
Gln Val Tyr Thr Leu Pro Pro Ser Gln Glu Glu Met Thr Lys Asn Gln
            130                 135                 140
Val Ser Leu Thr Cys Leu Val Lys Gly Phe Tyr Pro Ser Asp Ile Ala
145                 150                 155                 160
Val Glu Trp Glu Ser Asn Gly Gln Pro Glu Asn Asn Tyr Lys Thr Thr
                165                 170                 175
Pro Pro Val Leu Asp Ser Asp Gly Ser Phe Phe Leu Tyr Ser Arg Leu
            180                 185                 190
Thr Val Asp Lys Ser Arg Trp Gln Glu Gly Asn Val Phe Ser Cys Ser
            195                 200                 205
Val Met His Glu Ala Leu His Asn Arg Phe Thr Gln Lys Ser Leu Ser
```

```
                210                 215                 220
Leu Ser Leu Gly Lys
225

<210> SEQ ID NO 364
<211> LENGTH: 1128
<212> TYPE: PRT
<213> ORGANISM: Artificial Sequence
<220> FEATURE:
<223> OTHER INFORMATION: scFv_H4H123450(VH-linker-VL)_linker_GAA

<400> SEQUENCE: 364

Gln Val Gln Leu Gln Glu Ser Gly Pro Lys Val Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Asn Trp Ile Arg Gln Ser Pro Gly Lys Gly Leu Glu Trp Ile
        35                  40                  45

Gly Tyr Thr Lys Arg Gly Tyr Thr Asp Tyr Asn Pro Ser Leu Arg Ser
    50                  55                  60

Arg Val Thr Ile Ser Glu Asp Thr Ser Lys Asn Gln Phe Ser Leu Arg
65                  70                  75                  80

Ile Ser Ser Val Thr Ala Ala Asp Thr Ala Val Tyr Tyr Cys Ala Gln
                85                  90                  95

Met Gly Trp Gly Ser His Ala Phe Asp Met Trp Gly Gln Gly Thr Met
            100                 105                 110

Val Ala Val Ser Ser Gly Gly Gly Gly Ser Gly Gly Gly Gly Ser Gly
        115                 120                 125

Gly Ser Gly Gly Glu Ile Val Leu Thr Gln Ser Pro Gly Thr Leu Ser
    130                 135                 140

Leu Ser Pro Gly Glu Arg Ala Thr Leu Ser Cys Arg Ala Ser Gln Ser
145                 150                 155                 160

Val Ser Ser Ser Tyr Leu Ala Trp Tyr Gln Gln Lys Pro Gly Gln Ala
                165                 170                 175

Pro Arg Leu Leu Ile Tyr Gly Ala Ser Ser Arg Ala Thr Gly Ile Pro
            180                 185                 190

Asp Arg Phe Ser Gly Ser Gly Ser Gly Thr Asp Phe Thr Leu Thr Ile
        195                 200                 205

Ser Arg Leu Glu Pro Glu Asp Phe Ala Val Tyr Tyr Cys Gln Gln Tyr
    210                 215                 220

Gly Ser Ser Pro Trp Thr Phe Gly Gln Gly Thr Lys Val Glu Ile Lys
225                 230                 235                 240

Gly Gly Gly Gly Ser Ala His Pro Gly Arg Pro Arg Ala Val Pro Thr
                245                 250                 255

Gln Cys Asp Val Pro Pro Asn Ser Arg Phe Asp Cys Ala Pro Asp Lys
            260                 265                 270

Ala Ile Thr Gln Glu Gln Cys Glu Ala Arg Gly Cys Cys Tyr Ile Pro
        275                 280                 285

Ala Lys Gln Gly Leu Gln Gly Ala Gln Met Gly Gln Pro Trp Cys Phe
    290                 295                 300

Phe Pro Pro Ser Tyr Pro Ser Tyr Lys Leu Glu Asn Leu Ser Ser Ser
305                 310                 315                 320

Glu Met Gly Tyr Thr Ala Thr Leu Thr Arg Thr Thr Pro Thr Phe Phe
                325                 330                 335

Pro Lys Asp Ile Leu Thr Leu Arg Leu Asp Val Met Met Glu Thr Glu
```

```
                340             345              350
Asn Arg Leu His Phe Thr Ile Lys Asp Pro Ala Asn Arg Arg Tyr Glu
            355             360             365

Val Pro Leu Glu Thr Pro His Val His Ser Arg Ala Pro Ser Pro Leu
    370             375             380

Tyr Ser Val Glu Phe Ser Glu Glu Pro Phe Gly Val Ile Val Arg Arg
385             390             395             400

Gln Leu Asp Gly Arg Val Leu Leu Asn Thr Thr Val Ala Pro Leu Phe
            405             410             415

Phe Ala Asp Gln Phe Leu Gln Leu Ser Thr Ser Leu Pro Ser Gln Tyr
            420             425             430

Ile Thr Gly Leu Ala Glu His Leu Ser Pro Leu Met Leu Ser Thr Ser
            435             440             445

Trp Thr Arg Ile Thr Leu Trp Asn Arg Asp Leu Ala Pro Thr Pro Gly
            450             455             460

Ala Asn Leu Tyr Gly Ser His Pro Phe Tyr Leu Ala Leu Glu Asp Gly
465             470             475             480

Gly Ser Ala His Gly Val Phe Leu Leu Asn Ser Asn Ala Met Asp Val
            485             490             495

Val Leu Gln Pro Ser Pro Ala Leu Ser Trp Arg Ser Thr Gly Gly Ile
            500             505             510

Leu Asp Val Tyr Ile Phe Leu Gly Pro Glu Pro Lys Ser Val Val Gln
            515             520             525

Gln Tyr Leu Asp Val Val Gly Tyr Pro Phe Met Pro Pro Tyr Trp Gly
            530             535             540

Leu Gly Phe His Leu Cys Arg Trp Gly Tyr Ser Ser Thr Ala Ile Thr
545             550             555             560

Arg Gln Val Val Glu Asn Met Thr Arg Ala His Phe Pro Leu Asp Val
            565             570             575

Gln Trp Asn Asp Leu Asp Tyr Met Asp Ser Arg Arg Asp Phe Thr Phe
            580             585             590

Asn Lys Asp Gly Phe Arg Asp Phe Pro Ala Met Val Gln Glu Leu His
            595             600             605

Gln Gly Gly Arg Arg Tyr Met Met Ile Val Asp Pro Ala Ile Ser Ser
            610             615             620

Ser Gly Pro Ala Gly Ser Tyr Arg Pro Tyr Asp Glu Gly Leu Arg Arg
625             630             635             640

Gly Val Phe Ile Thr Asn Glu Thr Gly Gln Pro Leu Ile Gly Lys Val
            645             650             655

Trp Pro Gly Ser Thr Ala Phe Pro Asp Phe Thr Asn Pro Thr Ala Leu
            660             665             670

Ala Trp Trp Glu Asp Met Val Ala Glu Phe His Asp Gln Val Pro Phe
            675             680             685

Asp Gly Met Trp Ile Asp Met Asn Glu Pro Ser Asn Phe Ile Arg Gly
            690             695             700

Ser Glu Asp Gly Cys Pro Asn Asn Glu Leu Glu Asn Pro Pro Tyr Val
705             710             715             720

Pro Gly Val Val Gly Gly Thr Leu Gln Ala Ala Thr Ile Cys Ala Ser
            725             730             735

Ser His Gln Phe Leu Ser Thr His Tyr Asn Leu His Asn Leu Tyr Gly
            740             745             750

Leu Thr Glu Ala Ile Ala Ser His Arg Ala Leu Val Lys Ala Arg Gly
            755             760             765
```

Thr Arg Pro Phe Val Ile Ser Arg Ser Thr Phe Ala Gly His Gly Arg
    770                 775                 780

Tyr Ala Gly His Trp Thr Gly Asp Val Trp Ser Ser Trp Glu Gln Leu
785                 790                 795                 800

Ala Ser Ser Val Pro Glu Ile Leu Gln Phe Asn Leu Leu Gly Val Pro
                805                 810                 815

Leu Val Gly Ala Asp Val Cys Gly Phe Leu Gly Asn Thr Ser Glu Glu
                820                 825                 830

Leu Cys Val Arg Trp Thr Gln Leu Gly Ala Phe Tyr Pro Phe Met Arg
                835                 840                 845

Asn His Asn Ser Leu Leu Ser Leu Pro Gln Glu Pro Tyr Ser Phe Ser
850                 855                 860

Glu Pro Ala Gln Gln Ala Met Arg Lys Ala Leu Thr Leu Arg Tyr Ala
865                 870                 875                 880

Leu Leu Pro His Leu Tyr Thr Leu Phe His Gln Ala His Val Ala Gly
                885                 890                 895

Glu Thr Val Ala Arg Pro Leu Phe Leu Glu Phe Pro Lys Asp Ser Ser
                900                 905                 910

Thr Trp Thr Val Asp His Gln Leu Leu Trp Gly Glu Ala Leu Leu Ile
                915                 920                 925

Thr Pro Val Leu Gln Ala Gly Lys Ala Glu Val Thr Gly Tyr Phe Pro
                930                 935                 940

Leu Gly Thr Trp Tyr Asp Leu Gln Thr Val Pro Val Glu Ala Leu Gly
945                 950                 955                 960

Ser Leu Pro Pro Pro Ala Ala Pro Arg Glu Pro Ala Ile His Ser
                965                 970                 975

Glu Gly Gln Trp Val Thr Leu Pro Ala Pro Leu Asp Thr Ile Asn Val
                980                 985                 990

His Leu Arg Ala Gly Tyr Ile Ile Pro Leu Gln Gly Pro Gly Leu Thr
                995                 1000                1005

Thr Thr Glu Ser Arg Gln Gln Pro Met Ala Leu Ala Val Ala Leu
    1010                1015                1020

Thr Lys Gly Gly Glu Ala Arg Gly Glu Leu Phe Trp Asp Asp Gly
    1025                1030                1035

Glu Ser Leu Glu Val Leu Glu Arg Gly Ala Tyr Thr Gln Val Ile
    1040                1045                1050

Phe Leu Ala Arg Asn Asn Thr Ile Val Asn Glu Leu Val Arg Val
    1055                1060                1065

Thr Ser Glu Gly Ala Gly Leu Gln Leu Gln Lys Val Thr Val Leu
    1070                1075                1080

Gly Val Ala Thr Ala Pro Gln Val Leu Ser Asn Gly Val Pro
    1085                1090                1095

Val Ser Asn Phe Thr Tyr Ser Pro Asp Thr Lys Val Leu Asp Ile
    1100                1105                1110

Cys Val Ser Leu Leu Met Gly Glu Gln Phe Leu Val Ser Trp Cys
    1115                1120                1125

<210> SEQ ID NO 365
<211> LENGTH: 141
<212> TYPE: DNA
<213> ORGANISM: Artificial
<220> FEATURE:
<223> OTHER INFORMATION: synthetic

<400> SEQUENCE: 365

```
cctgcaggca gctgcgcgct cgctcgctca ctgaggccgc ccgggcaaag cccgggcgtc    60
gggcgacctt tggtcgcccg gcctcagtga gcgagcgagc gcgcagagag ggagtggcca   120
actccatcac tagggggttcc t                                             141
```

<210> SEQ ID NO 366
<211> LENGTH: 141
<212> TYPE: DNA
<213> ORGANISM: Artificial
<220> FEATURE:
<223> OTHER INFORMATION: synthetic

<400> SEQUENCE: 366

```
aggaacccct agtgatggag ttggccactc cctctctgcg cgctcgctcg ctcactgagg    60
ccgggcgacc aaaggtcgcc cgacgcccgg gctttgcccg gcggcctca gtgagcgagc    120 gagcgcgcag ctgcctgcag g                                              141
```

<210> SEQ ID NO 367
<211> LENGTH: 72
<212> TYPE: DNA
<213> ORGANISM: Artificial
<220> FEATURE:
<223> OTHER INFORMATION: synthetic

<400> SEQUENCE: 367

```
gggggaggct gctggtgaat attaaccaag gtcaccccag ttatcggagg agcaaacagg    60
ggctaagtcc ac                                                         72
```

<210> SEQ ID NO 368
<211> LENGTH: 224
<212> TYPE: DNA
<213> ORGANISM: Artificial
<220> FEATURE:
<223> OTHER INFORMATION: synthetic

<400> SEQUENCE: 368

```
gtctgtctgc acatttcgta gagcgagtgt tccgatactc taatctccct aggcaaggtt    60
catatttgtg taggttactt attctccttt tgttgactaa gtcaataatc agaatcagca   120
ggtttggagt cagcttggca gggatcagca gcctgggttg aaggagggg gtataaaagc   180 cccttcacca ggagaagccg tcacacagat ccacaagctc ctga                   224
```

<210> SEQ ID NO 369
<211> LENGTH: 952
<212> TYPE: PRT
<213> ORGANISM: Homo sapiens

<400> SEQUENCE: 369

```
Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45

Leu Glu Glu Thr His Pro Ala His Gln Gln Gly Ala Ser Arg Pro Gly
    50                  55                  60

Pro Arg Asp Ala Gln Ala His Pro Gly Arg Pro Arg Ala Val Pro Thr
65                  70                  75                  80

Gln Cys Asp Val Pro Pro Asn Ser Arg Phe Asp Cys Ala Pro Asp Lys
```

```
                    85                  90                  95
Ala Ile Thr Gln Glu Gln Cys Glu Ala Arg Gly Cys Cys Tyr Ile Pro
                100                 105                 110

Ala Lys Gln Gly Leu Gln Gly Ala Gln Met Gly Gln Pro Trp Cys Phe
            115                 120                 125

Phe Pro Pro Ser Tyr Pro Ser Tyr Lys Leu Glu Asn Leu Ser Ser Ser
        130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro His Val His Ser Arg Ala Pro Ser Pro Leu
        195                 200                 205

Tyr Ser Val Glu Phe Ser Glu Glu Pro Phe Gly Val Ile Val Arg Arg
    210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                245                 250                 255

Ile Thr Gly Leu Ala Glu His Leu Ser Pro Leu Met Leu Ser Thr Ser
            260                 265                 270

Trp Thr Arg Ile Thr Leu Trp Asn Arg Asp Leu Ala Pro Thr Pro Gly
        275                 280                 285

Ala Asn Leu Tyr Gly Ser His Pro Phe Tyr Leu Ala Leu Glu Asp Gly
    290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
            340                 345                 350

Gln Tyr Leu Asp Val Val Gly Tyr Pro Phe Met Pro Pro Tyr Trp Gly
        355                 360                 365

Leu Gly Phe His Leu Cys Arg Trp Gly Tyr Ser Ser Thr Ala Ile Thr
    370                 375                 380

Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
                405                 410                 415

Asn Lys Asp Gly Phe Arg Asp Phe Pro Ala Met Val Gln Glu Leu His
            420                 425                 430

Gln Gly Gly Arg Arg Tyr Met Met Ile Val Asp Pro Ala Ile Ser Ser
        435                 440                 445

Ser Gly Pro Ala Gly Ser Tyr Arg Pro Tyr Asp Glu Gly Leu Arg Arg
    450                 455                 460

Gly Val Phe Ile Thr Asn Glu Thr Gly Gln Pro Leu Ile Gly Lys Val
465                 470                 475                 480

Trp Pro Gly Ser Thr Ala Phe Pro Asp Phe Thr Asn Pro Thr Ala Leu
                485                 490                 495

Ala Trp Trp Glu Asp Met Val Ala Glu Phe His Asp Gln Val Pro Phe
            500                 505                 510
```

```
Asp Gly Met Trp Ile Asp Met Asn Glu Pro Ser Asn Phe Ile Arg Gly
        515                 520                 525

Ser Glu Asp Gly Cys Pro Asn Asn Leu Glu Asn Pro Pro Tyr Val
    530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
                565                 570                 575

Leu Thr Glu Ala Ile Ala Ser His Arg Ala Leu Val Lys Ala Arg Gly
                580                 585                 590

Thr Arg Pro Phe Val Ile Ser Arg Ser Thr Phe Ala Gly His Gly Arg
            595                 600                 605

Tyr Ala Gly His Trp Thr Gly Asp Val Trp Ser Ser Trp Glu Gln Leu
            610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
                645                 650                 655

Leu Cys Val Arg Trp Thr Gln Leu Gly Ala Phe Tyr Pro Phe Met Arg
                660                 665                 670

Asn His Asn Ser Leu Leu Ser Leu Pro Gln Glu Pro Tyr Ser Phe Ser
            675                 680                 685

Glu Pro Ala Gln Gln Ala Met Arg Lys Ala Leu Thr Leu Arg Tyr Ala
            690                 695                 700

Leu Leu Pro His Leu Tyr Thr Leu Phe His Gln Ala His Val Ala Gly
705                 710                 715                 720

Glu Thr Val Ala Arg Pro Leu Phe Leu Glu Phe Pro Lys Asp Ser Ser
                725                 730                 735

Thr Trp Thr Val Asp His Gln Leu Leu Trp Gly Glu Ala Leu Leu Ile
                740                 745                 750

Thr Pro Val Leu Gln Ala Gly Lys Ala Glu Val Thr Gly Tyr Phe Pro
            755                 760                 765

Leu Gly Thr Trp Tyr Asp Leu Gln Thr Val Pro Val Glu Ala Leu Gly
            770                 775                 780

Ser Leu Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
                805                 810                 815

His Leu Arg Ala Gly Tyr Ile Ile Pro Leu Gln Gly Pro Gly Leu Thr
            820                 825                 830

Thr Thr Glu Ser Arg Gln Gln Pro Met Ala Leu Ala Val Ala Leu Thr
            835                 840                 845

Lys Gly Gly Glu Ala Arg Gly Glu Leu Phe Trp Asp Asp Gly Glu Ser
850                 855                 860

Leu Glu Val Leu Glu Arg Gly Ala Tyr Thr Gln Val Ile Phe Leu Ala
865                 870                 875                 880

Arg Asn Asn Thr Ile Val Asn Glu Leu Val Arg Val Thr Ser Glu Gly
                885                 890                 895

Ala Gly Leu Gln Leu Gln Lys Val Thr Val Leu Gly Val Ala Thr Ala
            900                 905                 910

Pro Gln Gln Val Leu Ser Asn Gly Val Pro Val Ser Asn Phe Thr Tyr
            915                 920                 925
```

```
Ser Pro Asp Thr Lys Val Leu Asp Ile Cys Val Ser Leu Leu Met Gly
    930                 935                 940

Glu Gln Phe Leu Val Ser Trp Cys
945                 950

<210> SEQ ID NO 370
<211> LENGTH: 21
<212> TYPE: DNA
<213> ORGANISM: Artificial
<220> FEATURE:
<223> OTHER INFORMATION: synthetic

<400> SEQUENCE: 370 ggaacccta gtgatggagt t                                              21

<210> SEQ ID NO 371
<211> LENGTH: 16
<212> TYPE: DNA
<213> ORGANISM: Artificial
<220> FEATURE:
<223> OTHER INFORMATION: synthetic

<400> SEQUENCE: 371
cggcctcagt gagcga                                                   16

<210> SEQ ID NO 372
<211> LENGTH: 21
<212> TYPE: DNA
<213> ORGANISM: Artificial
<220> FEATURE:
<223> OTHER INFORMATION: synthetic

<400> SEQUENCE: 372
cactccctct ctgcgcgctc g                                             21
```

ANTI-CD63 ANTIBODIES, CONJUGATES, AND USES THEREOF

This application is a U.S. National Phase Application filed under 35 U.S.C. § 371 of PCT Application No. PCT/US2019/032922, filed May 17, 2019, which claims priority to U.S. Provisional Application Ser. No. 62/777,592, filed Dec. 10, 2018, U.S. Provisional Patent Application Ser. No. 62/681,563, filed Jun. 6, 2018, and U.S. Provisional Patent Application Ser. No. 62/673,098, filed May 17, 2018, each of which application is incorporated by reference in its entirety.

FIELD OF THE INVENTION

This application is generally directed to human antibodies and antigen-binding fragments of human antibodies that bind human CD63, and methods of use thereof, e.g., in methods of treating a disorder in a patient in need thereof. The application also relates to antigen-binding molecules comprising at least an antigen-binding fragment of an anti-CD63 antibody, wherein complexation of the antigen-binding molecule to CD63 mediates internalization of the antigen-binding molecule/CD63 complex. The application further relates to conjugates comprising an anti-CD63 antibody (or antigen-binding molecules comprising an antigen-binding fragment of an anti-CD63 antibody) and a therapeutic agent (e.g., a replacement enzyme, cytotoxic drug, etc.), which conjugates may be useful in treating diseases.

BACKGROUND

The human antigen CD63, also referred to as lysosome-associated glycoprotein 3 (LAMP3), is a member of the tetraspanin superfamily. Its cell expression is ubiquitous and primarily within intracellular endosomal or lysosomal compartments, although some expression is seen on the cell surface. CD63 is an internalizing protein capable of mediating internalization and transport of targets into endosomal/lysosomal compartments when such targets are physically linked to CD63 in some manner, e.g., via an antigen-binding protein conjugated to a payload or a bispecific antigen binding protein that binds the target and CD63.

There is a need in the art for new anti-human CD63 antibodies, including monovalent antigen-binding fragments thereof for use in bispecific binding proteins, capable of binding CD63 and effecting its internalization.

SUMMARY

The present invention provides antibodies and antigen-binding fragments thereof that bind to human CD63. The antibodies according to this aspect of the invention are useful, inter alia, for specifically directing the internalization and/or lysosomal trafficking of a target protein, an enzyme (e.g., GAA or GLA), a drug conjugate, etc. As such, this aspect of the invention also provides bispecific antibodies, antigen-binding fragments thereof that bind human CD63, antibody-protein fusion constructs (see, e.g., FIG. 1), and antibody drug conjugates.

Exemplary anti-CD63 antibodies of the present invention are listed in Table 1. Table 1sets forth the amino acid and nucleic acid sequence identifiers of the heavy chain variable regions (HCVRs) and light chain variable regions (LCVRs), as well as heavy chain complementarity determining regions (HCDR1, HCDR2 and HCDR3), and light chain complementarity determining regions (LCDR1, LCDR2 and LCDR3) of the exemplary anti-CD63 antibodies.

The present invention provides antibodies, or antigen-binding fragments thereof, comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

The present invention also provides antibodies, or antigen-binding fragments thereof, comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

The present invention also provides antibodies, or antigen-binding fragments thereof, comprising an HCVR and an LCVR amino acid sequence pair (HCVR/LCVR) comprising any of the HCVR amino acid sequences listed in Table 1 paired with any of the LCVR amino acid sequences listed in Table 1. According to certain embodiments, the present invention provides antibodies, or antigen-binding fragments thereof, comprising an HCVR/LCVR amino acid sequence pair contained within any of the exemplary anti-CD63 antibodies listed in Table 1. In certain embodiments, the HCVR/LCVR amino acid sequence pair is selected from the group consisting of SEQ ID NOs: 2/10, SEQ ID NOs: 18/26, SEQ ID NOs: 34/42, SEQ ID NOs: 50/58, SEQ ID NOs: 66/74, SEQ ID NOs: 82/90, SEQ ID NOs: 98/106, SEQ ID NOs: 114/122, SEQ ID NOs: 130/138, SEQ ID NOs: 146/154, SEQ ID NOs: 162/170, SEQ ID NOs: 178/186, SEQ ID NOs: 194/202, SEQ ID NOs: 210/218, SEQ ID NOs: 226/234, SEQ ID NOs: 242/250, SEQ ID NOs: 258/266, SEQ ID NOs: 274/282, SEQ ID NOs:290/282, SEQ ID NOs: 298/282, SEQ ID NOs: 306/282, SEQ ID NOs: 314/282, SEQ ID NOs: 322/282, and SEQ ID NOs: 330/282.

The present invention also provides antibodies, or antigen-binding fragments thereof, comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR3 (LCDR3) comprising an amino acid sequence selected from any of the LCDR3 amino acid sequences listed in Table for a substantially similar sequence thereof having at least 90%, at least 95%, at least 98% or at least 99% sequence identity.

The present invention also provides antibodies, or antigen-binding fragments thereof, comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the present invention provides antibodies, or antigen-binding fragments thereof, comprising an HCDR3/LCDR3 amino acid sequence pair contained within any of the exemplary anti-CD63 antibodies listed in Table 1. In certain embodiments, the HCDR3/LCDR3 amino acid sequence pair is selected from the group consisting of SEQ ID NOs: 8/16, SEQ ID NOs: 24/32, SEQ ID NOs: 40/48, SEQ ID NOs: 56/64, SEQ ID NOs: 72/80, SEQ ID NOs:88/96, SEQ ID NOs: 104/112, SEQ ID NOs:120/128, SEQ ID NOs:136/144, SEQ ID NOs; 152/160, SEQ ID NOs:168/176, SEQ ID NOs: 184/192, SEQ ID NOs:200/208; SEQ ID NOs:216/224; SEQ ID NOs:232/240; SEQ ID NOs:248/256; SEQ ID NOs:264/272; SEQ ID NOs:280/288; SEQ ID NOs:296/288; SEQ ID NOs: 304/288; SEQ ID NOs: 312/288; SEQ ID NOs: 320/288; SEQ ID NOs: 328/288; SEQ ID NOs:336/288.

The present invention also provides antibodies, or antigen-binding fragments thereof, comprising a set of six CDRs (i.e., HCDR1-HCDR2-HCDR3-LCDR1-LCDR2-LCDR3) contained within any of the exemplary anti-CD63 antibodies listed in Table 1. In certain embodiments, the HCDR1-HCDR2-HCDR3-LCDR1-LCDR2-LCDR3 amino acid sequences set is selected from the group consisting of SEQ ID NOs:4-6-8-12-14-16, SEQ ID NOs: 20-22-24-26-28-30-32, SEQ ID NOs:36-38-40-44-46-48, SEQ ID NOs: 52-54-56-60-62-64; SEQ ID NOs: 68-70-72-76-78-80; SEQ ID NOs: 84-86-88-92-94-96; SEQ ID NOs: 100-102-104-108-110-112; SEQ ID NOs: 116-118-120-124-126-128; SEQ ID NOs:132-134-136-140-142-144; SEQ ID NOs: 148-150-152-156-158-160; SEQ ID NOs:164-166-168-172-174-176; SEQ ID NOs:180-182-184-188-190-192; SEQ ID NOs: 196-198-200-204-206-208; SEQ ID NOs: 212-214-216-220-222-224; SEQ ID NOs: 228-230-232-236-238-240; SEQ ID NOs: 244-246-248-252-254-256; SEQ ID NOs: 260-262-264-268-270-272; SEQ ID NOs: 276-278-280-284-286-288; SEQ ID NOs: 292-294-296-284-286-288; SEQ ID NOs:300-302-304-284-286-288; SEQ ID NOs: 308-310-312-284-286-288; SEQ ID NOs: 316-318-320-284-286-288; SEQ ID NOs:324-326-328-284-286-288, and SEQ ID NOs:332-334-336-284-286-288.

In a related embodiment, the present invention provides antibodies, or antigen-binding fragments thereof, comprising a set of six CDRs (i.e., HCDR1-HCDR2-HCDR3-LCDR1-LCDR2-LCDR3) contained within an HCVR/LCVR amino acid sequence pair as defined by any of the exemplary anti-CD63 antibodies listed in Table 1. For example, the present invention includes antibodies, or antigen-binding fragments thereof, comprising the HCDR1-HCDR2-HCDR3-LCDR1-LCDR2-LCDR3 amino acid sequences set contained within an HCVR/LCVR amino acid sequence pair selected from the group consisting of SEQ ID NOs: 2/10, SEQ ID NOs: 18/26, SEQ ID NOs: 34/42, SEQ ID NOs: 50/58, SEQ ID NOs: 66/74, SEQ ID NOs: 82/90, SEQ ID NOs: 98/106, SEQ ID NOs: 114/122, SEQ ID NOs: 130/138, SEQ ID NOs: 146/154, SEQ ID NOs: 162/170, SEQ ID NOs: 178/186, SEQ ID NOs: 194/202, SEQ ID NOs: 210/218, SEQ ID NOs: 226/234, SEQ ID NOs: 242/250, SEQ ID NOs: 258/266, SEQ ID NOs: 274/282, SEQ ID NOs:290/282, SEQ ID NOs: 298/282, SEQ ID NOs: 306/282, SEQ ID NOs: 314/282, SEQ ID NOs: 322/282, and SEQ ID NOs: 330/282. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

The present invention also provides nucleic acid molecules encoding anti-CD63 antibodies or portions thereof. For example, the present invention provides nucleic acid molecules encoding any of the HCVR amino acid sequences listed in Table 1; in certain embodiments the nucleic acid molecule comprises a polynucleotide sequence selected from any of the HCVR nucleic acid sequences listed in Table 1, or a substantially similar sequence thereof having at least 90%, at least 95%, at least 98% or at least 99% sequence identity thereto.

The present invention also provides nucleic acid molecules encoding any of the LCVR amino acid sequences listed in Table 1; in certain embodiments the nucleic acid molecule comprises a polynucleotide sequence selected from any of the LCVR nucleic acid sequences listed in Table 1, or a substantially similar sequence thereof having at least 90%, at least 95%, at least 98% or at least 99% sequence identity thereto.

The present invention also provides nucleic acid molecules encoding any of the HCDR1 amino acid sequences listed in Table 1; in certain embodiments the nucleic acid molecule comprises a polynucleotide sequence selected from any of the HCDR1 nucleic acid sequences listed in Table 1, or a substantially similar sequence thereof having at least 90%, at least 95%, at least 98% or at least 99% sequence identity thereto.

The present invention also provides nucleic acid molecules encoding any of the HCDR2 amino acid sequences listed in Table 1; in certain embodiments the nucleic acid molecule comprises a polynucleotide sequence selected from any of the HCDR2 nucleic acid sequences listed in Table 1, or a substantially similar sequence thereof having at least 90%, at least 95%, at least 98% or at least 99% sequence identity thereto.

The present invention also provides nucleic acid molecules encoding any of the HCDR3 amino acid sequences listed in Table 1; in certain embodiments the nucleic acid molecule comprises a polynucleotide sequence selected from any of the HCDR3 nucleic acid sequences listed in Table 1, or a substantially similar sequence thereof having at least 90%, at least 95%, at least 98% or at least 99% sequence identity thereto.

The present invention also provides nucleic acid molecules encoding any of the LCDR1 amino acid sequences listed in Table 1; in certain embodiments the nucleic acid molecule comprises a polynucleotide sequence selected from any of the LCDR1 nucleic acid sequences listed in Table 1, or a substantially similar sequence thereof having at least 90%, at least 95%, at least 98% or at least 99% sequence identity thereto.

The present invention also provides nucleic acid molecules encoding any of the LCDR2 amino acid sequences listed in Table 1; in certain embodiments the nucleic acid molecule comprises a polynucleotide sequence selected from any of the LCDR2 nucleic acid sequences listed in Table 1, or a substantially similar sequence thereof having at least 90%, at least 95%, at least 98% or at least 99% sequence identity thereto.

The present invention also provides nucleic acid molecules encoding any of the LCDR3 amino acid sequences listed in Table 1; in certain embodiments the nucleic acid molecule comprises a polynucleotide sequence selected from any of the LCDR3 nucleic acid sequences listed in Table 1, or a substantially similar sequence thereof having at least 90%, at least 95%, at least 98% or at least 99% sequence identity thereto.

The present invention also provides nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined by any of the exemplary anti-CD63 antibodies listed in Table 1.

The present invention also provides nucleic acid molecules encoding an LCVR, wherein the LCVR comprises a set of three CDRs (i.e., LCDR1-LCDR2-LCDR3), wherein the LCDR1-LCDR2-LCDR3 amino acid sequence set is as defined by any of the exemplary anti-CD63 antibodies listed in Table 1.

The present invention also provides nucleic acid molecules encoding both an HCVR and an LCVR, wherein the HCVR comprises an amino acid sequence of any of the HCVR amino acid sequences listed in Table 1, and wherein the LCVR comprises an amino acid sequence of any of the LCVR amino acid sequences listed in Table 1. In certain embodiments, the nucleic acid molecule comprises a polynucleotide sequence selected from any of the HCVR nucleic acid sequences listed in Table 1, or a substantially similar sequence thereof having at least 90%, at least 95%, at least 98% or at least 99% sequence identity thereto, and a polynucleotide sequence selected from any of the LCVR nucleic acid sequences listed in Table 1, or a substantially similar sequence thereof having at least 90%, at least 95%, at least 98% or at least 99% sequence identity thereto. In certain embodiments according to this aspect of the invention, the nucleic acid molecule encodes an HCVR and LCVR, wherein the HCVR and LCVR are both derived from the same anti-CD63 antibody listed in Table 1.

The present invention also provides recombinant expression vectors capable of expressing a polypeptide comprising a heavy or light chain variable region of an anti-CD63 antibody. For example, the present invention includes recombinant expression vectors comprising any of the nucleic acid molecules mentioned above, i.e., nucleic acid molecules encoding any of the HCVR, LCVR, and/or CDR sequences as set forth in Table 1. Also included within the scope of the present invention are host cells into which such vectors have been introduced, as well as methods of producing the antibodies or portions thereof by culturing the host cells under conditions permitting production of the antibodies or antibody fragments, and recovering the antibodies and antibody fragments so produced.

In some aspects, the present invention includes antibodies or antigen-binding fragments thereof, such as anti-CD63 antibodies, having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shields et al. (2002) JBC 277:26733), where cytotoxicity is desirable. In other applications, modification of galactosylation can be made in order to modify complement dependent cytotoxicity (CDC).

In another aspect, the invention provides a pharmaceutical composition comprising a recombinant human antibody or fragment thereof which specifically binds CD63 and a pharmaceutically acceptable carrier. In a related aspect, the invention features a composition which is a combination of an anti-CD63 antibody and a second therapeutic agent. In one embodiment, the second therapeutic agent is any agent that is advantageously combined with an anti-CD63 antibody. Additional combination therapies and co-formulations involving the anti-CD63 antibodies of the present invention are disclosed elsewhere herein.

In another aspect, the invention provides therapeutic methods for targeting/killing tumor cells expressing CD63 using an anti-CD63 antibody of the invention, wherein the therapeutic methods comprise administering a therapeutically effective amount of a pharmaceutical composition comprising an anti-CD63 antibody of the invention to a subject in need thereof. In some cases, the anti-CD63 antibodies (or antigen-binding fragments thereof) may be modified to be more cytotoxic by methods, including but not limited to, modified Fc domains to increase ADCC (see e.g. Shields, R. L. et al. (2002) JBC 277:26733), radioimmunotherapy, antibody-drug conjugates, or other methods for increasing the efficiency of tumor ablation.

The present invention also includes the use of an anti-CD63 antibody of the invention in the manufacture of a medicament for the treatment of a disease or disorder (e.g., cancer) related to or caused by CD63-expressing cells. In one aspect, the invention relates to a compound comprising an anti-CD63 antibody or antigen-binding fragment, or a bispecific anti-TAAxCD63 antibody, for use in medicine. In one aspect, the invention relates to a compound comprising an antibody-drug conjugate (ADC) as disclosed herein, for use in medicine.

In yet another aspect, the invention provides monospecific anti-CD63 antibodies for diagnostic applications, such as, e.g., imaging reagents.

In yet another aspect, the invention provides therapeutic methods for enhancing CD63 internalization into and/or degradation by a lysosome using an anti-CD63 antibody or antigen-binding portion of an antibody of the invention, wherein the therapeutic methods comprise administering a therapeutically effective amount of a pharmaceutical composition comprising an antibody.

In another aspect, the present invention provides an antibody or antigen-binding fragment thereof that binds CD63-expressing cells with a KD of greater than 100 nM as measured by surface plasmon resonance, or equivalent assay. In another aspect, the present invention provides an antibody or antigen-binding fragment thereof that binds CD63-expressing cells with an EC50 of greater than 100 nM as measured by FACS analysis. In another aspect, the present invention provides an antibody or antigen-binding fragment thereof that binds and is internalized into lysosomes of CD63-expressing cells in the event that the antibody also binds to CD63 expressed on the same cell.

The invention further provides an antibody or antigen-binding fragment that competes for binding to human CD63 with a reference antibody comprising an HCVR/LCVR amino acid sequence pair as set forth in Table 1. In another aspect, the invention provides an antibody or antigen-binding fragment that competes for binding to human CD63 with a reference antibody comprising an HCVR/LCVR amino acid sequence pair selected from the group consisting of SEQ ID NOs: 2/10, SEQ ID NOs: 18/26, SEQ ID NOs: 34/42, SEQ ID NOs: 50/58, SEQ ID NOs: 66/74, SEQ ID NOs: 82/90, SEQ ID NOs: 98/106, SEQ ID NOs: 114/122, SEQ ID NOs: 130/138, SEQ ID NOs: 146/154, SEQ ID NOs: 162/170, SEQ ID NOs: 178/186, SEQ ID NOs: 194/202, SEQ ID NOs: 210/218, SEQ ID NOs: 226/234, SEQ ID NOs: 242/250, SEQ ID NOs: 258/266, SEQ ID NOs: 274/282, SEQ ID NOs:290/282, SEQ ID NOs: 298/282, SEQ ID NOs: 306/282, SEQ ID NOs: 314/282, SEQ ID NOs: 322/282, and SEQ ID NOs: 330/282.

The invention furthermore provides an antibody or antigen-binding fragment, wherein the antibody or antigen-binding fragment thereof binds to the same epitope on human CD63 as a reference antibody comprising an HCVR/LCVR amino acid sequence pair as set forth in Table 2. In another aspect, the antibody or antigen-binding fragment binds to the same epitope on human CD63 as a reference antibody comprising an HCVR/LCVR amino acid sequence pair selected from the group consisting of SEQ ID NOs: 2/10, SEQ ID NOs: 18/26, SEQ ID NOs: 34/42, SEQ ID NOs: 50/58, SEQ ID NOs: 66/74, SEQ ID NOs: 82/90, SEQ ID NOs: 98/106, SEQ ID NOs: 114/122, SEQ ID NOs: 130/138, SEQ ID NOs: 146/154, SEQ ID NOs: 162/170, SEQ ID NOs: 178/186, SEQ ID NOs: 194/202, SEQ ID NOs: 210/218, SEQ ID NOs: 226/234, SEQ ID NOs: 242/250, SEQ ID NOs: 258/266, SEQ ID NOs: 274/282, SEQ ID NOs:290/282, SEQ ID NOs: 298/282, SEQ ID NOs: 306/282, SEQ ID NOs: 314/282, SEQ ID NOs: 322/282, and SEQ ID NOs: 330/282.

The invention further provides an isolated antibody or antigen-binding fragment thereof that binds human CD63, wherein the antibody or antigen-binding fragment comprises: the complementarity determining regions (CDRs) of a heavy chain variable region (HCVR) having an amino acid sequence as set forth in Table 1; and the CDRs of a light chain variable region (LCVR) having an amino acid sequence as set forth in Table 1. In another aspect, the isolated antibody or antigen-binding fragment comprises the heavy and light chain CDRs of a HCVR/LCVR amino acid sequence pair selected from the group consisting of SEQ ID NOs: 2/10, SEQ ID NOs: 18/26, SEQ ID NOs: 34/42, SEQ ID NOs: 50/58, SEQ ID NOs: 66/74, SEQ ID NOs: 82/90, SEQ ID NOs: 98/106, SEQ ID NOs: 114/122, SEQ ID NOs: 130/138, SEQ ID NOs: 146/154, SEQ ID NOs: 162/170, SEQ ID NOs: 178/186, SEQ ID NOs: 194/202, SEQ ID NOs: 210/218, SEQ ID NOs: 226/234, SEQ ID NOs: 242/250, SEQ ID NOs: 258/266, SEQ ID NOs: 274/282, SEQ ID NOs:290/282, SEQ ID NOs: 298/282, SEQ ID NOs: 306/282, SEQ ID NOs: 314/282, SEQ ID NOs: 322/282, and SEQ ID NOs: 330/282. In yet another aspect, the isolated antibody or antigen-binding fragment comprises HCDR1-HCDR2-HCDR3-LCDR1-LCDR2-LCDR3 domains, respectively, selected from the group consisting SEQ ID NOs: 4-6-8-12-14-16, SEQ ID NOs: 20-22-24-26-28-30-32, SEQ ID NOs:36-38-40-44-46-48, SEQ ID NOs: 52-54-56-60-62-64; SEQ ID NOs: 68-70-72-76-78-80; SEQ ID NOs: 84-86-88-92-94-96; SEQ ID NOs: 100-102-104-108-110-112; SEQ ID NOs: 116-118-120-124-126-128; SEQ ID NOs:132-134-136-140-142-144; SEQ ID NOs: 148-150-152-156-158-160; SEQ ID NOs:164-166-168-172-174-176; SEQ ID NOs:180-182-184-188-190-192; SEQ ID NOs: 196-198-200-204-206-208; SEQ ID NOs: 212-214-216-220-222-224; SEQ ID NOs: 228-230-232-236-238-240; SEQ ID NOs: 244-246-248-252-254-256; SEQ ID NOs: 260-262-264-268-270-272; SEQ ID NOs: 276-278-280-284-286-288; SEQ ID NOs: 292-294-296-284-286-288; SEQ ID NOs:300-302-304-284-286-288; SEQ ID NOs: 308-310-312-284-286-288; SEQ ID NOs: 316-318-320-284-286-288; SEQ ID NOs:324-326-328-284-286-288, and SEQ ID NOs:332-334-336-284-286-288. In another aspect, the invention provides an isolated antibody or antigen-binding fragment thereof that binds human CD63, wherein the antibody or antigen-binding fragment comprises: (a) a heavy chain variable region (HCVR) having an amino acid sequence selected from the group consisting of SEQ ID NOs: 2, 18, 34, 50, 66, 82, 98, 114, 130, 146, 162, 178, 194, 210, 226, 242, 258, 274, 290, 298, 306, 314, 322, and 330; and (b) a light chain variable region (LCVR) having an amino acid sequence selected from the group consisting of SEQ ID NOs: 10, 26, 42, 58, 74, 90, 106, 122, 138, 154, 170, 186, 202, 218, 234, 250, 266, and 282. In a further aspect, the isolated antibody or antigen-binding fragment comprises a HCVR/LCVR amino acid sequence pair selected from the group consisting of SEQ ID NOs: SEQ ID NOs: 2/10, SEQ ID NOs: 18/26, SEQ ID NOs: 34/42, SEQ ID NOs: 50/58, SEQ ID NOs: 66/74, SEQ ID NOs: 82/90, SEQ ID NOs: 98/106, SEQ ID NOs: 114/122, SEQ ID NOs: 130/138, SEQ ID NOs: 146/154, SEQ ID NOs: 162/170, SEQ ID NOs: 178/186, SEQ ID NOs: 194/202, SEQ ID NOs: 210/218, SEQ ID NOs: 226/234, SEQ ID NOs: 242/250, SEQ ID NOs: 258/266, SEQ ID NOs: 274/282, SEQ ID NOs:290/282, SEQ ID NOs: 298/282, SEQ ID NOs: 306/282, SEQ ID NOs: 314/282, SEQ ID NOs: 322/282, and SEQ ID NOs: 330/282.

According to another aspect, the present invention provides antibody-drug conjugates comprising an anti-CD63 antibody, antigen-binding fragment thereof, or a multispecific binding protein comprising said antigen-binding fragment thereof, as described herein and a therapeutic agent (e.g., a cytotoxic agent). In some embodiments, the (a) anti-CD63 antibody, antigen-binding fragment and/or multispecific binding protein and (b) the cytotoxic agent are covalently attached via a linker, as discussed herein. In various embodiments, the anti-CD63 antibody or antigen-binding fragment can be any of the anti-CD63 antibodies or fragments described herein.

In some embodiments, the cytotoxic agent is selected from an auristatin, a maytansinoid, a tubulysin, a tomaymycin, calicheamicin, or a dolastatin derivative. In some cases, the cytotoxic agent is an auristatin selected from MMAE or MMAF, or a maytansinoid selected from DM1 or DM4. In some embodiments, the cytotoxic agent is a maytansinoid having the structure of Formulae, as discussed herein.

In some embodiments, the cytotoxic agent is a maytansinoid having the structure:

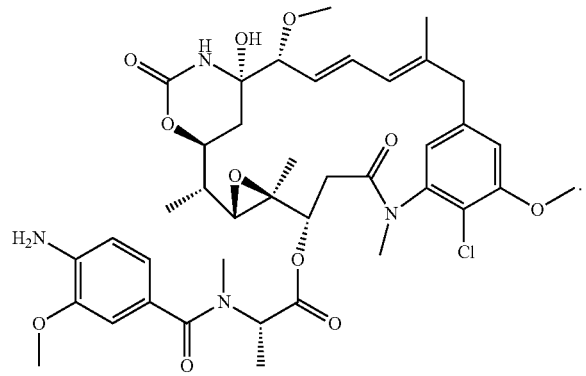 [SMILES: COc1cc(C(=O)N(C)[C@@H](C)C(=O)O[C@H]2CC(=O)N(C)c3cc(cc(OC)c3Cl)C/C(C)=C/C=C/[C@@H](OC)[C@@]3(O)C[C@H](OC(=O)N3)[C@@H](C)[C@@H]3O[C@@]23C)ccc1N]

In some embodiments, the cytotoxic agent is a maytansinoid having the structure:

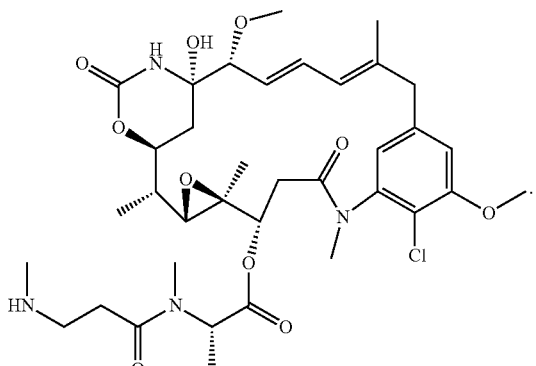

In some embodiments, the antibody-drug conjugate comprises an antigen binding protein, including a multispecific binding protein, comprising an anti-CD63 antigen-binding protein or antigen binding portion thereof, and

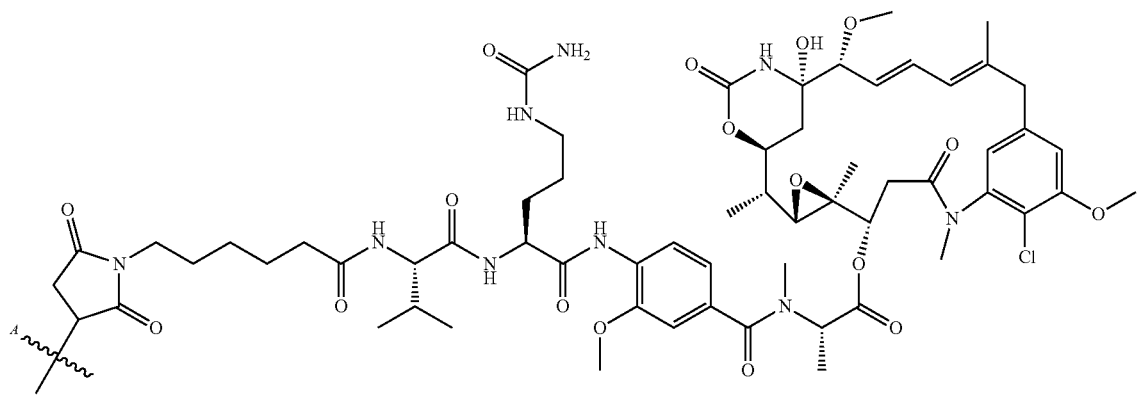

wherein

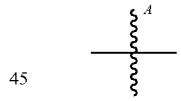

is a bond to the antibody or fragment thereof.

In some embodiments, the antibody-drug conjugate comprises an antigen binding protein, including a multispecific binding protein, comprising an anti-CD63 antigen-binding protein or antigen binding portion thereof, and

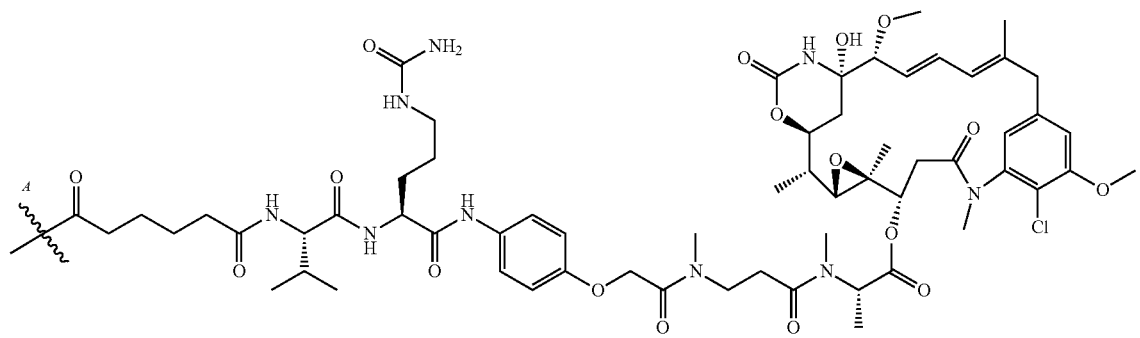

wherein

is a bond to the antibody or fragment thereof.

In some embodiments, the antibody-drug conjugate comprises an antigen binding protein, including a multispecific binding protein, comprising an anti-CD63 antigen-binding protein or antigen binding portion thereof, and In any of the various embodiments of the antibody-drug conjugates discussed above or herein, the antibody-drug conjugate can comprise from 1 to 10 cytotoxic agents per antigen binding protein, including a multispecific binding protein, comprising an anti-CD63 antigen-binding protein or antigen binding portion thereof.

DRAWINGS

FIG. 1 schematically represents multidomain therapeutic proteins. Panel A depicts a multidomain therapeutic protein comprising a bispecific antibody (ii) and a replacement enzyme (i). Panel B depicts an enzyme-Fc fusion polypep-

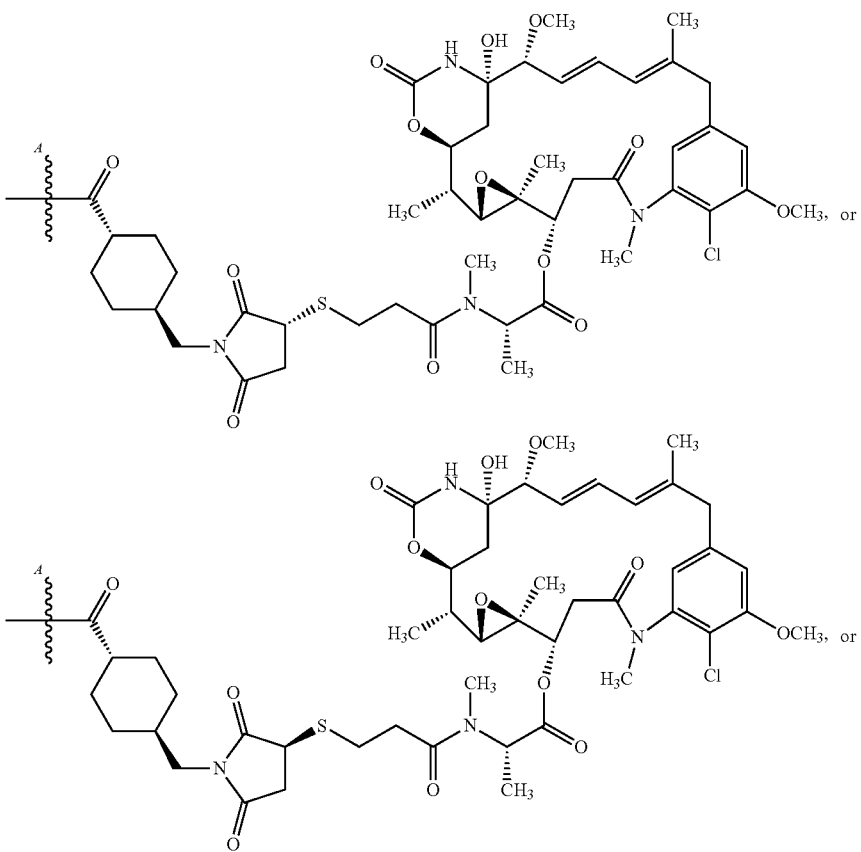

or
a mixture thereof,
wherein

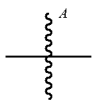

is a bond to the antibody or fragment thereof.

In some embodiments, the bond contacts the antibody or fragment thereof via a sulfur constituent of a cysteine residue.

In some embodiments, the bond contacts the antibody or fragment thereof via a nitrogen constituent of a lysine residue.

tide (i) associating with an internalization effector-specific half-body (ii) to form the multidomain therapeutic protein. Panel C depicts a replacement enzyme (hexagon) covalently linked to the C-terminus of the heavy chain of an anti-internalization effector antibody. Panel D depicts a replacement enzyme (hexagon) covalently linked to the N-terminus of the heavy chain of an anti-internalization effector antibody. Panel E depicts a replacement enzyme (hexagon) covalently linked to the C-terminus of the light chain of an anti-internalization effector antibody. Panel F depicts a replacement enzyme (hexagon) covalently linked to the N-terminus of the light chain of an anti-internalization effector antibody. Panel G depicts a replacement enzyme (hexagon) covalently linked to the C-terminus of a single-chain variable fragment (scFv) containing a VH region (shaded bar) and a VL region (open bar). Panel H depicts a replacement enzyme (hexagon) covalently linked to two scFv domains, the first scFv (i) which serves as a first delivery domain, and the second scFv (ii) which serves as a second delivery domain. Exemplary anti-CD63 $V_H$ and $V_L$ amino acid sequences (and nucleotide sequences encoding same) that may be used to construct a multidomain therapeutic protein comprising an anti-CD63 antibody or antigen binding portion thereof are provided in Table 1.

Figure 2:
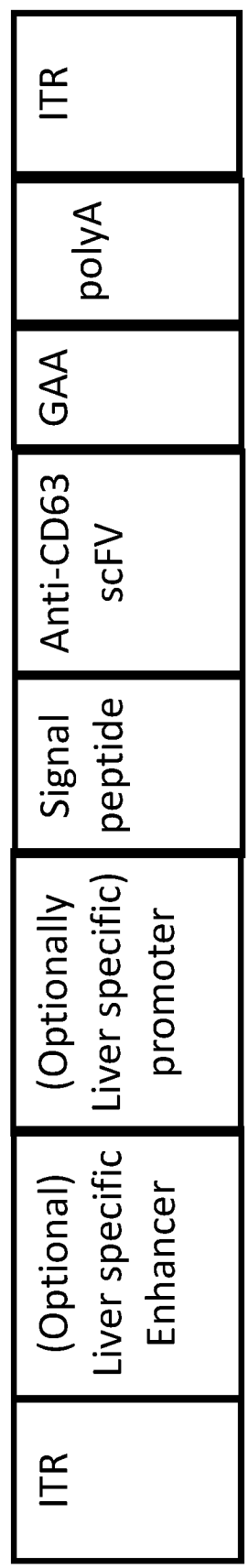

FIG. 2 is a non-limiting exemplary illustration of an AAV gene therapy vector that encodes a multidomain therapeutic protein represented in panel, wherein the scFv is an anti-human CD63 scFv and the replacement enzyme is GAA (e.g., anti-hCD63scFv::hGAA; see, e.g., the amino acid sequence set forth as SEQ ID NO:364 wherein the anti-hCD63scFv is derived from the H4H12450N antibody. Amino acids 1-117 of SEQ ID NO:364 provide the amino acid sequence of the heavy chain variable domain ($V_H$) of the H4H12450N antibody; amino acids 118-132 of SEQ ID NO:364 provide an amino acid linker sequence between the heavy and light chain variable domains of H4H12450N; amino acids 133-240 of SEQ ID NO:364 provide the amino acid sequence of the light chain variable domain ($V_L$) of the H4H12450N antibody; amino acids 241-245 of SEQ ID NO:364 provides an amino acid linker sequence between the anti-hCD63scFv and GAA; and amino acids 246-1128 of SEQ ID NO:364 provides the amino acid sequence of the replacement enzyme GAA, or biologically active portion thereof. Exemplary 5'ITR and 3' ITR sequences are respectively set forth as SEQ ID NO:365 and SEQ ID NO:366. An exemplary liver specific enhancer (serpina 1) is set forth as SEQ ID NO:367. An exemplary liver specific promoter (TTR) is set forth as SEQ ID NO:368. Additional exemplary anti-CD63 $V_H$ and $V_L$ amino acid sequences (and nucleotide sequences encoding same) that may be used to construct a multidomain therapeutic protein, e.g., for the treatment of Pompe disease in a patient in need thereof, comprising an anti-CD63 antibody or antigen binding portion thereof are provided in Table 1.

DESCRIPTION

Provided herein are novel anti-human CD63 antibodies, and monovalent antigen binding fragments thereof, which are useful in mediating internalization of CD63. The anti-human CD63 antibodies, and monovalent antigen binding fragments thereof may be useful, e.g., in the treatment of diseases, as part of multispecific antigen binding protein and/or multidomain therapeutic protein, and/or as an antibody drug conjugate.

This invention is not limited to particular embodiments, compositions, methods and experimental conditions described, as such embodiments, compositions, methods and conditions may vary. The terminology used herein is for the purpose of describing particular embodiments only, and is not intended to be limiting, since the scope of the present invention will be limited only by the appended claims.

Although any methods and materials similar or equivalent to those described herein can be used in the practice or testing of the present invention, some preferred methods and materials are now described. All publications cited herein are incorporated herein by reference to describe in their entirety. Unless defined otherwise, all technical and scientific terms used herein have the same meaning as commonly understood by one of ordinary skill in the art to which this invention belongs.

Unless defined otherwise, all technical and scientific terms used herein have the same meaning as commonly understood by one of ordinary skill in the art to which this invention belongs. The term "about," when used in reference to a particular recited numerical value, means that the value may vary from the recited value by no more than 1%. For example, the expression "about 100" includes 99 and 101 and all values in between (e.g., 99.1, 99.2, 99.3, 99.4, etc.). Although any methods and materials similar or equivalent to those described herein can be used in the practice or testing of the present invention, the preferred methods and materials are now described. All patents, applications and non-patent publications mentioned in this specification are incorporated herein by reference in their entireties.

"CD63" includes a protein that in humans is encoded by the CD63 gene and has an amino acid sequence set forth as SEQ ID NO:337. CD63, is a member of the tetraspanin superfamily of cell surface proteins that span the cell membrane four times. CD63 is expressed in virtually all tissues and is thought to be involved in forming and stabilizing signaling complexes. CD63 localizes to the cell membrane, lysosomal membrane, and late endosomal membrane. CD63 is known to associate with integrins and may be involved in epithelial-mesenchymal transitioning. See H. Maecker et al., "The tetraspanin superfamily: molecular facilitators," 11(6) FASEB J. 428-42, May 1997; and M. Metzelaar et al., "CD63 antigen. A novel lysosomal membrane glycoprotein, cloned by a screening procedure for intracellular antigens in eukaryotic cells," 266 J. Biol. Chem. 3239-3245, 1991. CD63 exhibits biological activities of an internalizing effector. All references to proteins, polypeptides and protein fragments herein are intended to refer to the human version of the respective protein, polypeptide or protein fragment unless explicitly specified as being from a non-human species. Thus, the expression "CD63" means human CD63 unless specified as being from a non-human species, e.g., "mouse CD63," "monkey CD63," etc.

An "internalizing effector" includes a protein that is capable of being internalized into a cell or that otherwise participates in or contributes to retrograde membrane trafficking. In some instances, the internalizing effector is a protein that undergoes transcytosis; that is, the protein is internalized on one side of a cell and transported to the other side of the cell (e.g., apical-to-basal). In many embodiments, the internalizing effector protein is a cell surface-expressed protein or a soluble extracellular protein. However, the present invention also contemplates embodiments in which the internalizing effector protein is expressed within an intracellular compartment such as the endosome, endoplasmic reticulum, Golgi, lysosome, etc. For example, proteins involved in retrograde membrane trafficking (e.g., pathways from early/recycling endosomes to the trans-Golgi network) may serve as internalizing effector proteins in various embodiments of the present invention. In any event, the binding of an antibody or antigen-binding portion thereof, including multidomain therapeutic proteins and multispecific binding proteins comprising same, to an internalizing effector protein causes the entire antibody or antigen-binding portion thereof, including multidomain therapeutic proteins and multispecific binding proteins comprising same, and any molecules associated therewith (e.g., enzyme, target molecule, drug conjugate), to also become internalized into the cell. As explained below, internalizing effector proteins include proteins that are directly internalized into a cell, as well as proteins that are indirectly internalized into a cell. Internalizing effector proteins that are directly internalized into a cell include membrane-associated molecules with at least one extracellular domain (e.g., transmembrane proteins, GPI-anchored proteins, etc.), which undergo cellular internalization, and are preferably processed via an intracellular degradative and/or recycling pathway.

The phrase "an antibody that binds CD63" or an "anti-CD63 antibody" includes antibodies and antigen-binding fragments thereof that specifically recognize a single CD63 molecule. The antibodies and antigen-binding fragments of the present invention may bind soluble CD63 and/or cell surface expressed CD63. Soluble CD63 includes natural CD63 proteins as well as recombinant CD63 protein variants that lack a transmembrane domain or are otherwise unassociated with a cell membrane, for example, but not limited to a recombinant C-terminal Myc-Myc-hexahistidine (hCD63 EC loop 2-MMH; SEQ ID NO:338) or recombinant human CD63 extracellular loop 2 expressed with a C-terminal human Fc tag (hCD63 EC loop 2-hFc; SEQ ID NO:339).

The expression "cell surface-expressed CD63" refers to one or more CD63 protein(s) that is/are expressed on the surface of a cell in vitro or in vivo, such that at least a portion of a CD63 protein is exposed to the extracellular side of the cell membrane and is accessible to an antigen-binding portion of an antibody. "Cell surface-expressed CD63" includes CD63 proteins contained within the context of a functional T cell receptor in the membrane of a cell. A "cell surface-expressed CD63" can comprise or consist of a CD63 protein expressed on the surface of a cell which normally expresses CD63 protein. Alternatively, "cell surface-expressed CD63" can comprise or consist of CD63 protein expressed on the surface of a cell that normally does not express human CD63 on its surface but has been artificially engineered to express CD63 on its surface.

The term "antigen-binding molecule" includes antibodies and antigen-binding fragments of antibodies, including, e.g., bispecific antibodies.

The term "avidity" refers to the ability of an antigen-binding molecule to reach a threshold of target engagement in order to achieve its desired effect. The phrase "avidity-driven binding" or "avidity-driven pairing" in the context of multiple target antigens and a multispecific antigen-binding molecule refers to the mechanism of action wherein the multispecific antigen-binding molecule provides at least two monovalent binding arms, and a first binding arm (or arms) binds to a first target antigen with high affinity. A second binding arm (or arms) binds a second target antigen with low affinity such that the second binding arm does not bind the second target antigen unless both antigens are in proximity to each other, such as present on the same cell. Thus, the high affinity binding to the first target antigen increases the avidity of the low affinity arm for the second binding arm and mediates binding to the second target (Rhoden, J. J., et al., May 20, 2016, *J Biol Chem.* 291, 11337-11347, first published on Mar. 28, 2016 doi: 10.1074/jbc.M116.714287; Jarantow, S. W., et al., Oct. 9, 2015, *J Biol Chem.* 290(41): 24689-704. doi: 10.1074/jbc.M115.651653. Epub 2015 Aug. 10).

The term "antibody" refers to any antigen-binding molecule or molecular complex comprising at least one complementarity determining region (CDR) that specifically binds to or interacts with a particular antigen (e.g., CD63). The term "antibody", as used herein, includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4 (heavy chain CDRs may be abbreviated as HCDR1, HCDR2 and HCDR3; light chain CDRs may be abbreviated as LCDR1, LCDR2 and LCDR3. The term "high affinity" antibody refers to those antibodies having a binding affinity to their target of at least $10^{-9}$ M, at least $10^{-10}$ M; at least $10^{-11}$ M; or at least $10^{-12}$ M, as measured by surface plasmon resonance, e.g., BIACORE™ or solution-affinity ELISA. The term "antibody" may encompass any type of antibody, such as e.g. monoclonal or polyclonal. Moreover, the antibody may be or any origin, such as e.g. mammalian or non-mammalian. In one embodiment, the antibody may be mammalian or avian. In a further embodiment, the antibody may be or human origin and may further be a human monoclonal antibody.

The term "antibody" also includes antigen-binding fragments of full antibody molecules. The terms "antigen-binding portion" of an antibody, "antigen-binding fragment" of an antibody, and the like include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment".

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-CL; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-CL. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The antibodies of the present invention may function through complement-dependent cytotoxicity (CDC) or antibody-dependent cell-mediated cytotoxicity (ADCC). "Complement-dependent cytotoxicity" (CDC) refers to lysis of antigen-expressing cells by an antibody of the invention in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al. (1998) Proc. Natl. Acad. Sci. (USA) 95:652-656). The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

In certain embodiments of the invention, the anti-CD63 antibodies of the invention are human antibodies. The term "human antibody" refers to antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody" is not intended to include antibodies in which CDR sequences derived from the germline of another mammalian species, such as a mouse, have been grafted onto human framework sequences.

The antibodies of the invention may, in some embodiments, be recombinant human antibodies. The term "recombinant human antibody" is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, CH2 or CH3 region which may be desirable, for example, in production, to improve the yield of the desired antibody form.

The antibodies of the invention may be isolated antibodies. An "isolated antibody" refers to an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The present invention also includes one-arm antibodies that bind CD63. The term "one-arm antibody" refers to an antigen-binding molecule comprising a single antibody heavy chain and a single antibody light chain. The one-arm antibodies of the present invention may comprise any of the HCVR/LCVR or CDR amino acid sequences as set forth in Table 1.

The anti-CD63 antibodies disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes anti-CD63 antibodies comprising variants of any of the HCVR, LCVR, and/or CDR amino acid sequences disclosed herein having one or more conservative substitutions. For example, the present invention includes anti-CD63 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth in Table 1 herein.

The phrase "bispecific antibody" includes an antibody capable of selectively binding two or more epitopes. Bispecific antibodies generally comprise two different heavy chains, with each heavy chain specifically binding a different epitope—either on two different molecules (e.g., antigens) or on the same molecule (e.g., on the same antigen). If a bispecific antibody is capable of selectively binding two different epitopes (a first epitope and a second epitope), the affinity of the first heavy chain for the first epitope will generally be at least one to two or three or four orders of magnitude lower than the affinity of the first heavy chain for the second epitope, and vice versa. The epitopes recognized by the bispecific antibody can be on the same or a different target (e.g., on the same or a different protein). Bispecific antibodies can be made, for example, by combining heavy chains that recognize different epitopes of the same antigen. For example, nucleic acid sequences encoding heavy chain variable sequences that recognize different epitopes of the same antigen can be fused to nucleic acid sequences encoding different heavy chain constant regions, and such sequences can be expressed in a cell that expresses an immunoglobulin light chain. A typical bispecific antibody has two heavy chains each having three heavy chain CDRs, followed by (N-terminal to C-terminal) a CH1 domain, a hinge, a CH2 domain, and a CH3 domain, and an immunoglobulin light chain that either does not confer antigen-binding specificity but that can associate with each heavy chain, or that can associate with each heavy chain and that can bind one or more of the epitopes bound by the heavy chain antigen-binding regions, or that can associate with each heavy chain and enable binding or one or both of the heavy chains to one or both epitopes.

The phrase "heavy chain," or "immunoglobulin heavy chain" includes an immunoglobulin heavy chain constant region sequence from any organism, and unless otherwise specified includes a heavy chain variable domain. Heavy chain variable domains include three heavy chain CDRs and four FR regions, unless otherwise specified. Fragments of heavy chains include CDRs, CDRs and FRs, and combinations thereof. A typical heavy chain has, following the variable domain (from N-terminal to C-terminal), a CH1 domain, a hinge, a CH2 domain, and a CH3 domain. A functional fragment of a heavy chain includes a fragment that is capable of specifically recognizing an antigen (e.g., recognizing the antigen with a KD in the micromolar, nanomolar, or picomolar range), that is capable of expressing and secreting from a cell, and that comprises at least one CDR.

The phrase "light chain" includes an immunoglobulin light chain constant region sequence from any organism, and unless otherwise specified includes human kappa and lambda light chains. Light chain variable (VL) domains typically include three light chain CDRs and four framework (FR) regions, unless otherwise specified. Generally, a full-length light chain includes, from amino terminus to carboxyl terminus, a VL domain that includes FR1-CDR1-FR2-CDR2-FR3-CDR3-FR4, and a light chain constant domain. Light chains that can be used with this invention include e.g., those, that do not selectively bind either the first or second antigen selectively bound by the antigen-binding protein. Suitable light chains include those that can be identified by screening for the most commonly employed light chains in existing antibody libraries (wet libraries or in silico), where the light chains do not substantially interfere with the affinity and/or selectivity of the antigen-binding domains of the antigen-binding proteins. Suitable light chains include those that can bind one or both epitopes that are bound by the antigen-binding regions of the antigen-binding protein.

The phrase "variable domain" includes an amino acid sequence of an immunoglobulin light or heavy chain (modified as desired) that comprises the following amino acid regions, in sequence from N-terminal to C-terminal (unless otherwise indicated): FR1, CDR1, FR2, CDR2, FR3, CDR3, FR4. A "variable domain" includes an amino acid sequence capable of folding into a canonical domain (VH or VL) having a dual beta sheet structure wherein the beta sheets are connected by a disulfide bond between a residue of a first beta sheet and a second beta sheet.

The phrase "complementarity determining region," or the term "CDR," includes an amino acid sequence encoded by a nucleic acid sequence of an organism's immunoglobulin genes that normally (i.e., in a wildtype animal) appears between two framework regions in a variable region of a light or a heavy chain of an immunoglobulin molecule (e.g., an antibody or a T cell receptor). A CDR can be encoded by, for example, a germline sequence or a rearranged or unrearranged sequence, and, for example, by a naive or a mature B cell or a T cell. In some circumstances (e.g., for a CDR3), CDRs can be encoded by two or more sequences (e.g., germline sequences) that are not contiguous (e.g., in an unrearranged nucleic acid sequence) but are contiguous in a B cell nucleic acid sequence, e.g., as the result of splicing or connecting the sequences (e.g., V-D-J recombination to form a heavy chain CDR3).

The term "antibody fragment", refers to one or more fragments of an antibody that retain the ability to specifically bind to an antigen. Examples of binding fragments encompassed within the term "antibody fragment" include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) *Nature* 241:544-546), which consists of a VH domain, (vi) an isolated CDR, and (vii) an scFv, which consists of the two domains of the Fv fragment, VL and VH, joined by a synthetic linker to form a single protein chain in which the VL and VH regions pair to form monovalent molecules. Other forms of single chain antibodies, such as diabodies are also encompassed under the term "antibody" (see e.g., Holliger et al. (1993) PNAS USA 90:6444-6448; Poljak et al. (1994) *Structure* 2:1121-1123).

The phrase "Fc-containing protein" includes antibodies, bispecific antibodies, immunoadhesins, and other binding proteins that comprise at least a functional portion of an immunoglobulin CH2 and CH3 region. A "functional portion" refers to a CH2 and CH3 region that can bind a Fc receptor (e.g., an FcγR; or an FcRn, i.e., a neonatal Fc receptor), and/or that can participate in the activation of complement. If the CH2 and CH3 region contains deletions, substitutions, and/or insertions or other modifications that render it unable to bind any Fc receptor and also unable to activate complement, the CH2 and CH3 region is not functional.

Fc-containing proteins can comprise modifications in immunoglobulin domains, including where the modifications affect one or more effector function of the binding protein (e.g., modifications that affect FcγR binding, FcRn binding and thus half-life, and/or CDC activity). Such modifications include, but are not limited to, the following modifications and combinations thereof, with reference to EU numbering of an immunoglobulin constant region: 238, 239, 248, 249, 250, 252, 254, 255, 256, 258, 265, 267, 268, 269, 270, 272, 276, 278, 280, 283, 285, 286, 289, 290, 292, 293, 294, 295, 296, 297, 298, 301, 303, 305, 307, 308, 309, 311, 312, 315, 318, 320, 322, 324, 326, 327, 328, 329, 330, 331, 332, 333, 334, 335, 337, 338, 339, 340, 342, 344, 356, 358, 359, 360, 361, 362, 373, 375, 376, 378, 380, 382, 383, 384, 386, 388, 389, 398, 414, 416, 419, 428, 430, 433, 434, 435, 437, 438, and 439.

For example, and not by way of limitation, the binding protein is an Fc-containing protein and exhibits enhanced serum half-life (as compared with the same Fc-containing protein without the recited modification(s)) and have a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at 428 and/or 433 (e.g., L/R/SI/P/Q or K) and/or 434 (e.g., H/F or Y); or a modification at 250 and/or 428; or a modification at 307 or 308 (e.g., 308F, V308F), and 434. In another example, the modification can comprise a 428L (e.g., M428L) and 434S (e.g., N434S) modification; a 428L, 259I (e.g., V259I), and a 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); a 307 and/or 308 modification (e.g., 308F or 308P).

The term "antigen-binding protein," as used herein, refers to a polypeptide or protein (one or more polypeptides complexed in a functional unit) that specifically recognizes an epitope on an antigen, such as a cell-specific antigen and/or a target antigen of the present invention. An antigen-binding protein may be multi-specific. The term "multi-specific" with reference to an antigen-binding protein means that the protein recognizes different epitopes, either on the same antigen or on different antigens. A multi-specific antigen-binding protein of the present invention can be a single multifunctional polypeptide, or it can be a multimeric complex of two or more polypeptides that are covalently or non-covalently associated with one another. The term "antigen-binding protein" includes antibodies or fragments thereof of the present invention that may be linked to or co-expressed with another functional molecule, e.g., another peptide or protein. For example, an antibody or fragment thereof can be functionally linked (e.g., by chemical coupling, genetic fusion, non-covalent association or otherwise) to one or more other molecular entities, such as a protein or fragment thereof to produce a bispecific or a multi-specific antigen-binding molecule with a second binding specificity.

"Multidomain therapeutic protein" includes (i) a single protein that contains more than one functional domain, (ii) a protein that contains more than one polypeptide chain, and (iii) a mixture of more than one protein or more than one polypeptide. The term polypeptide is generally taken to mean a single chain of amino acids linked together via peptide bonds. The term protein encompasses the term polypeptide, but also includes more complex structures. That is, a single polypeptide is a protein, and a protein can contain one or more polypeptides associated in a higher order structure. For example, hemoglobin is a protein containing four polypeptides: two alpha globin polypeptides and two beta globin polypeptides. Myoglobin is also a protein, but it contains only a single myoglobin polypeptide.

The multidomain therapeutic protein comprises one or more polypeptide(s) and at least two domains providing two functions. One of those domains is the "enzyme domain" which provides the replacement of a defective protein activity associated with an enzyme deficiency disease. The other of those domains is the "delivery domain" which provides binding to an internalization effector, e.g., CD63, such as an anti-CD63 antibody as disclosed herein or antigen-binding fragment thereof. Thus, a single polypeptide that provides an enzyme replacement activity and the ability to bind to an internalization effector (a.k.a. internalization effector-binding protein (delivery domain activity) is a multidomain therapeutic protein. Also, a mixture of proteins, wherein one protein provides the enzyme function, and another protein provides the internalization effector binding activity, is a multidomain therapeutic protein The term "protein" means any amino acid polymer having more than about 20 amino acids covalently linked via amide bonds. Proteins contain one or more amino acid polymer chains, generally known in the art as "polypeptides". Thus, a polypeptide may be a protein, and a protein may contain multiple polypeptides to form a single functioning biomolecule. Disulfide bridges (i.e., between cysteine residues to form cystine) may be present in some proteins. These covalent links may be within a single polypeptide chain, or between two individual polypeptide chains. For example, disulfide bridges are essential to proper structure and function of insulin, immunoglobulins, protamine, and the like. For a recent review of disulfide bond formation, see Oka and Bulleid, "Forming disulfides in the endoplasmic reticulum," 1833(11) Biochim Biophys Acta 2425-9 (2013).

As used herein, "protein" includes biotherapeutic proteins, recombinant proteins used in research or therapy, trap proteins and other Fc-fusion proteins, chimeric proteins, antibodies, monoclonal antibodies, human antibodies, bispecific antibodies, antibody fragments, nanobodies, recombinant antibody chimeras, scFv fusion proteins, cytokines, chemokines, peptide hormones, and the like. Proteins may be produced using recombinant cell-based production systems, such as the insect bacculovirus system, yeast systems (e.g., *Pichia* sp.), mammalian systems (e.g., CHO cells and CHO derivatives like CHO-K1 cells). For a recent review discussing biotherapeutic proteins and their production, see Ghaderi et al., "Production platforms for biotherapeutic glycoproteins. Occurrence, impact, and challenges of non-human sialylation," 28 Biotechnol Genet Eng Rev. 147-75 (2012).

As used herein, the term "epitope" refers to the portion of the antigen which is recognized by the multi-specific antigen-binding polypeptide. A single antigen (such as an antigenic polypeptide) may have more than one epitope. Epitopes may be defined as structural or functional. Functional epitopes are generally a subset of structural epitopes and are defined as those residues that directly contribute to the affinity of the interaction between the antigen-binding polypeptide and the antigen. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics. Epitopes formed from contiguous amino acids are typically retained on exposure to denaturing solvents, whereas epitopes formed by tertiary folding are typically lost on treatment with denaturing solvents.

The term "domain" refers to any part of a protein or polypeptide having a particular function or structure. Preferably, domains of the present invention bind to cell-specific or target antigens. Cell-specific antigen- or target antigen-binding domains, and the like, as used herein, include any naturally occurring, enzymatically obtainable, synthetic, or genetically engineered polypeptide or glycoprotein that specifically binds an antigen.

The term "half-body" or "half-antibody", which are used interchangeably, refers to half of an antibody, which essentially contains one heavy chain and one light chain. Antibody heavy chains can form dimers, thus the heavy chain of one half-body can associate with heavy chain associated with a different molecule (e.g., another half-body) or another Fc-containing polypeptide. Two slightly different Fc-domains may "heterodimerize" as in the formation of bispecific antibodies or other heterodimers, -trimers, -tetramers, and the like. See Vincent and Murini, "Current strategies in antibody engineering: Fc engineering and pH-dependent antigen binding, bispecific antibodies and antibody drug conjugates," 7 Biotechnol. J. 1444-1450 (20912); and Shimamoto et al., "Peptibodies: A flexible alternative format to antibodies," 4(5) MAbs 586-91 (2012).

In one embodiment, the half-body variable domain specifically recognizes the internalization effector and the half body Fc-domain dimerizes with an Fc-fusion protein that comprises a replacement enzyme (e.g., a peptibody) Id, 586.

The term "single-chain variable fragment" or "scFv" includes a single chain fusion polypeptide containing an immunoglobulin heavy chain variable region ($V_H$) and an immunoglobulin light chain variable region ($V_L$). In some embodiments, the $V_H$ and $V_L$ are connect by a linker sequence of 10 to 25 amino acids. ScFv polypeptides may also include other amino acid sequences, such as CL or CH1 regions. ScFv molecules can be manufactured by phage display or made by directly subcloning the heavy and light chains from a hybridoma or B-cell. Ahmad et al., Clinical and Developmental Immunology, volume 2012, article ID 98025 is incorporated herein by reference for methods of making scFv fragments by phage display and antibody domain cloning.

Bispecific Antigen-Binding Molecules

The anti-CD63 antibodies and antigen-binding fragments thereof (including multispecific antigen-binding molecules and multidomain therapeutic proteins comprising anti-CD63 antibodies or antigen-binding fragments thereof) of the present invention may be monospecific, bi-specific, or multispecific. Multispecific antibodies may be specific for different epitopes of one target polypeptide or may contain antigen-binding domains specific for more than one target polypeptide. See, e.g., Tutt et al., 1991, J. Immunol. 147: 60-69; Kufer et al., 2004, Trends Biotechnol. 22:238-244. The anti-CD63 antibodies and antigen-binding fragments thereof (including multispecific antigen-binding molecules and multidomain therapeutic proteins comprising anti-CD63 antibodies or antigen-binding fragments thereof) of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second or additional binding specificity.

Use of the expression "anti-CD63 antibody" herein is intended to include both monospecific anti-CD63 antibodies as well as bispecific antibodies comprising a CD63-binding arm and a "target"-binding arm. Thus, the present invention includes bispecific antibodies wherein one arm of an immunoglobulin binds human CD63, and the other arm of the immunoglobulin is specific for another target molecule. The CD63-binding arm can comprise any of the HCVR/LCVR or CDR amino acid sequences as set forth in Table 1 herein.

In certain embodiments, the CD63-binding arm binds to human CD63 and induces internalization of the CD63 and antibody bound thereto. In certain embodiments, the CD63-binding arm binds weakly to human CD63 and induces internalization of CD63 and antibody bound thereto. In other embodiments, the CD63-binding arm binds weakly to human CD63 and induces tumor-associated antigen-expressing cell killing in the context of a bispecific or multispecific antibody, e.g., comprising a CD63-binding arm and a "target"-binding arm, where the "target"-binding arm is a tumor associated antigen (TAA). Non-limiting examples of specific tumor-associated antigens include, e.g., AFP, ALK, BAGE proteins, β-catenin, brc-abl, BRCA1, BORIS, CA9, carbonic anhydrase IX, caspase-8, CD40, CDK4, CEA, CTLA4, cyclin-B1, CYP1B1, EGFR, EGFRvIII, ErbB2/Her2, ErbB3, ErbB4, ETV6-AML, EphA2, Fra-1, FOLR1, GAGE proteins (e.g., GAGE-1, -2), GD2, GD3, GloboH, glypican-3, GM3, gp100, Her2, HLA/B-raf, HLA/k-ras, HLA/MAGE-A3, hTERT, LMP2, MAGE proteins (e.g., MAGE-1, -2, -3, -4, -6, and -12), MART-1, mesothelin, ML-IAP, Mucl, Muc16 (CA-125), MUM1, NA17, NY-BR1, NY-BR62, NY-BR85, NY-ESO1, OX40, p15, p53, PAP, PAX3, PAX5, PCTA-1, PLAC1, PRLR, PRAME, PSMA (FOLH1), RAGE proteins, Ras, RGS5, Rho, SART-1, SART-3, Steap-1, Steap-2, survivin, TAG-72, TGF-β, TMPRSS2, Tn, TRP-1, TRP-2, tyrosinase, and uroplakin-3. In other embodiments, the CD63-binding arm binds or associated weakly with human and cynomolgus (monkey) CD63, yet the binding interaction is not detectable by in vitro assays known in the art.

In certain exemplary embodiments of the present invention, the bispecific antigen-binding molecule is a bispecific antibody. Each antigen-binding domain of a bispecific antibody comprises a heavy chain variable domain (HCVR) and a light chain variable domain (LCVR). In the context of a bispecific antigen-binding molecule comprising a first and a second antigen-binding domain (e.g., a bispecific antibody), the CDRs of the first antigen-binding domain may be designated with the prefix "A1" and the CDRs of the second antigen-binding domain may be designated with the prefix "A2". Thus, the CDRs of the first antigen-binding domain may be referred to herein as A1-HCDR1, A1-HCDR2, and A1-HCDR3; and the CDRs of the second antigen-binding domain may be referred to herein as A2-HCDR1, A2-HCDR2, and A2-HCDR3.

The first antigen-binding domain and the second antigen-binding domain may be directly or indirectly connected to one another to form a bispecific antigen-binding molecule of the present invention. Alternatively, the first antigen-binding domain and the second antigen-binding domain may each be connected to a separate multimerizing domain. The association of one multimerizing domain with another multimerizing domain facilitates the association between the two antigen-binding domains, thereby forming a bispecific antigen-binding molecule. A "multimerizing domain" is any macromolecule, protein, polypeptide, peptide, or amino acid that has the ability to associate with a second multimerizing domain of the same or similar structure or constitution. For example, a multimerizing domain may be a polypeptide comprising an immunoglobulin CH3 domain. A non-limiting example of a multimerizing component is an Fc portion of an immunoglobulin (comprising a CH2-CH3 domain), e.g., an Fc domain of an IgG selected from the isotypes IgG1, IgG2, IgG3, and IgG4, as well as any allotype within each isotype group.

Bispecific antigen-binding molecules of the present invention will typically comprise two multimerizing domains, e.g., two Fc domains that are each individually part of a separate antibody heavy chain. The first and second multimerizing domains may be of the same IgG isotype such as, e.g., IgG1/IgG1, IgG2/IgG2, IgG4/IgG4. Alternatively, the first and second multimerizing domains may be of different IgG isotypes such as, e.g., IgG1/IgG2, IgG1/IgG4, IgG2/IgG4, etc.

In certain embodiments, the multimerizing domain is an Fc fragment or an amino acid sequence of from 1 to about 200 amino acids in length containing at least one cysteine residue. In other embodiments, the multimerizing domain is a cysteine residue, or a short cysteine-containing peptide. Other multimerizing domains include peptides or polypeptides comprising or consisting of a leucine zipper, a helix-loop motif, or a coiled-coil motif.

Any bispecific antibody format or technology may be used to make the bispecific antigen-binding molecules of the present invention. For example, an antibody or fragment thereof having a first antigen binding specificity can be functionally linked (e.g., by chemical coupling, genetic fusion, noncovalent association or otherwise) to one or more other molecular entities, such as another antibody or antibody fragment having a second antigen-binding specificity to produce a bispecific antigen-binding molecule. Specific exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED)body, leucine zipper, Duobody, IgG1/IgG2, dual acting Fab (DAF)-IgG, and Mab$^{e2}$ bispecific formats (see, e.g., Klein et al. 2012, mAbs 4:6, 1-11, and references cited therein, for a review of the foregoing formats).

In the context of bispecific antigen-binding molecules of the present invention, the multimerizing domains, e.g., Fc domains, may comprise one or more amino acid changes (e.g., insertions, deletions or substitutions) as compared to the wild-type, naturally occurring version of the Fc domain. For example, the invention includes bispecific antigen-binding molecules comprising one or more modifications in the Fc domain that results in a modified Fc domain having a modified binding interaction (e.g., enhanced or diminished) between Fc and FcRn. In one embodiment, the bispecific antigen-binding molecule comprises a modification in a CH2 or a CH3 region, wherein the modification increases the affinity of the Fc domain to FcRn in an acidic environment (e.g., in an endosome where pH ranges from about 5.5 to about 6.0). Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

The present invention also includes bispecific antigen-binding molecules comprising a first CH3 domain and a second Ig CH3 domain, wherein the first and second Ig CH3 domains differ from one another by at least one amino acid, and wherein at least one amino acid difference reduces binding of the bispecific antibody to Protein A as compared to a bi-specific antibody lacking the amino acid difference. In one embodiment, the first Ig CH3 domain binds Protein A and the second Ig CH3 domain contains a mutation that reduces or abolishes Protein A binding such as an H95R modification (by IMGT exon numbering; H435R by EU numbering). The second CH3 may further comprise a Y96F modification (by IMGT; Y436F by EU). See, for example, U.S. Pat. No. 8,586,713. Further modifications that may be found within the second CH3 include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies.

In certain embodiments, the Fc domain may be chimeric, combining Fc sequences derived from more than one immunoglobulin isotype. For example, a chimeric Fc domain can comprise part or all of a CH2 sequence derived from a human IgG1, human IgG2 or human IgG4 CH2 region, and part or all of a CH3 sequence derived from a human IgG1, human IgG2 or human IgG4. A chimeric Fc domain can also contain a chimeric hinge region. For example, a chimeric hinge may comprise an "upper hinge" sequence, derived from a human IgG1, a human IgG2 or a human IgG4 hinge region, combined with a "lower hinge" sequence, derived from a human IgG1, a human IgG2 or a human IgG4 hinge region. A particular example of a chimeric Fc domain that can be included in any of the antigen-binding molecules set forth herein comprises, from N- to C-terminus: [IgG4 CH1]-[IgG4 upper hinge]-[IgG2 lower hinge]-[IgG4 CH2]-[IgG4 CH3]. Another example of a chimeric Fc domain that can be included in any of the antigen-binding molecules set forth herein comprises, from N- to C-terminus: [IgG1 CH1]-[IgG1 upper hinge]-[IgG2 lower hinge]-[IgG4 CH2]-[IgG1 CH3]. These and other examples of chimeric Fc domains that can be included in any of the antigen-binding molecules of the present invention are described in US Publication 2014/0243504, published Aug. 28, 2014, which is herein incorporated in its entirety. Chimeric Fc domains having these general structural arrangements, and variants thereof, can have altered Fc receptor binding, which in turn affects Fc effector function.

In certain embodiments, the invention provides an antibody heavy chain wherein the heavy chain constant region (CH) region comprises an amino acid sequence at least 95%, at least 96%, at least 97%, at least 98%, at least 99% identical to any one of SEQ ID NO:340, SEQ ID NO:341, SEQ ID NO:342, SEQ ID NO:343, SEQ ID NO:344, SEQ ID NO:345, SEQ ID NO:346, SEQ ID NO:347, SEQ ID NO:348, SEQ ID NO:349, SEQ ID NO:350, or SEQ ID NO:351. In some embodiments, the heavy chain constant region (CH) region comprises an amino acid sequence selected from the group consisting of SEQ ID NO:340, SEQ ID NO:341, SEQ ID NO:342, SEQ ID NO:343, SEQ ID NO:344, SEQ ID NO:345, SEQ ID NO:346, SEQ ID NO:347, SEQ ID NO:348, SEQ ID NO:349, SEQ ID NO:350, or SEQ ID NO:351.

In other embodiments, the invention provides an antibody heavy chain wherein the Fc domain comprises an amino acid sequence at least 95%, at least 96%, at least 97%, at least 98%, at least 99% identical to any one of SEQ ID NO:352, SEQ ID NO:353, SEQ ID NO:354, SEQ ID NO:355, SEQ ID NO:356, SEQ ID NO:357, SEQ ID NO:358, SEQ ID NO:359, SEQ ID NO:360, SEQ ID NO:361, SEQ ID NO:362, or SEQ ID NO:363. In some embodiments, the Fc domain comprises an amino acid sequence selected form the group consisting of SEQ ID NO:352, SEQ ID NO:353, SEQ ID NO:354, SEQ ID NO:355, SEQ ID NO:356, SEQ ID NO:357, SEQ ID NO:358, SEQ ID NO:359, SEQ ID NO:360, SEQ ID NO:361, SEQ ID NO:362, or SEQ ID NO:363.

Multidomain Therapeutic Proteins

FIG. 1 depicts various exemplars of multidomain therapeutic proteins. In one example (FIG. 1, panel A), the multidomain therapeutic protein contains an enzyme (represented by the hexagon) and a bispecific antibody (the IE-BP) that binds the enzyme (hashed lines) and an internalization effector (solid lines). Here, one arm of the bispecific antibody binds non-covalently to the enzyme, and the other arm binds non-covalently to the internalization effector, thereby enabling the internalization of the replacement enzyme into the cell or subcellular compartment. In another example (panel B), the multidomain therapeutic protein comprises a single protein containing two polypeptides, one polypeptide having enzyme function and the other having delivery domain function. Here, the enzyme is fused to an immunoglobulin Fc domain or heavy chain constant region, which associates with the Fc domain of the enzyme half-antibody to form the bifunctional multidomain therapeutic protein. The embodiment depicted in panel B is similar to that in panel A, except that the enzyme is covalently attached to one of the half-antibodies, rather than through antigen-antibody interaction at the immunoglobulin variable domain of the half-antibody.

In other examples, the multidomain therapeutic protein consists of the enzyme covalently linked (directly or indirectly through a linker) to the delivery domain. In one embodiment, the enzyme is attached to the C-terminus of an immunoglobulin molecule (e.g., the heavy chain or alternatively the light chain). In another embodiment, the enzyme is attached to the N-terminus of the immunoglobulin molecule (e.g., the heavy chain or alternatively the light chain). In these exemplars, the immunoglobulin molecule is the delivery domain. In yet another embodiment, the enzyme is attached to the C-terminus of a scFv molecule that binds the internalization effector.

In one embodiment, the multidomain therapeutic protein comprises two delivery domains. In one embodiment, the first delivery domain binds to a lysosomal trafficking molecule or other internalization effector (e.g., CD63). In another embodiment, the second delivery domain binds to a transcytosis effector to facilitate transcellular transport of the multidomain therapeutic protein. In one embodiment, the transcytosis effector is inter alia an LDL receptor, an IgA receptor, a transferrin receptor, or a neonatal Fc receptor (FcRn). In a specific embodiment, the transcytosis delivery domain comprises a molecule that binds to a transferrin receptor, such as e.g., an anti-transferrin receptor antibody or an anti-transferrin receptor scFv molecule. Tuma and Hubbard, "Transcytosis: Crossing Cellular Barriers," Physiological Reviews, 83(3): 871-935 (1 Jul. 2003) is incorporated herein by reference for cell surface receptors that mediate transcytosis that are useful in the practice of the subject invention.

"Enzyme domain" or "enzyme" denotes any protein associated with the etiology or physiological effect of an enzyme deficiency disease. An enzyme includes the actual enzyme, transport protein, receptor, or other protein that is defective and which is attributed as the molecular lesion that caused the disease. An enzyme also includes any protein that can provide a similar or sufficient biochemical or physiological activity that replaces or circumvents the molecular lesion of the disease. For example, an "isozyme" may be used as an enzyme.

In some embodiments, the enzyme is a hydrolase, including esterases, glycosylases, hydrolases that act on ether bonds, peptidases, linear amidases, diphosphatases, ketone hydrolases, halogenases, phosphoamidases, sulfohydrolases, sulfinases, desulfinases, and the like. In some embodiments, the enzyme is a glycosylase, including glycosidases and N-glycosylases. In some embodiments, the enzyme is a glycosidase, including alpha-amylase, beta-amylase, glucan 1,4-alpha-glucosidase, cellulose, endo-1,3(4)-beta-glucanase, inulinase, endo-1,4-beta-xylanase, endo-1,4-b-xylanase, dextranase, chitinase, polygalacturonidase, lysozyme, exo-alpha-sialidase, alpha-glucosidase, beta-glucosidase, alpha-galactosidase, beta-galactosidase, alpha-mannosidase, beta-mannosidase, beta-fructofuranosidase, alpha,alpha-trehalose, beta-glucuronidase, xylan endo-1,3-beta-xylosidase, amylo-alpha-1,6-glucosidase, hyaluronoglucosaminidase, hyaluronoglucuronidase, and the like.

In the case of Pompe disease, in which the molecular defect is a defect in α-glucosidase activity, enzymes include human alpha-glucosidase (GAA), and "isozymes" such as other alpha-glucosidases, engineered recombinant alpha-glucosidase, other glucosidases, recombinant glucosidases, any protein engineered to hydrolyze a terminal non-reducing 1-4 linked alpha-glucose residue to release a single alpha-glucose molecule, any EC 3.2.1.20 enzyme, natural or recombinant low pH carbohydrate hydrolases for glycogen or starches, and glucosyl hydrolases such as sucrase isomaltase, maltase glucoamylase, glucosidase II, and neutral alpha-glucosidase. An exemplary gene therapy vector Germline Mutations The anti-CD63 antibodies disclosed herein may comprise one or more amino acid substitutions, insertions and/or deletions in the framework and/or CDR regions of the heavy chain variable domains as compared to the corresponding germline sequences from which the antibodies were derived.

The present invention also includes anti-CD63 antibodies and antigen-binding fragments thereof (including multispecific antigen-binding molecules and multidomain therapeutic proteins comprising anti-CD63 antibodies or antigen-binding fragments thereof) of the present invention which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"), and having weak or no detectable binding to a CD63 antigen. Several such exemplary antibodies that recognize CD63 are described in Table 1 herein.

Furthermore, the anti-CD63 antibodies and antigen-binding fragments thereof (including multispecific antigen-binding molecules and multidomain therapeutic proteins comprising anti-CD63 antibodies or antigen-binding fragments thereof) of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be tested for one or more desired properties such as, improved binding specificity, weak or reduced binding affinity, improved or enhanced pharmacokinetic properties, reduced immunogenicity, etc. Antibodies and antigen-binding fragments obtained in this general manner given the guidance of the present disclosure are encompassed within the present invention.

The present invention also includes anti-CD63 antibodies and antigen-binding fragments thereof (including multispecific antigen-binding molecules and multidomain therapeutic proteins comprising anti-CD63 antibodies or antigen-binding fragments thereof) comprising variants of any of the HCVR, LCVR, and/or CDR amino acid sequences disclosed herein having one or more conservative substitutions. For example, the present invention includes anti-CD63 antibodies and antigen-binding fragments thereof (including multispecific antigen-binding molecules and multidomain therapeutic proteins comprising anti-CD63 antibodies or antigen-binding fragments thereof) having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth in Table 1 herein. The antibodies, antigen-binding fragments thereof, multispecific antigen-binding molecules, and multidomain therapeutic proteins of the present invention may comprise one or more amino acid substitutions, insertions and/or deletions in the framework and/or CDR regions of the heavy and light chain variable domains as compared to the corresponding germline sequences from which the individual antigen-binding domains were derived, while maintaining or improving the desired weak-to-no detectable binding to, e.g., CD63. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein, i.e. the amino acid substitution maintains or improves the desired weak to no detectable binding affinity in the case of anti-CD63 binding molecules. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445. A "moderately conservative" replacement is any change having a nonnegative value in the PAM250 log-likelihood matrix.

The present invention also includes anti-CD63 antibodies and antigen-binding fragments thereof (including multispecific antigen-binding molecules and multidomain therapeutic proteins comprising anti-CD63 antibodies or antigen-binding fragments thereof) comprising an antigen-binding domain with an HCVR and/or CDR amino acid sequence that is substantially identical to any of the HCVR and/or CDR amino acid sequences disclosed herein, while maintaining or improving the desired weak affinity to CD63 antigen. The term "substantial identity" or "substantially identical," when referring to an amino acid sequence means that two amino acid sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402.

Once obtained, antigen-binding domains that contain one or more germline mutations were tested for decreased binding affinity utilizing one or more in vitro assays. Although antibodies that recognize a particular antigen are typically screened for their purpose by testing for high (i.e. strong) binding affinity to the antigen, the antibodies of the present invention exhibit weak binding or no detectable binding. Bispecific antigen-binding molecules comprising one or more antigen-binding domains obtained in this general manner are also encompassed within the present invention and were found to be advantageous as avidity-driven tumor therapies.

Unexpected benefits, for example, improved pharmacokinetic properties and low toxicity to the patient may be realized from further modifying the antibodies of the invention by the methods described herein.

Binding Properties of the Antibodies

The term "binding" in the context of the binding of an antibody, immunoglobulin, antibody-binding fragment, or Fc-containing protein to either, e.g., a predetermined antigen, such as a cell surface protein or fragment thereof, typically refers to an interaction or association between a minimum of two entities or molecular structures, such as an antibody-antigen interaction.

For instance, binding affinity typically corresponds to a $K_D$ value of about $10^{-7}$ M or less, such as about $10^{-8}$ M or less, such as about $10^{-9}$ M or less when determined by, for instance, surface plasmon resonance (SPR) technology in a BIAcore 3000 instrument using the antigen as the ligand and the antibody, Ig, antibody-binding fragment, or Fc-containing protein as the analyte (or antiligand). Cell-based binding strategies, such as fluorescent-activated cell sorting (FACS) binding assays, are also routinely used and provide binding characterization data with respect to cell-surface expressed proteins. FACS data correlates well with other methods such as radioligand competition binding and SPR (Benedict, C A, *J Immunol Methods*. 1997, 201(2):223-31; Geuijen, C A, et al. *J Immunol Methods*. 2005, 302(1-2):68-77).

Accordingly, the anti-CD63 antibodies and antigen-binding fragments thereof (including multispecific antigen-binding molecules and multidomain therapeutic proteins comprising anti-CD63 antibodies or antigen-binding fragments thereof) of the invention binds to the predetermined antigen or cell surface molecule (receptor) having an affinity corresponding to a $K_D$ value that is at least ten-fold lower than its affinity for binding to a non-specific antigen (e.g., BSA, casein). According to the present invention, the affinity of an antibody corresponding to a $K_D$ value that is equal to or less than ten-fold lower than a non-specific antigen may be considered non-detectable binding, however such an antibody may be paired with a second antigen binding arm for the production of a bispecific antibody of the invention.

The term "$K_D$" or "KD" in molar (M) refers to the dissociation equilibrium constant of a particular antibody-antigen interaction, or the dissociation equilibrium constant of an antibody or antibody-binding fragment binding to an antigen. There is an inverse relationship between $K_D$ and binding affinity, therefore the smaller the $K_D$ value, the higher, i.e. stronger, the affinity. Thus, the terms "higher affinity" or "stronger affinity" relate to a higher ability to form an interaction and therefore a smaller $K_D$ value, and conversely the terms "lower affinity" or "weaker affinity" relate to a lower ability to form an interaction and therefore a larger $K_D$ value. In some circumstances, a higher binding affinity (or $K_D$) of a particular molecule (e.g. antibody) to its interactive partner molecule (e.g. antigen X) compared to the binding affinity of the molecule (e.g. antibody) to another interactive partner molecule (e.g. antigen Y) may be expressed as a binding ratio determined by dividing the larger $K_D$ value (lower, or weaker, affinity) by the smaller $K_D$ (higher, or stronger, affinity), for example expressed as 5-fold or 10-fold greater binding affinity, as the case may be.

In some embodiments, a bispecific antigen-binding molecule of the invention, or conjugate thereof, binds to a target molecule with a binding affinity ($K_D$ value) greater than 10-fold its binding affinity to CD63. As such, the bispecific molecule has a much stronger binding affinity to the target molecule than its binding affinity to CD63. In some cases, the binding affinity is measured by a surface plasmon resonance assay at 37° C., or equivalent assay.

The term "$k_d$" (sec-1 or 1/s) refers to the dissociation rate constant of a particular antibody-antigen interaction, or the dissociation rate constant of an antibody or antibody-binding fragment. Said value is also referred to as the $k_{off}$ value.

The term "$k_a$" (M-1×sec-1 or 1/M) refers to the association rate constant of a particular antibody-antigen interaction, or the association rate constant of an antibody or antibody-binding fragment.

The term "$K_A$" (M-1 or 1/M) refers to the association equilibrium constant of a particular antibody-antigen interaction, or the association equilibrium constant of an antibody or antibody-binding fragment. The association equilibrium constant is obtained by dividing the $k_a$ by the $k_d$.

The term "EC50" or "$EC_{50}$" refers to the half maximal effective concentration, which includes the concentration of an antibody which induces a response halfway between the baseline and maximum after a specified exposure time. The $EC_{50}$ essentially represents the concentration of an antibody where 50% of its maximal effect is observed. In certain embodiments, the $EC_{50}$ value equals the concentration of an antibody of the invention that gives half-maximal binding to cells expressing CD63 or tumor-associated antigen, as determined by e.g. a FACS binding assay. Thus, reduced or weaker binding is observed with an increased $EC_{50}$, or half maximal effective concentration value.

In one embodiment, decreased binding can be defined as an increased $EC_{50}$ antibody concentration which enables binding to the half-maximal amount of target cells.

Sequence Variants

The anti-CD63 antibodies and antigen-binding fragments thereof (including multispecific antigen-binding molecules and multidomain therapeutic proteins comprising anti-CD63 antibodies or antigen-binding fragments thereof) of the present invention may comprise one or more amino acid substitutions, insertions and/or deletions in the framework and/or CDR regions of the heavy and light chain variable domains as compared to the corresponding germline sequences from which the individual antigen-binding domains were derived. Such mutations can be readily ascertained by comparing the amino acid sequences disclosed herein to germline sequences available from, for example, public antibody sequence databases. The antigen-binding molecules of the present invention may comprise antigen-binding domains which are derived from any of the exemplary amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antigen-binding domain was originally derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antigen-binding domain was originally derived). Furthermore, the antigen-binding domains may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antigen-binding domains that contain one or more germline mutations can be easily tested for one or more desired property such as, improved binding specificity, increased binding affinity, improved or enhanced antagonistic or agonistic biological properties (as the case may be), reduced immunogenicity, etc. Bispecific antigen-binding molecules comprising one or more antigen-binding domains obtained in this general manner are encompassed within the present invention.

The present invention also includes antigen-binding molecules wherein one or both antigen-binding domains comprise variants of any of the HCVR, LCVR, and/or CDR amino acid sequences disclosed herein having one or more conservative substitutions. For example, the present invention includes antigen-binding molecules comprising an antigen-binding domain having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

The present invention also includes antigen-binding molecules comprising an antigen-binding domain with an HCVR, LCVR, and/or CDR amino acid sequence that is substantially identical to any of the HCVR, LCVR, and/or CDR amino acid sequences disclosed herein. The term "substantial identity" or "substantially identical," when referring to an amino acid sequence means that two amino acid sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

pH-Dependent Binding

The present invention includes anti-CD63 antibodies and antigen-binding fragments thereof (including multispecific antigen-binding molecules and multidomain therapeutic proteins comprising anti-CD63 antibodies or antigen-binding fragments thereof) with pH-dependent binding characteristics. For example, an anti-CD63 antibody of the present invention may exhibit reduced binding to CD63 at acidic pH as compared to neutral pH. Alternatively, anti-CD63 antibodies of the invention may exhibit enhanced binding to CD63 at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. The expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding . . . at acidic pH as compared to neutral pH" is expressed in terms of a ratio of the $K_D$ value of the antibody binding to its antigen at acidic pH to the $K_D$ value of the antibody binding to its antigen at neutral pH (or vice versa). For example, an antibody or antigen-binding fragment thereof may be regarded as exhibiting "reduced binding to CD63 at acidic pH as compared to neutral pH" for purposes of the present invention if the antibody or antigen-binding fragment thereof exhibits an acidic/neutral $K_D$ ratio of about 3.0 or greater. In certain exemplary embodiments, the acidic/neutral $K_D$ ratio for an antibody or antigen-binding fragment of the present invention can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0. 25.0, 30.0, 40.0, 50.0, 60.0, 70.0, 100.0 or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained.

Antibodies Comprising Fc Variants

According to certain embodiments of the present invention, anti-CD63 antibodies and antigen-binding fragments thereof (including multispecific antigen-binding molecules and multidomain therapeutic proteins comprising anti-CD63 antibodies or antigen-binding fragments thereof) are provided comprising an Fc domain comprising one or more mutations which enhance or diminish antibody binding to the FcRn receptor, e.g., at acidic pH as compared to neutral pH. For example, the present invention includes antibodies comprising a mutation in the CH2 or a CH3 region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

For example, the present invention includes anti-CD63 antibodies and antigen-binding fragments thereof (including multispecific antigen-binding molecules and multidomain therapeutic proteins comprising anti-CD63 antibodies or antigen-binding fragments thereof) comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains disclosed herein, are contemplated within the scope of the present invention.

Biological Characteristics of the Antibodies and Bispecific Antigen-Binding Molecules The present invention includes antibodies and antigen-binding fragments thereof that bind human CD63 with high, medium or low affinity, depending on the therapeutic context and particular targeting properties that are desired. For example, in the context of a bispecific antigen-binding molecule, wherein one arm binds CD63 and another arm binds a target antigen (e.g., a tumor associated antigen), it may be desirable for the target antigen-binding arm to bind the target antigen with high affinity while the anti-CD63 arm binds CD63 with only moderate or low affinity. In this manner, preferential targeting of the antigen-binding molecule to cells expressing the target antigen may be achieved while avoiding general/untargeted CD63 binding and the consequent adverse side effects associated therewith.

The present invention includes antibodies, antigen-binding fragments, and bispecific antibodies thereof that bind human CD63 with weak (i.e. low) or even no detectable affinity. According to certain embodiments, the present invention includes antibodies and antigen-binding fragments of antibodies that bind human CD63 (e.g., at 37° C.) with a $K_D$ of greater than about 100 nM as measured by surface plasmon resonance. In certain embodiments, the antibodies or antigen-binding fragments of the present invention bind CD63 with a $K_D$ of greater than about greater than about 110 nM, at least 120 nM, greater than about 130 nM, greater than about 140 nM, greater than about 150 nM, at least 160 nM, greater than about 170 nM, greater than about 180 nM, greater than about 190 nM, greater than about 200 nM, greater than about 250 nM, greater than about 300 nM, greater than about 400 nM, greater than about 500 nM, greater than about 600 nM, greater than about 700 nM, greater than about 800 nM, greater than about 900 nM, or greater than about 1 µM, or with no detectable affinity, as measured by surface plasmon resonance (e.g., mAb-capture or antigen-capture format), or a substantially similar assay.

The present invention includes antibodies, antigen-binding fragments, and bispecific antibodies thereof that bind monkey (i.e. cynomolgus) CD63 with weak (i.e. low) or even no detectable affinity.

Epitope Mapping and Related Technologies

The epitope on CD63 to which the anti-CD63 antibodies and antigen-binding fragments thereof (including multispecific antigen-binding molecules and multidomain therapeutic proteins comprising anti-CD63 antibodies or antigen-binding fragments thereof) of the present invention bind may consist of a single contiguous sequence of 3 or more (e.g., 3, 4, 5, 6, 7, 8, 9, 10, 11, 12, 13, 14, 15, 16, 17, 18, 19, 20 or more) amino acids of a CD63 protein. Alternatively, the epitope may consist of a plurality of non-contiguous amino acids (or amino acid sequences) of CD63. The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstances, an epitope may include moieties of saccharides, phosphoryl groups, or sulfonyl groups on the antigen.

Various techniques known to persons of ordinary skill in the art can be used to determine whether an antigen-binding domain of an antibody "interacts with one or more amino acids" within a polypeptide or protein. Exemplary techniques include, e.g., routine cross-blocking assay such as that described *Antibodies*, Harlow and Lane (Cold Spring Harbor Press, Cold Spring Harb., NY), alanine scanning mutational analysis, peptide blots analysis (Reineke, 2004, Methods Mol Biol 248:443-463), and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antigen-binding domain of an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) *Anal. Chem.* 73:256A-265A. X-ray crystallography of the antigen/antibody complex may also be used for epitope mapping purposes.

The present invention further includes anti-CD63 antibodies that bind to the same epitope as any of the specific exemplary antibodies described herein (e.g. antibodies comprising any of the amino acid sequences as set forth in Table 1 herein). Likewise, the present invention also includes anti-CD63 antibodies that compete for binding to CD63 with any of the specific exemplary antibodies described herein (e.g. antibodies comprising any of the amino acid sequences as set forth in Table 1 herein).

One can easily determine whether a particular antigen-binding molecule (e.g., antibody) or antigen-binding domain thereof binds to the same epitope as, or competes for binding with, a reference antigen-binding molecule of the present invention by using routine methods known in the art. For example, to determine if a test antibody binds to the same epitope on CD63 as a reference bispecific antigen-binding molecule of the present invention, the reference bispecific molecule is first allowed to bind to a CD63 protein. Next, the ability of a test antibody to bind to the CD63 molecule is assessed. If the test antibody is able to bind to CD63 following saturation binding with the reference bispecific antigen-binding molecule, it can be concluded that the test antibody binds to a different epitope of CD63 than the reference bispecific antigen-binding molecule. On the other hand, if the test antibody is not able to bind to the CD63 molecule following saturation binding with the reference bispecific antigen-binding molecule, then the test antibody may bind to the same epitope of CD63 as the epitope bound by the reference bispecific antigen-binding molecule of the invention. Additional routine experimentation (e.g., peptide mutation and binding analyses) can then be carried out to confirm whether the observed lack of binding of the test antibody is in fact due to binding to the same epitope as the reference bispecific antigen-binding molecule or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antigen-binding proteins bind to the same (or overlapping) epitope if, e.g., a 1-, 5-, 10-, 20- or 100-fold excess of one antigen-binding protein inhibits binding of the other by at least 50% but preferably 75%, 90% or even 99% as measured in a competitive binding assay (see, e.g., Junghans et al., Cancer Res. 1990:50:1495-1502). Alternatively, two antigen-binding proteins are deemed to bind to the same epitope if essentially all amino acid mutations in the antigen that reduce or eliminate binding of one antigen-binding protein reduce or eliminate binding of the other. Two antigen-binding proteins are deemed to have "overlapping epitopes" if only a subset of the amino acid mutations that reduce or eliminate binding of one antigen-binding protein reduce or eliminate binding of the other.

To determine if an antibody or antigen-binding domain thereof competes for binding with a reference antigen-binding molecule, the above-described binding methodology is performed in two orientations: In a first orientation, the reference antigen-binding molecule is allowed to bind to a CD63 protein under saturating conditions followed by assessment of binding of the test antibody to the CD63 molecule. In a second orientation, the test antibody is allowed to bind to a CD63 molecule under saturating conditions followed by assessment of binding of the reference antigen-binding molecule to the CD63 molecule. If, in both orientations, only the first (saturating) antigen-binding molecule is capable of binding to the CD63 molecule, then it is concluded that the test antibody and the reference antigen-binding molecule compete for binding to CD63. As will be appreciated by a person of ordinary skill in the art, an antibody that competes for binding with a reference antigen-binding molecule may not necessarily bind to the same epitope as the reference antibody, but may sterically block binding of the reference antibody by binding an overlapping or adjacent epitope.

Preparation of Antigen-Binding Domains and Construction of Bispecific Molecules

Antigen-binding domains specific for particular antigens can be prepared by any antibody generating technology known in the art. Once obtained, two different antigen-binding domains, specific for two different antigens (e.g., CD63 and a target antigen), can be appropriately arranged relative to one another to produce a bispecific antigen-binding molecule of the present invention using routine methods. (A discussion of exemplary bispecific antibody formats that can be used to construct the bispecific antigen-binding molecules of the present invention is provided elsewhere herein). In certain embodiments, one or more of the individual components (e.g., heavy and light chains) of the multispecific antigen-binding molecules of the invention are derived from chimeric, humanized or fully human antibodies. Methods for making such antibodies are well known in the art. For example, one or more of the heavy and/or light chains of the bispecific antigen-binding molecules of the present invention can be prepared using VELOCIMMUNE™ technology. Using VELOCIMMUNE™ technology (or any other human antibody generating technology), high affinity chimeric antibodies to a particular antigen (e.g., CD63) are initially isolated having a human variable region and a mouse constant region. The antibodies are characterized and selected for desirable characteristics, including affinity, selectivity, epitope, etc. The mouse constant regions are replaced with a desired human constant region to generate fully human heavy and/or light chains that can be incorporated into the bispecific antigen-binding molecules of the present invention.

Genetically engineered animals may be used to make human bispecific antigen-binding molecules. For example, a genetically modified mouse can be used which is incapable of rearranging and expressing an endogenous mouse immunoglobulin light chain variable sequence, wherein the mouse expresses only one or two human light chain variable domains encoded by human immunoglobulin sequences operably linked to the mouse kappa constant gene at the endogenous mouse kappa locus. Such genetically modified mice can be used to isolate heavy chain and light chain variable regions to produce fully human bispecific antigen-binding molecules. As such, the fully human bispecific antigen-binding molecules comprise two different heavy chains that associate with the same light chain. (See, e.g., US 2011/0195454). Fully human refers to an antibody, or antigen-binding fragment or immunoglobulin domain thereof, comprising an amino acid sequence encoded by a DNA derived from a human sequence over the entire length of each polypeptide of the antibody or antigen-binding fragment or immunoglobulin domain thereof. In some instances, the fully human sequence is derived from a protein endogenous to a human. In other instances, the fully human protein or protein sequence comprises a chimeric sequence wherein each component sequence is derived from human sequence. While not being bound by any one theory, chimeric proteins or chimeric sequences are generally designed to minimize the creation of immunogenic epitopes in the junctions of component sequences, e.g. compared to any wild-type human immunoglobulin regions or domains.

Bispecific antigen-binding molecules may be constructed with one heavy chain having a modified Fc domain that abrogates its binding to Protein A, thus enabling a purification method that yields a heterodimeric protein. See, for example, U.S. Pat. No. 8,586,713. As such, the bispecific antigen-binding molecules comprise a first $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation/modification that reduces or abolishes Protein A binding such as an H95R modification (by IMGT exon numbering; H435R by EU numbering). The second $C_H3$ may further comprise a Y96F modification (by IMGT; Y436F by EU).

Bioequivalents

The present invention encompasses antigen-binding molecules having amino acid sequences that vary from those of the exemplary molecules disclosed herein but that retain the ability to bind CD63. Such variant molecules may comprise one or more additions, deletions, or substitutions of amino acids when compared to parent sequence, but exhibit biological activity that is essentially equivalent to that of the described bispecific antigen-binding molecules.

The present invention includes antigen-binding molecules that are bioequivalent to any of the exemplary antigen-binding molecules set forth herein. Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antigen-binding proteins will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antigen-binding protein.

Bioequivalent variants of the exemplary bispecific antigen-binding molecules set forth herein may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antigen-binding proteins may include variants of the exemplary bispecific antigen-binding molecules set forth herein comprising amino acid changes which modify the glycosylation characteristics of the molecules, e.g., mutations which eliminate or remove glycosylation.

Species Selectivity and Species Cross-Reactivity

According to certain embodiments of the invention, antigen-binding molecules are provided which bind to human CD63 but not to CD63 from other species. The present invention also includes antigen-binding molecules that bind to human CD63 and to CD63 from one or more non-human species.

According to certain exemplary embodiments of the invention, antigen-binding molecules are provided which bind to human CD63 may bind or not bind, as the case may be, to one or more of mouse, rat, guinea pig, hamster, gerbil, pig, cat, dog, rabbit, goat, sheep, cow, horse, camel, cynomolgus, marmoset, rhesus or chimpanzee CD63.

Antibody-Drug Conjugates (ADCs)

The present invention provides antibody-drug conjugates (ADCs) comprising an anti-CD63 antibodies and antigen-binding fragments thereof (including multispecific antigen-binding molecules and multidomain therapeutic proteins comprising anti-CD63 antibodies or antigen-binding fragments thereof) thereof conjugated to a therapeutic moiety such as a cytotoxic agent, a chemotherapeutic drug, immunosuppressant or a radioisotope. Anti-CD63 antibodies, or antigen-binding fragment thereof, conjugated to a therapeutic moiety are also provided. In general terms, the ADCs comprise: A-[L-P]$_y$, in which A is an antigen-binding molecule, e.g. an anti-CD63 antibody, or a fragment thereof (e.g., a fragment comprising at least a HCDR3 selected from any of the HCDR3 amino acid sequences listed in Table 1), L is a linker, P is the payload or therapeutic moiety (e.g., cytotoxic agent), and y is an integer from 1 to 30.

In various embodiments, the ADC comprises an anti-CD63 antibody or antigen-binding fragment thereof (e.g., an anti-target (TAA)×anti-CD63 antibody) that comprises the CDRs of a HCVR or a LCVR having the amino acid sequences of the SEQ ID NOs (e.g., SEQ ID NOs: 2, 18, 34, 50, 66, 82, 98, 114, 130, 146, 162, 178, 194, 210, 226, 242, 258, 274, 290, 298, 306, 314, 322, 330, 10, 26, 42, 58, 74, 90, 106, 122, 138, 154, 170, 186, 202, 218, 234, 250, 266, and 282) set forth in Table 1, or specific HCVR/LCVR pairs (e.g., SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/282, 298/282, 306/282, 314/282, 322/282, and 330/282). In some cases, the anti-CD63 antibody or fragment comprises CDRs with the amino acid sequences of the SEQ ID NOs (e.g., SEQ ID NOs: 4-6-8-12-14-16, 20-22-24-26-28-30-32, 36-38-40-44-46-48, 52-54-56-60-62-64; 68-70-72-76-78-80 84-86-88-92-94-96; 100-102-104-108-110-112, 116-118-120-124-126-128; 132-134-136-140-142-144; 148-150-152-156-158-160; 164-166-168-172-174-176; 180-182-184-188-190-192; 196-198-200-204-206-208; 212-214-216-220-222-224; 228-230-232-236-238-240; 244-246-248-252-254-256; 260-262-264-268-270-272; 276-278-280-284-286-288; 292-294-296-284-286-288; 300-302-304-284-286-288; 308-310-312-284-286-288; 316-318-320-284-286-288; 324-326-328-284-286-288, and 332-334-336-284-286-288) set forth in Table 1. In some cases, the anti-CD63 antibody or fragment comprises a HCVR and a LCVR having the amino acid sequences of the SEQ ID NOs (e.g., SEQ ID NOs: 2, 18, 34, 50, 66, 82, 98, 114, 130, 146, 162, 178, 194, 210, 226, 242, 258, 274, 290, 298, 306, 314, 322, 330, 10, 26, 42, 58, 74, 90, 106, 122, 138, 154, 170, 186, 202, 218, 234, 250, 266, and 282) set forth in Table 1, or specific amino acid sequence pairs (e.g., SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/282, 298/282, 306/282, 314/282, 322/282, and 330/282).

Cytotoxic agents include any agent that is detrimental to the growth, viability or propagation of cells, including, but not limited to, tubulin-interacting agents and DNA-damaging agents. Examples of suitable cytotoxic agents and chemotherapeutic agents that can be conjugated to anti-CD63 antibodies in accordance with this aspect of the disclosure include, e.g., 1-(2chloroethyl)-1,2-dimethanesulfonyl hydrazide, 1,8-dihydroxy-bicyclo[7.3.1]trideca-4,9-diene-2,6-diyne-13-one, 1-dehydrotestosterone, 5-fluorouracil, 6-mercaptopurine, 6-thioguanine, 9-amino camptothecin, actinomycin D, amanitins, aminopterin, anguidine, anthracycline, anthramycin (AMC), auristatins, bleomycin, busulfan, butyric acid, calicheamicins (e.g., calicheamicin yl), camptothecin, carminomycins, carmustine, cemadotins, cisplatin, colchicin, combretastatins, cyclophosphamide, cytarabine, cytochalasin B, dactinomycin, daunorubicin, decarbazine, diacetoxypentyldoxorubicin, dibromomannitol, dihydroxy anthracin dione, disorazoles, dolastatin (e.g., dolastatin 10), doxorubicin, duocarmycin, echinomycins, eleutherobins, emetine, epothilones, esperamicin, estramustines, ethidium bromide, etoposide, fluorouracils, geldanamycins, gramicidin D, glucocorticoids, irinotecans, kinesin spindle protein (KSP) inhibitors, leptomycins, leurosines, lidocaine, lomustine (CCNU), maytansinoids, mechlorethamine, melphalan, mercatopurines, methopterins, methotrexate, mithramycin, mitomycin, mitoxantrone, N8-acetyl spermidine, podophyllotoxins, procaine, propranolol, pteridines, puromycin, pyrrolobenzodiazepines (PBDs), rhizoxins, streptozotocin, tallysomycins, taxol, tenoposide, tetracaine, thioepa chlorambucil, tomaymycins, topotecans, tubulysin, vinblastine, vincristine, vindesine, vinorelbines, and derivatives of any of the foregoing.

According to certain embodiments, the cytotoxic agent that is conjugated to an anti-CD63 antibody is a maytansinoid such as DM1 or DM4, a tomaymycin derivative, or a dolastatin derivative. According to certain embodiments, the cytotoxic agent that is conjugated to an anti-CD63 antibody is an auristatin such as MMAE, MMAF, or derivatives thereof. Other cytotoxic agents known in the art are contemplated within the scope of the present disclosure, including, e.g., protein toxins such ricin, *C. difficile* toxin, *pseudomonas* exotoxin, ricin, diphtheria toxin, botulinum toxin, bryodin, saporin, pokeweed toxins (i.e., phytolaccatoxin and phytolaccigenin), and others such as those set forth in Sapra et al., *Pharmacol. & Therapeutics,* 2013, 138:452-469.

In certain embodiments, the cytotoxic agent is a maytansinoid, e.g., derivative of maytansine. Suitable maytansinoids include DM1, DM4, or derivatives, stereoisomers, or isotopologues thereof. Suitable maytansinoids also include, but are not limited to, those disclosed in WO 2014/145090A1, WO 2015/031396A1, US 2016/0375147A1, and US 2017/0209591A1, incorporated herein by reference in their entireties.

In some embodiments, the maytansinoid has the following structure:

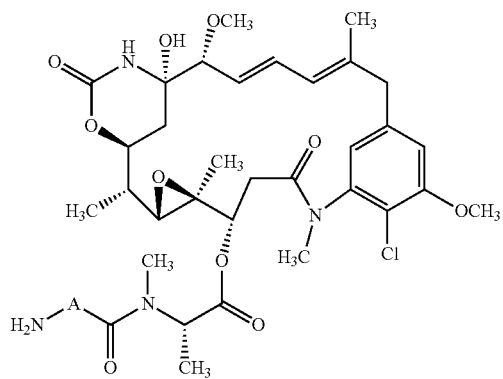

wherein A is an optionally substituted arylene or heteroarylene.

In some embodiments, the maytansinoid has the following structure:

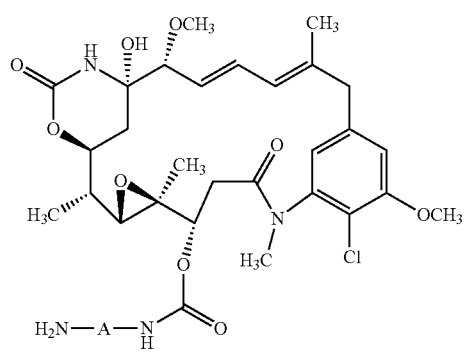

wherein A is an optionally substituted arylene or heteroarylene.

In some embodiments, the maytansinoid has the following structure:

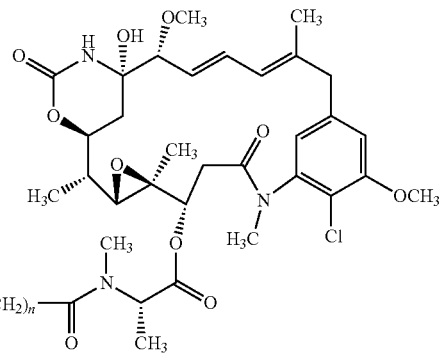

wherein n is an integer from 1-12 and $R^1$ is alkyl.

In some embodiments, the maytansinoid is:

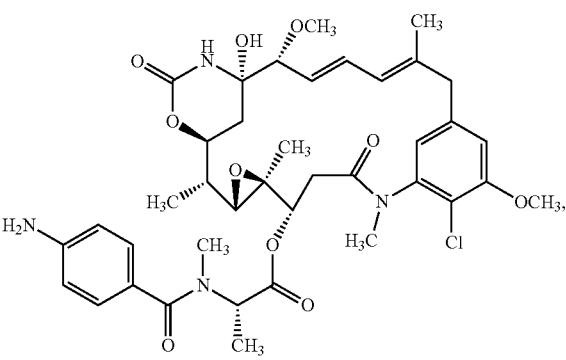

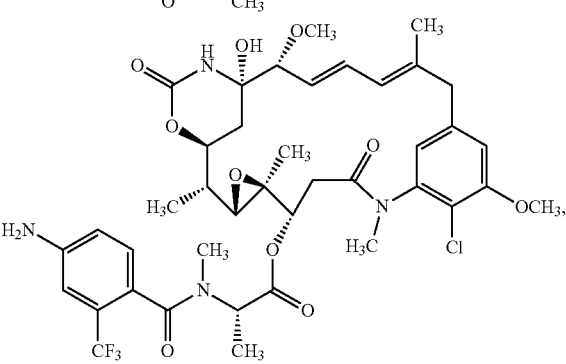

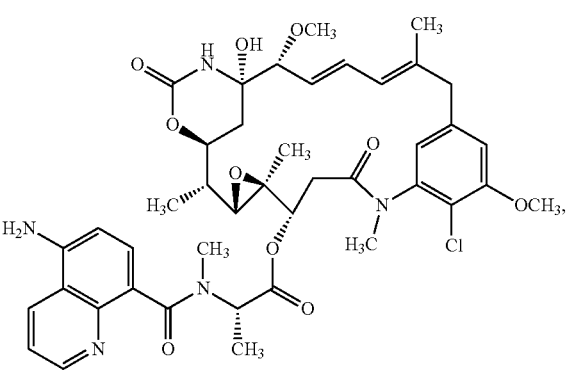

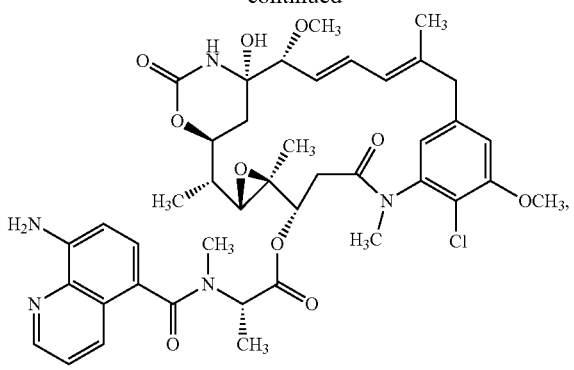
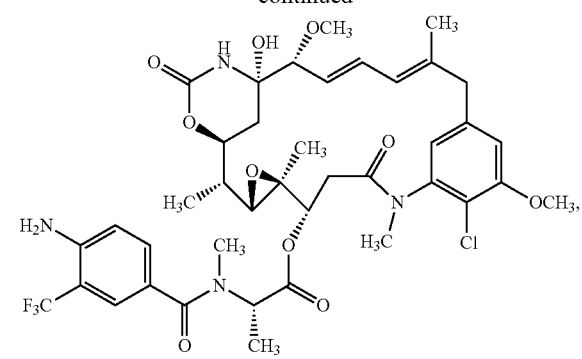
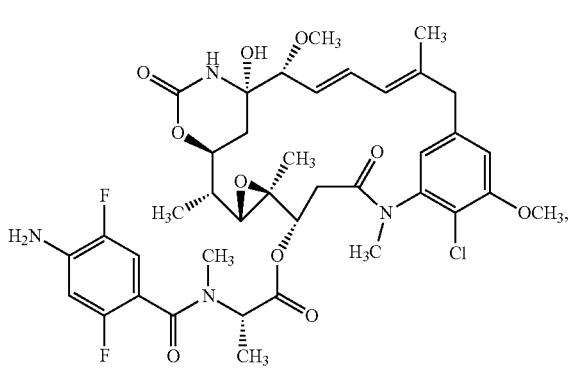
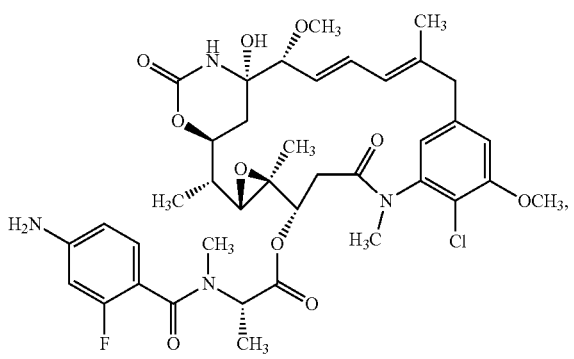
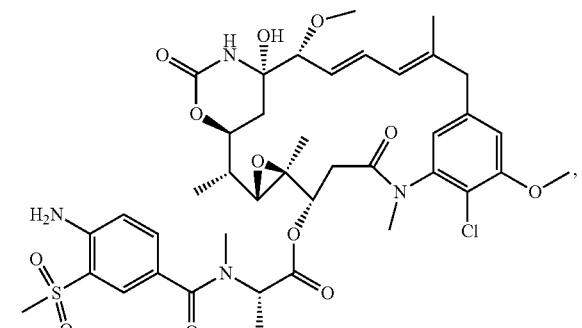
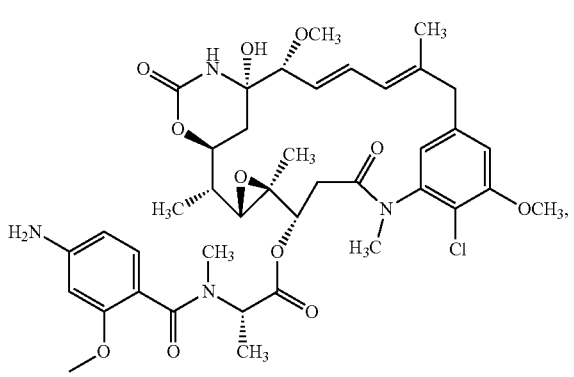
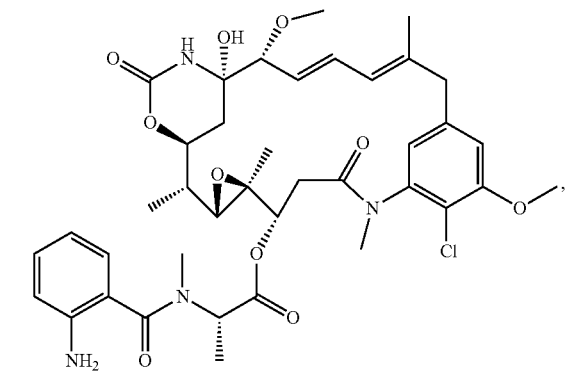

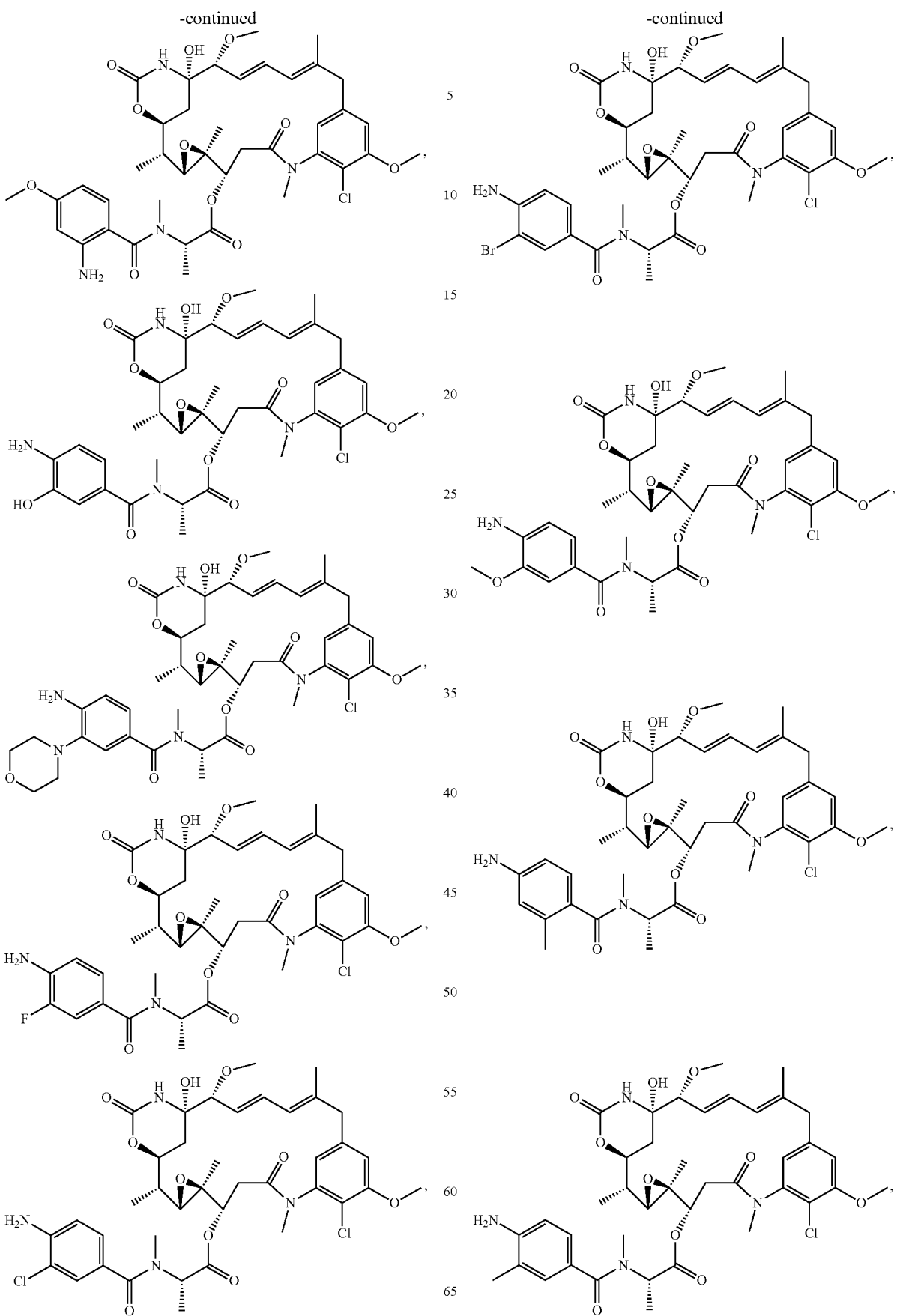

49
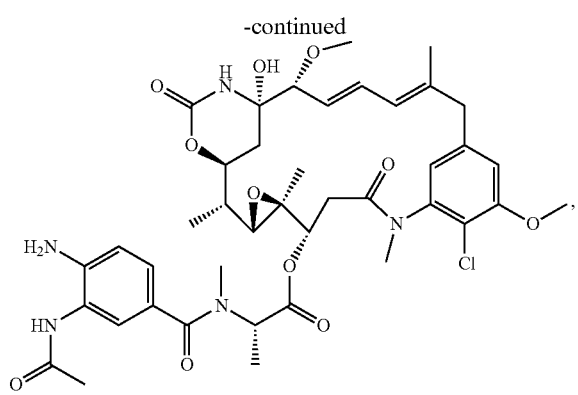
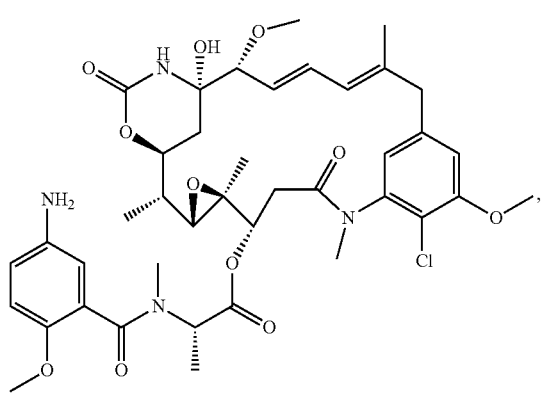
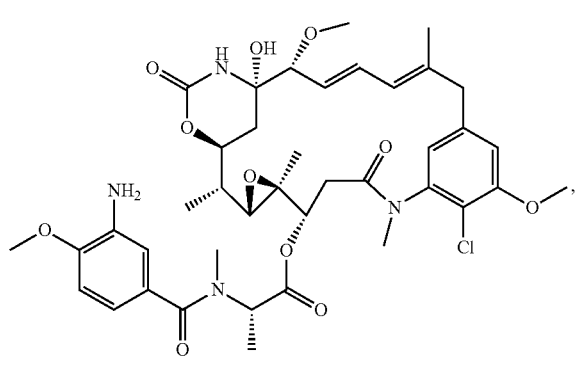
50
-continued
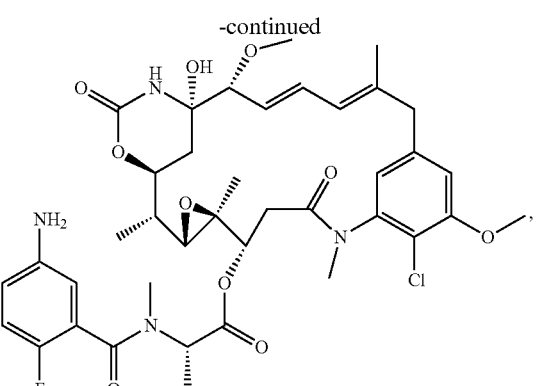
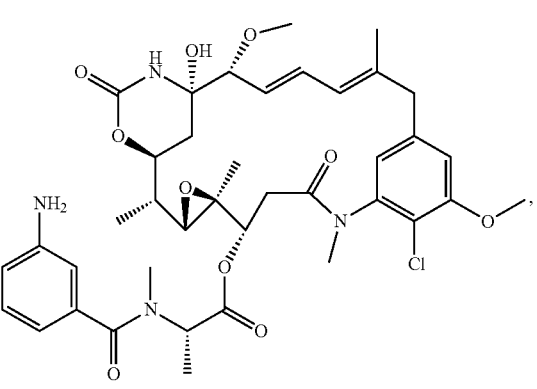
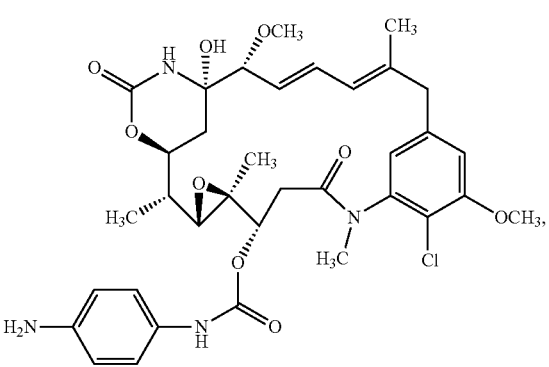

-continued

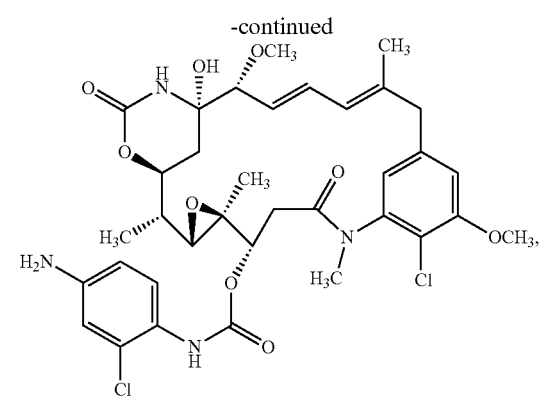

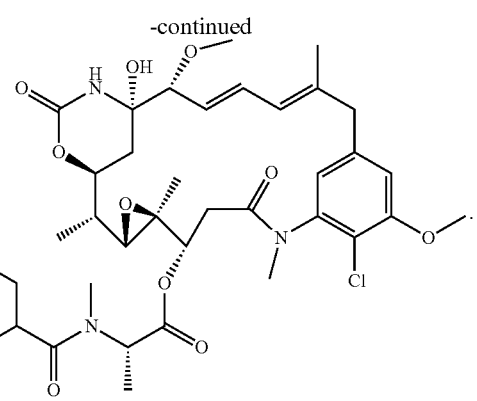

In some embodiments, the maytansinoid is:

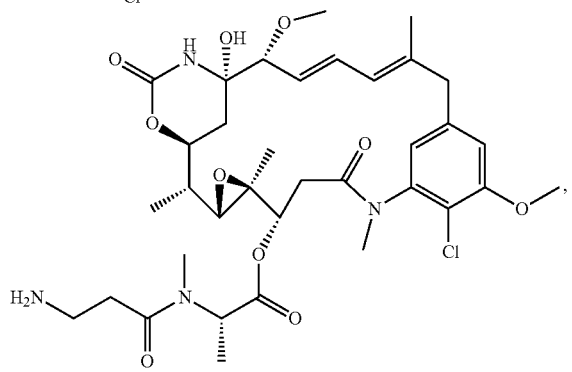

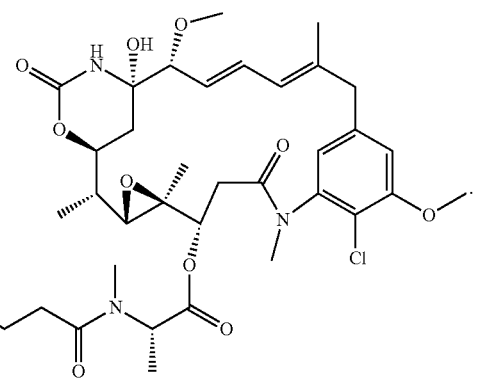

In some embodiments, the maytansinoid is:

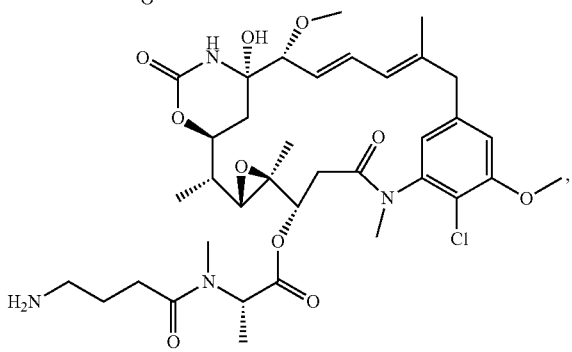

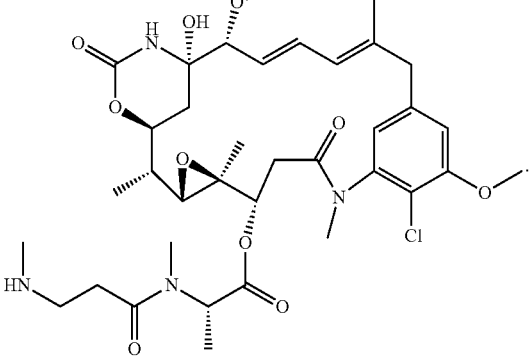

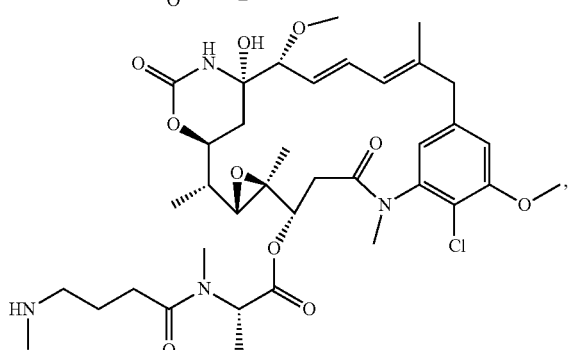

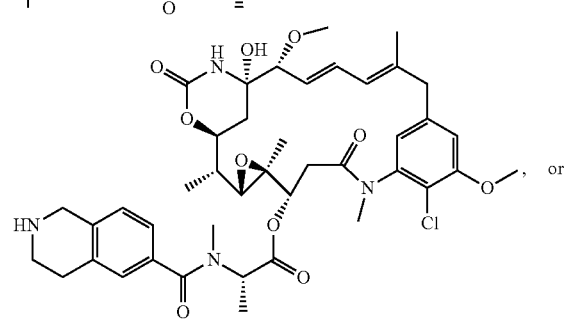

or

Also provided herein are antibody-radionuclide conjugates (ARCs) comprising anti-CD63 antibodies conjugated to one or more radionuclides. Exemplary radionuclides that can be used in the context of this aspect of the disclosure include, but are not limited to, e.g., $^{225}$Ac, $^{212}$Bi, $^{213}$Bi, $^{131}$I, $^{186}$Re, $^{227}$Th, $^{222}$Rn, $^{223}$Ra, $^{224}$Ra, and $^{90}$Y.

In certain embodiments provided herein, ADCs are provided comprising, e.g., an anti-TAA×anti-CD63 bispecific antigen-binding protein conjugated to a cytotoxic agent (e.g., any of the cytotoxic agents disclosed above) via a linker molecule. Linkers are any group or moiety that links, connects, or bonds the antibody or antigen-binding proteins described herein with a therapeutic moiety, e.g. cytotoxic agent. Suitable linkers may be found, for example, in

*Antibody-Drug Conjugates and Immunotoxins*; Phillips, G. L., Ed.; Springer Verlag: New York, 2013; *Antibody-Drug Conjugates*; Ducry, L., Ed.; Humana Press, 2013; *Antibody-Drug Conjugates*; Wang, J., Shen, W.-C., and Zaro, J. L., Eds.; Springer International Publishing, 2015, the contents of each incorporated herein in their entirety by reference. Generally, suitable binding agent linkers for the antibody conjugates described herein are those that are sufficiently stable to exploit the circulating half-life of the antibody and, at the same time, capable of releasing its payload after antigen-mediated internalization of the conjugate. Linkers can be cleavable or non-cleavable. Cleavable linkers include linkers that are cleaved by intracellular metabolism following internalization, e.g., cleavage via hydrolysis, reduction, or enzymatic reaction. Non-cleavable linkers include linkers that release an attached payload via lysosomal degradation of the antibody following internalization. Suitable linkers include, but are not limited to, acid-labile linkers, hydrolysis-labile linkers, enzymatically cleavable linkers, reduction labile linkers, self-immolative linkers, and non-cleavable linkers. Suitable linkers also include, but are not limited to, those that are or comprise peptides, glucuronides, succinimide-thioethers, polyethylene glycol (PEG) units, hydrazones, mal-caproyl units, dipeptide units, valine-citruline units, and para-aminobenzyl (PAB) units.

Any linker molecule or linker technology known in the art can be used to create or construct an ADC of the present disclosure. In certain embodiments, the linker is a cleavable linker. According to other embodiments, the linker is a non-cleavable linker. Exemplary linkers that can be used in the context of the present disclosure include, linkers that comprise or consist of e.g., MC (6-maleimidocaproyl), MP (maleimidopropanoyl), val-cit (valine-citrulline), val-ala (valine-alanine), val-gly (valine-glycine), dipeptide site in protease-cleavable linker, ala-phe (alanine-phenylalanine), dipeptide site in protease-cleavable linker, PAB (p-amino-benzyloxycarbonyl), SPP (N-Succinimidyl 4-(2-pyridylthio) pentanoate), SMCC (N-Succinimidyl 4-(N-maleimidomethyl)cyclohexane-1 carboxylate), SIAB (N-Succinimidyl (4-iodo-acetyl)aminobenzoate), and variants and combinations thereof. Additional examples of linkers that can be used in the context of the present disclosure are provided, e.g., in U.S. Pat. No. 7,754,681 and in Ducry, Bioconjugate Chem., 2010, 21:5-13, and the references cited therein, the contents of which are incorporated by reference herein in their entireties.

In certain embodiments, the linkers are stable in physiological conditions. In certain embodiments, the linkers are cleavable, for instance, able to release at least the payload portion in the presence of an enzyme or at a particular pH range or value. In some embodiments, a linker comprises an enzyme-cleavable moiety. Illustrative enzyme-cleavable moieties include, but are not limited to, peptide bonds, ester linkages, hydrazones, and disulfide linkages. In some embodiments, the linker comprises a cathepsin-cleavable linker.

In some embodiments, the linker comprises a non-cleavable moiety.

Suitable linkers also include, but are not limited to, those that are chemically bonded to two cysteine residues of a single binding agent, e.g., antibody. Such linkers can serve to mimic the antibody's disulfide bonds that are disrupted as a result of the conjugation process.

In some embodiments, the linker comprises one or more amino acids. Suitable amino acids include natural, non-natural, standard, non-standard, proteinogenic, non-proteinogenic, and L- or D-α-amino acids. In some embodiments, the linker comprises alanine, valine, glycine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, or combination thereof. In certain embodiments, one or more side chains of the amino acids is linked to a side chain group, described below. In some embodiments, the linker comprises valine and citrulline. In some embodiments, the linker comprises lysine, valine, and citrulline. In some embodiments, the linker comprises lysine, valine, and alanine. In some embodiments, the linker comprises valine and alanine.

In some embodiments, the linker comprises a self-immolative group. The self-immolative group can be any such group known to those of skill. In particular embodiments, the self-immolative group is p-aminobenzyl (PAB), or a derivative thereof. Useful derivatives include p-aminobenzyloxycarbonyl (PABC). Those of skill will recognize that a self-immolative group is capable of carrying out a chemical reaction which releases the remaining atoms of a linker from a payload.

In some embodiments, the linker is:

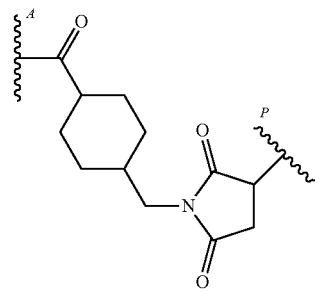

wherein

is a bond to the antibody or antigen-binding protein (e.g., via lysine residue) and

is a bond to the cytotoxic agent (e.g., DM1). In some embodiments, the linker is:

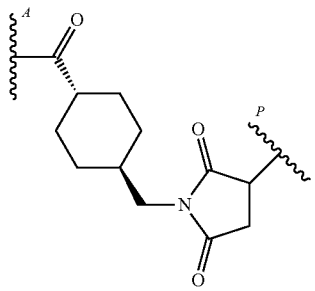

wherein

is a bond to the antibody or antigen-binding protein (e.g., via lysine residue) and is a bond to the cytotoxic agent (e.g., DM1). In certain embodiments, the linker is:

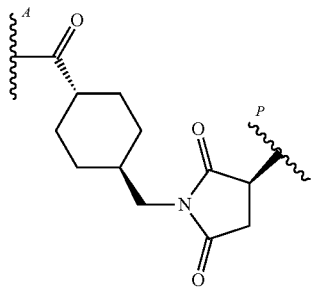

In certain embodiments, the linker is:

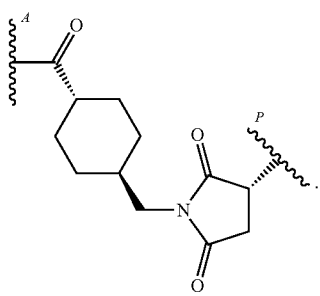

In some embodiments, the linker is derived from maleimidylmethyl-4-trans-cyclohexanecarboxysuccinate:

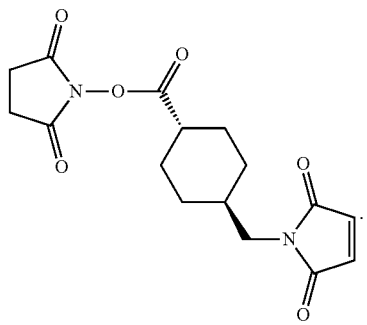 [SMILES: O=C1C=CC(=O)N1C[C@H]1CC[C@H](C(=O)ON2C(=O)CCC2=O)CC1]

In some embodiments, the linker is:

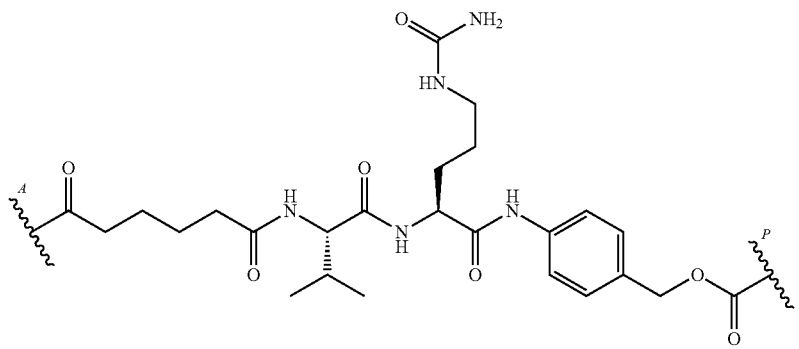

wherein

is a bond to the antibody or antigen-binding protein (e.g., via lysine residue) and

is a bond to the cytotoxic agent (e.g., a compound having the following formula:

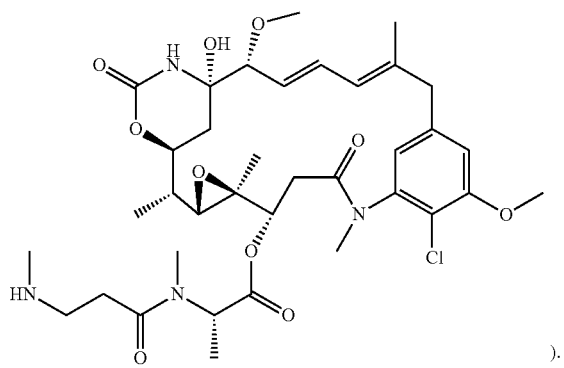 [SMILES: CNCCC(=O)N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

).

*Bioconjugate Chem.*, 2008, 19:358-361; WO 2005/089808; U.S. Pat. No. 5,714,586; and US 2013/0101546), cysteine (see, e.g., US 2007/0258987; WO 2013/055993; WO 2013/055990; WO 2013/053873; WO 2013/053872; WO 2011/130598; US 2013/0101546; and U.S. Pat. No. 7,750,116), selenocysteine (see, e.g., WO 2008/122039; and Hofer et al., *Proc. Natl. Acad. Sci., USA,* 2008, 105:12451-12456), formyl glycine (see, e.g., Carrico et al., *Nat. Chem. Biol.,* 2007, 3:321-322; Agarwal et al., *Proc. Natl. Acad. Sci., USA,* 2013, 110:46-51, and Rabuka et al., *Nat. Protocols,* 2012, 10:1052-1067), non-natural amino acids (see, e.g., WO 2013/068874, and WO 2012/166559), and acidic amino acids (see, e.g., WO 2012/05982). Linkers can also be conjugated to an antigen-binding protein via attachment to carbohydrates (see, e.g., US 2008/0305497, WO 2014/065661, and Ryan et al., *Food & Agriculture Immunol.,* 2001, 13:127-130) and disulfide linkers (see, e.g., WO 2013/085925, WO 2010/010324, WO 2011/018611, and Shaunak et al., *Nat. Chem. Biol.,* 2006, 2:312-313). Site specific conjugation techniques can also be employed to direct conjugation to particular residues of the antibody or antigen binding protein (see, e.g., Schumacher et al. *J Clin Immunol* (2016) 36(Suppl 1): 100). Site specific conjugation techniques, include, but are not limited to glutamine conjugation via transglutaminase (see e.g., Schibli, Angew Chemie Inter Ed. 2010, 49, 9995).

According to certain embodiments, the present disclosure provides ADCs, wherein an anti-TAA×anti-CD63 bispecific antigen-binding protein as described herein is conjugated to a linker-drug composition as set forth in International Patent Publication WO2014/145090, (e.g., compound "7," also referred to herein as "M0026" and depicted below), the disclosure of which is hereby incorporated by reference herein in its entirety:

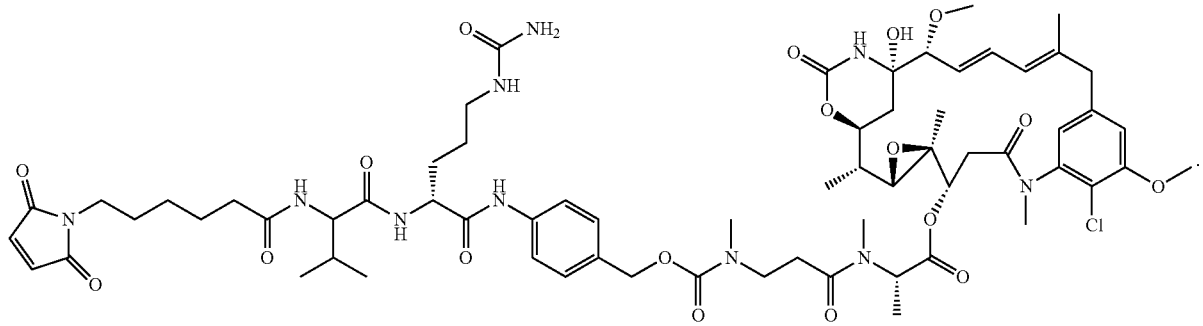

The present disclosure comprises ADCs in which a linker connects an anti-TAA×anti-CD63 bispecific antigen-binding protein to a drug or cytotoxin through an attachment at a particular amino acid within the antibody or antigen-binding molecule. Exemplary amino acid attachments that can be used in the context of this aspect, e.g., lysine (see, e.g., U.S. Pat. No. 5,208,020; US 2010/0129314; Hollander et al., Provided herein are also antibody-drug conjugates comprising the anti-TAA×anti-CD63 bispecific antigen-binding proteins, where said anti-TAA×anti-CD63 bispecific antigen-binding protein is conjugated to a cytotoxic agent. In certain embodiments, the cytotoxic agent is a maytansinoid. In certain embodiments, the maytansinoid is a compound having the following formula:

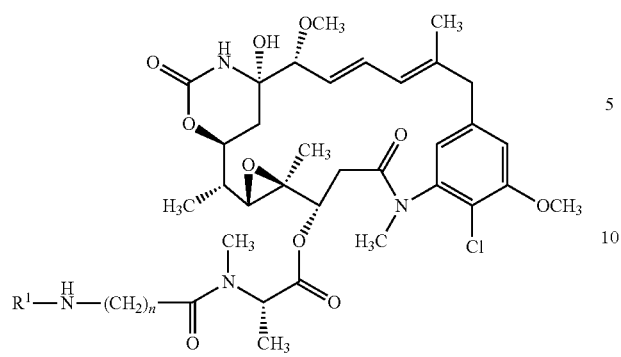

wherein n is an integer from 1-12 and R¹ is alkyl. In certain embodiments, the maytansinoid is

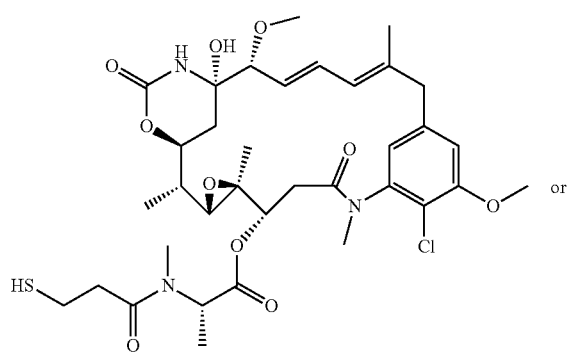

or

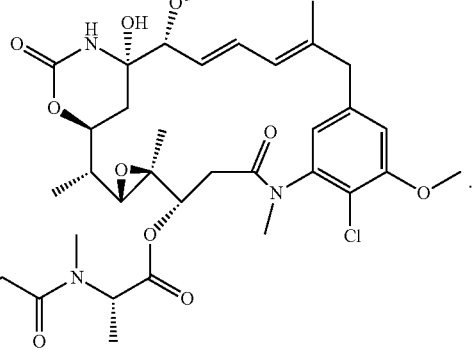

In certain embodiments, the cytotoxic agent is a maytansinoid, and the maytansinoid is covalently attached to the antibody via non-cleavable linker. In certain embodiments, the cytotoxic agent is a maytansinoid, and the maytansinoid is covalently attached to the antibody via cleavable linker.

In one embodiment, the antibody is conjugated to:

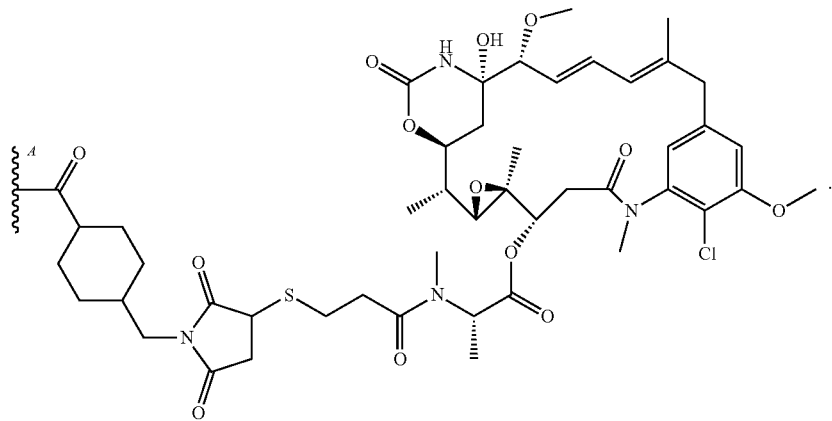

wherein

is a bond to the antibody.

In one embodiment, the antibody is conjugated to:
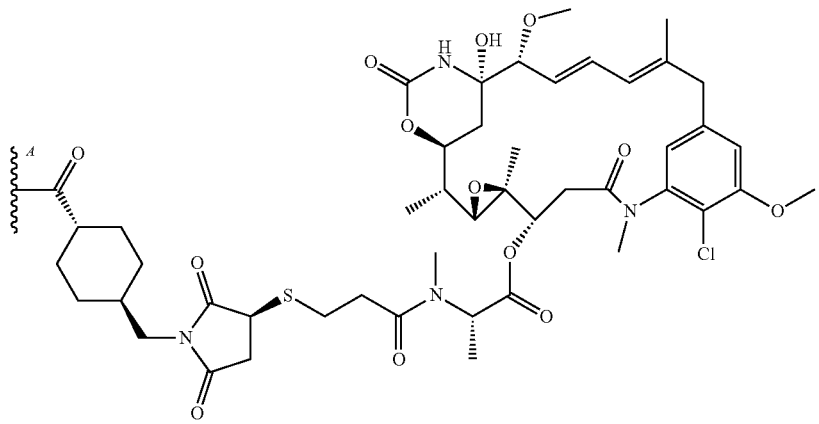
wherein
is a bond to the antibody.
In one embodiment, the antibody is conjugated to:
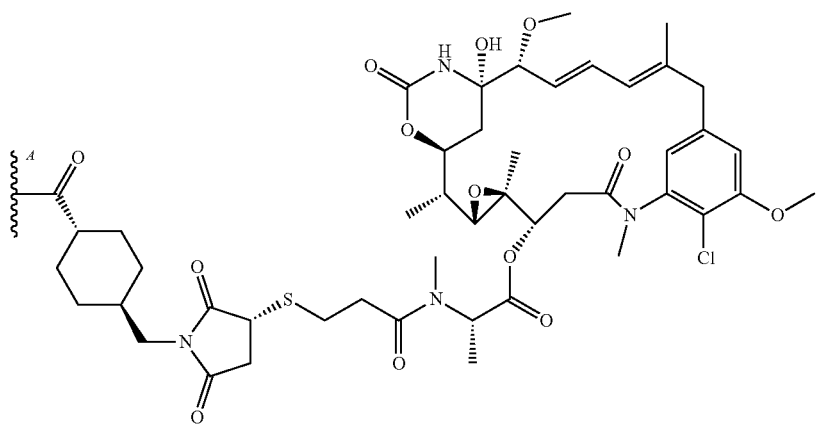
wherein
is a bond to the antibody.

In one embodiment, the antibody is conjugated to:

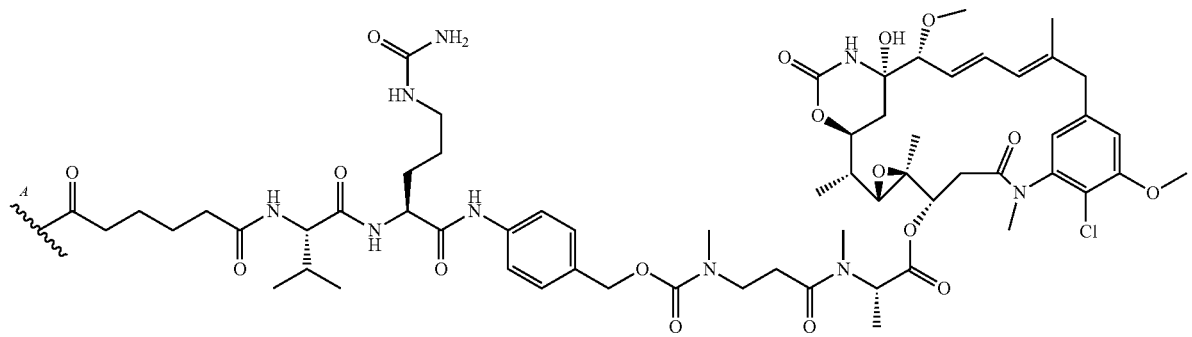

wherein

is a bond to the antibody.

In some embodiments, the conjugates have the following structure:

Ab-[L-Pay]$_n$ wherein:
Ab is an anti-TAA×anti-CD63 bispecific antigen-binding protein as described herein;
L is a linker;
Pay is a cytotoxic agent; and
n is an integer from 1-10.

In some embodiments, Ab is any of the antibodies or antigen-binding proteins described in Table 1.

In some embodiments, Payload is a maytansinoid.

In some embodiments, Pay is:

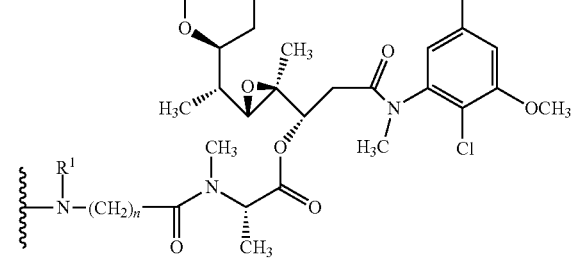

wherein R$^1$ is alkyl.

In some embodiments, Pay is:

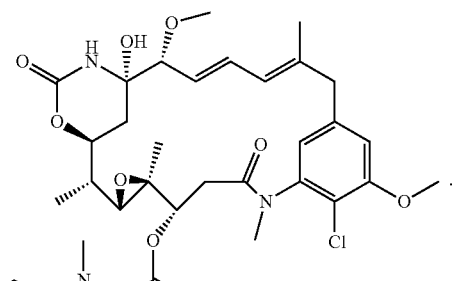

In some embodiments, Pay is:

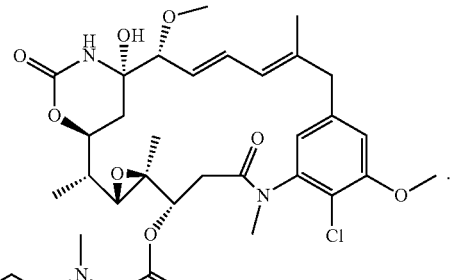

In some embodiments, n is an integer from 2 to 5.

In some embodiments, -L-Pay is:
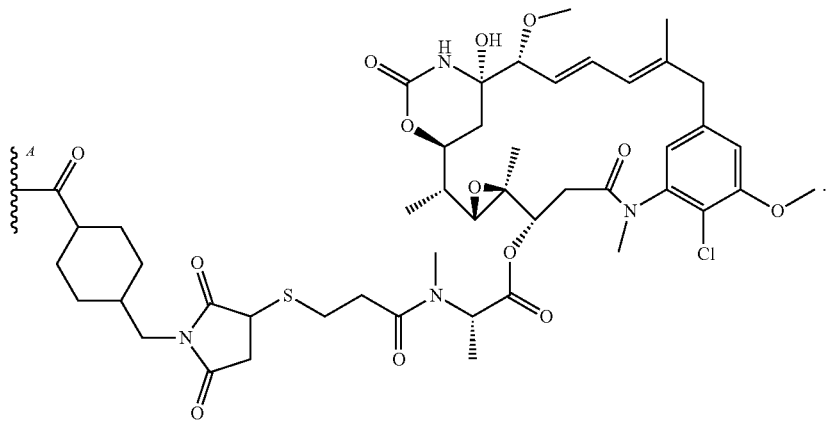
wherein
is a bond to the antibody.
In some embodiments, -L-Pay is:
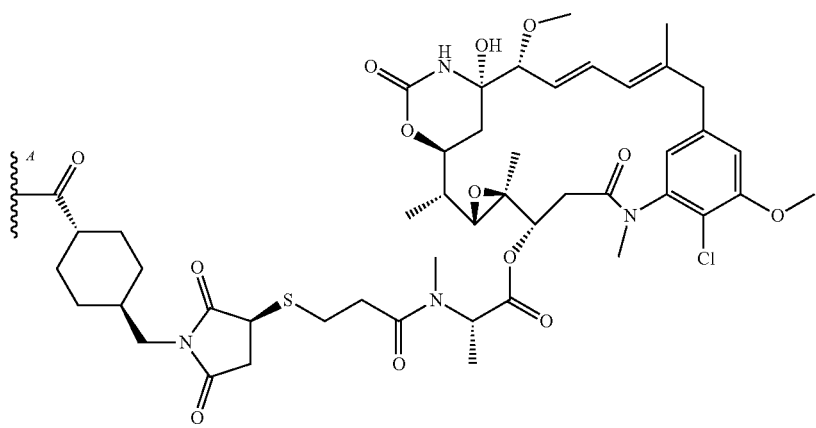
wherein
is a bond to the antibody.

In some embodiments, -L-Pay is:
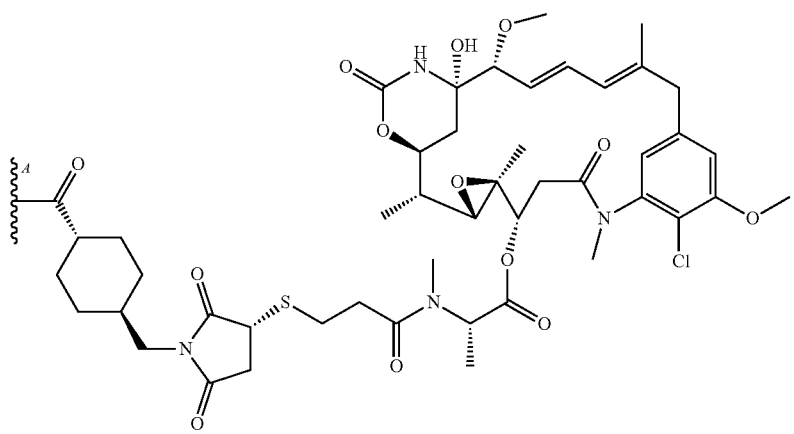
wherein
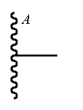
is a bond to the antibody.
In some embodiments, -L-Pay is:
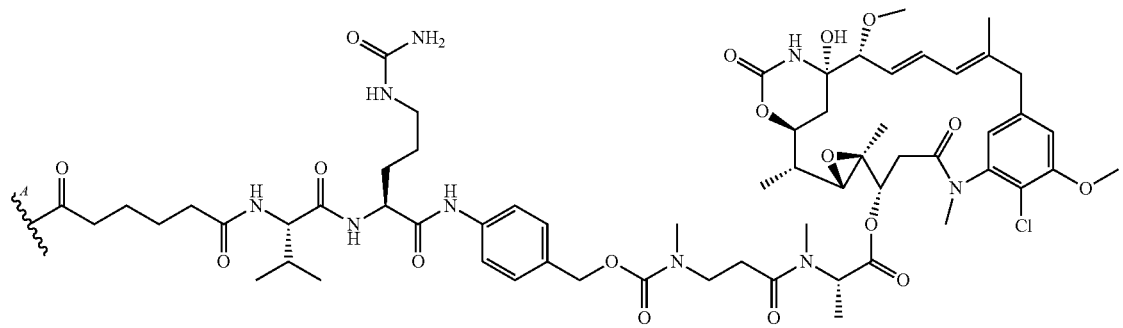
wherein
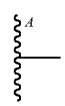
is a bond to the antibody.
In some embodiments, -L-Pay is:
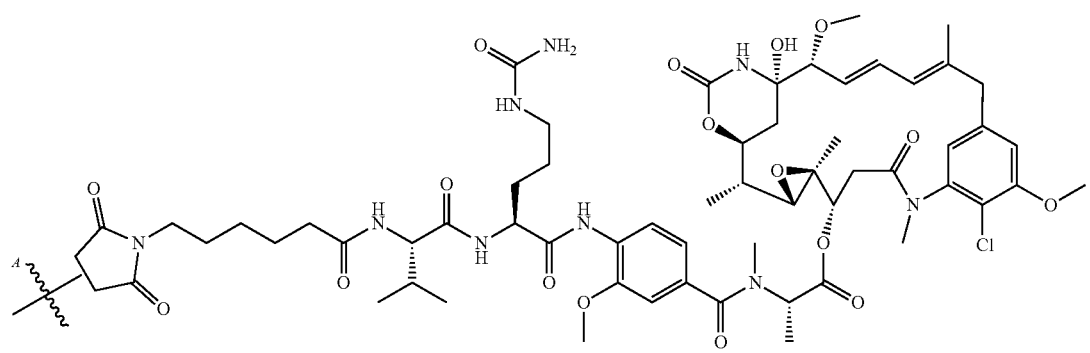

wherein

is a bond to the antibody.

The antibody drug conjugates described herein can be prepared using conjugation conditions known to those of ordinary skill in the art, (see, e.g., Doronina et al. *Nature Biotechnology* 2003, 21, 7, 778, which is incorporated herein by reference in its entirety). In some embodiments an anti-TAA×anti-CD63 bispecific antigen-binding protein drug conjugate is prepared by contacting an anti-TAA×anti-CD63 bispecific antigen-binding protein described herein with a compound comprising the desired linker and cytotoxic agent, wherein said linker possesses a moiety that is reactive with the antibody or antigen-binding protein, e.g., at the desired residue of the antibody or antigen-binding protein.

In some embodiments, provided herein are processes for preparing an antibody-drug conjugate comprising contacting an anti-TAA×anti-CD63 bispecific antigen-binding protein described herein with a compound having the following formula $A^1$:

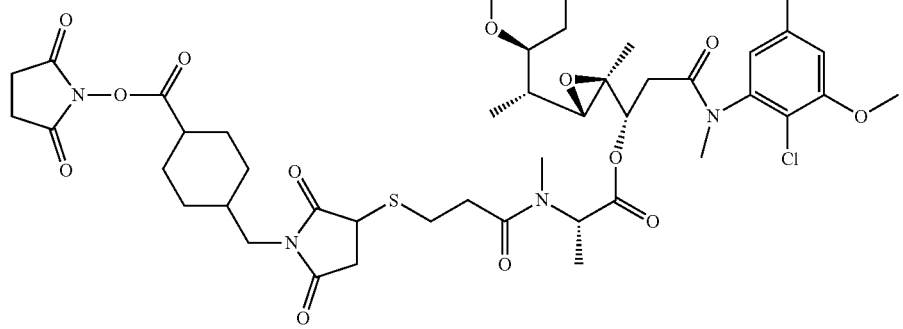

and aqueous diluent.

In some embodiments, the compound of formula $A^1$ is present in stoichiometric excess. In some embodiments, the compound of formula $A^1$ is present in 5-6 fold stoichiometric excess. In some embodiments, the aqueous diluent comprises HEPES. In some embodiments, the aqueous diluent comprises DMA.

In some embodiments, the compound of formula $A^1$ is a compound of formula $A^2$ or $A^3$:

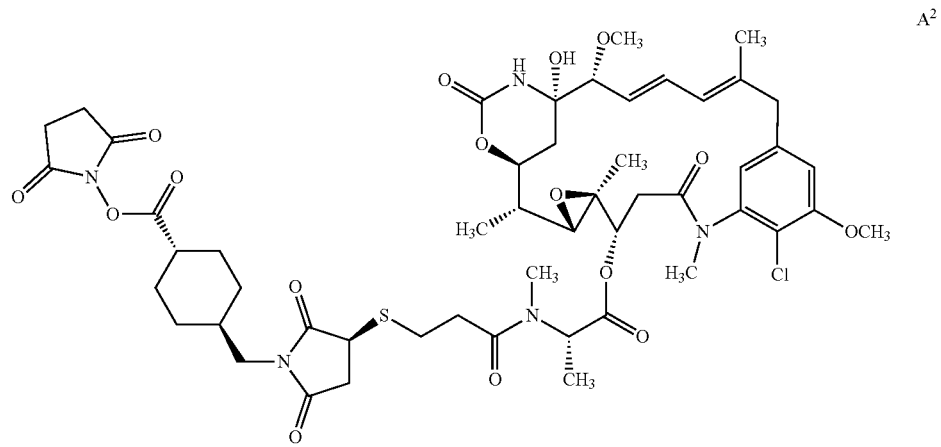

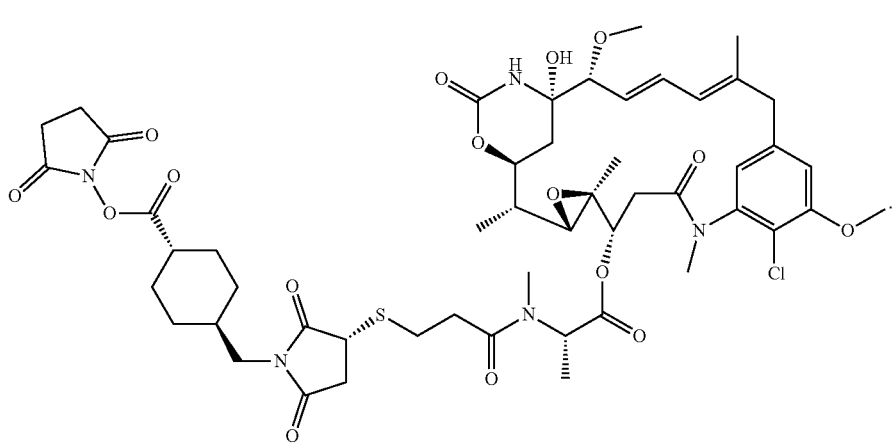

In some embodiments, the compound of formula $A^2$ is $A^3$ stereomerically pure. In some embodiments, the compound of formula $A^1$ comprises a compound of formula $A^1$ or $A^2$, wherein the compound of $A^1$ or $A^2$ is present in a diastereomeric excess of more than 50%. In certain embodiments, the diastereomeric excess is more than 70%. In certain embodiments, the diastereomeric excess is more than 90%. In certain embodiments, the diastereomeric excess is more than 95%. Structures $A^1$, $A^2$ and $A^3$ individually or collectively are known as SMCC-DM1.

The term "diastereomeric excess" refers to the difference between the mole fraction of the desired single diastereomer as compared to the remaining diastereomers in a composition. Diastereomeric excess is calculated as follows: (amount of single diastereomer)–(amount of other diastereomers)/1. For example, a composition that contains 90% of 1 and 10% of 2, 3, 4, or a mixture thereof has a diastereomeric excess of 80% [(90-10)/1]. A composition that contains 95% of 1 and 5% of 2, 3, 4, or a mixture thereof has a diastereomeric excess of 90% [(95–5)/1]. A composition that contains 99% of 1 and 1% of 2, 3, 4, or a mixture thereof has a diastereomeric excess of 98% [(99-1)/1]. The diastereomeric excess can similarly be calculated for any one of 1, 2, 3, or 4.

In some embodiments, the compound of formula $A^1$ is prepared by contacting a compound of formula (a):

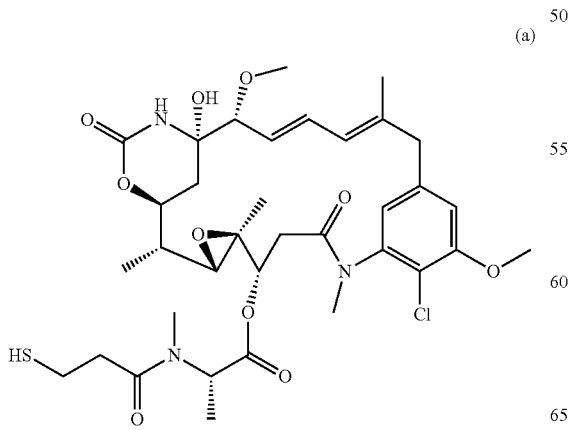

(a)

with a compound of formula (b)

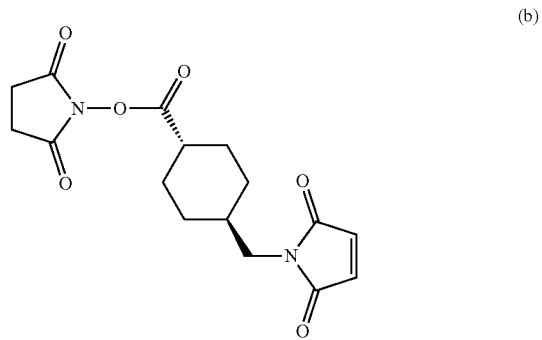 [SMILES: O=C1C=CC(=O)N1C[C@H]1CC[C@H](C(=O)ON2C(=O)CCC2=O)CC1]

(b)

in the presence of silica gel and diluent. In some embodiments, the diluent comprises an organic solvent and water.

Provided herein is also the product prepared by the process of:

(i) contacting a compound of formula (a):

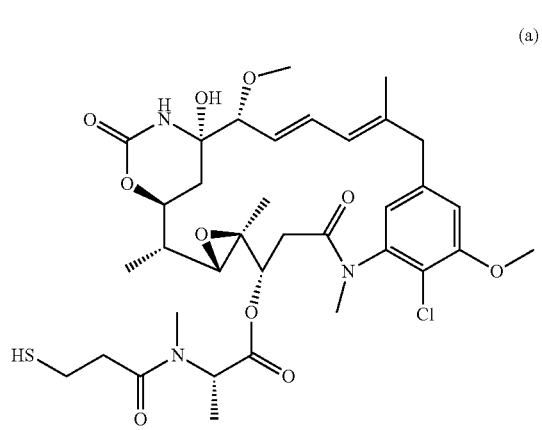 [SMILES: COc1cc2cc(c1Cl)N(C)C(=O)C[C@H](OC(=O)[C@H](C)N(C)C(=O)CCS)[C@]1(C)O[C@H]1[C@H](C)[C@@H]1C[C@@](O)(NC(=O)O1)[C@H](OC)/C=C/C=C(\C)C2]

(a)

with a compound of formula (b):

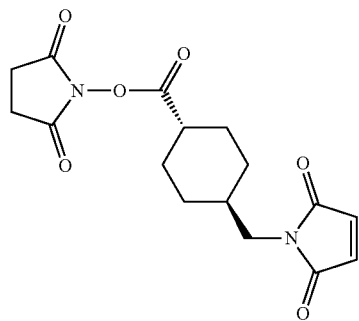

(b)

in the presence of silica gel and diluent to synthesize an intermediate; and (ii) contacting an anti-TAA×anti-CD63 bispecific antigen-binding protein with the intermediate and aqueous diluent.

In some embodiments, provided herein are processes for preparing an antibody-drug conjugate comprising contacting an anti-TAA×anti-CD63 bispecific antigen-binding protein described herein with a compound having the following formula B:

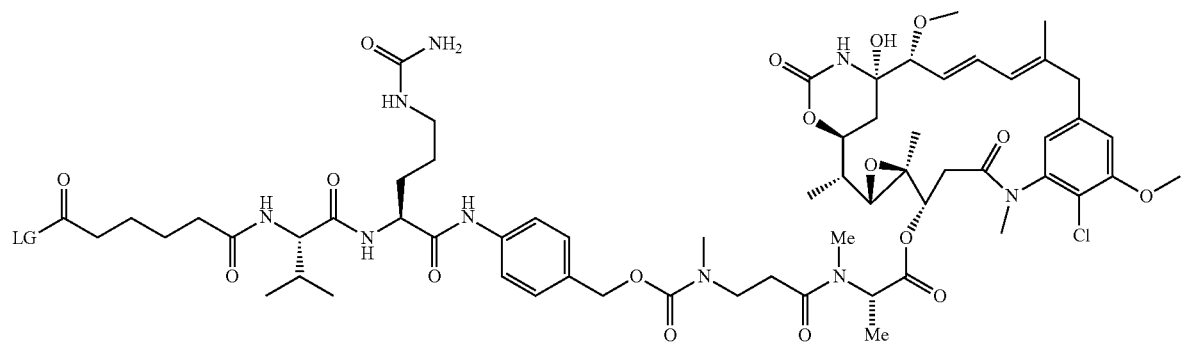

B wherein LG is a leaving group, and aqueous diluent.

In some embodiments, the compound of formula B is present in stoichiometric excess. In some embodiments, the compound of formula B is present in 5-6 fold stoichiometric excess. In some embodiments, the aqueous diluent comprises HEPES. In some embodiments, the aqueous diluent comprises DMA. In some embodiments, the —C(O)-LG is an ester, e.g., NHS or pentafluorophenyl ester.

In some embodiments, the compound of formula B is a compound of formula $B^1$ known as Compound I:

(Compound I)

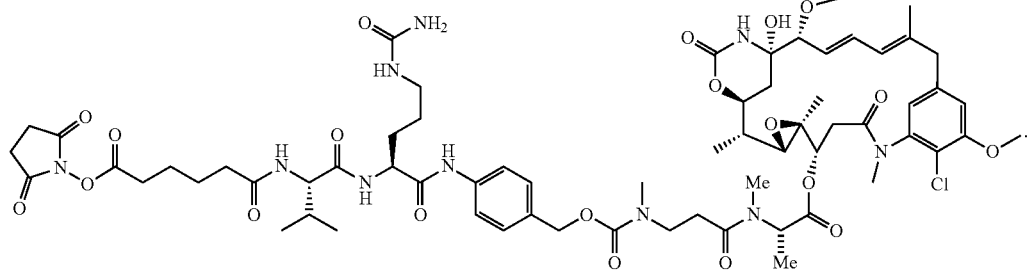

$B^1$

In some embodiments, the compound of formula C is known as Compound II:

(Compound II)

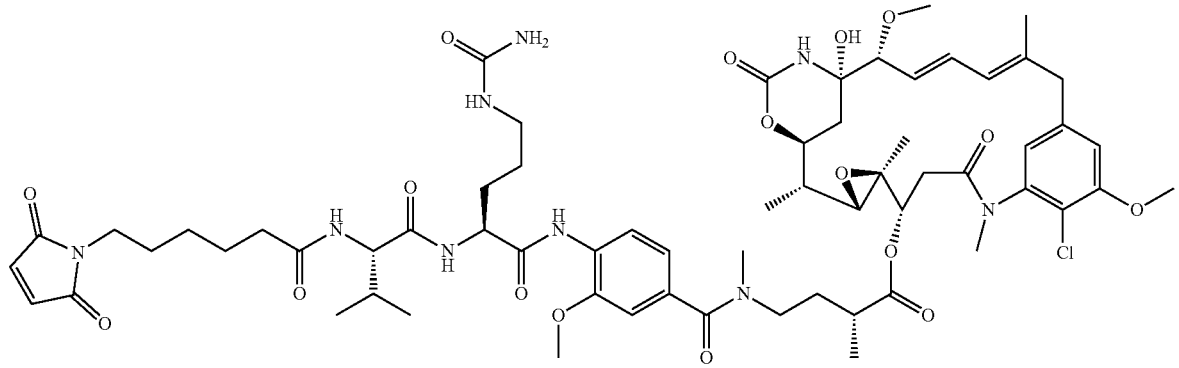

Drug-to-antibody ratio (DAR) is the average number of drugs conjugated to the antibody or antigen-binding fragment, which has an important effect on the efficacy, potency and pharmacokinetics of the ADC. In various embodiments, the DAR is from 1, 2, 3, 4, 5, 6, 7, or 8 drug molecules per antibody. In some embodiments, the DAR is from 1 to 4. In certain embodiments, the DAR is from 2 to 4. In some cases, the DAR is from 2 to 3. In certain cases, the DAR is from 3 to 4. In some embodiments, the DAR is from 1 to 10, 1 to 20 or 1 to 30 (i.e., from 1 to 30 drug molecules per antibody or antigen-binding fragment thereof).

Therapeutic Formulation and Administration

The present invention provides pharmaceutical compositions comprising the antigen-binding molecules of the present invention. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, PA These formulations include, for example, powders, pastes, ointments, jellies, waxes, oils, lipids, lipid (cationic or anionic) containing vesicles (such as LIPOFECTIN™, Life Technologies, Carlsbad, CA), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antigen-binding molecule administered to a patient may vary depending upon the age and the size of the patient, target disease, conditions, route of administration, and the like. The preferred dose is typically calculated according to body weight or body surface area. When a bispecific antigen-binding molecule of the present invention is used for therapeutic purposes in an adult patient, it may be advantageous to intravenously administer the bispecific antigen-binding molecule of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering a bispecific antigen-binding molecule may be determined empirically; for example, patient progress can be monitored by periodic assessment, and the dose adjusted accordingly. Moreover, interspecies scaling of dosages can be performed using well-known methods in the art (e.g., Mordenti et al., 1991, Pharmaceut. Res. 8:1351).

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN (Dey, L.P.), and the HUMIRA™ Pen (Abbott Labs, Abbott Park IL), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Florida. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic and Diagnostic Uses thereof

Disclosed herein are also methods comprising administering to a subject in need thereof a therapeutic composition comprising an anti-CD63 antibody or antigen-binding fragment thereof (including a multispecific binding molecule or multidomain therapeutic protein comprising same) or an antibody-drug conjugate comprising an anti-CD63 antibody (e.g., an anti-CD63 antibody or ADC comprising any of the HCVR/LCVR or CDR sequences as set forth in Table 1 herein). The therapeutic composition can comprise any of the anti-CD63 antibodies, antigen-binding fragments thereof, or ADCs disclosed herein, and a pharmaceutically acceptable carrier or diluent.

The antibodies, antigen-binding fragment thereof (including a multispecific binding molecule or multidomain therapeutic protein comprising same) or an antibody-drug conjugate comprising an anti-CD63 antibody of the invention may be useful, inter alia, for the treatment, prevention and/or amelioration of any disease or disorder associated with or mediated by CD63. For example, the antibodies and ADCs of the present invention are useful for the treatment of tumors that express CD63, and in some embodiments a TAA which may be targeted by a bispecific antibody of the invention. The antibodies, antigen-binding fragment thereof (including a multispecific binding molecule or multidomain therapeutic protein comprising same) or an antibody-drug conjugate comprising an anti-CD63 antibody of the invention may also be useful in treating mast cell (MC-) dependent diseases, rheumatoid arthritis, IgE-dependent allergic reactions and Fc-ER1-mediated allergic reaction, asthma, cancer and/or metastases, etc. See, e.g., Kraft et al. (2005) JEM201:385; Valadi (2007) Nat. Cell Biol. 9:654

The anti-CD63 antibodies of the invention have various utilities. In one embodiment, the anti-CD63 antibodies are useful for the affinity purification of exosomes, e.g., in which the anti-CD63 antibodies disclosed herein can be immobilized on a suitable support, such as a Sephadex resin or filter paper, using methods well known in the art, and then contacted with a sample containing the desired exosomes containing CD63 to be purified, and thereafter the support is washed with a suitable solvent that will remove substantially all the material in the sample except the exosomes which are bound to the immobilized antibody. Finally, the support can be washed with another suitable solvent that will release the exosomes from the antibody. In another embodiment, anti-CD63 antibodies may be used in diagnostic assays for CD63, e.g., detecting its expression in specific cells, tissues, or serum, e.g., as a reagent to identify/label exosomes. See, e.g., Valadi et al. (2007) Nature Cell. Biol: 9(6):654-9. Various diagnostic and prognostic assay techniques known in the art may be used, such as competitive binding assays, direct or indirect sandwich assays and immunoprecipitation assays conducted in either heterogeneous or homogeneous phases (Zola (1987) Monoclonal Antibodies: A Manual of Techniques, CRC Press, Inc. pp. 147-1581). The antibodies used in the assays can be labeled with a detectable moiety. The detectable moiety should be capable of producing, either directly or indirectly, a detectable signal. Any method known in the art for conjugating the antibody to the detectable moiety may be employed.

In another embodiment, provided is a method of treatment of a disease, such as cancer. The method of the invention preferably includes the step of providing an antibody or CD63 antigen-binding fragment thereof, as described above, to a subject requiring said treatment.

Methods of immunotargeting cancer cells using antibodies or antibody fragments are well known in the art. U.S. Pat. No. 6,306,393, for instance, describes the use of anti-CD22 antibodies in the immunotherapy of B-cell malignancies, and U.S. Pat. No. 6,329,503 describes immunotargeting of cells that express serpentine transmembrane antigens. Antibodies described herein (including humanized or human monoclonal antibodies or fragments or other modifications thereof, optionally conjugated to cytotoxic or other agents) can be introduced into a patient such that the antibody binds to cancer cells and mediates the destruction of the cells and the tumor and/or inhibits the growth of the cells or the tumor.

Without intending to limit the disclosure, mechanisms by which such antibodies can exert a therapeutic effect may include, for example, complement-mediated cytolysis, antibody-dependent cellular cytotoxicity (ADCC)1 modulating the physiologic function of the tumor antigen, inhibiting binding or signal transduction pathways, modulating tumor cell differentiation, altering tumor angiogenesis factor profiles, modulating the secretion of immune stimulating or tumor suppressing cytokines and growth factors, modulating cellular adhesion, and/or by inducing apoptosis.

Example 1: Exemplary CD63 Antibodies

Generation of Anti-Human CD63 Antibodies

Anti-human CD63 antibodies were obtained by immunizing a mouse (e.g., an engineered mouse comprising DNA encoding human immunoglobulin heavy and human kappa light chain variable regions), with human CD63.

Following immunization, splenocytes were harvested from each mouse and either (1) fused with mouse myeloma cells to preserve their viability and form hybridoma cells and screened for human CD63 specificity, or (2) B-cell sorted (as described in US 2007/0280945A1) using a either a human CD63 fragment as the sorting reagent that binds and identifies reactive antibodies (antigen-positive B cells).

Chimeric antibodies to human CD63 were initially isolated having a human variable region and a mouse constant region using, e.g., VELOCIMMUNE technology as described in U.S. Pat. Nos. 7,105,348; 8,642,835; and 9,622,459, each of which is incorporated herein by reference.

In some antibodies, for testing purposes, mouse constant regions were replaced with a desired human constant region, for example wild-type human CH or modified human CH (e.g. IgG1, IgG2 or IgG4 isotypes), and light chain constant region (CL), to generate a fully human anti-hCD63, including a fully human bispecific antibody comprising an anti-hCD63antibody or antigen binding portion thereof. While the constant region selected may vary according to specific use, high affinity antigen-binding and target specificity characteristics reside in the variable region.

Certain biological properties of the exemplary bispecific antibodies comprising an anti-human CD63 binding arm generated in accordance with the methods of this Example are described in detail in the Examples set forth below.

Heavy and Light Chain Variable Region Amino Acid and Nucleic Acid Sequences of Anti-CD63 Antibodies Table 1 sets forth sequence identifiers of a nucleic acid (NA) sequence encoding, and in parentheses an amino acid (AA) sequence of, a heavy or light chain variable region (HCVR or LCVR, respectively), or a heavy or light chain CDR (HCDR and LCDR, respectively) of selected anti-CD63 antibodies used to generate the multidomain therapeutic anti-CD63 proteins disclosed herein.

TABLE 1 anti-CD63 Sequence Identifiers

| Antibody Designation | SEQ ID NOs: | | | | | | | |
|---|---|---|---|---|---|---|---|---|
| | HCVR NA (AA) | HCDR1 NA (AA) | HCDR2 NA (AA) | HCDR3 NA (AA) | LCVR NA (AA) | LCDR1 NA (AA) | LCDR2 NA (AA) | LCDR3 NA (AA) |
| H1M12451N | 1 (2) | 3 (4) | 5 (6) | 7 (8) | 9 (10) | 11 (12) | 13 (14) | 15 (16) |
| H2M12395N | 17 (18) | 19 (20) | 21 (22) | 23 (24) | 25 (26) | 27 (28) | 29 (30) | 31 (32) |
| H4H12450N | 33 (34) | 35 (36) | 37 (38) | 39 (40) | 41 (42) | 43 (44) | 45 (46) | 47 (48) |
| H2M12450N | 49 (50) | 51 (52) | 53 (54) | 55 (56) | 57 (58) | 59 (60) | 61 (62) | 63 (64) |
| H1M12362N | 65 (66) | 67 (68) | 69 (70) | 71 (72) | 73 (74) | 75 (76) | 77 (78) | 79 (80) |
| H1M12366N | 81 (82) | 83 (84) | 85 (86) | 87 (88) | 89 (90) | 91 (92) | 93 (94) | 95 (96) |
| H1M12386N | 97 (98) | 99 (100) | 101 (102) | 103 (104) | 105 (106) | 107 (108) | 109 (110) | 111 (112) |
| H1M12388N | 113 (114) | 115 (116) | 117 (118) | 119 (120) | 121 (122) | 123 (124) | 125 (126) | 127 (128) |
| H1M12390N | 129 (130) | 131 (132) | 133 (134) | 135 (136) | 137 (138) | 139 (140) | 141 (142) | 143 (144) |
| H2M12385N | 145 (146) | 147 (148) | 149 (150) | 151 (152) | 153 (154) | 155 (156) | 157 (158) | 159 (160) |
| H2M12387N | 161 (162) | 163 (164) | 165 (166) | 167 (168) | 169 (170) | 171 (172) | 173 (174) | 175 (176) |
| H2M12392N | 177 (178) | 179 (180) | 181 (182) | 183 (184) | 185 (186) | 187 (188) | 189 (190) | 191 (192) |
| H2M12394N | 193 (194) | 195 (196) | 197 (198) | 199 (200) | 201 (202) | 203 (204) | 205 (206) | 207 (208) |
| H2M12452N | 209 (210) | 211 (212) | 213 (214) | 215 (216) | 217 (218) | 219 (220) | 221 (222) | 223 (224) |
| H2M12454N | 225 (226) | 227 (228) | 229 (230) | 231 (232) | 233 (234) | 235 (236) | 237 (238) | 239 (240) |

TABLE 1-continued anti-CD63 Sequence Identifiers

| Antibody Designation | SEQ ID NOs: | | | | | | | |
|---|---|---|---|---|---|---|---|---|
| | HCVR NA (AA) | HCDR1 NA (AA) | HCDR2 NA (AA) | HCDR3 NA (AA) | LCVR NA (AA) | LCDR1 NA (AA) | LCDR2 NA (AA) | LCDR3 NA (AA) |
| H2M13022N | 241 (242) | 243 (244) | 245 (246) | 247 (248) | 249 (250) | 251 (252) | 253 (254) | 255 (256) |
| H3M12361N | 257 (258) | 259 (260) | 261 (262) | 263 (264) | 265 (266) | 267 (268) | 269 (270) | 271 (272) |
| H4H11990P2 | 273 (274) | 275 (276) | 277 (278) | 279 (280) | 281 (282) | 283 (284) | 285 (286) | 287 (288) |
| H4H11992P2 | 289 (290) | 291 (292) | 293 (294) | 295 (296) | 281 (282) | 283 (284) | 285 (286) | 287 (288) |
| H4H11993P2 | 297 (298) | 299 (300) | 301 (302) | 303 (304) | 281 (282) | 283 (284) | 285 (286) | 287 (288) |
| H4H11995P2 | 305 (306) | 307 (308) | 309 (310) | 311 (312) | 281 (282) | 283 (284) | 285 (286) | 287 (288) |
| H4H11996P2 | 313 (314) | 315 (316) | 317 (318) | 319 (320) | 281 (282) | 283 (284) | 285 (286) | 287 (288) |
| H4H11997P2 | 321 (322) | 323 (324) | 325 (326) | 327 (328) | 281 (282) | 283 (284) | 285 (286) | 287 (288) |
| H4H11998P2 | 329 (330) | 331 (332) | 333 (334) | 335 (336) | 281 (282) | 283 (284) | 285 (286) | 287 (288) |

Binding by Parental Anti-Human CD63 Antibodies

Relative cell surface binding of the anti-CD63 antibodies to human CD63 expressing cells was accessed via flow cytometry using CD63 positive HEK293 cells (ATCC, Cat #CRL-1573), which endogenously express human CD63, and CD63 negative HEK293/CD63 knock out cells. For the assay, cells were plated in PBS without calcium and magnesium (VWR, Cat #45000-446), containing 2% FBS (Saradigm Cat #1500-500) (Staining Buffer) in 96 well V-bottom plates (Axygen Scientific, Cat #P-96-450-V-C-S). Cells were then incubated with anti-CD63 antibodies or isotype control antibodies at concentrations ranging from 100 nM to 1.7 pM for 30 minutes on ice. Wells containing no antibody were used as controls. HEK293/CD63KO cells were stained with only the highest concentration (100 nM) of the antibodies. The cells were then washed once with staining buffer and were incubated with a PE conjugated anti-mouse Fc secondary antibody (Jackson ImmunoResearch, Cat #115-115-164) at 100 nM for 30 minutes at 4° C. Cells were then washed and fixed using a 50% solution of Cytofix (BD Biosciences, Cat #554655) diluted in PBS. Samples were run on the Intellicyte Hypercyt flow cytometer and results were analyzed in ForeCyt software (Intellicyte) to calculate the mean fluorescent intensity (MFI). Measured values were analyzed using a four parameter logistic equation over a 12-point response curve using GraphPad Prism and the resulting $EC_{50}$ values are reported (Table 12). The signal to noise ratio (S/N) was determined by calculating the ratio of the anti-CD63 antibodies or the control antibodies MFI to the wells containing no antibodies (Table 12).

As shown in Table 2, three of the anti-CD63 antibodies of the invention demonstrated binding to HEK293 cells with S/N values ranging from 21.0 to 31.6 and $EC_{50}$ values ranging from 0.5 nM to 1.9 nM. The non-binding controls did not demonstrate binding to HEK293 cells (S/N≤1.5). Both the anti-CD63 antibodies and the isotype control antibodies demonstrated weak to little binding to the HEK293/CD63KO cells (S/N≤4.4).

TABLE 2

Binding of anti-CD63 antibodies to HEK293 and HEK293/CD63 KO cells as measured by flow cytometry

| Antibody | HEK293 $EC_{50}$ (nM) | HEK293 (S/N) | HEK293/CD63 KO (S/N) |
|---|---|---|---|
| H2M12450N | 0.5 | 26.7 | 2.9 |
| H1M12451N | 1.8 | 31.6 | 4.1 |
| H2M12395N | 1.9 | 21.0 | 2.9 |
| Isotype Control 1 | ND | 1.4 | 4.4 |
| Isotype Control 2 | ND | 1.5 | 1.6 |

ND = Not determined

The ability of the anti-CD63 monoclonal antibodies of the invention to bind to human CD63 expressing cells was also determined using an electrochemiluminescence (ECL) based detection assay.

To generate overexpressing cells, mouse embryonic fibroblast NIH3T3 cells (ATCC, Cat #CRL-1658) were transfected to form a cell line "NIH3T3/hCD63" that stably expresses human CD63 (hCD63; amino acids M1-M238 of accession number NP_001771; SEQ ID NO:337). Expression levels of human CD63 in endogenously expressing cells, a human androgen-sensitive prostate adenocarcinoma cell line, LNCAP (ATCC, Cat #CRL-1740), and human primary glioblastoma cell line, U87MG (ATCC, Cat #HTB-14) were analyzed with a Quantum™ Alexa Fluor® 647 MESF (Bangs Laboratories, Cat #647B) and a Simply Cellular® anti-Mouse IgG (Bangs Laboratories Inc, Cat #815) following the manufacturer's instructions. LNCAP cells were determined to have a lower human CD63 copy number than U87MG cells. Non-transfected NIH3T3 cells, which have no detectable expression of human CD63 by fluorescence activated cell sorting (FACS), were included as a negative control.

Briefly, cell lines were rinsed once in PBS buffer without $Ca^{2+}/Mg^{2+}$ and incubated for 10 minutes at 37° C. with Enzyme Free Cell Dissociation Solution (Millipore, Cat #S-004-C) to detach the cells. Cells were then washed once with PBS with $Ca^{2+}/Mg^{2+}$ and counted with a Cellometer™ Auto T4 cell counter (Nexcelom Bioscience, LLC). Approximately $2.0 \times 10^4$ NIH3T3/hCD63, LNCAP, U87MG or NIH3T3 cells were seeded separately onto 96-well carbon electrode plates (Meso Scale Discovery, Cat #L15)CB-6) and were then incubated for one hour at 37° C. Nonspecific binding sites were blocked with 2% BSA (w/v) in PBS with $Ca^{2+}/Mg^{2+}$ for one hour at room temperature (RT). Solutions containing anti-CD63 antibodies or isotype control antibodies at a range of concentrations (1.7 pM to 100 nM) in 0.5% BSA (w/v) in PBS with $Ca^{2+}/Mg^{2+}$, as well as control buffer alone, were then added in duplicate to the plate-bound NIH3T3/hCD63, LNCAP, U87MG or NIH3T3 cells and incubated for one hour at RT. Plates were subsequently washed to remove unbound antibodies using an Aqua-Max2000 plate washer with a cell washing head (MDS Analytical Technologies). The plate-bound antibodies were detected with 1 μg/mL of either a SULFO-TAG™-conjugated goat polyclonal anti-human IgG antibody specific for Fcγ fragment (Jackson Immunoresearch, Cat #109-005-098) or a SULFO-TAG™-conjugated goat polyclonal anti-mouse IgG antibody specific for Fcγ fragment (Jackson Immunoresearch, Cat #115-005-164) for one hour at RT. Plates were washed and then incubated with Read Buffer (MSD, Cat #R92TD-2) according to the manufacturer's instructions.

Luminescent signals were measured using a SECTOR Imager (MSD). Luminescence intensity, measured in relative light units (RLU), was recorded to indicate the binding intensity of each antibody at the range of concentrations tested. The ratio of signal detected with 3.7 nM antibody binding to human CD63 expressing cells compared to the same concentration of antibody binding to negative cells was reported as an indication of specificity of CD63 binding. Antibodies with the binding ratio of greater than 3 were classified as specific binders and antibodies with the binding ratio less than or equal to 3 were classified as non-binders and marked as NB in Table 13. In addition, the direct binding signals (in RLU) were analyzed as a function of the antibody concentration and the data were fitted with a sigmoidal (four-parameter logistic) dose-response model using GraphPad Prism™ software. The $EC_{50}$ value for binding to human CD63 expressing cells, defined as the concentration of antibody at which 50% of the maximal binding signal is detected, was determined to indicate potency of each antibody and reported in Table 3 only for specific binders. The data for two separate experiments testing different antibodies are reported in Tables 3A and 3B.

As shown in Table 3A, the four anti-CD63 antibodies generated as described in Exathis Example and a Comparator Ab (Comparator 1) bound specifically to human CD63 expressed on engineered NIH3T3/hCD63 cells as well as that endogenously expressed on LNCAP and U87MG cell lines. The four anti-CD63 antibodies described in this Example bound to NIH3T3/hCD63 cells with $EC_{50}$ values ranging from 280 pM to 970 pM and binding ratios over the negative cell line ranging from 91 to 281-fold. The four anti-CD63 antibodies of the invention bound to U87MG cells with $EC_{50}$ values ranging from 500 pM to 1.4 nM and binding ratios over the negative cell line ranging from 52 to 272-fold. The four anti-CD63 antibodies generated as described in this Example bound to LNCAP cells with $EC_{50}$ values ranging from 210 pM to 1.7 nM and binding ratios over the negative cell line ranging from 7 to 20-fold. The lower binding ratios on LNCAP cells are in agreement with lower CD63 copy number on these cells compared to U87MG cells. The isotype control antibodies were non-binders, as expected, with cell binding ratios less than or equal to 3.

TABLE 3A

Anti-CD63 Antibodies Binding to Human CD63 expressing cells as measured by Electrochemiluminescence based detection

| Antibody | Cell Binding Potency, $EC_{50}$ (M) | | | Ratio at 3.7 nM Ab concentration of Cell Binding Signal (RLU) to human CD63 cells relative to negative NIH3T3 | | |
|---|---|---|---|---|---|---|
| | NIH3T3/hCD63 | U87MG | LNCAP | NIH3T3/hCD63 | U87MG | LNCAP |
| H1M12451N | 2.9E−10 | 7.9E−10 | 3.5E−10 | 256 | 171 | 18 |
| H2M12395N | 5.7E−10 | 9.5E−10 | 1.7E−09 | 91 | 52 | 7 |
| H4H12450N | 2.8E−10 | 5.0E−10 | 2.1E−10 | 230 | 175 | 20 |
| H2M12450N | 9.7E−10 | 1.4E−09 | 1.4E−09 | 281 | 272 | 20 |
| CONTROLS | | | | | | |
| Comparator Ab 1 | 5.7E−10 | 6.7E−10 | 2.0E−09 | 253 | 271 | 16 |
| Human IgG4 isotype control | NB | NB | NB | 1 | 1 | 1 |
| Mouse IgG2 isotype control | NB | NB | NB | 3 | 2 | 2 |

NB—non-binder; antibodies with a binding ratio of less than or equal to 3 were classified as non-binders.

As shown in Table 3B, nineteen of the twenty anti-CD63 antibodies tested, as well as a Comparator Ab (Comparator 1), bound specifically to human CD63 expressed on engineered NIH3T3/hCD63 cells and on endogenously expressing U87MG and LNCAP cell lines. One anti-CD63 antibody, H4H11998P2, specifically bound to NIH3T3/hCD63 and U87MG, but did not bind to LNCAP. The twenty anti-CD63 antibodies tested bound to NIH3T3/hCD63 cells with EC50 values ranging from 0.320 nM to 7.4 nM with binding ratios over the negative cell line ranging from 14 to 608-fold and bound to U87MG cells with EC50 values ranging from 0.29 nM to 17 nM with binding ratios ranging from 5 to 405-fold. Nineteen anti-CD63 antibodies bound to LNCAP cells with EC50 values ranging from 0.15 pM to 55 nM with binding ratios over the negative cell line ranging from 4 to 51-fold. The one anti-CD63 antibody, H4H11998P2, was non-binder to LNCAP cells with a cell binding ratio of 1. The lower binding ratios on LNCAP cells are in agreement with lower CD63 copy number on these cells compared to U87MG cells. The isotype control antibodies were non-binders, as expected, with cell binding ratios less than or equal to 3 or binding signal less than 100 RLU on the human CD63 cell lines tested.

TABLE 3B

Anti-CD63 Antibodies Binding to Human CD63 expressing cells as measured by Electrochemiluminescence based detection

| Antibody | Cell Binding Potency, $EC_{50}$ (M) | | | Ratio at 3.7 nM Ab concentration of Cell Binding Signal (RLU) to human CD63 cells relative to negative NIH3T3 | | |
|---|---|---|---|---|---|---|
| | NIH3T3/hCD63 | U87MG | LNCAP | NIH3T3/hCD63 | U87MG | LNCAP |
| H2bM12454N | 3.2E−10 | 4.7E−10 | 1.8E−10 | 175 | 132 | 14 |
| H2aM12394N | 3.8E−10 | 1.4E−09 | 7.5E−10 | 61 | 50 | 4 |
| H2aM12387N | 3.9E−10 | 2.9E−10 | 1.5E−10 | 228 | 172 | 18 |
| H2aM12392N | 4.0E−10 | 5.3E−10 | 2.3E−10 | 608 | 405 | 51 |
| H2bM12385N | 4.5E−10 | 6.4E−10 | 2.9E−10 | 71 | 47 | 5 |
| H2bM13022N | 4.5E−10 | 8.5E−10 | 3.2E−10 | 95 | 71 | 8 |
| H1M12390N | 4.8E−10 | 3.6E−10 | 3.0E−10 | 559 | 339 | 31 |
| H1M12388N | 5.2E−10 | 3.0E−10 | 2.5E−10 | 434 | 284 | 31 |
| H1M12386N | 5.2E−10 | 3.1E−10 | 2.9E−10 | 220 | 129 | 16 |
| H2aM12452N | 6.1E−10 | 2.0E−09 | 7.4E−10 | 593 | 260 | 37 |
| H1M12362N | 6.3E−10 | 5.6E−10 | 5.7E−10 | 283 | 174 | 16 |
| H3M12361N | 8.1E−10 | 1.3E−09 | 1.1E−09 | 243 | 111 | 19 |
| H3M12366N | 8.3E−10 | 2.0E−09 | 1.8E−09 | 310 | 107 | 7 |
| H4H11990P2 | 9.3E−10 | 4.8E−09 | 5.1E−09 | 168 | 66 | 6 |
| H4H11997P2 | 9.4E−10 | 1.7E−09 | 1.9E−09 | 266 | 99 | 11 |
| H4H11996P2 | 9.8E−10 | 8.1E−09 | 4.4E−09 | 188 | 57 | 7 |
| H4H11992P2 | 1.5E−09 | 5.5E−09 | 3.6E−09 | 87 | 33 | 4 |
| H4H11993P2 | 2.5E−09 | 1.7E−08 | 6.7E−09 | 227 | 62 | 8 |
| H4H11995P2 | 5.0E−09 | 1.3E−08 | 5.5E−08 | 212 | 61 | 5 |
| H4H11998P2 | 7.4E−09 | IC | NB | 14 | 5 | 1 |
| CONTROLS | | | | | | |
| Comparator Ab 1 | 9.6E−10 | 1.1E−09 | 5.3E−10 | 589 | 243 | 25 |
| Human IgG4 isotype control | NB | NB | NB | 1 | 4(*) | 1 |
| Mouse IgG2 isotype control | NB | NB | NB | 3 | 2 | 2 |

NB—non-binder; antibodies with a binding ratio of less than or equal to 3 or binding signal of less than 100 RLU.
(*)—binding signal on U87MG was less than 100 RLU and isotype control was classified as non-binder.
IC—inconclusive; no sigmoidal fit observed to calculate $EC_{50}$ value.

Internalization/Cytotoxicity Mediated by Parental Anti-Human CD63 Antibodies

The ability of the anti-CD63 antibodies disclosed herein to bind and internalize on CD63 expressing cells was assessed. For the assay, T47D cells (ATCC, Cat #HTB-133) were seeded into 96 well Collagen coated plates (Greiner, Cat #655956) in RPMI (Irvine Scientific, Cat #9160) containing 10% FBS (ATCC, Cat #30-2020), pencillin/streptomycin/L-glutamine (Gibco, Cat #10378-016), 100 µM sodium pyruvate (Millipore, Cat #TM5-005-C), 1 mM HEPES (ThermoFisher, Cat #15630080), 10 µg/mL Insulin bovine (Gemini BioProducts, Cat #700-912P) (growth media) and allowed to incubate overnight at 37° C. in 5% $CO_2$. To stain, quadruplicate plates of cells were incubated with 10 µg/mL of anti-CD63 antibodies that was diluted in 2% FBS in PBS, without Calcium and Magnesium (Irving, Cat #9240) (staining buffer) for 30 minutes at 4° C. Cells were washed twice with staining buffer, then incubated with an Alexa-Flour 488 conjugated secondary Ab (Jackson Immunoresearch, Cat #115-547-003 or Jackson Immunoresearch, Cat #109-547-003) at 10 µg/mL for 30 minutes at 4° C., and subsequently washed twice more with staining buffer. Two plates were immediately fixed and stained with 4% paraformaldehyde (PFA; ThermoFisher, Cat #28908)+5 uM DRAQ5 (ThermoFisher, Cat #62251) in PBS for 20 minutes (non-internalization plates). The remaining two plates were incubated with growth media at 37° C. for 2 hours followed by fixation and staining for 20 minutes using a solution of 4% PFA+5 µM DRAQ5 diluted in PBS (internalization plates). After fixation, all plates were washed once with PBS. One non-internalization plate and one internalization plate were incubated with an anti-Alexa Fluor 488 antibody (Regeneron) at 50 µg/mL in PBS overnight at 4° C. to quench surface Alexa Fluor 488 fluorescence. The remaining plates were incubated with PBS only. Confocal images were acquired on the Opera Phenix (Perkin Elmer) at 40× magnification. Harmony analysis software (Perkin Elmer) was utilized to identify DRAQ5-labeled cells and the total Alexa-Fluor 488 relative fluorescent units (RFU) per cell was determined. The total binding at 4° C. (RFU values of 4° C. unquenched wells), total binding at 37° C. (RFU values of 37° C. unquenched wells), the total internalized RFU, and the % Internalization were determined for each antibody as shown in Table 1. For all calculations, background fluorescence from $2^{nd}$ Ab only control wells were subtracted from every well. Total internalized RFU was calculated as follows: Total RFU of 37° C. unquenched samples−Surface RFU at 37° C. Surface RFU is defined as unquenched RFU at 37° C.−quenched RFU at 37° C.)/QE. QE (quenching efficiency) is defined as: 1−(Total RFU of 4° C. quenched sample/Total RFU of 4° C. unquenched sample). The % Internalization was determined from the following formula: (Total internalized RFU at 37° C./Total RFU at 37° C.)*100.

As shown in Table 4, all 4 anti-CD63 antibodies of the invention demonstrated internalization into T47D cells ranging from 60.9% to 73.7% internalization. The isotype controls did not demonstrate any measurable internalization.

TABLE 4

Internalization and Surface Binding of anti-CD63 Antibodies in T47D Cells

| Antibody | Total RFU at 4° C. | Total RFU at 37° C. (2 h) | Total Internalized RFU | % Internalization |
|---|---|---|---|---|
| H4H12450N | 2098644 | 2083920 | 1419840 | 68.1 |
| hIgG4 Isotype control | 137648 | −80525 | −75133 | ND* |
| H2aM12450N | 2359553 | 2938050 | 1790248 | 60.9 |
| H1M12451N | 1902759 | 2321763 | 1710839 | 73.7 |
| H2M12395N | 1499634 | 1693000 | 1238752 | 73.2 |
| mIgG1 Isotype control | −93885 | 57417 | 66563 | ND* |
| mIgG2a Isotype control | −73427 | 65365 | 73850 | ND* |

ND*: % internalization could not be determined due to weak binding and/or inability to determine quenching efficiency In order to assess the ability of an anti-CD63 antibody described herein to internalize in CD63 expressing cells, an in vitro indirect cytotoxicity assay was performed. Human CD63 positive T47D cells (ATCC, Cat #HTB-133) and human CD63 negative NIH3T3 cells (ATCC, Cat #CRL-1658) were respectively seeded in PDL-coated 96-well plates (BD Biocoat, Cat #356461) at either 6,000 cells per well in RPMI (Irvine Scientific, Cat #9160) containing 10% FBS (ATCC, Cat #30-2020), pencillin/streptomycin/L-glutamine (Gibco, Cat #10378-016), 50 uM Beta-Mercaptoethanol (Sigma, Cat #M7522) (growth media), Sodium Pyruvate 100 mM (Millipore, Cat #TMS-005-C), HEPES 1M (Irvine Scientific, Cat #9319), and Insulin bovine 10 ug/mL (Gemini BioProducts, Cat #700-912P) or 2,000 cells per well in DME high glucose (Irvine Scientific, Cat #9033), 10% Bovine calf serum (Hyclone, Cat #SH30072.03), plus pencillin/streptomycin/L-glutamine (Gibco, Cat #10378-016) and grown overnight at 37° C. in 5% $CO_2$. For cell viability curves, cells were incubated for 5 minutes at 37° C. with a serially diluted anti-CD63 antibody (H2M12450N) or a non-binding isotype control antibody at concentrations ranging from 3.0 pM to 2.2 nM. A Fab anti-mFc secondary antibody conjugated to the cytotoxic payload MMAF (Moradec, Cat #AM-201AF-50) was then added at 20 nM to each well. Media alone served as a negative control, and 33 µM of digitonin (Promega, Cat #G9441) was used to determine the maximum cytotoxicity. Following a 72 hour incubation, cell viability was measured using Cell Counting Kit-8 (Dojindo, Cat #CK04) as per manufacturer's protocols with an incubation time range of 1-3 hours. The absorbance at 450 nm ($OD_{450}$) was measured on an Envision plate reader (PerkinElmer). Background $OD_{450}$ levels from digitonin treated cells were subtracted from all wells and viability was expressed as a percentage of the untreated controls (% viability). $IC_{50}$ values were determined from a four-parameter logistic equation over an 8-point response curve (GraphPad Prism). All $IC_{50}$ values are expressed in nM concentration and the minimum % viable cells remaining after treatment is reported.

As summarized in Table 5, the anti-CD63 antibody, H2M12450N, reduced T47D viability to 21% with an $IC_{50}$ value of 0.24 nM, whereas the isotype control reduced viability to only 64%. The antibodies had little to no impact on the viability of the NIH3T3 cell line.

TABLE 5

Anti-CD63 antibody internalization measured by an indirect cytotoxicity assay in T47D and NIH3T3 cells

| Antibody | T47D (nM) $IC_{50}$ | T47D % Viability | NIH3T3 (nM) $IC_{50}$ | NIH3T3% Viability |
|---|---|---|---|---|
| H2M12450N | 0.24 | 21 | ND | 83 |
| Isotype Control | ND | 64 | ND | 91 |

ND = Not determined

Biacore Binding Kinetics of Anti-CD63 Monoclonal Antibodies Binding to CD63 (EC2) Loop Reagents Measured at 25° C. and 37° C.

Equilibrium dissociation constants ($K_D$) for different CD63 (EC2) loop reagents binding to purified anti-CD63 monoclonal antibodies were determined using a real-time surface plasmon resonance based Biacore T200 biosensor or Biacore 2000 biosensor. All binding studies were performed in 10 mM HEPES, 150 mM NaCl, 3 mM EDTA, and 0.05% v/v Surfactant Tween-20, pH 7.4 (HBS-ET) running buffer at 25° C. and 37° C. The Biacore CM5 sensor chip surface was first derivatized by amine coupling with either a rabbit anti-mouse Fc specific polyclonal antibody (GE Healthcare, Cat #BR100838) or an anti-human Fab kit (GE Healthcare, Cat #28958325) to capture anti-CD63 monoclonal antibodies. Binding studies were performed on either recombinant human CD63 extracellular loop 2 expressed with a C-terminal Myc-Myc-hexahistidine (hCD63 EC loop 2-MMH; SEQ ID NO:338) or recombinant human CD63 extracellular loop 2 expressed with a C-terminal human Fc tag (hCD63 EC loop 2-hFc; SEQ ID NO:339). Different concentrations of hCD63 EC loop 2-MMH or hCD63 EC loop 2-hFc (either tested at 50 nM-12.5 nM in a 4-fold dilution or at 90 nM-0.37 nM in 3-fold serial dilutions) were first prepared in HBS-ET running buffer and were injected over the captured anti-CD63 monoclonal antibody surface for 4 minutes at a flow rate of 35 µL/minute or 50 µL/minute, while the dissociation of monoclonal antibody bound CD63 reagent was monitored for 8 or 10 minutes in HBS-ET running buffer. The association rate ($K_a$) and dissociation rate ($k_d$) were determined by fitting the real-time binding sensorgrams to a 1:1 binding model with mass transport limitation using Scrubber 2.0c curve-fitting software. Binding dissociation equilibrium constant ($K_D$) and dissociative half-life (t½) were calculated from the kinetic rates as:

$$K_D(M) = \frac{kd}{ka}, \text{ and } t1/2(\min) = \frac{\ln(2)}{60*kd}$$

Binding kinetics parameters for human CD63 EC loop 2 protein binding to different anti-CD63 monoclonal antibodies of the invention at 25° C. and 37° C. are shown in Tables 6 through 9.

At 25° C., 20 of 23 of the anti-CD63 monoclonal antibodies of the invention bound to human CD63 EC loop 2-MMH with $K_D$ values ranging from 676 pM to 11.7 uM, as shown in Table 6. At 37° C., 21 of 23 of the anti-CD63 monoclonal antibodies of the invention bound to human CD63 EC loop 2-MMH with $K_D$ values ranging from 1.15 nM to 12.3 as shown in Table 7. At 25° C., 22 of 23 of the anti-CD63 monoclonal antibodies of the invention bound to human CD63 EC loop 2-Fc with $K_D$ values ranging from 129 pM to 10.1 nM, as shown in Table 8. At 37° C., 22 of 23 of the anti-CD63 monoclonal antibodies of the invention bound to human CD63 EC loop 2-Fc with $K_D$ values ranging from 45.0 pM to 14.5 nM, as shown in Table 9.

TABLE 6

Binding kinetics parameters of human CD63 EC loop 2-MMH binding to anti-CD63 monoclonal antibodies at 25° C.

| Antibody | mAb Capture Level (RU) | 100 nM Ag Bound (RU) | $k_a$ (1/Ms) | $k_d$ (1/s) | $K_D$ (M) | $t\frac{1}{2}$ (min) |
|---|---|---|---|---|---|---|
| H2aM12450N | 592 | 65 | 2.27E+05 | 2.79E-04 | 1.23E-09 | 41 |
| H2aM12395N | 472 | 42 | 1.66E+05 | 1.82E-03 | 1.10E-08 | 6 |
| H1M12451N | 525 | 52 | 8.59E+04 | 4.30E-04 | 5.00E-09 | 27 |
| H1M12386N | 405 | 65 | 5.40E+05 | 3.65E-04 | 6.76E-10 | 32 |
| H1M12388N | 408 | 59 | 8.15E+05 | 5.87E-04 | 7.20E-10 | 20 |
| H2aM12387N | 532 | 74 | 5.43E+05 | 5.40E-04 | 9.94E-10 | 21 |
| H3M12361N | 367 | 43 | 2.58E+05 | 8.05E-04 | 3.12E-09 | 14 |
| H2aM12452N | 348 | 35 | 8.13E+04 | 5.96E-04 | 7.33E-09 | 19 |
| H2aM12392N | 595 | 79 | 2.98E+05 | 9.22E-04 | 3.10E-09 | 13 |
| H2bM12454N | 485 | 61 | 3.84E+05 | 1.88E-03 | 4.89E-09 | 6 |
| H1M12362N | 308 | 51 | 1.13E+05 | 1.44E-03 | 1.27E-08 | 8 |
| H2bM13022N | 350 | 48 | 1.02E+05 | 1.32E-03 | 1.30E-08 | 9 |
| H1M12390N | 418 | 54 | 3.23E+05 | 3.36E-03 | 1.04E-08 | 3 |
| H2bM12385 | 536 | 48 | 3.22E+05 | 3.31E-03 | 1.03E-08 | 3 |
| H2aM12394N | 670 | 27 | 5.91E+04 | 5.53E-04 | 9.36E-09 | 21 |
| H3M12366N | 239 | 21 | IC | IC | IC | IC |
| H4H11990P2 | 707 | 94 | 1.93E+05 | 5.91E-03 | 3.06E-08 | 2 |
| H4H11997P2 | 819 | 106 | 1.86E+05 | 3.71E-03 | 1.99E-08 | 3.1 |
| H4H11998P2 | 633 | 11 | 2.64E+03 | 3.09E-02 | 1.17E-05 | 0.4 |
| H4H11996P2 | 628 | 61 | 1.65E+05 | 1.40E-02 | 8.49E-08 | 0.8 |
| H4H11995P2 | 643 | 8 | IC | IC | IC | IC |
| H4H11992P2 | 743 | 53 | 1.25E+05 | 2.67E-02 | 2.13E-07 | 0.4 |
| H4H11993P2 | 601 | 10 | IC | IC | IC | IC |

IC = inconclusive binding

TABLE 7

Binding kinetics parameters of human CD63 EC loop2-MMH binding to anti-CD63 monoclonal antibodies at 37° C.

| Antibody | mAb Capture Level (RU) | 100 nM Ag Bound (RU) | $k_a$ (1/Ms) | $k_d$ (1/s) | $K_D$ (M) | $t\frac{1}{2}$ (min) |
|---|---|---|---|---|---|---|
| H2aM12450N | 617 | 58 | 1.75E+05 | 2.01E-04 | 1.15E-09 | 57 |
| H2aM12395N | 535 | 31 | 1.65E+05 | 9.32E-03 | 5.64E-08 | 1 |
| H1M12451N | 597 | 44 | 8.89E+04 | 1.90E-03 | 2.14E-08 | 6 |
| H1M12386N | 455 | 65 | 6.50E+05 | 2.35E-03 | 3.61E-09 | 5 |
| H1M12388N | 462 | 60 | 6.51E+05 | 3.27E-03 | 5.02E-09 | 4 |
| H2aM12387N | 590 | 77 | 6.79E+05 | 3.54E-03 | 5.21E-09 | 3 |
| H3M12361N | 425 | 39 | 4.95E+05 | 2.89E-03 | 5.85E-09 | 4 |
| H2aM12452N | 421 | 34 | 3.85E+05 | 2.69E-03 | 6.98E-09 | 4 |
| H2aM12392N | 626 | 68 | 4.47E+05 | 3.24E-03 | 7.25E-09 | 4 |
| H2bM12454N | 586 | 56 | 5.59E+05 | 5.91E-03 | 1.06E-08 | 2 |
| H1M12362N | 369 | 32 | 3.69E+05 | 7.20E-03 | 1.95E-08 | 2 |
| H2bM13022N | 395 | 31 | 3.11E+05 | 6.71E-03 | 2.15E-08 | 2 |
| H1M12390N | 440 | 38 | 4.19E+05 | 1.49E-02 | 3.56E-08 | 1 |
| H2bM12385 | 642 | 44 | 2.71E+05 | 1.09E-02 | 4.00E-08 | 1 |
| H2aM12394N | 753 | 19 | 3.62E+04 | 2.77E-03 | 7.67E-08 | 4 |
| H3M12366N | 292 | 0 | NB | NB | NB | NB |
| H4H11990P2 | 840 | 81 | 1.60E+05 | 1.98E-02 | 1.24E-07 | 0.6 |
| H4H11997P2 | 899 | 74 | 1.32E+05 | 1.92E-02 | 1.45E-07 | 0.6 |
| H4H11998P2 | 639 | 3 | 5.28E+05 | 9.17E-02 | 1.74E-07 | 0.1 |
| H4H11996P2 | 704 | 46 | 1.08E+05 | 3.89E-02 | 3.61E-07 | 0.3 |
| H4H11995P2 | 674 | 3 | 7.94E+04 | 1.28E-01 | 1.62E-06 | 0.1 |
| H4H11992P2 | 889 | 30 | 6.60E+03 | 8.14E-02 | 1.23E-05 | 0.1 |
| H4H11993P2 | 723 | 3 | IC | IC | IC | IC |

IC = inconclusive binding
NB = no binding

TABLE 8

Binding kinetics parameters of human CD63 EC loop2-hFC binding to anti-CD63 monoclonal antibodies at 25° C.

| Antibody | mAb Capture Level (RU) | 100 nM Ag Bound (RU) | $k_a$ (1/Ms) | $k_d$ (1/s) | $K_D$ (M) | $t^{1/2}$ (min) |
|---|---|---|---|---|---|---|
| H2aM12450N | 592 | 134 | 3.20E+05 | 4.66E−05 | 1.50E−10 | 248 |
| H2aM12395N | 472 | 117 | 6.77E+05 | 5.10E−04 | 7.53E−10 | 23 |
| H1M12451N | 525 | 107 | 1.19E+05 | 8.40E−05 | 7.04E−10 | 138 |
| H1M12386N | 405 | 160 | 6.54E+05 | 1.13E−04 | 1.73E−10 | 102 |
| H1M12388N | 408 | 131 | 7.28E+05 | 1.73E−04 | 2.38E−10 | 67 |
| H2aM12387N | 532 | 164 | 8.54E+05 | 1.10E−04 | 1.29E−10 | 105 |
| H3M12361N | 367 | 83 | 4.41E+05 | 1.32E−04 | 2.99E−10 | 87 |
| H2aM12452N | 348 | 91 | 1.22E+05 | 2.28E−04 | 1.87E−09 | 51 |
| H2aM12392N | 595 | 169 | 5.10E+05 | 1.99E−04 | 3.91E−10 | 58 |
| H2bM12454N | 485 | 142 | 6.88E+05 | 3.60E−04 | 5.23E−10 | 32 |
| H1M12362N | 308 | 125 | 4.77E+05 | 3.99E−04 | 8.40E−10 | 29 |
| H2bM13022N | 350 | 117 | 4.60E+05 | 2.80E−04 | 6.10E−10 | 41 |
| H1M12390N | 418 | 150 | 5.23E+05 | 9.91E−04 | 1.89E−09 | 12 |
| H2bM12385 | 536 | 121 | 5.92E+05 | 9.84E−04 | 1.66E−09 | 12 |
| H2aM12394N | 670 | 59 | 8.18E+04 | 1.44E−04 | 1.76E−09 | 80 |
| H3M12366N | 239 | 51 | IC | IC | IC | IC |
| H4H11990P2 | 707 | 275 | 4.30E+05 | 8.99E−05 | 2.09E−10 | 128 |
| H4H11997P2 | 819 | 291 | 4.17E+05 | 6.20E−05 | 1.49E−10 | 186 |
| H4H11998P2 | 633 | 136 | 1.75E+05 | 4.53E−04 | 2.58E−09 | 26 |
| H4H11996P2 | 628 | 257 | 4.61E+05 | 1.35E−04 | 2.92E−10 | 86 |
| H4H11995P2 | 643 | 198 | 5.52E+05 | 5.55E−03 | 1.01E−08 | 2 |
| H4H11992P2 | 743 | 304 | 6.41E+05 | 2.57E−04 | 4.01E−10 | 45 |
| H4H11993P2 | 601 | 194 | 3.64E+05 | 7.28E−04 | 2.00E−09 | 16 |

IC = inconclusive binding

TABLE 9

Binding kinetics parameters of human CD63 EC loop2-hFC binding to anti-CD63 monoclonal antibodies at 37° C.

| Antibody | mAb Capture Level (RU) | 100 nM Ag Bound (RU) | $k_a$ (1/Ms) | $k_d$ (1/s) | $K_D$ (M) | $t^{1/2}$ (min) |
|---|---|---|---|---|---|---|
| H2aM12450N | 617 | 138 | 4.11E+05 | 4.89E−05 | 1.19E−10 | 236 |
| H2aM12395N | 535 | 123 | 5.29E+05 | 1.79E−03 | 3.38E−09 | 6 |
| H1M12451N | 597 | 118 | 6.51E+05 | 3.31E−04 | 5.09E−10 | 35 |
| H1M12386N | 455 | 170 | 9.21E+05 | 6.31E−04 | 6.85E−10 | 18 |
| H1M12388N | 462 | 158 | 1.03E+06 | 8.87E−04 | 8.63E−10 | 13 |
| H2aM12387N | 590 | 196 | 1.10E+06 | 6.57E−04 | 5.96E−10 | 18 |
| H3M12361N | 425 | 97 | 6.51E+05 | 3.70E−04 | 5.68E−10 | 31 |
| H2aM12452N | 421 | 104 | 7.79E+05 | 8.57E−04 | 1.10E−09 | 13 |
| H2aM12392N | 626 | 177 | 7.65E+05 | 4.45E−04 | 5.82E−10 | 26 |
| H2bM12454N | 586 | 160 | 8.68E+05 | 7.77E−04 | 8.95E−10 | 15 |
| H1M12362N | 369 | 118 | 6.85E+05 | 6.69E−04 | 9.77E−10 | 17 |
| H2bM13022N | 395 | 107 | 5.57E+05 | 5.62E−04 | 1.01E−09 | 21 |
| H1M12390N | 440 | 134 | 9.07E+05 | 4.95E−04 | 5.46E−10 | 23 |
| H2bM12385 | 642 | 133 | 8.27E+05 | 1.70E−03 | 2.05E−09 | 7 |
| H2aM12394N | 753 | 67 | 3.27E+05 | 5.04E−04 | 1.54E−09 | 23 |
| H3M12366N | 292 | 0 | NB | NB | NB | NB |
| H4H11990P2 | 840 | 338 | 4.82E+05 | 4.96E−05 | 1.04E−10 | 233 |
| H4H11997P2 | 899 | 342 | 4.25E+05 | 1.91E−05 | 4.50E−11 | 603 |
| H4H11998P2 | 639 | 111 | 3.18E+05 | 2.07E−03 | 6.50E−09 | 6 |
| H4H11996P2 | 704 | 294 | 5.38E+05 | 1.42E−04 | 2.64E−10 | 81 |
| H4H11995P2 | 674 | 116 | 1.29E+06 | 1.88E−02 | 1.45E−08 | 1 |
| H4H11992P2 | 889 | 358 | 6.47E+05 | 6.82E−04 | 1.05E−09 | 17 |
| H4H11993P2 | 723 | 156 | 5.77E+05 | 4.57E−03 | 7.92E−09 | 3 |

IC = inconclusive binding

Octet Cross-Competition Between Different Anti-CD63 Monoclonal Antibodies

Binding competition between a panel of anti-CD63 monoclonal antibodies was determined using a real time, label-free bio-layer interferometry assay on the Octet HTX biosensor platform (Pall ForteBio Corp.). The entire experiment was performed at 25° C. in 10 mM HEPES, 150 mM NaCl, 3 mM EDTA, and 0.05% v/v Surfactant Tween-20, 1 mg/mL BSA, pH7.4 (HBS-EBT) buffer with the plate shaking at the speed of 1000 rpm. To assess whether 2 antibodies are able to compete with one another for binding to their respective epitopes on the recombinant human CD63 EC loop 2 expressed with a C-terminal myc-myc-hexahistidine tag (hCD63 EC Loop 2-MMH; SEQ ID: xx), around ~0.61 nm of hCD63 EC Loop 2-MMH was first captured onto anti-Penta-His antibody coated Octet biosensor tips (Fortebio Inc, #18-5122) by submerging the biosensor tips for 3 minutes in wells containing 20 μg/mL solution of hCD63 EC Loop 2-MMH. The antigen captured biosensor tips were then saturated with first anti-CD63 monoclonal antibody (subsequently referred to as mAb-1) by dipping into wells containing 50 μg/mL solution of mAb-1 for 210 seconds. The biosensor tips were then subsequently dipped into wells containing 50 μg/mL solution of a second anti-CD63 monoclonal antibody (subsequently referred to as mAb-2) for 120 seconds. The biosensor tips were washed in HBS-EBT buffer in between every step of the experiment. The real-time binding response was monitored during the entire course of the experiment and the binding response at the end of every step was recorded. The response of mAb-2 binding to hCD63 EC Loop 2-MMH pre-complexed with mAb-1 was compared and competitive/non-competitive behavior of different anti-CD63 monoclonal antibodies was determined as shown in Table 10.

TABLE 10

Cross-competition between anti-CD63 monoclonal antibodies

| mAb-1 | mAb-2 Competing with mAb-1 |
|---|---|
| H1M12451N | H2aM12394N |
|  | H2aM12395N |
|  | H2aM12450N |
|  | H2aM12452N |
|  | H3M12366N |
|  | H2bM12454N |
|  | H2bM13022N |
|  | H4H11992P2 |
|  | H4H11993P2 |
|  | H4H11995P2 |
|  | H4H11996P2 |
|  | H4H11997P2 |
|  | H4H11998P2 |
|  | H4H11990P2 |
|  | H1M12386N |
|  | H1M12390N |
|  | H2aM12387N |
|  | H2aM12392N |
|  | H3M12361N |
| H2aM12394N | H1M12451N |
|  | H2aM12395N |
|  | H2aM12450N |
|  | H2aM12452N |
|  | H3M12366N |
|  | H2bM12454N |
|  | H2bM13022N |
|  | H4H11992P2 |
|  | H4H11993P2 |
|  | H4H11995P2 |
|  | H4H11996P2 |
|  | H4H11997P2 |
|  | H4H11998P2 |
|  | H4H11990P2 |
|  | H1M12386N |
|  | H1M12390N |
|  | H2aM12387N |
|  | H2aM12392N |
|  | H3M12361N |
| H2aM12395N | H1M12451N |
|  | H2aM12394N |
|  | H2aM12450N |
|  | H2aM12452N |
|  | H3M12366N |
|  | H2bM12454N |
|  | H2bM13022N |
|  | H4H11992P2 |
|  | H4H11993P2 |
|  | H4H11995P2 |
|  | H4H11996P2 |
|  | H4H11997P2 |
|  | H4H11998P2 |
|  | H4H11990P2 |
|  | H1M12386N |
|  | H1M12390N |
|  | H2aM12387N |
|  | H2aM12392N |
|  | H3M12361N |
| H2aM12450N | H1M12451N |
|  | H2aM12394N |
|  | H2aM12395N |
|  | H2aM12452N |
|  | H3M12366N |
|  | H2bM12454N |
|  | H2bM13022N |
|  | H4H11992P2 |
|  | H4H11993P2 |
|  | H4H11995P2 |
|  | H4H11996P2 |
|  | H4H11997P2 |
|  | H4H11998P2 |
|  | H4H11990P2 |
|  | H1M12386N |
|  | H1M12390N |
|  | H2aM12387N |
|  | H2aM12392N |
|  | H3M12361N |
| H2aM12452N | H1M12451N |
|  | H2aM12394N |
|  | H2aM12395N |
|  | H2aM12450N |
|  | H3M12366N |
|  | H2bM12454N |
|  | H2bM13022N |
|  | H4H11992P2 |
|  | H4H11993P2 |
|  | H4H11995P2 |
|  | H4H11996P2 |
|  | H4H11997P2 |
|  | H4H11998P2 |
|  | H4H11990P2 |
|  | H1M12386N |
|  | H1M12390N |
|  | H2aM12387N |
|  | H2aM12392N |
|  | H3M12361N |
| H3M12366N | H1M12451N |
|  | H2aM12394N |
|  | H2aM12395N |
|  | H2aM12450N |
|  | H2aM12452N |
|  | H2bM12454N |
|  | H2bM13022N |
|  | H4H11992P2 |
|  | H4H11993P2 |
|  | H4H11995P2 |
|  | H4H11996P2 |
|  | H4H11997P2 |
|  | H4H11998P2 |
|  | H4H11990P2 |
|  | H1M12386N |
|  | H1M12390N |
|  | H2aM12387N |
|  | H2aM12392N |
|  | H3M12361N |
| H2bM12454N | H1M12451N |
|  | H2aM12394N |
|  | H2aM12395N |
|  | H2aM12450N |
|  | H2aM12452N |
|  | H3M12366N |
|  | H2bM13022N |
|  | H4H11992P2 |
|  | H4H11993P2 |
|  | H4H11995P2 |

TABLE 10-continued

Cross-competition between anti-CD63 monoclonal antibodies

| mAb-1 | mAb-2 Competing with mAb-1 |
|---|---|
| H2bM13022N | H4H11996P2 |
|  | H4H11997P2 |
|  | H4H11998P2 |
|  | H4H11990P2 |
|  | H1M12386N |
|  | H1M12390N |
|  | H2aM12387N |
|  | H2aM12392N |
|  | H1M12451N |
|  | H2aM12394N |
|  | H2aM12395N |
|  | H2aM12450N |
|  | H2aM12452N |
|  | H3M12366N |
|  | H2bM12454N |
| H4H11992P2 | H4H11993P2 |
|  | H4H11995P2 |
|  | H4H11996P2 |
|  | H4H11997P2 |
|  | H4H11998P2 |
|  | H4H11990P2 |
|  | H1M12386N |
|  | H1M12390N |
|  | H2aM12387N |
|  | H2aM12392N |
|  | H1M12451N |
|  | H2aM12394N |
|  | H2aM12395N |
|  | H2aM12450N |
|  | H2aM12452N |
|  | H3M12366N |
|  | H2bM12454N |
|  | H2bM13022N |
| H4H11993P2 | H4H11992P2 |
|  | H4H11995P2 |
|  | H4H11996P2 |
|  | H4H11997P2 |
|  | H4H11998P2 |
|  | H4H11990P2 |
|  | H1M12386N |
|  | H1M12390N |
|  | H2aM12387N |
|  | H2aM12392N |
|  | H1M12451N |
|  | H2aM12394N |
|  | H2aM12395N |
|  | H2aM12450N |
|  | H2aM12452N |
|  | H3M12366N |
|  | H2bM12454N |
|  | H2bM13022N |
| H4H11995P2 | H4H11992P2 |
|  | H4H11993P2 |
|  | H4H11996P2 |
|  | H4H11997P2 |
|  | H4H11998P2 |
|  | H4H11990P2 |
|  | H1M12386N |
|  | H1M12390N |
|  | H2aM12387N |
|  | H2aM12392N |
|  | H1M12451N |
|  | H2aM12394N |
|  | H2aM12395N |
|  | H2aM12450N |
|  | H2aM12452N |
|  | H3M12366N |
|  | H2bM12454N |
|  | H2bM13022N |
|  | H4H11992P2 |
|  | H4H11993P2 |
|  | H4H11996P2 |
|  | H4H11997P2 |
|  | H4H11998P2 |
| H4H11996P2 | H4H11990P2 |
|  | H1M12386N |
|  | H1M12390N |
|  | H2aM12387N |
|  | H2aM12392N |
|  | H1M12451N |
|  | H2aM12394N |
|  | H2aM12395N |
|  | H2aM12450N |
|  | H2aM12452N |
|  | H3M12366N |
|  | H2bM12454N |
|  | H2bM13022N |
|  | H4H11992P2 |
|  | H4H11993P2 |
|  | H4H11995P2 |
|  | H4H11997P2 |
|  | H4H11998P2 |
|  | H4H11990P2 |
|  | H1M12386N |
|  | H1M12390N |
|  | H2aM12387N |
|  | H2aM12392N |
| H4H11997P2 | H1M12451N |
|  | H2aM12394N |
|  | H2aM12395N |
|  | H2aM12450N |
|  | H2aM12452N |
|  | H3M12366N |
|  | H2bM12454N |
|  | H2bM13022N |
|  | H4H11992P2 |
|  | H4H11993P2 |
|  | H4H11995P2 |
|  | H4H11996P2 |
|  | H4H11998P2 |
|  | H4H11990P2 |
|  | H1M12386N |
|  | H1M12390N |
|  | H2aM12387N |
|  | H2aM12392N |
| H4H11998P2 | H1M12451N |
|  | H2aM12394N |
|  | H2aM12395N |
|  | H2aM12450N |
|  | H2aM12452N |
|  | H3M12366N |
|  | H2bM12454N |
|  | H2bM13022N |
|  | H4H11992P2 |
|  | H4H11993P2 |
|  | H4H11995P2 |
|  | H4H11996P2 |
|  | H4H11997P2 |
|  | H4H11990P2 |
|  | H1M12386N |
|  | H1M12390N |
|  | H2aM12387N |
|  | H2aM12392N |
| H4H11990P2 | H1M12451N |
|  | H2aM12394N |
|  | H2aM12395N |
|  | H2aM12450N |
|  | H2aM12452N |
|  | H3M12366N |
|  | H2bM12454N |
|  | H2bM13022N |
|  | H4H11992P2 |
|  | H4H11993P2 |
|  | H4H11995P2 |
|  | H4H11996P2 |
|  | H4H11997P2 |
|  | H4H11998P2 |
|  | H1M12386N |
|  | H1M12390N |

TABLE 10-continued

Cross-competition between anti-CD63 monoclonal antibodies

| mAb-1 | mAb-2 Competing with mAb-1 |
|---|---|
| H1M12386N | H2aM12387N |
|  | H2aM12392N |
|  | H1M12451N |
|  | H2aM12394N |
|  | H2aM12395N |
|  | H2aM12450N |
|  | H2aM12452N |
|  | H3M12366N |
|  | H2bM12454N |
|  | H2bM13022N |
|  | H4H11992P2 |
|  | H4H11993P2 |
|  | H4H11995P2 |
|  | H4H11996P2 |
|  | H4H11997P2 |
|  | H4H11998P2 |
|  | H4H11990P2 |
|  | H1M12390N |
|  | H2aM12387N |
|  | H2aM12392N |
| H1M12390N | H1M12451N |
|  | H2aM12394N |
|  | H2aM12395N |
|  | H2aM12450N |
|  | H2aM12452N |
|  | H3M12366N |
|  | H2bM12454N |
|  | H2bM13022N |
|  | H4H11992P2 |
|  | H4H11993P2 |
|  | H4H11995P2 |
|  | H4H11996P2 |
|  | H4H11997P2 |
|  | H4H11998P2 |
|  | H4H11990P2 |
|  | H1M12386N |
|  | H2aM12387N |
|  | H2aM12392N |
| H2aM12387N | H1M12451N |
|  | H2aM12394N |
|  | H2aM12395N |
|  | H2aM12450N |
|  | H2aM12452N |
|  | H3M12366N |
|  | H2bM12454N |
|  | H2bM13022N |
|  | H4H11992P2 |
|  | H4H11993P2 |
|  | H4H11995P2 |
|  | H4H11996P2 |
|  | H4H11997P2 |
|  | H4H11998P2 |
|  | H4H11990P2 |
|  | H1M12386N |
|  | H1M12390N |
|  | H2aM12392N |
| H2aM12392N | H1M12451N |
|  | H2aM12394N |
|  | H2aM12395N |
|  | H2aM12450N |
|  | H2aM12452N |
|  | H3M12366N |
|  | H2bM12454N |
|  | H2bM13022N |
|  | H4H11992P2 |
|  | H4H11993P2 |
|  | H4H11995P2 |
|  | H4H11996P2 |
|  | H4H11997P2 |
|  | H4H11998P2 |
|  | H4H11990P2 |
|  | H1M12386N |
|  | H1M12390N |
|  | H2aM12387N |
| H3M12361N | H1M12451N |
|  | H2aM12394N |
|  | H2aM12395N |
|  | H2aM12450N |
|  | H2aM12452N |
|  | H3M12366N |

Generation of Bispecific Antibodies to Determine Internalization of Bispecific Complex Having an Anti-CD63 Binding Arm To assess the ability of anti-CD63 antibodies generated as described in this example to internalize as part of a bispecific antigen-binding molecule, the antibodies were reconstructed into bispecific formats where one binding arm was the anti-CD63 antibody VH/VL pair (see Table 1 parental antibodies) and the other was an irrelevant binding arm. Standard methods of making bispecific antibodies were used, and exemplary methods are described in, e.g., US Application Publication No. 2010/0331527, and U.S. Pat. No. 5,731,168, each of which is incorporated herein by reference. The bispecific antibodies were tested for their ability to internalize using human CD63 expressing cells. For the assay, HEK293 cells, which endogenously express human CD63, were plated at a density of 10,000 cells/well in DMEM containing 10% FBS and penicillin-streptomycin/L-glutamine (Gibco, Cat #10378016) in clear bottom black Poly-D-Lysine coated 96-well plates (Greiner, Cat #655946). Two days later, the media was replaced with fresh media containing anti-CD63 bispecific antibodies and a negative control antibody in a 2-fold dilution series beginning at 10 μg/mL to 0.157 μg/mL, along with a media only control. Cells were then incubated at 37° C. for 3 hours to allow for antibody internalization. Following the incubation, cells were washed with PBS, fixed in 4% paraformaldehyde (Thermo Scientific, Cat #28908) for 20 minutes at room temperature, and subsequently permeabalized with 0.2% Triton X-100 (Spectrum Chemical, Cat #TR135) in 5% normal goat serum (NGS) (Gibco, Cat #PCN5000) for 20 minutes at room temperature. Cells were then incubated with either 2 ug/mL of donkey anti-mouse IgG Alexa Fluor-647 Fab (Manufacture, Cat #115-606-006) or 2 μg/mL of goat anti-human IgG Alexa Fluor-647 Fab (Jackson ImmunoResearch, Cat #115-606-006) in 5% NGS for 1 hour at room temperature. The secondary antibody solution was removed, then cells were washed with PBS, and subsequently fresh PBS containing 2 drops/mL of NucBlue (Invitrogen, CAT #R37605) was added to stain live cell nuclei. Antibody internalization and nuclei were imaged at 40× on the ImageXpress High-Content Imaging System (Molecular Devices) and antibody internalization was quantified using the MetaXpress Software Transfluor Application Module (Molecular Devices). Antibody internalization is reported as pit integrated intensity per cell±standard deviation (SD).

As shown in Table 11, all of the bispecific antibodies incorporating a single arm binding to human CD63 (derived from either H1M12451, H2M12450, or H2M12395) and an irrelevant non-binding arm demonstrated efficient internalization into HEK293 cells. The bispecific antibody incorporating one binding arm of mAb12450 demonstrated a higher amount of internalization than the other bispecific antibodies tested.

TABLE 11

Internalization of anti-CD63 bispecific antibodies by HEK293 cells

| Concentration of antibody (µg/mL) | Internalization of antibody (pit integrated intensity) ± SD | | | |
|---|---|---|---|---|
| | H2M12395N bispecific | H2M12450N bispecific | H1M12451N bispecific | Negative control Ab |
| 10 | 1.05E+06 ± 4.56E+05 | 4.34E+06 ± 8.77E+05 | 8.26E+05 ± 2.67E+05 | 4.58E+03 ± 6.50E+03 |
| ~5 | 1.07E+06 ± 4.06E+05 | 4.31E+06 ± 5.48E+05 | 5.45E+05 ± 5.20E+04 | 1.23E+03 ± 8.85E+02 |
| 2.5 | 2.73E+05 ± 6.01E+04 | 3.92E+06 ± 5.80E+05 | 3.27E+05 ± 1.06E+05 | 7.70E+02 ± 6.09E+02 |
| 1.25 | 1.89E+05 ± 6.61E+04 | 2.72E+06 ± 2.63E+05 | 1.20E+05 ± 3.91E+04 | 1.43E+03 ± 1.19E+03 |
| 0.625 | 2.03E+05 ± 9.37E+04 | 1.75E+06 ± 1.39E+05 | 7.87E+04 ± 1.07E+04 | 3.37E+03 ± 5.22E+03 |
| 0.3125 | 3.95E+04 ± 8.23E+03 | 8.57E+05 ± 1.60E+05 | 3.77E+04 ± 1.22E+04 | 1.99E+03 ± 2.19E+03 |
| 0.15625 | 2.81E+04 ± 1.30E+04 | 2.42E+05 ± 2.54E+04 | 7.23E+03 ± 6.09E+03 | 1.87E+03 ± 1.16E+03 |
| 0 | 3.72E+03 ± 1.66E+03 | 8.21E+03 ± 3.47E+03 | 1.66E+04 ± 1.80E+04 | 1.10E+03 ± 1.56E+03 |

Example 2: Construction of Anti-hCD63 ScFv::GAA Polynucleotide and Gene Therapy Vector AAV2/8 viruses encoding for the expression of human GAA (hGAA; SEQ ID NO:369) or an anti-human CD63 single chain variable fragment (ScFv) fused on its C-terminus to human GAA (anti-hCD63 ScFv-hGAA) are generated using a standard triple transfection protocol (Gray et al. 2011; see also "Production of recombinant adeno-associated viral vectors and use in vitro and in vivo administration", Current Protocols in Neuroscience, John Wiley & Sons, New York (1999), pp. 4.17.1-4.17.25, Vol 1). For the production, $1 \times 10^7$ HEK293 cells are plated onto 15 cm plates. The following day the cells are transfected with (A) either 8 µg of a control pAAV vector comprising a liver specific serpina 1 enhancer (SEQ ID NO:367) and encoding TTR promoter (SEQ ID NO:368) driven human GAA or test pAAV comprising a liver specific serpina 1 enhancer (SEQ ID NO:367) and encoding a TTR promoter (SEQ ID NO:368) driven hCD63 ScFv-hGAA (see, e.g., FIG. 2) and (B) pAAV RC2/8-derived vector (Gao, 2002) and 16 µg of pHelper (Agilent, Cat #240074) using PEIpro (Polyplus transfection, New York, NY catalog #115-100)-mediated transfection at ratio of 1:1 (1 ul PEIpro:1 µg DNA). Seventy-two hours after transfection, the cells are collected and lysed in a buffer comprised of 20 mM Tris-HCl, 1 mM MgCl2, 2.5 mM KCl, 100 mM NaCl using a standard freeze-thaw method. Next, benzonase (Sigma, Cat #E1014-25KU) is added to the samples at a final concentration of 0.5 U/µL, and then incubated at 37° C. for 60 minutes. Viruses are purified using iodixanol gradient ultracentrifugation as described in (Zolotukhin et al., 1999, Gene Ther 1999; 6:973-985) and subsequently titrated by qPCR.

AAV samples are treated with DNaseI (Thermofisher Scientific, Cat #EN0525) at 37° C. for one hour and lysed using DNA extract All Reagents (Thermofisher Scientific Cat #4403319). Encapsidated viral genomes are quantified using an QuantStudio 3 Real-Time PCR System (Thermofisher Scientific) using primers directed to the AAV2 ITRs. The sequences of the AAV2 ITRs primers are 5'-GGAACCCCTAGTGATGGAGTT-3' (fwd ITR; SEQ ID NO:370) and 5'-CGGCCTCAGTGAGCGA-3' (rev ITR; SEQ ID NO:371) (Aurnhammer et al., 2012), derived the left internal inverted repeat (ITR) sequence from of the AAV (SEQ ID NO:365) and the right internal inverted repeat (ITR) sequence from of the AAV (SEQ ID NO:366), respectively. The sequence of the AAV2 ITRs probe is 5'-6-FAM-CACTCCCTCTCTGCGCGCTCG-TAMRA-3' (SEQ ID NO:372) (Aurnhammer C., Haase M., Muether N., et al., 2012, Hum. Gene Ther. Methods 23, 18-28). After a 95° C. activation step for 10 min, a two-step PCR cycle is performed at 95° C. for 15 seconds and 60° C. for 30 seconds for 40 cycles. The TaqMan Universal PCR Master Mix (Thermofisher Scientific, Cat #4304437) is used in the qPCR. DNA plasmid (Agilent, Cat #240074) is used as standard to determine absolute titers.

Anti-human CD63 antibodies and their fusions use the anti-CD63 variable domains set forth in Table 1. ScFv versions of the antibodies are cloned with variable domains in heavy-light order with a glycine-serine linker in between (5'-VH-Gly-Ser-VL-3').

AAV encoding an anti-hCD63 scFv::GAA multidomain therapeutic having an amino acid sequence set forth as SEQ ID NO:364 (FIG. 2) were generated and tested for efficacy in providing enzyme replacement treatment

Example 3: Glycogen Content in Murine Pompe Model Post-AAV

To determine the effect of AAV delivered anti-hCD63 ScFv-GAA fusion (SEQ ID NO:364) versus AAV delivered GAA, in a relevant glycogen storage in vivo model, both therapies are delivered to a Pompe disease mouse model where mice are homozygous for the deletion of the mouse GAA gene and are homozygous for the expression of human CD63 in place of mouse CD63 with a strain background of 75% C57BL/6; 25% 129SvJ. These mice are herein referred to as CD63 HumIn GAA KO mice or alternatively as CD63hu/hu; GAA$^{-/-}$ mice.

For the experiment, 2-month-old CD63 HumIn GAA KO are were administered via tail vein injection with either AAV2/8 virus containing a genome with either the TTR liver specific promoter driving human GAA (AAV-hGAA; described in Example 2) or the TTR liver specific promoter driving anti-human CD63 ScFv fused at its C-terminus with human GAA (AAV-anti-hCD63 ScFv-hGAA; described in Example 2). Both AAV2/8 viruses are delivered at either one of two doses, 1e10 vg/mouse or 1e11 vg/mouse. As controls, untreated CD63 HumIn GAA KO mice and untreated CD63 HumIn with the mouse GAA gene intact are included in the assay. Mice are housed for 3 months after treatment and bled incrementally (monthly) during this period for serum measurements of GAA levels and anti-GAA antibodies. After 3 months, all mice are sacrificed and individual tissues are harvested for glycogen measurements, PAS-H staining, quantification of central nuclei, measurement of lysosomal proliferation, and measurement of LC3b expression. Experimental dosing and treatment protocol for groups of mice are shown in Table 12.

TABLE 12

Experimental dosing and treatment protocol for groups of mice

| Group | Mice | Number of Mice | Treatment | Dosage |
|---|---|---|---|---|
| 1 | CD63 Humin GAA KO | 4 | None | N/A |
| 2 | CD63 Humin GAA KO | 4 | AAV-hGAA | 1e10 vg/mouse |

TABLE 12-continued

Experimental dosing and treatment protocol for groups of mice

| Group | Mice | Number of Mice | Treatment | Dosage |
|---|---|---|---|---|
| 3 | CD63 Humin GAA KO | 4 | AAV-hGAA | 1e11 vg/mouse |
| 4 | CD63 Humin GAA KO | 5 | AAV-anti-hCD63 ScFv-hGAA | 1e10 vg/mouse |
| 5 | CD63 Humin GAA KO | 4 | AAV-anti-hCD63 ScFv-hGAA | 1e11 vg/mouse |
| 6 | CD63 Humin GAA WT | 2 | None | N/A |

Example 4: Immunological Response to GAA

To measure anti-human GAA antibody serum levels, serum from all the treatment groups is separated from the blood collected during the terminal bleed using serum separator tubes (BD Biosciences, Cat #365967) as per the manufacturer's specifications. Separately, 96-well high protein binding plates (ThermoFisher, Cat #15041) are coated with 20 μg of hGAA (R&D Systems, Cat #8329-GH-025) diluted in PBS overnight. Plates are washed with PBS+ 0.05% Tween (PBS-T) 3 times. Plates are blocked with 0.5% BSA in PBS-T, and serial dilutions of mouse serum ranging from 1:300 to 1:5.1e7 are added to the plate overnight. Total anti-mouse IgG (subclasses 1+2a+2b+3) is measured using a HRP conjugated goat anti-mouse IgG antibody (Jackson Immuno Research, Cat #115-035-164) and the BD Opt EIA substrate kit. The colormetric reactions are stopped using 1 N phosphoric acid. Absorbance is then read at 450 nm on a Spectramax i3 plate reader (Molecular Devices). Dilution curves are fit to sigmoidal curves, and titers are calculated from the curves.

In similarly performed experiments, higher levels of GAA or anti-hCD63scFv::GAA (SEQ ID NO:364) after AAV administration was correlated with lower anti-GAA titers (data not shown). The serum of GAA null mice treated with high or low titers of AAV-anti-hCD63scFv::GAA (SEQ ID NO:364) or AAV-GAA were assessed for anti-GAA antibodies over the course of the three months post-injection. A negative correlation between antibody titer and serum exposure to GAA, and an inverse correlation between doses of construct and titer of anti-GAA antibodies was seen (data not shown).

Example 5: Serum GAA

To measure human GAA serum levels over the course of the experiment, samples are collected at monthly time points via tail bleed. Serum is separated from the blood using serum separator tubes (BD Biosciences, Cat #365967) as per the manufacturer's specifications. 1 μL of isolated serum is then loaded onto a 4-20% Novex wedgewell pre-cast gel, run at 220V for 45 minutes and transferred to nitrocellulose membrane at 200 mA for 1 hour using standard procedures. The nitrocellulose membrane is then probed with an anti-GAA primary antibody (Abcam, #ab137068) used at a dilution of 1:2000 and an anti-GAPDH antibody (Abcam, #AB9484) used at a dilution of 1:1000 in 12 mL and incubated overnight at 4° C. After primary antibody incubation, the membrane is washed three times with 1×TBST for 5 minutes per wash. Anti-rabbit IgG (LiCor, 926-32211) and anti-mouse IgG (LiCor, 925-68070) (LiCor, Lincoln, NE) secondary antibodies at a dilution of 1:15000 in 12 mL are then added to the membrane and incubated for 1 hour at room temperature. After secondary antibody incubation, the membrane is washed two times with 1×TBST for 5 minutes per wash and one time with 1×TBS for 5 minutes. The membrane is then imaged and quantified using a LiCor Odyssey instrument (LI-COR Biotechnology).

In experiments similar to those described above, CD63 HumIn GAA KO mice treated with the high dose (10" vg/mouse) of AAV-anti-hCD63 ScFv-hGAA (SEQ ID NO:364) or AAV-hGAA demonstrated sustained levels of GAA in the serum over the course of the experiment (data not shown).

Real-time PCR quantifications of expression in liver, heart, and quadriceps lysates 3 months after injection was performed. Liver expression was detected for all injections of AAV construct, and a comparison of serum GAA level to RNA expression level of GAA was also made. The data (not shown) suggested that the AAV encoding the fusion protein set forth as SEQ ID NO:364 (and expression is driven by a liver-specific promoter) attains an improved secretion profile for GAA.

Example 6: Tissue Measurement of Glycogen and Histological Characterization of Muscle Tissue Tissue Measurements of Glycogen:

To measure the glycogen content in individual tissues, heart, quadriceps, gastrocnemius, diaphragm, soleus, and EDL tissue are dissected from mice from all groups immediately after $CO_2$ asphyxiation, and then snap frozen in liquid nitrogen, and stored at −80° C. ~50 mg of each tissue is lysed on a benchtop homogenizer with stainless steel beads in distilled water at a ratio of 1 mg to 25 μL water for glycogen measurements. Glycogen analysis lysates are heated at 105° for 15 minutes and centrifuged at 21000×g to clear debris. Glycogen measurements are performed using a Glycogen Assay Kit (Sigma-Aldrich, #MAK016) according to manufacturer's instructions for fluorometric assays. The fluorescence of each sample is measured at 535 nm excitation and 587 nm emission on a fluorescence plate reader (Molecular Devices, Spectramax i3). The calculated amount of glycogen is calculated using the following formula provided by the manufacturer.

Quadricep Harvest for Histopathology and Quantification:

Quadricep tissue samples from mice from each group besides the low dose (1e10 vg/mouse) treatment group are either snap frozen immediately after dissection in liquid nitrogen and stored at −80° C. for quantification of LC3b expression or are placed onto blocks containing O.C.T medium (Tissue-Tek, #4583).

Tissues samples in O.C.T medium are sent to Histoserv, Inc (Germantown, MD) for sectioning and periodic acid Schiff (PAS) staining to detect polysaccharides. Additional sections are prepared and returned for staining of central nuclei and lysosomal proliferation.

Pas Staining:

PAS stain sections are imaged using a Leica slide scanner at 20× magnification.

Quantification of Central Nuclei and Lysosomal Proliferation:

Unstained sections from Histoserv are removed from the freezer and then fixed with 4% paraformaldehyde in PBS for 15 minutes in a staining chamber. The fixed slides are then washed twice for 5 minutes in PBS and subsequently incubated with blocking buffer (eBiosciences, 00-4953-54) for 1 hour at room temperature. Slides are then either stained with either a rat anti-Lamp-1 antibody (Abcam, #AB25245) at a dilution of 1:50 in blocking buffer, a rabbit anti-Laminin antibody (Sigma, #L9393) at a dilution of 1:1000 in blocking buffer, or blocking buffer with no added antibody while in a humidified staining chamber and then transferred to 4° C. for overnight incubation. The following day, slides are then washed twice for 5 minutes in PBS and subsequently stained with either goat anti-rabbit IgG (H+L) superclonal secondary antibody conjugated with Alexa Fluor 647 (Life Tech Thermo, #A27040) or goat anti-rat IgG (H+L) cross-adsorbed secondary antibody conjugated with Alexa Fluor 555 (Life Tech Thermo, #A21434) in a staining chamber then allowed to incubate for 1 hour at room temperature. Stained slides are then washed twice for 5 minutes in PBS before they being mounted with Fluoromount-G with DAPI (Life Tech Thermo, #00-4959-52) and imaged on a Zeiss LSM710 instrument (Carl Zeiss Microscopy GmbH). The number of centralized nuclei is quantified using Halo software (Indica Labs, NM)

Quantification of LC3b Expression:

For quantification of LC3b expression, snap frozen samples are thawed, homogenized and then lysed in RIPA buffer at a 1 mg tissue to 254, RIPA buffer ratio (150 mM NaCl, 1.0% IGEPAL® CA-630, 0.5% sodium deoxycholate, 0.1% SDS, 50 mM Tris, pH 8.0, Sigma Aldrich, R0278) by bead impaction for 45 seconds (MP Biomedical). Lysates are cleared of insoluble material by centrifugation at 21,000×g and then 300 µg of lysate in RIPA buffer is loaded on a 4-20% Novex wedgewell pre-cast gel, transferred to a nitrocellulose membrane and analyzed by western blot using a similar protocol as previously described for the analysis of serum GAA levels, substituting the use of primary antibody that recognizes mouse LC3b-I and LC3b-II (Sigma, #L7543) in place of the primary antibody against GAA. The membrane was then imaged and quantified using a LiCor Odyssey instrument (LI-COR Biotechnology). LC3b-I and LC3b-II levels expressed as (mean+/−standard deviation) in arbitrary units.

What is claimed:

1. An anti-CD63 antibody or antigen-binding fragment thereof, wherein the antibody or antigen-binding fragment thereof comprises three heavy chain complementarity determining regions (HCDRs) within the heavy chain variable region (HCVR) amino acid sequence and three light chain complementarity determining regions (LCDRs) within the light chain variable region (LCVR) amino acid sequence of an HCVR/LCVR pair selected from the group consisting of SEQ ID NOs: 2/10, SEQ ID NOs: 18/26, SEQ ID NOs: 34/42, SEQ ID NOs: 50/58, SEQ ID NOs: 66/74, SEQ ID NOs: 82/90, SEQ ID NOs: 98/106, SEQ ID NOs: 114/122, SEQ ID NOs: 130/138, SEQ ID NOs: 146/154, SEQ ID NOs: 162/170, SEQ ID NOs: 178/186, SEQ ID NOs: 194/202, SEQ ID NOs: 210/218, SEQ ID NOs: 226/234, SEQ ID NOs: 242/250, SEQ ID NOs: 258/266, SEQ ID NOs: 274/282, SEQ ID NOs: 290/282, SEQ ID NOs: 298/282, SEQ ID NOs: 306/282, SEQ ID NOs: 314/282, SEQ ID NOs: 322/282, and SEQ ID NOs: 330/282.

2. The anti-CD63 antibody or antigen-binding fragment thereof of claim 1, wherein the antibody or antigen-binding fragment thereof comprises a set of six CDRs selected from the group consisting of SEQ ID NOs: 4-6-8-12-14-16, SEQ ID NOS: 20-22-24-28-30-32, SEQ ID NOs: 36-38-40-44-46-48, SEQ ID NOs: 52-54-56-60-62-64; SEQ ID NOs: 68-70-72-76-78-80; SEQ ID NOs: 84-86-88-92-94-96; SEQ ID NOs: 100-102-104-108-110-112; SEQ ID NOs: 116-118-120-124-126-128; SEQ ID NOs: 132-134-136-140-142-144; SEQ ID NOS: 148-150-152-156-158-160; SEQ ID NOs: 164-166-168-172-174-176; SEQ ID NOs: 180-182-184-188-190-192; SEQ ID NOs: 196-198-200-204-206-208; SEQ ID NOs: 212-214-216-220-222-224; SEQ ID NOs: 228-230-232-236-238-240; SEQ ID NOs: 244-246-248-252-254-256; SEQ ID NOs: 260-262-264-268-270-272; SEQ ID NOs: 276-278-280-284-286-288; SEQ ID NOs: 292-294-296-284-286-288; SEQ ID NOS: 300-302-304-284-286-288; SEQ ID NOs: 308-310-312-284-286-288; SEQ ID NOS: 316-318-320-284-286-288; SEQ ID NOs: 324-326-328-284-286-288, and SEQ ID NOs: 332-334-336-284-286-288.

3. The anti-CD63 antibody or antigen-binding fragment thereof of claim 1, wherein the antibody or antigen-binding fragment thereof comprises an HCVR/LCVR amino acid sequence pair selected from the group consisting of SEQ ID NOs: 2/10, SEQ ID NOs: 18/26, SEQ ID NOs: 34/42, SEQ ID NOS: 50/58, SEQ ID NOs: 66/74, SEQ ID NOs: 82/90, SEQ ID NOs: 98/106, SEQ ID NOS: 114/122, SEQ ID NOs: 130/138, SEQ ID NOs: 146/154, SEQ ID NOs: 162/170, SEQ ID NOs: 178/186, SEQ ID NOs: 194/202, SEQ ID NOs: 210/218, SEQ ID NOs: 226/234, SEQ ID NOs: 242/250, SEQ ID NOs: 258/266, SEQ ID NOs: 274/282, SEQ ID NOS: 290/282, SEQ ID NOs: 298/282, SEQ ID NOs: 306/282, SEQ ID NOs: 314/282, SEQ ID NOs: 322/282, and SEQ ID NOs: 330/282.

4. A bispecific antigen-binding molecule comprising:
   (i) a first antigen-binding domain comprising the anti-CD63 antibody or antigen-binding fragment thereof of claim 1, and (ii) a second antigen-binding domain that binds a target antigen.

5. The bispecific antigen-binding molecule of claim 4, wherein the target antigen is a tumor associated antigen.

6. The bispecific antigen-binding molecule of claim 4, wherein the first antigen-binding domain does not bind human cells that express CD63 but not the target antigen.

7. The bispecific antigen-binding molecule of claim 4, wherein each of the first antigen-binding domain and the second antigen-binding domain is fully human.

8. The bispecific antigen-binding molecule of claim 4, wherein the bispecific antigen-binding molecule binds both human CD63 and a human target antigen expressed on a cell and induces CD63 internalization and/or degradation of the human target antigen in that cell.

9. The bispecific antigen-binding molecule of claim 4, wherein the bispecific antigen-binding molecule is not internalized by cells that express human CD63 but do not express the human target antigen.

10. The bispecific antigen-binding molecule of claim 4, wherein the bispecific antigen-binding molecule is fully human.

11. The bispecific antigen-binding molecule of claim 4, wherein the first antigen-binding domain binds human CD63 with a low binding affinity such that the bispecific antigen-binding molecule does not bind cells that express human CD63 alone but binds to cells that express both human CD63 and the target antigen.

12. A multidomain therapeutic protein comprising the anti-CD63 antibody or antigen-binding fragment thereof of claim 1 and an enzyme domain.

13. The multidomain therapeutic protein of claim 12, wherein the enzyme domain comprises GAA, or a biologically active portion thereof.

14. The multidomain therapeutic protein of claim 12, comprising an amino acid sequence set forth as SEQ ID NO: 364.

15. A polynucleotide comprising a sequence encoding the anti-CD63 antibody or antigen-binding fragment thereof of claim 1.

16. A polynucleotide comprising a sequence encoding the multidomain therapeutic protein of claim 12, wherein the polynucleotide is comprised within an AAV vector.

17. The polynucleotide of claim 16, wherein the polynucleotide further comprises the sequences set forth as SEQ ID NO: 365 and SEQ ID NO: 366.

18. The polynucleotide of claim 17, wherein the polynucleotide further comprises a liver specific enhancer and/or liver specific promoter.

19. The polynucleotide of claim 18, wherein the liver specific enhancer comprises a sequence set forth as SEQ ID NO: 367 and/or the liver specific promoter comprises a sequence set forth as SEQ ID NO: 368.

20. A pharmaceutical composition comprising the anti-CD63 antibody or antigen-binding fragment thereof of claim 1 and a pharmaceutically acceptable carrier.

21. A compound comprising the anti-CD63 antibody or antigen-binding fragment thereof of claim 1 for use in medicine.

22. The compound of claim 21, for use in treating a CD63-associated disorder.

23. The compound of claim 22, wherein the CD63-associated disorder is selected from the group consisting of mast cell (MC-) dependent diseases, rheumatoid arthritis, IgE-dependent allergic reactions and Fc-ER1-mediated allergic reaction, asthma, cancer and/or metastases.

24. The compound of claim 21, for use in the identification and/or isolation of exosomes.

* * * * *